United States Patent
Xiang et al.

(10) Patent No.: US 10,449,258 B2
(45) Date of Patent: Oct. 22, 2019

(54) ANTIBODY DRUG CONJUGATE, INTERMEDIATE, PREPARATION METHOD, PHARMACEUTICAL COMPOSITION AND USES THEREOF

(71) Applicant: XDCEXPLORER (SHANGHAI) CO., LTD., Shanghai (CN)

(72) Inventors: Jason Shaoyun Xiang, Shanghai (CN); Shifeng Liu, Shanghai (CN); Hongyu Yang, Shanghai (CN); Xingquan Ma, Shanghai (CN)

(73) Assignee: XDCEXPLORER (SHANGHAI) CO., LTD., Shanghai (CN)

(*) Notice: Subject to any disclaimer, the term of this patent is extended or adjusted under 35 U.S.C. 154(b) by 0 days.

(21) Appl. No.: 15/580,895

(22) PCT Filed: Jun. 8, 2016

(86) PCT No.: PCT/CN2016/085275
§ 371 (c)(1),
(2) Date: Dec. 8, 2017

(87) PCT Pub. No.: WO2016/197946
PCT Pub. Date: Dec. 15, 2016

(65) Prior Publication Data
US 2018/0161446 A1    Jun. 14, 2018

(30) Foreign Application Priority Data
Jun. 9, 2015 (CN) .......................... 2015 1 0313585

(51) Int. Cl.
| C07D 498/18 | (2006.01) |
| A61K 31/537 | (2006.01) |
| C07K 16/30 | (2006.01) |
| C07K 16/32 | (2006.01) |
| A61K 47/68 | (2017.01) |
| A61P 35/00 | (2006.01) |
| A61K 31/5365 | (2006.01) |

(52) U.S. Cl.
CPC ...... *A61K 47/6803* (2017.08); *A61K 31/5365* (2013.01); *A61K 47/6855* (2017.08); *A61P 35/00* (2018.01); *C07D 498/18* (2013.01); *C07K 16/32* (2013.01)

(58) Field of Classification Search
CPC .... C07D 498/18; A61K 31/537; C07K 16/30; C07K 16/32
See application file for complete search history.

(56) References Cited

U.S. PATENT DOCUMENTS

| 389,611 A | 9/1888 | Strom |
| 5,208,020 A | 5/1993 | Chari et al. |
| 5,416,064 A | 5/1995 | Chari et al. |
| 9,314,536 B2 | 4/2016 | Qin et al. |
| 2005/0276812 A1 | 12/2005 | Ebens et al. |

FOREIGN PATENT DOCUMENTS

| CN | 103269712 A | 8/2013 |
| CN | 103319599 A | 9/2013 |
| EP | 0 425 235 B1 | 9/1996 |
| JP | 63-233986 A | 9/1988 |
| JP | 01-006282 A | 1/2001 |
| WO | WO-2004/103272 A1 | 12/2004 |
| WO | WO-2005/037992 | 4/2005 |
| WO | WO-2009/134976 A1 | 11/2009 |
| WO | WO-2011/039721 A1 | 4/2011 |
| WO | WO-2012/061590 A1 | 5/2012 |
| WO | WO-2013/173391 A1 | 11/2013 |
| WO | WO-2014/094355 A1 | 6/2014 |
| WO | WO-2014/094453 A1 | 6/2014 |
| WO | WO-2014/145090 A1 | 9/2014 |
| WO | WO-2014/134483 A1 | 10/2014 |
| WO | WO-2014/134457 A1 | 12/2014 |
| WO | WO-2014/194030 A3 | 1/2015 |

(Continued)

OTHER PUBLICATIONS

Erickson et al. (Cancer Research (2006), 66(8), 4426-4433).*
Kawai et al, "Chemical Modification of Ansamitocins. III. Sythesis and Biological Effects of 3-Acyl Esters of Maytansinol", Chem. Pharma. Bull., vol. 32(9), 3441-3451, 1984.
Widdison et al, "Semisynthetic Maytansine Analogues for the Targeted Treatment of Cancer", J. Med. Chem. vol. 49, 4392-4408, 2006.

(Continued)

*Primary Examiner* — Bruck Kifle
(74) *Attorney, Agent, or Firm* — Foley & Lardner LLP

(57) ABSTRACT

Disclosed are an antibody drug conjugate IB, which uses ether linkages for connection, and improves the water solubility, stability and cytotoxicity in vivo and in intro, and an intermediate, a pharmaceutical composition, and uses of the antibody drug conjugate. The antibody drug conjugate has simple synthetic steps and a high yield.

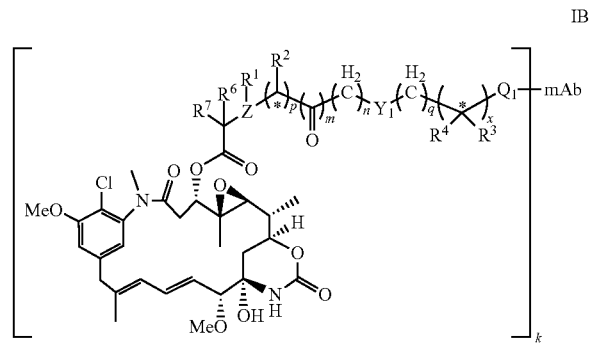

18 Claims, 3 Drawing Sheets

(56) References Cited

FOREIGN PATENT DOCUMENTS

| WO | WO-2015/000062 A1 | 1/2015 |
|---|---|---|
| WO | WO-2014/134486 A3 | 3/2015 |

OTHER PUBLICATIONS

Cassady et al, "Recent Development in the Maytansinoid Antitumor Agents", Chem. Pharm. Bull., vol. 52 (1) ,1-26, 2004.
Kupchan et al, "Structural Requirements for Antileukemic Activity among the Naturally Occurring and Semisynthetic Maytansinoids", Journal of Medicinal Chemistry, vol. 21(1), pp. 31-37, 1978.
Junttila et al, "Trastuzumab-DM1 (T-DM1) retains all the mechanisms of action of trastuzumab and efficiently inhibits growth of lapatinib insensitive breast cancer", Breast. Cancer. Res. Treat., vol. 128, 347-356, 2011.
Chinese Patent Application No. 201510313585.7 (withdrawn), with English translation.
Extended European Search Report issued in European patent application No. 16806844.3 dated Jan. 24, 2019.
Jain et al., "Current ADC linker chemistry," Pharmaceutical Research, Springer New York LLC, US, vol. 32, No. 11, Mar. 2015, pp. 3526-3540.
Phillips et al., "Targeting HER2-positive breast cancer with trastuzumab-DM1, an antibody-cytotoxic drug conjugate," Cancer Research, vol. 68, No. 22, Nov. 2008, pp. 9280-9290.
Jain et al., "Current ADC Linker Chemistry", Pharmres, vol. 32, No. 11, Mar. 2015, pp. 3526-3540.
Lewis et al., "Targeting HER2-Positive Breast Cancer with Trastuzumab-DM1, an Antibody-Cytotoxic Drug Conjugate," Cancer Research, vol. 68, No. 22, 2008, pp. 9280-9290.
International Search Report with English Translation and Written Opinion issued in corresponding application No. PCT/CN2016/085275 dated Sep. 14, 2016.

* cited by examiner

ANTIBODY DRUG CONJUGATE, INTERMEDIATE, PREPARATION METHOD, PHARMACEUTICAL COMPOSITION AND USES THEREOF

CROSS REFERENCE TO RELATED APPLICATIONS

The present application is a national stage entry of PCT/CN/2016/085275, filed Jun. 8, 2016, which claims the benefit of Chinese Patent Application CN201510313585.7 filed on Jun. 9, 2015, the contents of which are incorporated herein by reference in their entireties.

FIELD OF INVENTION

The present invention relates to an antibody drug conjugate, an intermediate (a toxin with a linker), a preparation method, a pharmaceutical composition and a use thereof.

BACKGROUND OF THE INVENTION

Typical antibody drug conjugates (ADC) contain monoclonal antibodies capable to bind to surface specific antigens of cancer cells. These antibodies include some proteins on the surface of immune system B cells and T cells, such as CD20, CD22, and human epidermal growth factor receptor 2 (Her2) and prostate specific membrane antigen (PSMA). These antibodies are connected with the highly toxic drugs through a cleavable linker unit. Drugs are designed to induce irreversible DNA damage or interfere with cell division, so as to lead to apoptosis of cancer cells.

The mechanism of antibody drug conjugates (ADC) is to recognize and bind to specific antigen through the antibodies, trigger a series of reactions, and then enter the cytoplasm through the endocytosis, where the highly toxic drug is dissociated from the lysosomal enzymes to kill cancer cells. Compared with the traditional chemotherapy which causes damage to both cancer cells and normal tissues indiscriminately, targeting drug delivery can make the drug act on cancer cells directly and reduce the damage to normal cells.

The first antibody drug conjugate approved by the FDA is Mylotarg (gemtuzumab/ozogamicin), developed by Wyeth in 2000 for the treatment of acute myeloid leukemia, but due to some adverse effects and safety consideration, the drug was withdrawn after ten years. Since then, much progress has been made in the technology of linking antibodies and drugs. By using a linker with a proper biological half-life, researchers are able to ensure that the antibody drug conjugate can reach target cells thereby reducing side effects.

In 2011, Adcetris (brentuximab vedotin) from Seattle Genetics was approved by the FDA for the treatment of Hodgkin's lymphoma and systematic anaplastic large cell lymphoma. The turnover of the antibody drug conjugate in the first quarter of 2012 reached $34,500,000 and continued increasing. It is expected that in the next ten years, the use of antibody drug conjugates will be increased by about 50% in cancer therapy drug market. At present, Roche and Genentech together have more than 25 antibody drug conjugates in the research and development, of which 9 are in clinical research.

The first antibody drug conjugate, a potential blockbuster, Kadcyla (trastuzumab emtansine, T-DM1) was approved on sale for the treatment of metastatic breast cancer in February 2013. Kadcyla was formulated by combining Herceptin which is an antibody used for the treatment of breast cancer with a toxin Maitansine licensed by ImmunoGen. The turnover of the drug in 2015 was nearly 700 million dollar.

Antibody drug conjugates are likely to become the next resounding drug field that will bring sustained income. The collaboration of biomedicine and clinical trials results in continuous success of antibody drug conjugate technology. These common results suggest the use of humanized monoclonal antibody technology as target directed therapeutic delivery. So far, most of the antibody drug conjugates that have been developed are using auristatins supplied by Seattle Genetics or maytansine supplied by ImmunoGen as effective toxins. In addition, Spirogen and other companies are also developing other toxins for the next generation of antibody drug conjugates, such as class PBD.

Maytansinoids alkaloid was first isolated from *Maytenus serrata*, a shrub in East African (US 389611, JP 01006282, JP 63233986), which is a compound with high cytotoxicity used as an anti-cancer agent. Many maytansine derivatives prepared artificially with high anticancer activity are 100 to 1000 times that of traditional anticancer drugs, such as vincaleukoblastinum or taxinol. (*J. Med. Chem.*, 1978, 21, 31-37, *Chem. Pharma. Bull.*, 1984, 3441-3451, *J. MAed. Chem.* 2006, 49, 4392-4408, *Chem. Pharm. Bull.* 2004, 52 (1) 1-26, WO 2011039721, WO 2012/061590, WO 2014/094453).

In patent documents U.S. Pat. Nos. 5,208,020, 5,416,064 and *J. Med. Chem*, 2006, 49, 4392-4408, Chari, R. V. J. et al. reported the maytansine analogues DM1 and DM4. Patent application WO 2004/103272, EP 0425235 reported the conjugates of maytansine analogues DM1 and DM4 and anticancer activities thereof. A series of articles and patents followed reported many conjugates of maytansine analogues used as antitumor drugs (WO 2011/039721, WO 2012/061590, WO 2014/134483, WO 2014/134457, WO 2014/194030, WO 2014/134486, WO 2014/094355, WO 2015/000062, WO 2014/145090, WO 2013/173391).

Typical antibody drug conjugate is comprised by three parts of a drug, a linker unit and an antibody. The choice of specific antibody and drug depends on specific diseases and has important effects on the safety and efficacy of the conjugate. The stability of the linker unit and the coupling method to the antibody play a decisive role in the development of ADC drug. Factors that determine the efficacy of antibody drug conjugates include the stability and fracture sensitivity of the linker unit, cell surface excitation internalization, transport, and release of the cytotoxin.

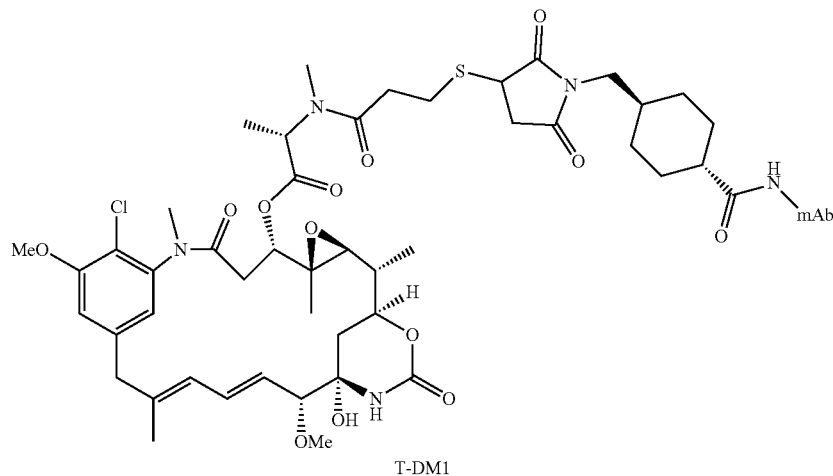

T-DM1

T-DM1, for example, is prone to degrade and release toxins prematurely before antigen binding protein (Abu) begins endocytosis, thereby causing side effects. Moreover, the drug/antibody ratio of T-DM1 is relatively low, and the distribution is greatly varied, and it is difficult to control the efficacy and safety precisely (WO 2012/061590 A1, WO 201139721). Therefore, the technical problem required to be solved is to search a linker with high stability and good water-solubility, thereby obtaining an antibody drug conjugate with high release efficiency of cytotoxin, high specificity, high cytotoxicity, good anti-cancer effect.

SUMMARY OF THE INVENTION

The technical problem to be solved in the present invention is to overcome the defects of antibody drug conjugates in prior art, such as low stability of linker units, low fracture sensitivity, low efficiency of cell surface excitation internalization, transport and release of cytotoxin, low cytotoxicity, poor specificity, side effects and others, and provides an antibody drug conjugate, an intermediate (a toxin with a linker), a preparation method, a pharmaceutical composition and a use thereof. The antibody drug conjugate of the present invention has very high cytotoxicity, good anti-cancer effect, and has good market application prospect.

The present invention provides an antibody drug conjugate, which is represented by formula IB,

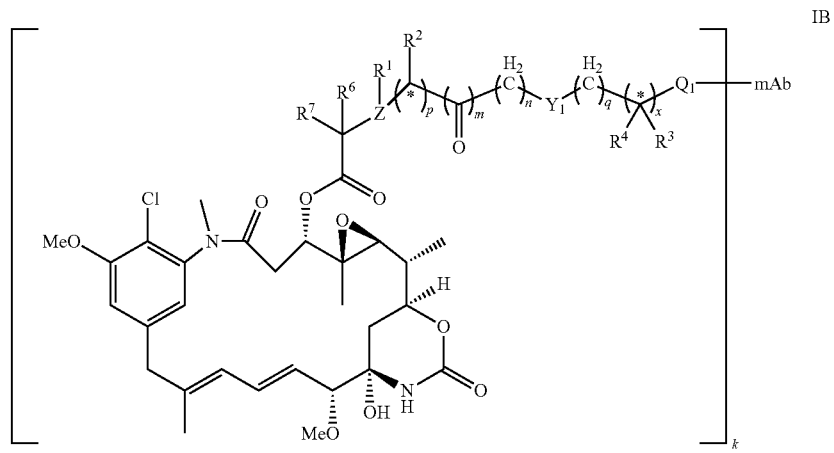

IB wherein:
Z is nitrogen atom,

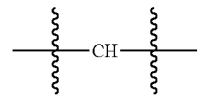

or oxygen atom, when Z is oxygen atom, $R^1$ is absence; when Z is

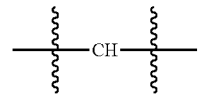

or nitrogen atom, $R^1$ is hydrogen or a $C_1$-$C_4$ alkyl (the $C_1$-$C_4$ alkyl, e.g. methyl, ethyl, n-propyl, n-butyl, iso-propyl, iso-butyl or tert-butyl, methyl is preferred) or $R^1$, Z as well as the carbon atom that they connected to and $R^6$ or $R^7$ together form a 4- to 6-membered cyclical structure (a 6-member cyclical structure is preferred, e.g.

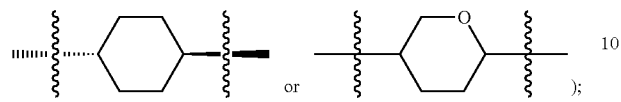
);

$R^2$ is hydrogen or a halogenated $C_1$-$C_4$ alkyl (the halogen in the halogenated $C_1$-$C_4$ alkyl can be fluorine, chlorine, or bromine, the halogenated $C_1$-$C_4$ alkyl can be a halogenated methyl, a halogenated ethyl, a halogenated propyl, a halogenated iso-propyl, a halogenated butyl, a halogenated iso-butyl or a halogenated tert-butyl, a halogenated methyl is preferred, the halogenated methyl is preferably

p is 0, 1, 2, 3, 4, 5, 6, 7, 8, 9 or 10 (0, 1 or 2 is preferred);
m is 0 or 1;
n is 0, 1, 2, 3, 4, 5, 6, 7, 8, 9 or 10 (0, 1 or 2 is preferred);
Y1 is an oxygen atom, a chemical bond (a single bond is preferred) or

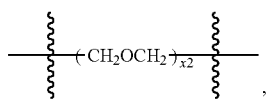

wherein x2 is an integer among 1-24 (e.g. 1, 2, 3, 4, 5, 6, 7, 8, 9 or 10);
q is 0, 1, 2, 3, 4, 5, 6, 7, 8, 9 or 10 (0, 1 or 2 is preferred);
$R^3$ and $R^4$ are independently hydrogen, cyano, or a substituted or unsubstituted $C_1$-$C_4$ alkyl (the unsubstituted $C_1$-$C_4$ alkyl e.g. methyl, ethyl, propyl, butyl, iso-propyl, iso-butyl or tert-butyl, methyl or iso-propyl is preferred; the substituted $C_1$-$C_4$ alkyl e.g. a substituted methyl, a substituted ethyl, a substituted propyl, a substituted butyl, a substituted iso-propyl, a substituted iso-butyl or a substituted tert-butyl, a substituted methyl is preferred; the substituted methyl is preferably

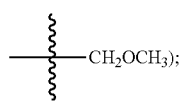

in $R^3$ or $R^4$, the substitutent contained in the substituted or unsubstituted $C_1$-$C_4$ alkyl refers to a $C_1$-$C_4$ alkoxy (the $C_1$-$C_4$ alkoxy e.g. methoxy, ethoxy, propoxy, butoxy, iso-propoxy, iso-butoxy, or tert-butoxy, methoxy is preferred);
x is 0, 1, 2, 3, 4, 5, 6, 7, 8, 9 or 10 (0, 1 or 2 is preferred);

Q1 is

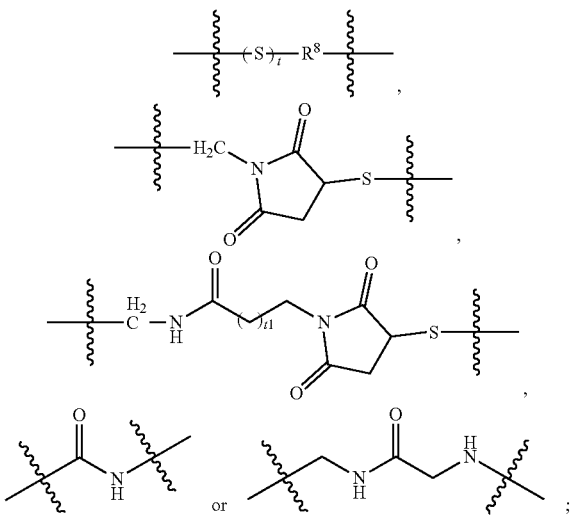

wherein, $R^8$ is a substituted or unsubstituted $C_1$-$C_4$ alkyl (the substituted or unsubstituted $C_1$-$C_4$ alkyl, e.g. a substituted or unsubstituted methyl, a substituted or unsubstituted ethyl, a substituted or unsubstituted propyl, a substituted or unsubstituted iso-propyl, a substituted or unsubstituted butyl, a substituted or unsubstituted iso-butyl or a substituted or unsubstituted tert-butyl, a substituted or unsubstituted propyl is preferred; the substituted propyl is preferably

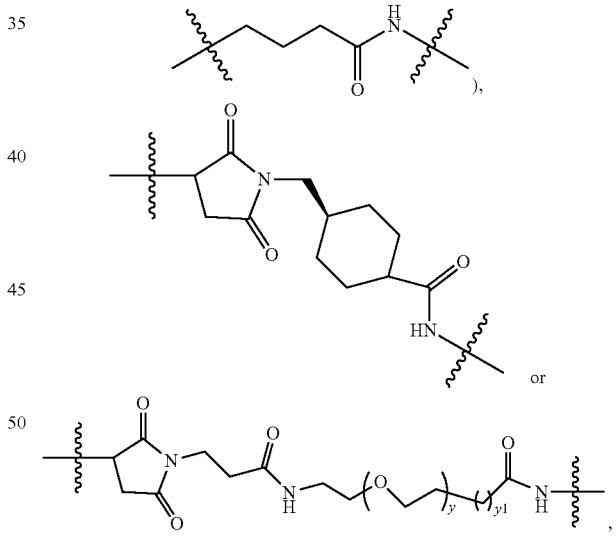

y is 1, 2, 3, 4, 5, 6, 7, 8, 9 or 10; y1 is 0 or 1; in $R^8$, the substituent contained in the substituted or unsubstituted $C_1$-$C_4$ alkyl refers to

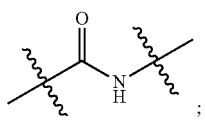 [SMILES: *NC(*)=O]

t is 1 or 2; t1 is 0, 1, 2, 3, 4, 5 or 6;

R⁶ is hydrogen, a substituted or unsubstituted C₁-C₁₂ alkyl (the substituted or unsubstituted C₁-C₁₂ alkyl is preferably a substituted or unsubstituted C₁-C₄ alkyl; the substituted or unsubstituted C₁-C₄ alkyl is preferably methyl, ethyl, propyl, iso-propyl, butyl, iso-butyl or tert-butyl, methyl is more preferred) or

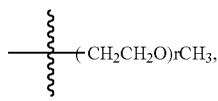

r is 1, 2, 3, 4, 5, 6, 7, 8, 9, 10, 11 or 12;

R⁷ is hydrogen, a substituted or unsubstituted C₁-C₁₂ alkyl (the substituted or unsubstituted C₁-C₁₂ alkyl is preferably a substituted or unsubstituted C₁-C₄ alkyl; the substituted or unsubstituted C₁-C₄ alkyl is preferably methyl, ethyl, propyl, iso-propyl, butyl, iso-butyl or tert-butyl, methyl is more preferred), a substituted or unsubstituted C₁-C₁₂ alkoxy (the substituted or unsubstituted C₁-C₁₂ alkoxy is preferably a substituted or unsubstituted C₁-C₄ alkoxy; the substituted or unsubstituted C₁-C₄ alkoxy is preferably methoxy, ethoxy, propoxy, iso-propoxy, butoxy, iso-butoxy or tert-butoxy, methoxy is more preferred) or

mAb represents a monoclonal antibody, such as Herceptin;

k is among 1-8 (preferably 1-6), refers to a molar ratio (or a rate, abbreviated as DAR) of the drug to the monoclonal antibody inside the bracket;

The antibody drug conjugate represented by formula IB does not include the compound below:

In another preferred embodiment of the present invention, Z is an oxygen atom or Y1 is an oxygen atom.

In a preferred embodiment of the present invention, when Z is a nitrogen atom, p or q is not 0 at the same time, R² is a halogenated C₁-C₄ alkyl; R³ and R⁴ are independently hydrogen, cyano or a substituted or unsubstituted C₁-C₄ alkyl, but R³ and R⁴ are not hydrogen at the same time.

The antibody drug conjugate represented by formula IB is preferably an antibody drug conjugate represented by formula Ib or Ib1, -continued

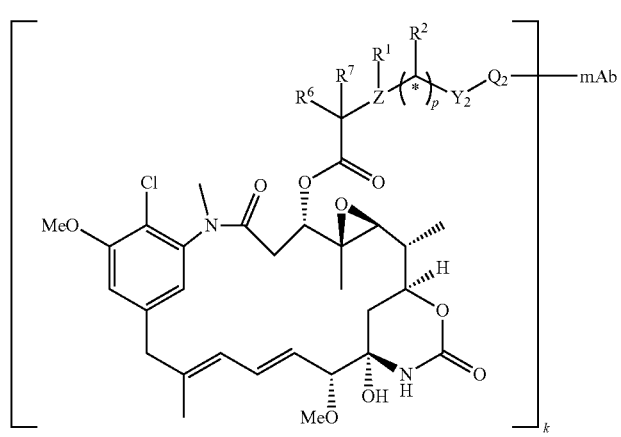

In the antibody drug conjugate represented by formula Ib or Ib1, Z is a nitrogen atom,

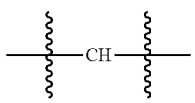 [SMILES: *C*]

or an oxygen atom, when Z is an oxygen atom, $R^1$ is absence; when Z is

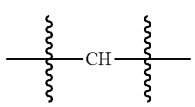 [SMILES: *C*]

or a nitrogen atom, $R^1$ is hydrogen or a $C_1$-$C_4$ alkyl (the $C_1$-$C_4$ alkyl e.g. methyl, ethyl, propyl, butyl, iso-propyl, iso-butyl or tert-butyl, methyl is preferred) or $R_1$, Z as well as the carbon atom that they connected to and $R^6$ or $R^7$ together form a 4- to 6-membered cyclical structure (a 6-member cyclical structure is preferred e.g.

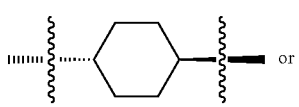

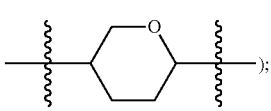

$R^2$ is hydrogen or a halogenated $C_1$-$C_4$ alkyl (the halogen in the halogenated $C_1$-$C_4$ alkyl can be fluorine, chlorine, or bromine, the halogenated $C_1$-$C_4$ alkyl can be a halogenated methyl, a halogenated ethyl, a halogenated propyl, a halogenated iso-propyl, a halogenated butyl, a halogenated iso-butyl or a halogenated tert-butyl, a halogenated methyl is preferred, the halogenated methyl is preferably

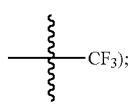

p is 0, 1, 2, 3, 4, 5, 6, 7, 8, 9 or 10 (0, 1 or 2 is preferred); $R^6$ is hydrogen, a substituted or unsubstituted $C_1$-$C_{12}$ alkyl (the substituted or unsubstituted $C_1$-$C_{12}$ alkyl is preferably a substituted or unsubstituted $C_1$-$C_4$ alkyl; the substituted or unsubstituted $C_1$-$C_4$ alkyl is preferably methyl, ethyl, propyl, iso-propyl, butyl, iso-butyl or tert-butyl, methyl is more preferred) or

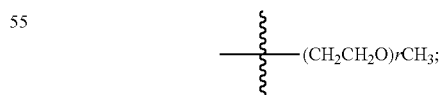

r is 1, 2, 3, 4, 5, 6, 7, 8, 9, 10, 11 or 12; $R^7$ is hydrogen, a substituted or unsubstituted $C_1$-$C_{12}$ alkyl (the substituted or unsubstituted $C_1$-$C_{12}$ alkyl is preferably a substituted or unsubstituted $C_1$-$C_4$ alkyl; the substituted or unsubstituted $C_1$-$C_4$ alkyl is preferably methyl, ethyl, propyl, iso-propyl, butyl, iso-butyl or tert-butyl, methyl is more preferred), a substituted or unsubstituted $C_1$-$C_{12}$ alkoxy (the substituted or unsubstituted $C_1$-$C_{12}$ alkoxy is preferably a substituted or unsubstituted $C_1$-$C_4$ alkoxy; the substituted or unsubstituted $C_1$-$C_4$ alkoxy is preferably methoxy, ethoxy, propoxy, iso-propoxy, butoxy, iso-butoxy or tert-butoxy, methoxy is more preferred) or

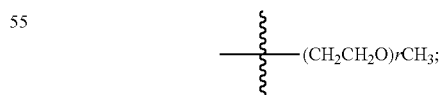

mAb represents a monoclonal antibody, such as Herceptin; k is among 1-8, which refers to a molar ratio of the drug to the monoclonal antibody inside the bracket;

In the antibody drug conjugate represented by formula Ib, m is 0 or 1; n is 0, 1, 2, 3, 4, 5, 6, 7, 8, 9 or 10 (0, 1 or 2 is preferred); Y1 is an oxygen atom or a chemical bond (a single bond is preferred); q is 0, 1, 2, 3, 4, 5, 6, 7, 8, 9 or 10 (0, 1 or 2 is preferred); $R^3$ and $R^4$ are independently hydrogen, cyano or a substituted or unsubstituted $C_1$-$C_4$ alkyl (the unsubstituted $C_1$-$C_4$ alkyl is for example a methyl, an ethyl, a propyl, a butyl, an iso-propyl, an iso-butyl or a tert-butyl, a methyl or an iso-propyl is preferred; the substituted $C_1$-$C_4$ alkyl is for example a substituted methyl, a substituted ethyl, a substituted propyl, a substituted butyl, a substituted iso-propyl, a substituted iso-butyl or a substituted tert-butyl, a substituted methyl is preferred; the substituted methyl is preferably

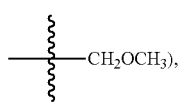

in $R^3$ or $R^4$, the substituent contained in the substituted or unsubstituted $C_1$-$C_4$ alkyl refers to a $C_1$-$C_4$ alkoxy (the $C_1$-$C_4$ alkoxy is for example a methoxy, an ethoxy, a propoxy, a butoxy, an iso-propoxy, an iso-butoxy or a tert-butoxy, a methoxy is preferred); x is 0, 1, 2, 3, 4, 5, 6, 7, 8, 9 or 10 (0, 1 or 2 is preferred); $R^8$ is a substituted or unsubstituted $C_1$-$C_4$ alkyl (the substituted or unsubstituted $C_1$-$C_4$ alkyl is for example a substituted or unsubstituted methyl, a substituted or unsubstituted ethyl, a substituted or unsubstituted propyl, a substituted or unsubstituted iso-propyl, a substituted or unsubstituted butyl, a substituted or unsubstituted iso-butyl or a substituted or unsubstituted tert-butyl, a substituted or unsubstituted propyl is preferred; the substituted propyl is preferably

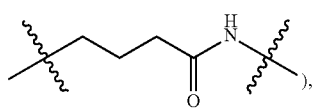

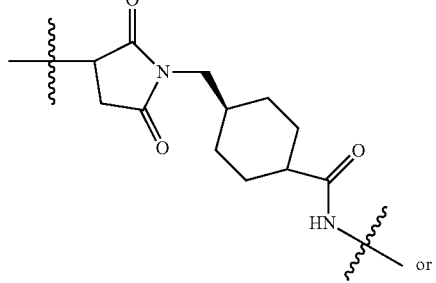

-continued

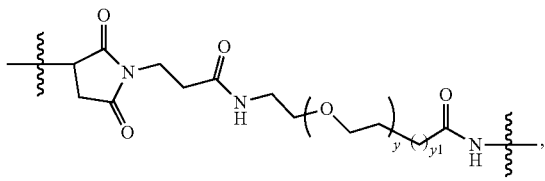

y is 1, 2, 3, 4, 5, 6, 7, 8, 9 or 10; y1 is 0 or 1; in $R^8$, the substituent contained in the substituted or unsubstituted $C_1$-$C_4$ alkyl refers to

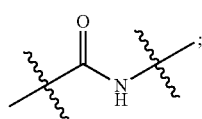 [SMILES: *NC(*)=O]

t is 1 or 2;

In the antibody drug conjugate represented by formula Ib1, Y2 is

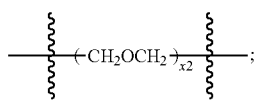

wherein x2 is an integer among 1-24; Q2 is

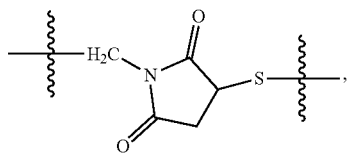

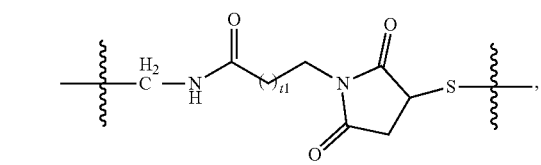

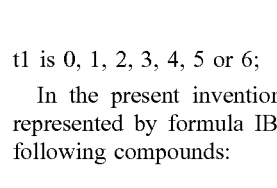

t1 is 0, 1, 2, 3, 4, 5 or 6;

In the present invention, the antibody drug conjugate represented by formula IB is more preferably one of the following compounds:

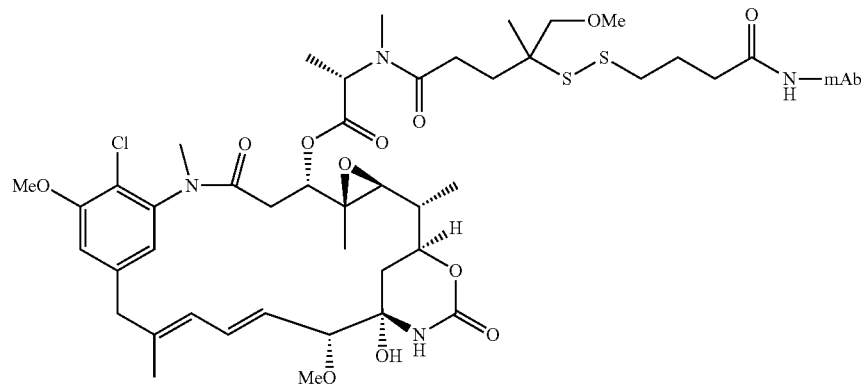
T-CE-004
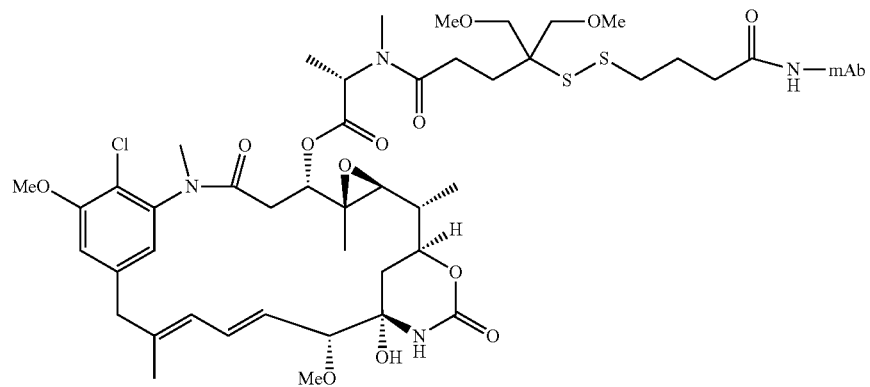
T-CE-005
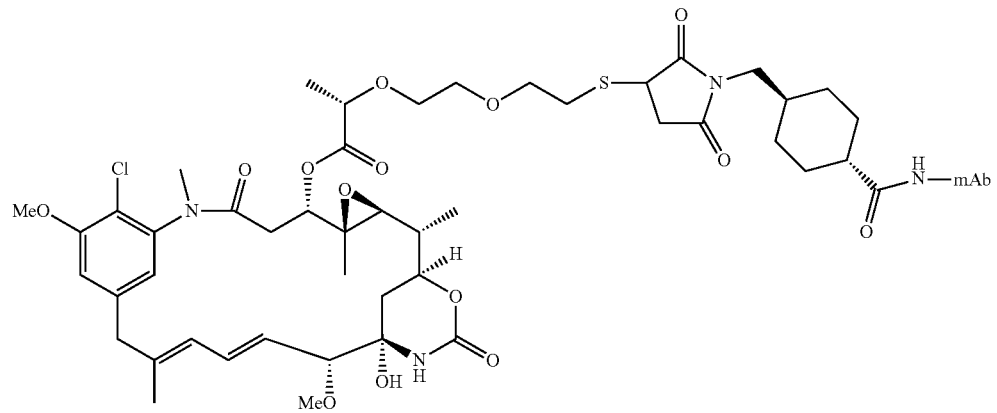
T-CE-034
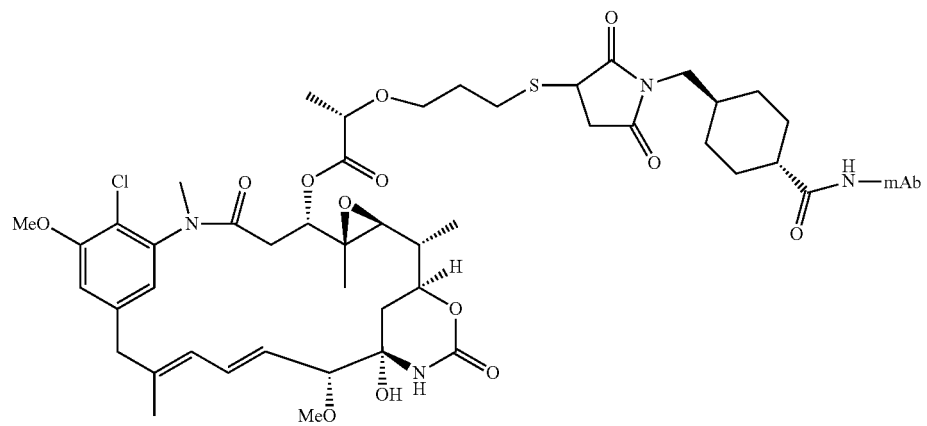
T-CE-035

-continued
T-CE-036
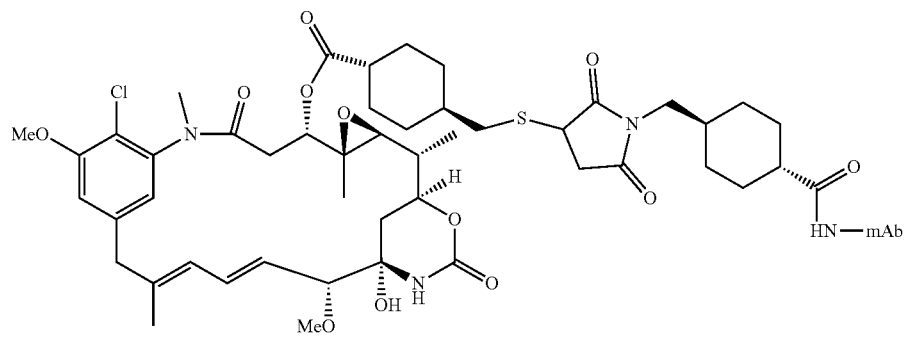
T-CE-037
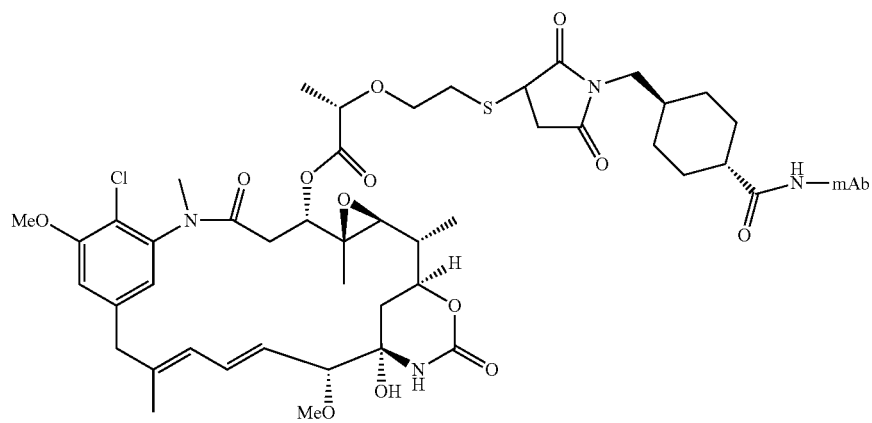
T-CE-041
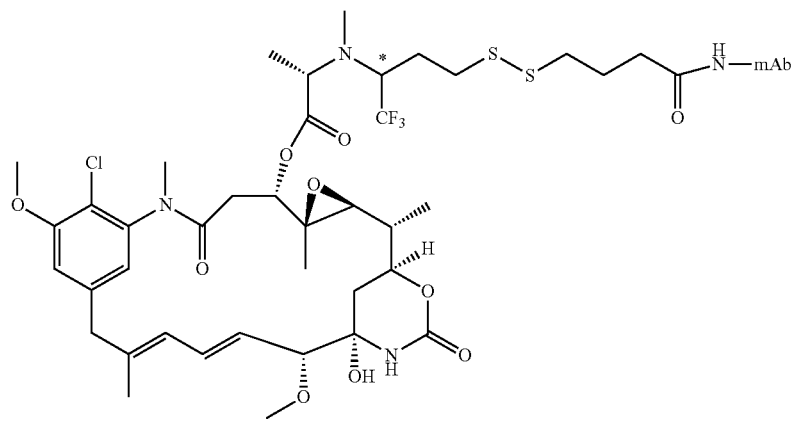
T-CE-038
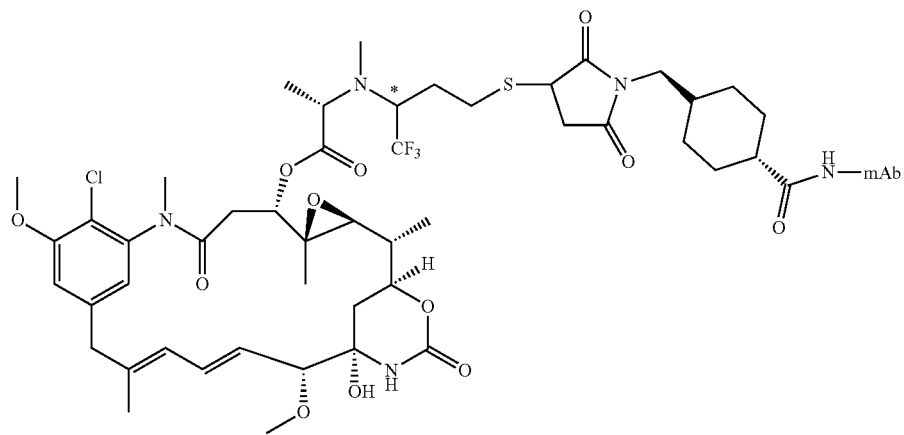

-continued
T-CE-039
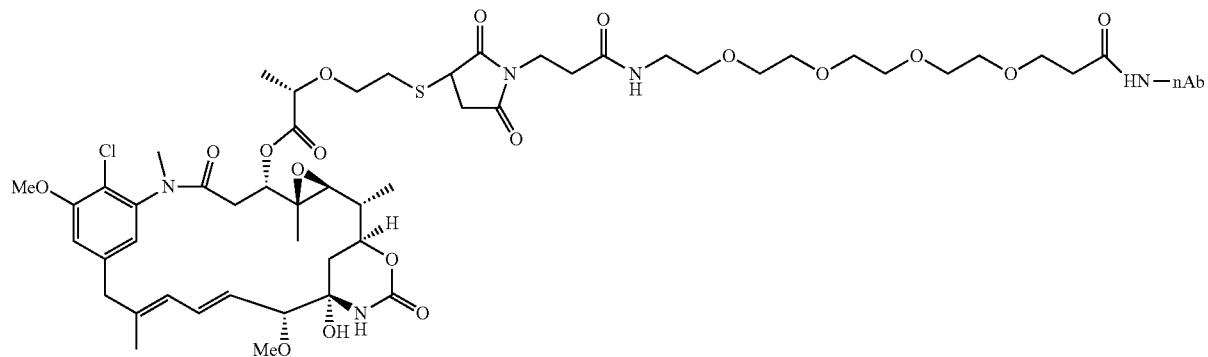
T-CE-040
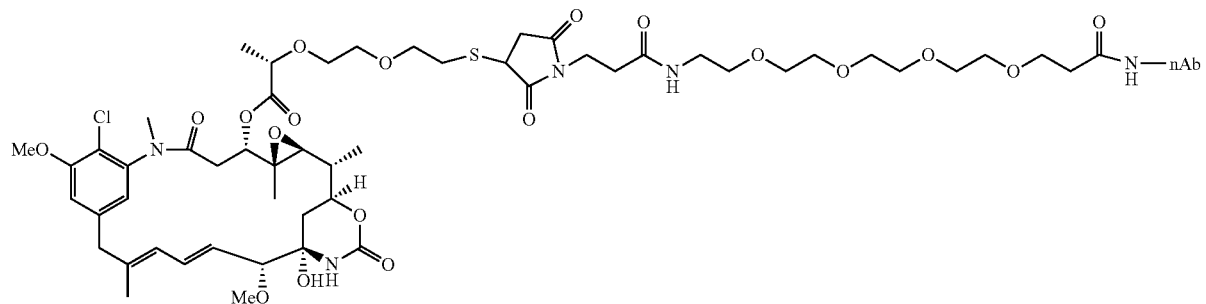
T-CE-043
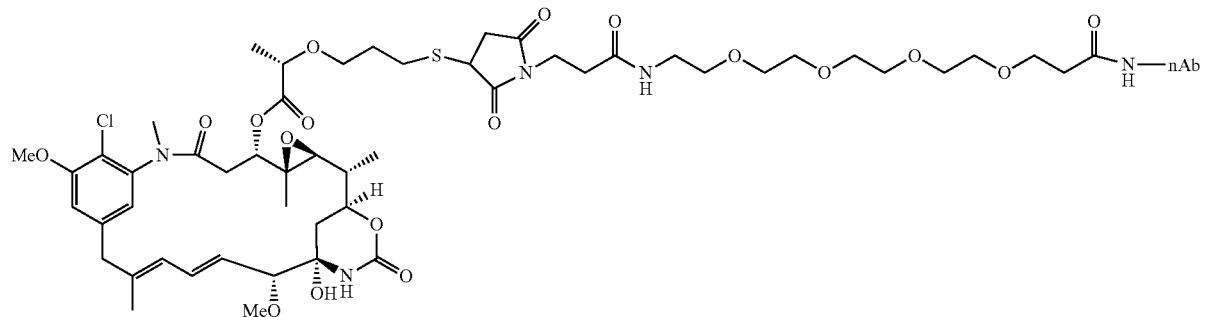
T-CE-048
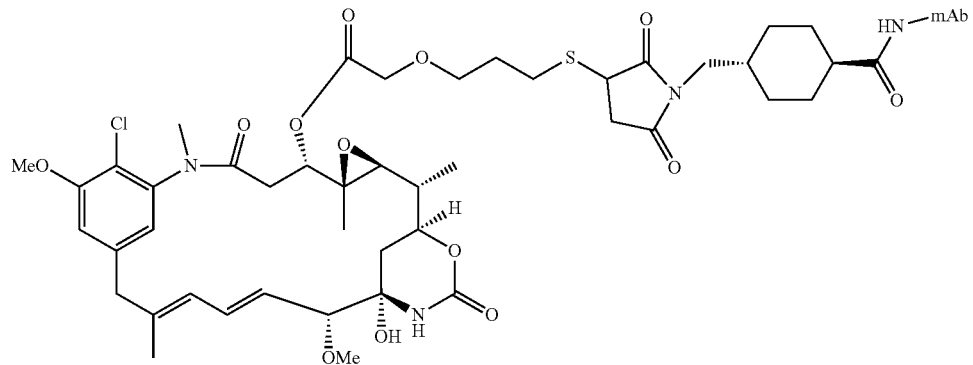

-continued
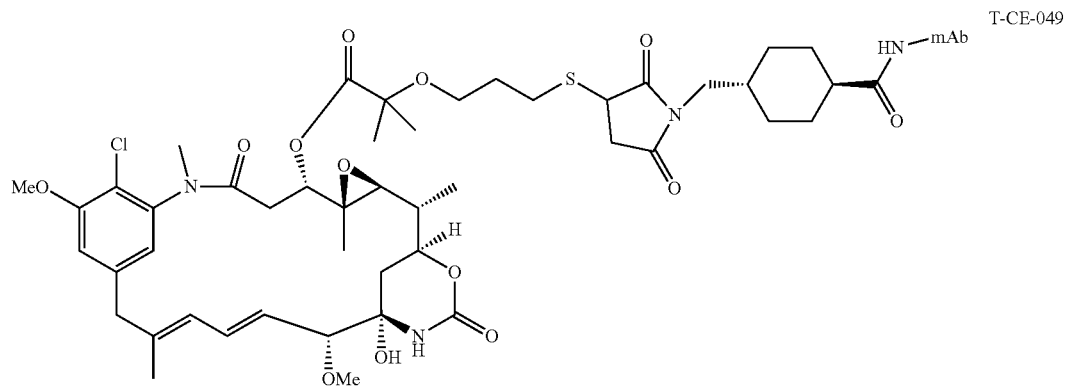
T-CE-049
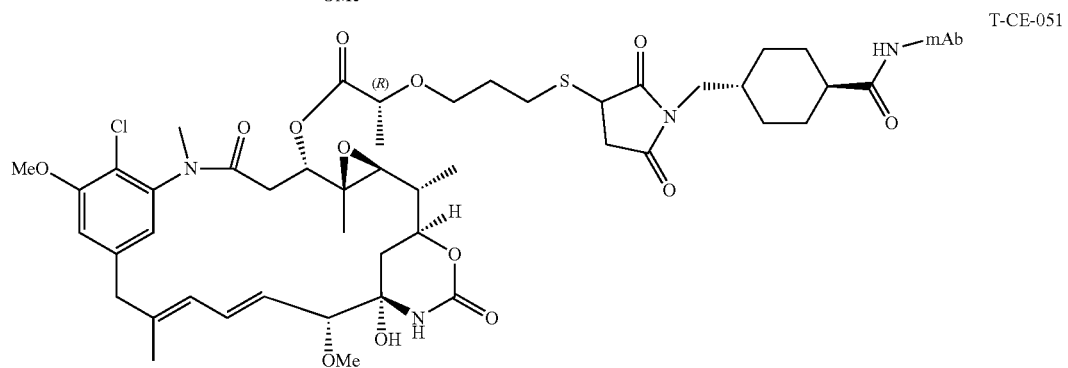
T-CE-051
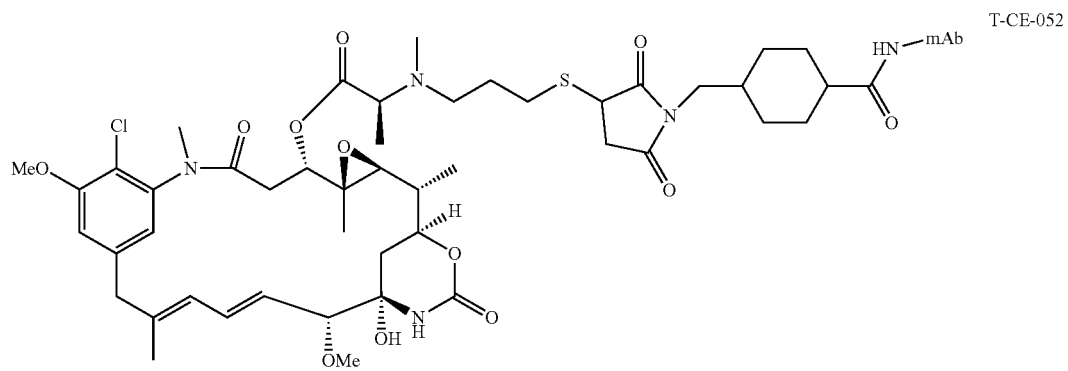
T-CE-052
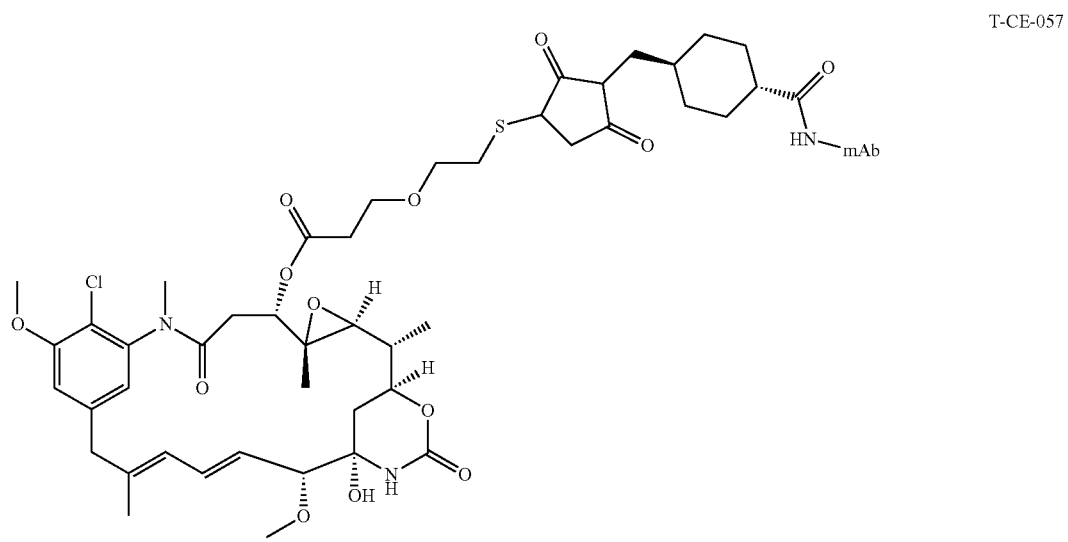
T-CE-057

T-CE-046
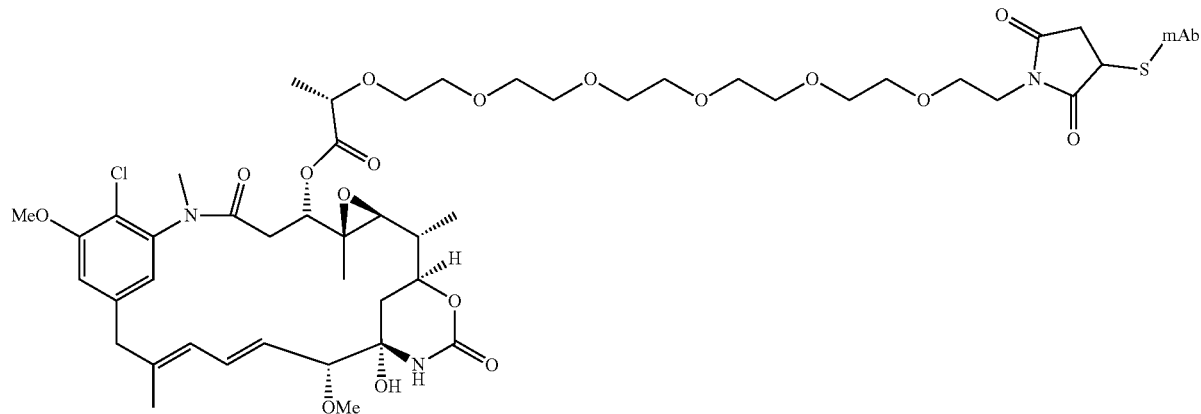
T-CE-047
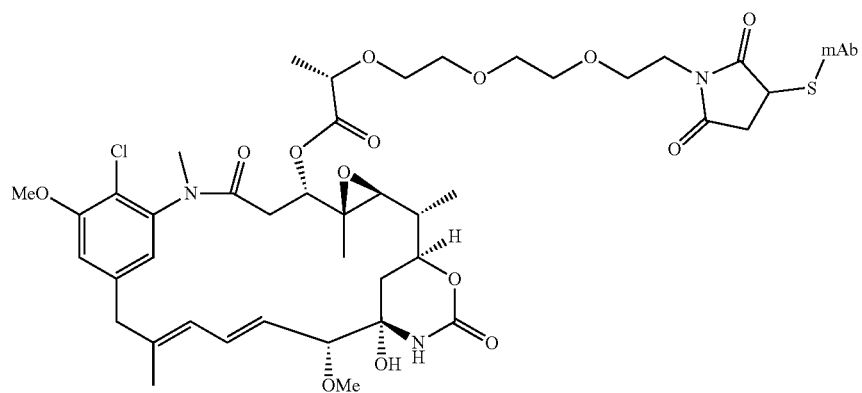
T-CE-063
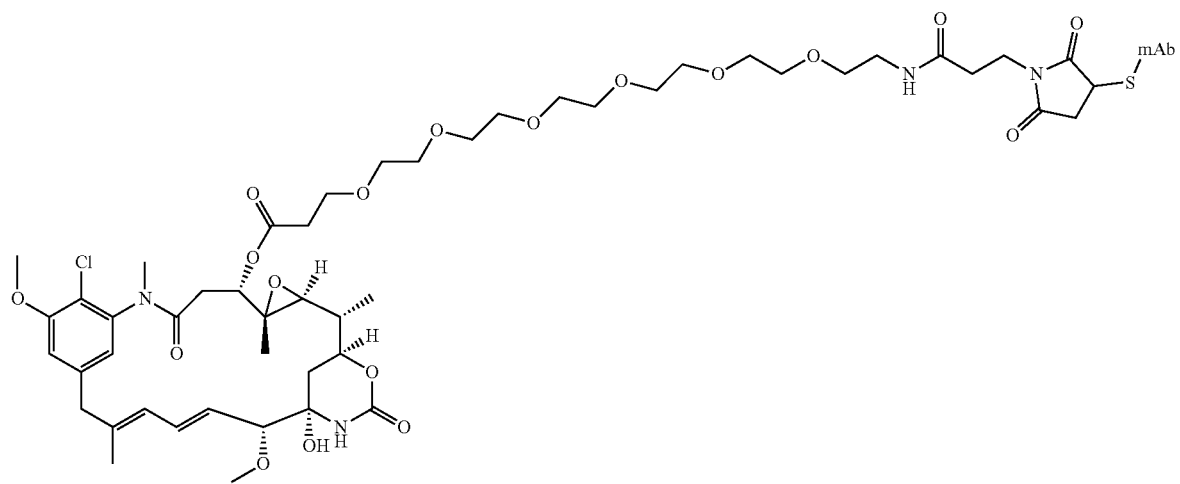

T-CE-045
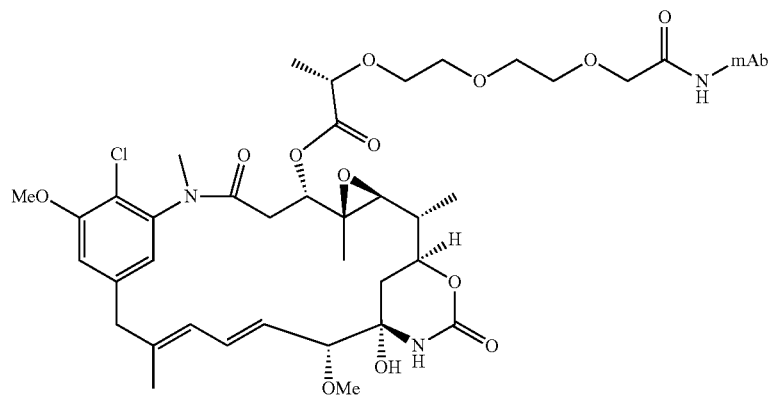
T-CE-050
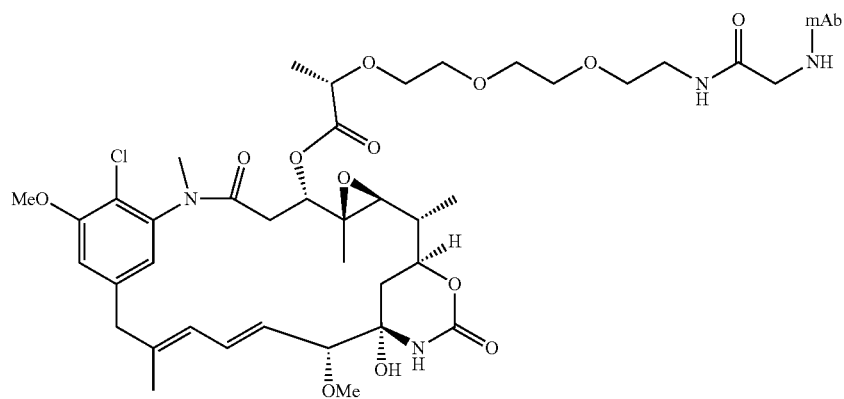
T-CE-052a
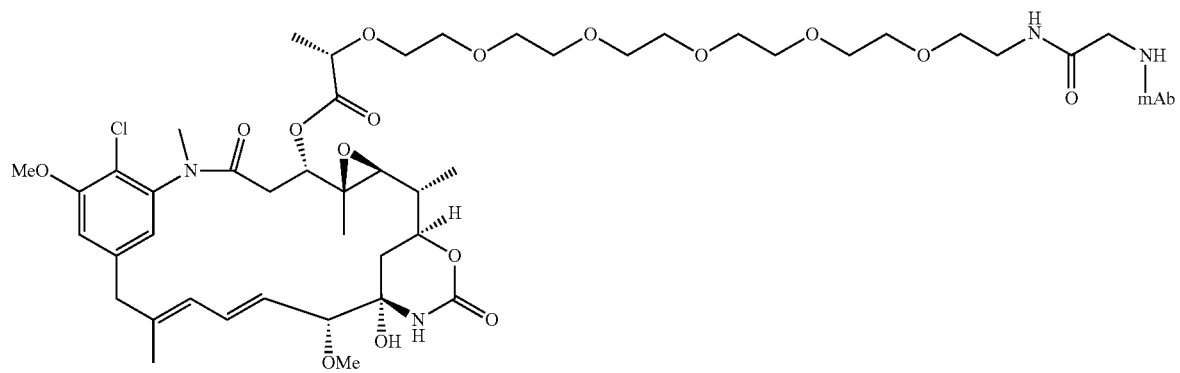
T-XDCE-M-001
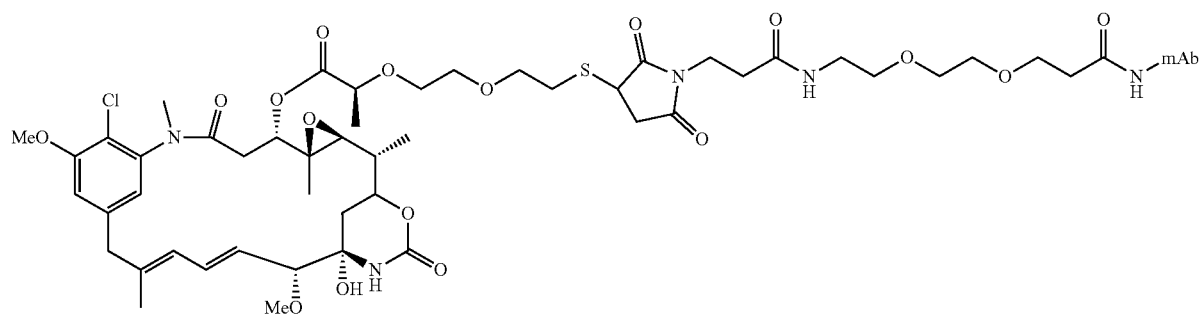

-continued

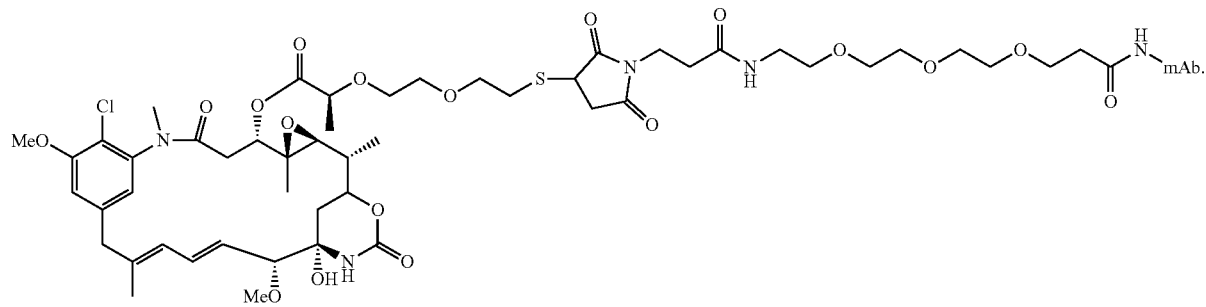

T-XDCE-M-002

The present invention also provides an intermediate (a toxin with a linker) represented by formula IA:

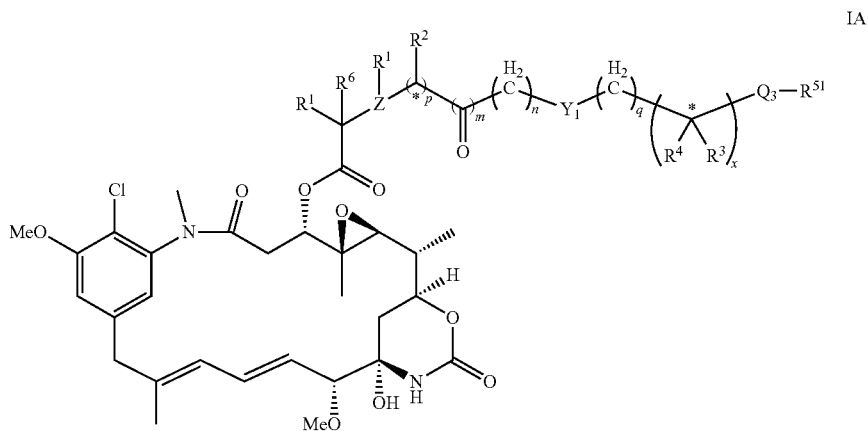

IA

In the compound represented by formula IA, the definition of each letter and group are the same as above; $Q_3$ is

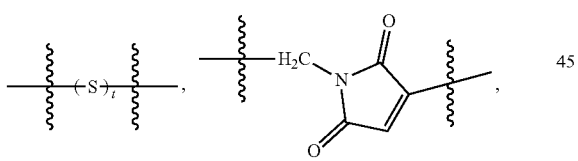

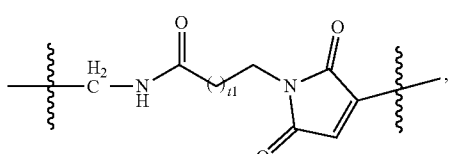

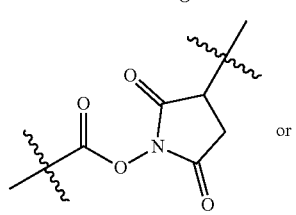
or

-continued

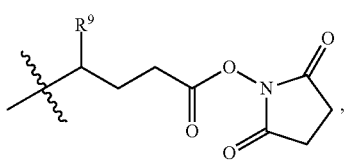

t is 1 or 2; t1 is 0, 1, 2, 3, 4, 5 or 6;

$R^{51}$ is H, a $C_1$-$C_4$ alkyl (the $C_1$-$C_4$ alkyl is for example a methyl, an ethyl, a propyl, a butyl, an iso-propyl, an iso-butyl or a tert-butyl, a methyl is more preferred), -continued

,

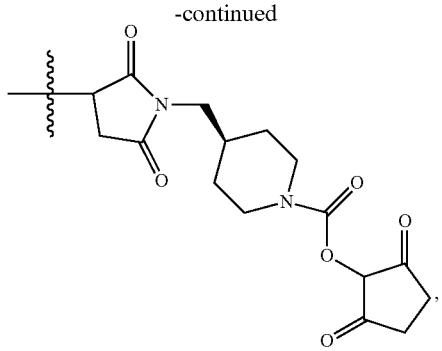

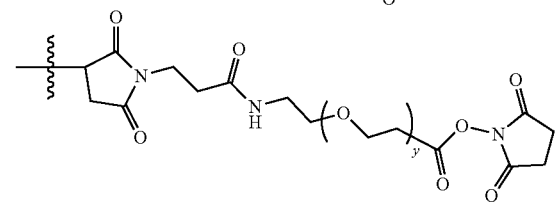

or a halogen (the halogen is preferably F, Cl, Br or I), y is 1, 2, 3, 4, 5, 6, 7, 8, 9 or 10, $R^9$ is H or a $C_1$-$C_4$ alkyl (the $C_1$-$C_4$ alkyl is for example a methyl, an ethyl, a propyl, a butyl, an iso-propyl, an iso-butyl or a tert-butyl).

The intermediate represented by formula IA, is preferably an intermediate represented by formula Ia or Ia1 (a toxin with a linker):

In the intermediate represented by formula Ia or Ia1, Z is a nitrogen atom,

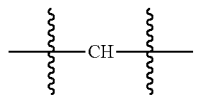 [SMILES: *C*]

an oxygen atom, when Z is an oxygen atom, $R^1$ is absence; when Z is or a nitrogen atom, $R^1$ is a $C_1$-$C_4$ alkyl (the $C_1$-$C_4$ alkyl is for example a methyl, an ethyl, a propyl, a butyl, an iso-propyl, an iso-butyl or a tert-butyl, a methyl is preferred) or $R_1$, Z as well as the carbon atom that they connected to and $R^6$ or $R^7$ together form a 4- to 6-membered cyclical structure (a 6-member cyclical structure is preferred e.g.

Ia

Ia1

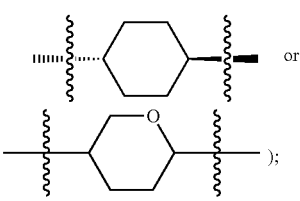 or $R^2$ is a halogenated $C_1$-$C_4$ alkyl (the halogen in the halogenated $C_1$-$C_4$ alkyl can be fluorine, chlorine or bromine, the halogenated $C_1$-$C_4$ alkyl can be a halogenated methyl, a halogenated ethyl, a halogenated propyl, a halogenated iso-propyl, a halogenated butyl, a halogenated iso-butyl or a halogenated tert-butyl, a halogenated methyl is preferred, the halogenated methyl is preferably

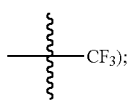

p is 0, 1, 2, 3, 4, 5, 6, 7, 8, 9 or 10 (0, 1 or 2 is preferred); $R^6$ is hydrogen or a substituted or unsubstituted $C_1$-$C_{12}$ alkyl (the substituted or unsubstituted $C_1$-$C_{12}$ alkyl is preferably a substituted or unsubstituted $C_1$-$C_4$ alkyl; the substituted or unsubstituted $C_1$-$C_4$ alkyl is preferably a methyl, an ethyl, a propyl, an iso-propyl, a butyl, an iso-butyl or a tert-butyl, a methyl is more preferred) or

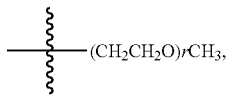

r is 1, 2, 3, 4, 5, 6, 7, 8, 9, 10, 11 or 12; $R^7$ is hydrogen, a substituted or unsubstituted $C_1$-$C_{12}$ alkyl (the substituted or unsubstituted $C_1$-$C_{12}$ alkyl is preferably a substituted or unsubstituted $C_1$-$C_4$ alkyl; the substituted or unsubstituted $C_1$-$C_4$ alkyl is preferably a methyl, an ethyl, a propyl, an iso-propyl, a butyl, an iso-butyl or a tert-butyl, a methyl is more preferred), a substituted or unsubstituted $C_1$-$C_{12}$ alkoxy (the substituted or unsubstituted $C_1$-$C_{12}$ alkoxy is preferably a substituted or unsubstituted $C_1$-$C_4$ alkoxy; the substituted or unsubstituted $C_1$-$C_4$ alkoxy is preferably a methoxy, an ethoxy, a propoxy, an iso-propoxy, a butoxy, an iso-butoxy or a tert-butoxy, a methoxy is more preferred) or

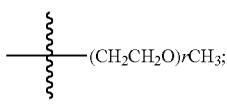

t is 1 or 2;

In the intermediate represented by formula Ia, m is 0 or 1; n is 0, 1, 2, 3, 4, 5, 6, 7, 8, 9 or 10 (0, 1 or 2 is preferred); Y1 is an oxygen atom or a chemical bond; q is 0, 1, 2, 3, 4, 5, 6, 7, 8, 9 or 10 (0, 1 or 2 is preferred); $R^3$ and $R^4$ are independently hydrogen, cyano, a substituted or unsubstituted $C_1$-$C_4$ alkyl (the unsubstituted $C_1$-$C_4$ alkyl is for example a methyl, an ethyl, a propyl, a butyl, an iso-propyl, an iso-butyl or a tert-butyl, a methyl or an iso-propyl is preferred; the substituted $C_1$-$C_4$ alkyl is for example a substituted methyl, a substituted ethyl, a substituted propyl, a substituted butyl, a substituted iso-propyl, a substituted iso-butyl or a substituted tert-butyl, a substituted methyl is preferred; the substituted methyl is preferably

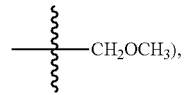

in R or $R^4$, the substituent in the substituted or unsubstituted $C_1$-$C_4$ alkyl refers to a $C_1$-$C_4$ alkoxy (the $C_1$-$C_4$ alkoxy is for example a methoxy, an ethoxy, a propoxy, a butoxy, an iso-propoxy, an iso-butoxy or a tert-butoxy, a methoxy is preferred); $R^5$ is hydrogen or a $C_1$-$C_4$ alkyl (the $C_1$-$C_4$ alkyl is for example a methyl, an ethyl, a propyl, a butyl, an iso-propyl, an iso-butyl or a tert-butyl, a methyl is preferred),

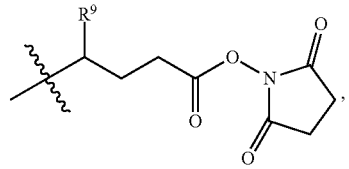

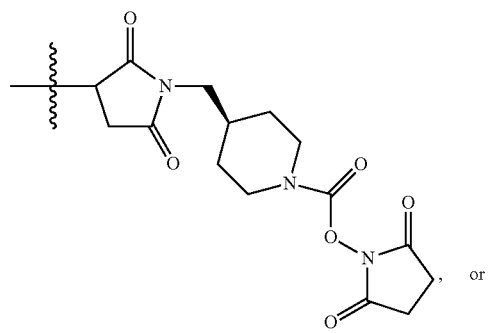, or

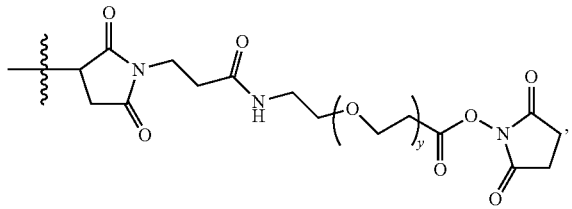

y is 1, 2, 3, 4, 5, 6, 7, 8, 9 or 10; y1 is 0 or 1; $R^9$ is hydrogen or a $C_1$-$C_4$ alkyl (the $C_1$-$C_4$ alkyl is for example a methyl, an ethyl, a propyl, a butyl, an iso-propyl, an iso-butyl or a tert-butyl);

In the intermediate represented by formula Ia1, Y2 is

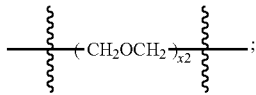

wherein x2 is an integer among 1-24; Q2 is
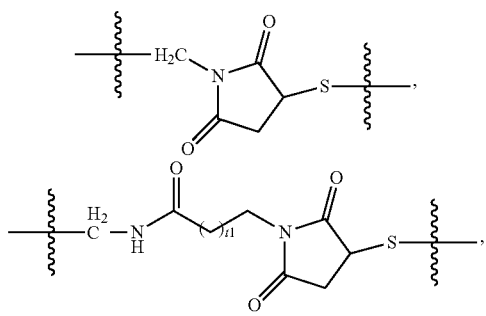
-continued
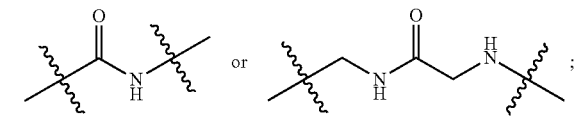
$R^{52}$ is hydrogen or a halogen (F, Cl, Br or I is preferred).
In the present invention, the intermediate (a toxin with a linker) represented by formula IA, is further preferably one of the following compounds:
CE-013
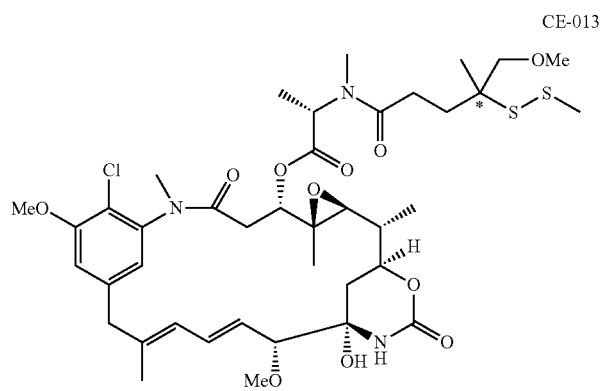
CE-015
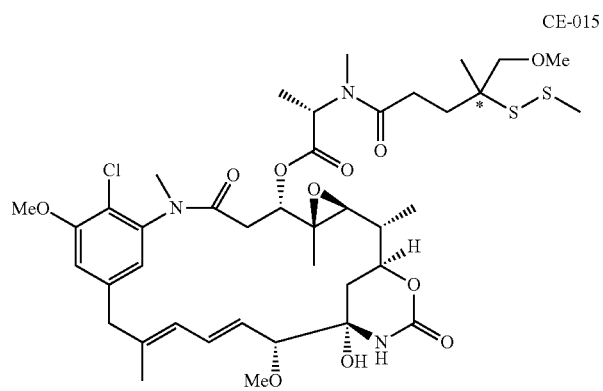
CE-017
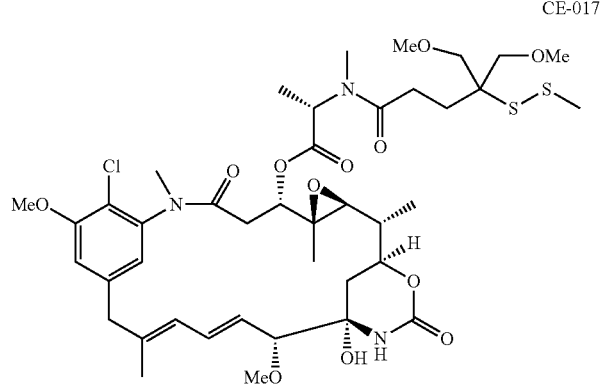
CE-019
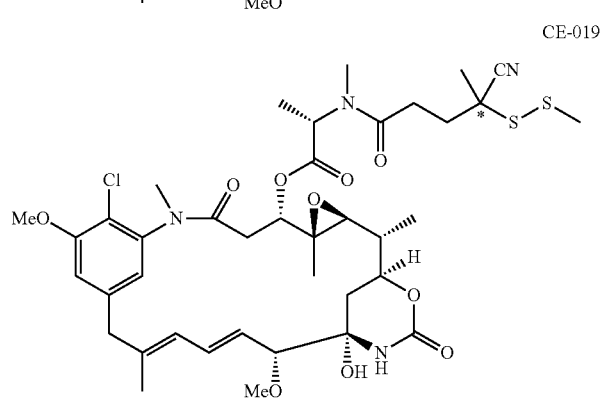
CE-022
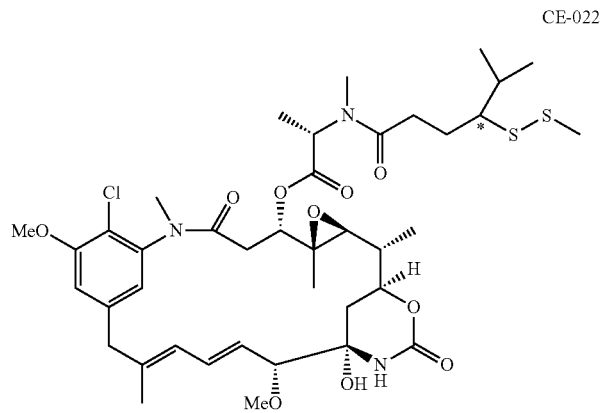
CE-011
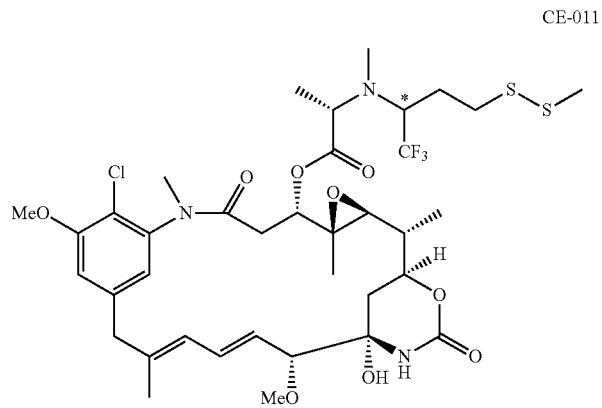

-continued
CE-029
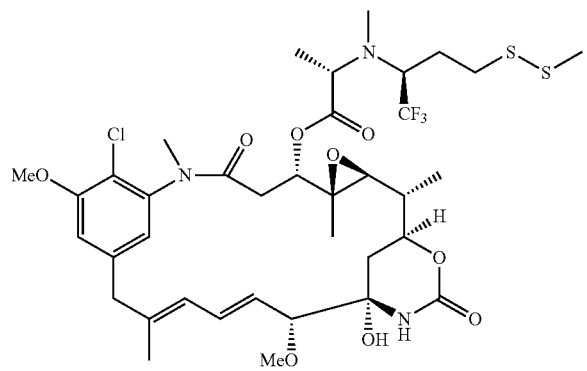
CE-030
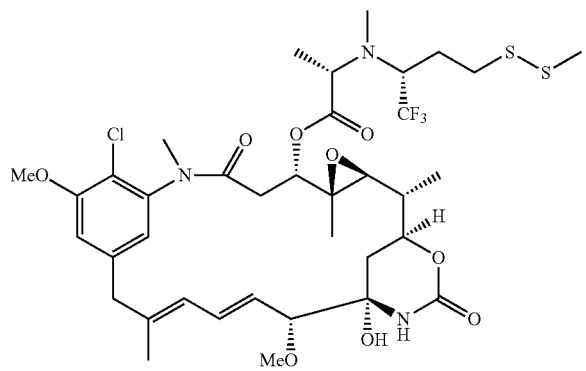
CE-026
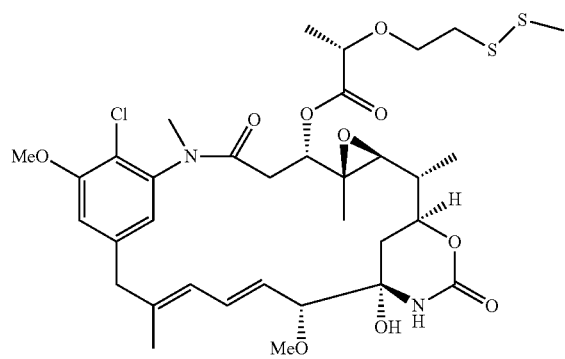
CE-027
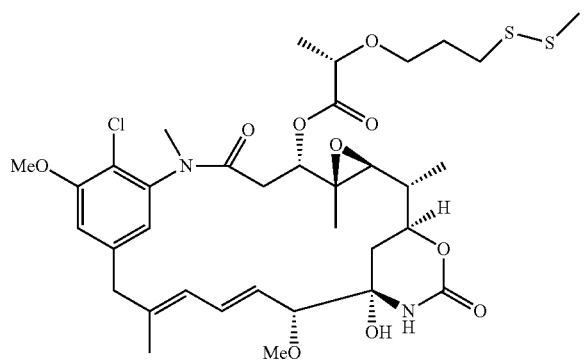
CE-028
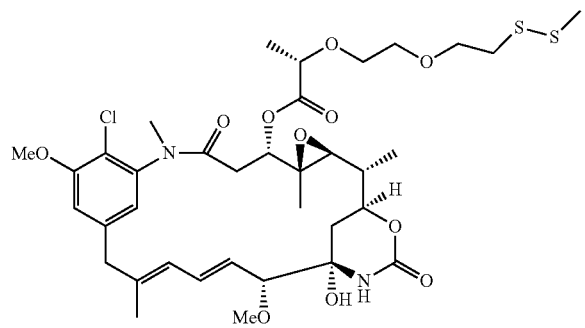
CE-031
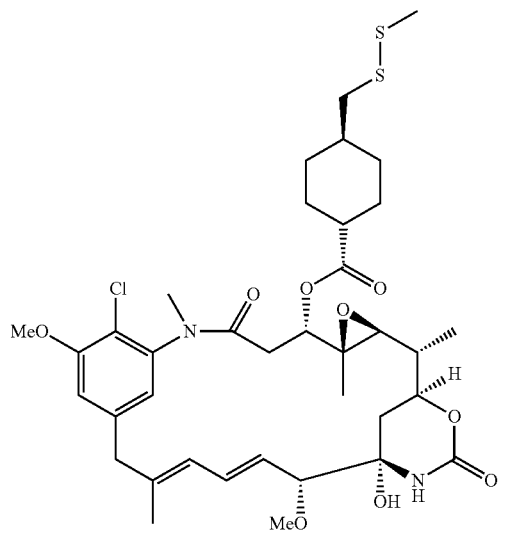

-continued
8-8
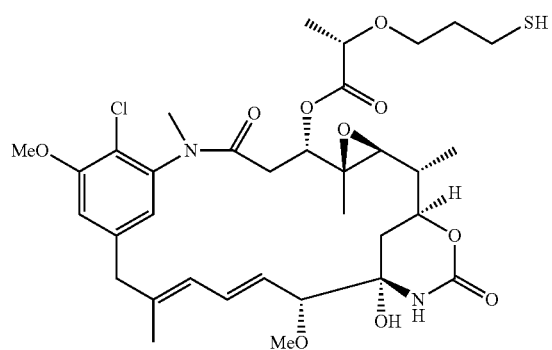
9-7
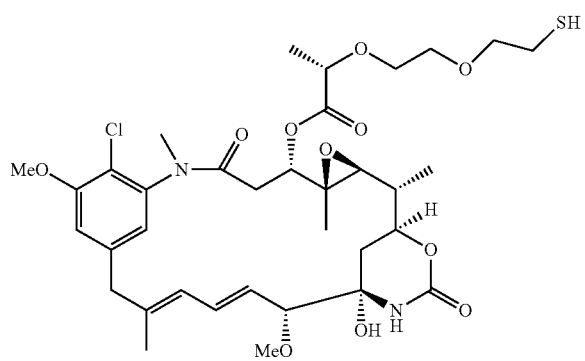
8-9
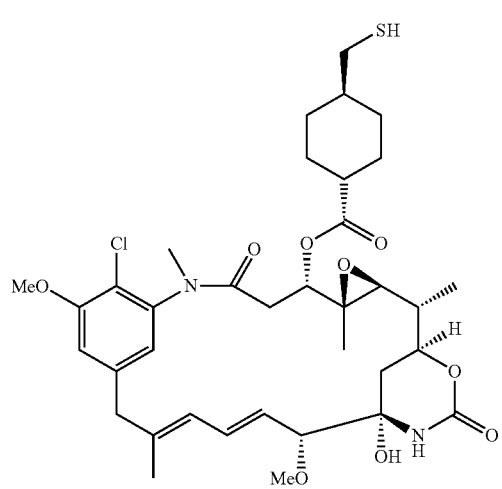
10-10
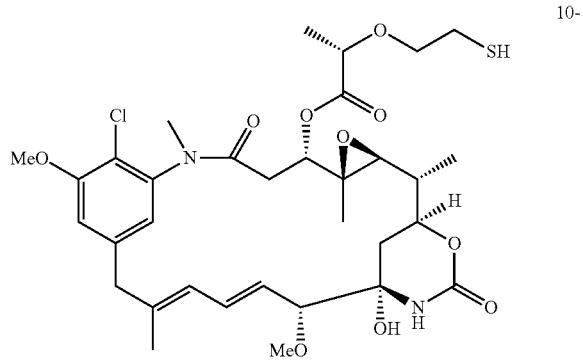
7-2
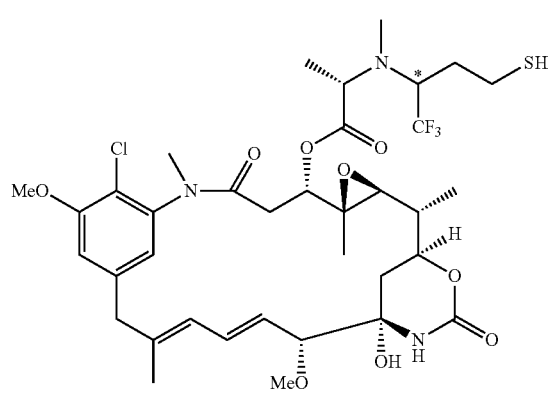
CE-024
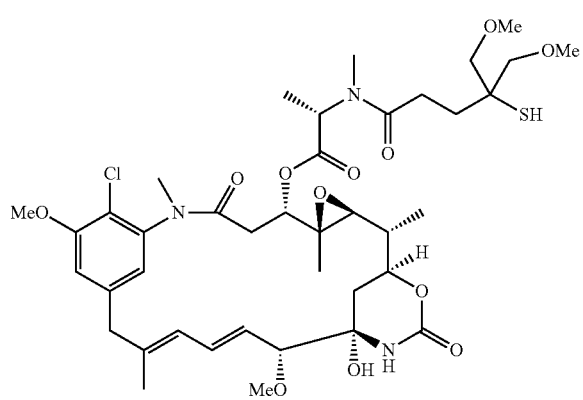
CE-032
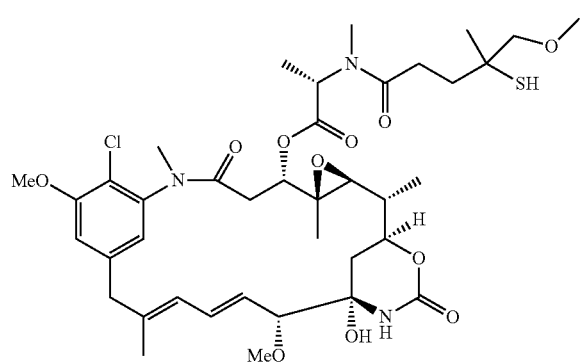
5-11
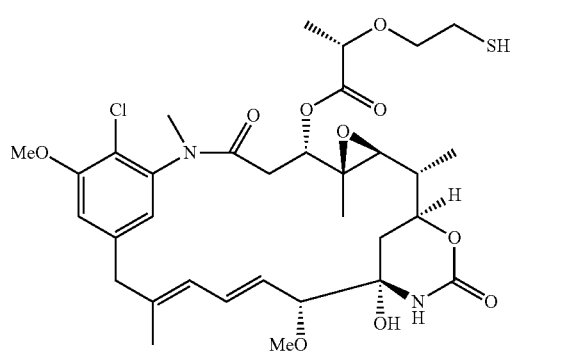

-continued
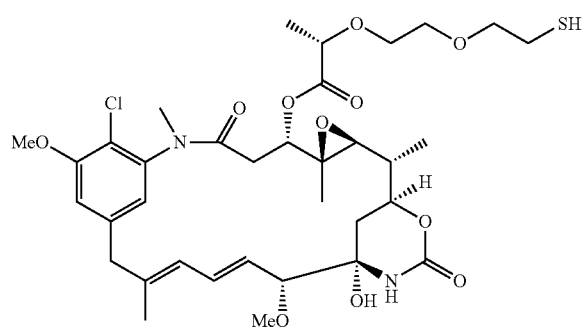
CE-053
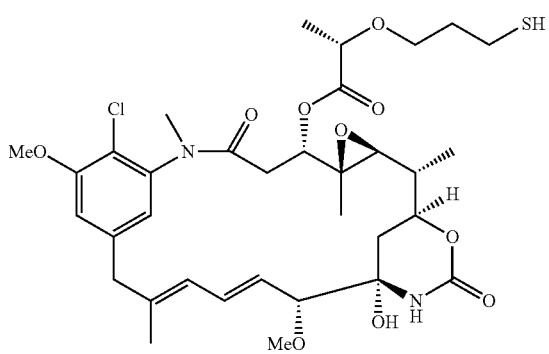
CE-054/055
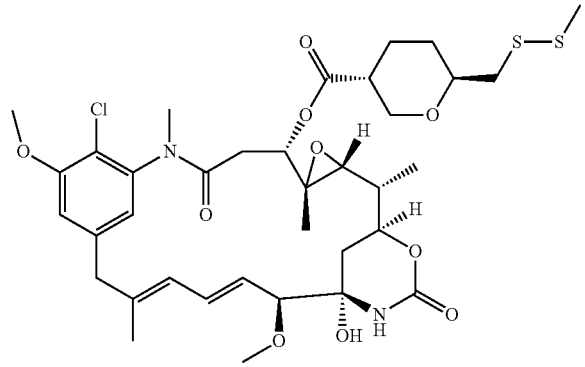
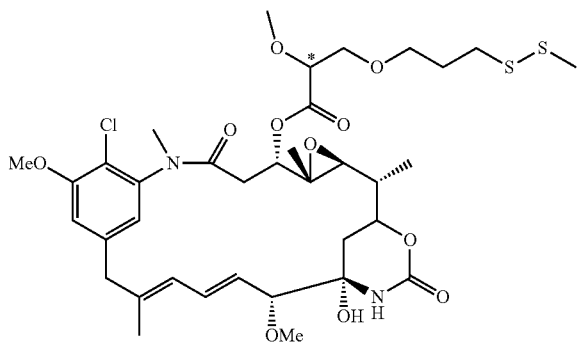
CE-056
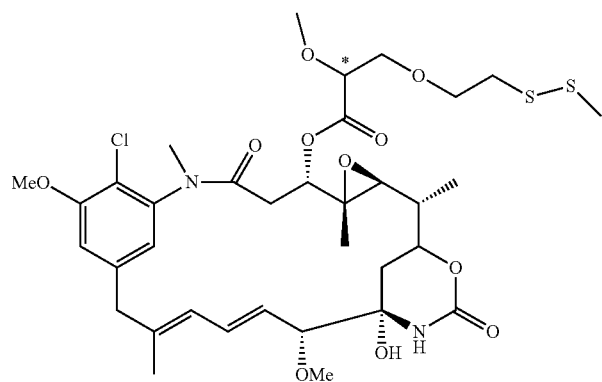
CE-002
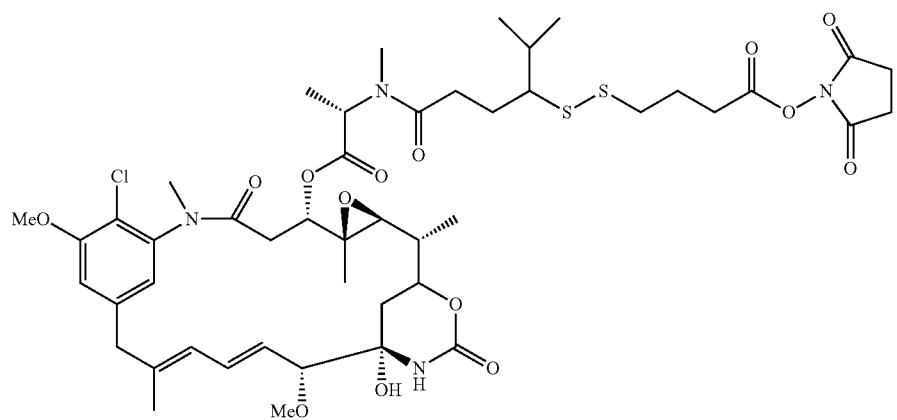

CE-004
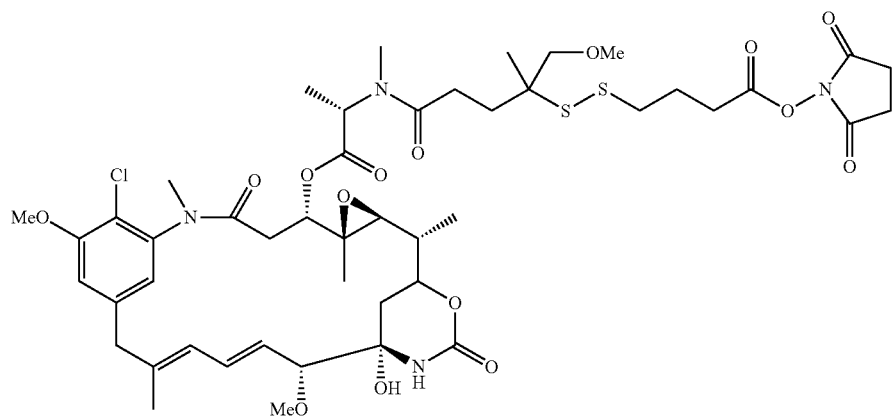
CE-005
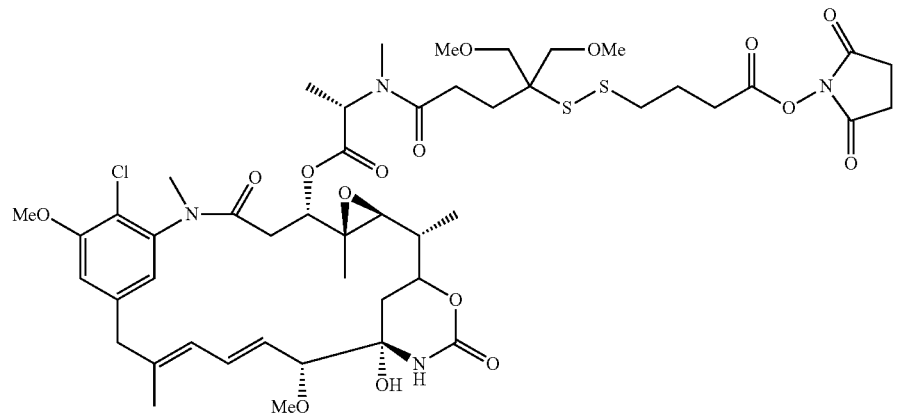
CE-033
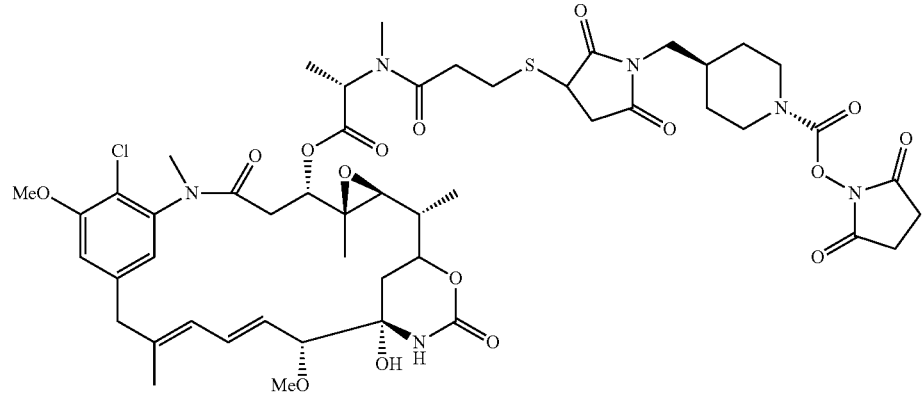
CE-034
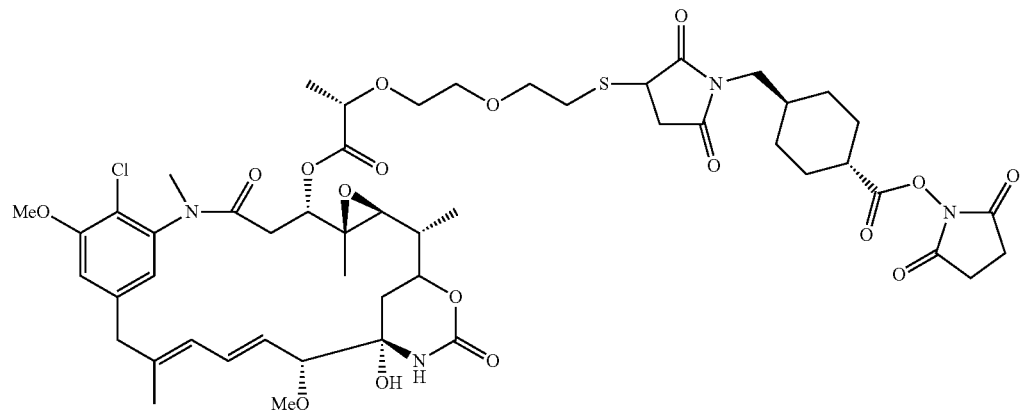

-continued
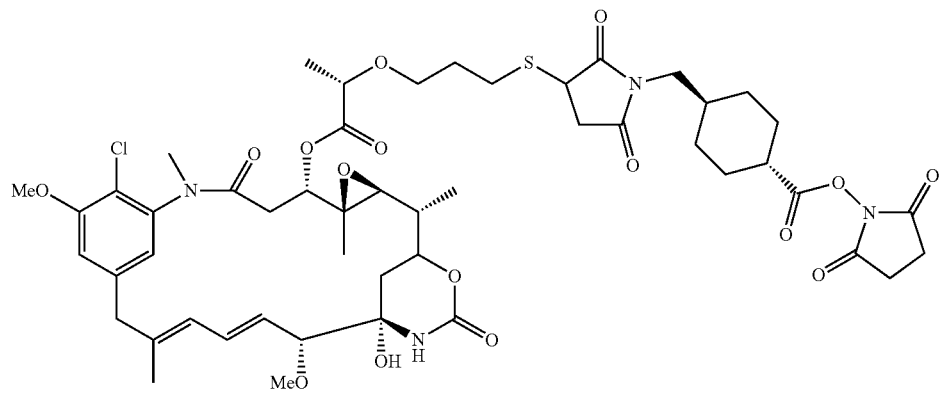
CE-035
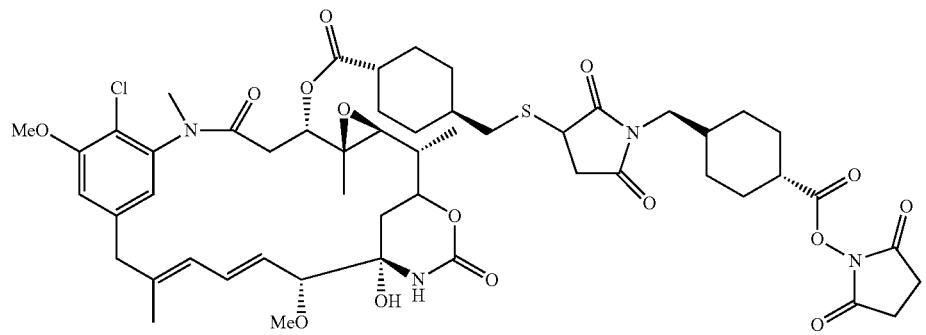
CE-036
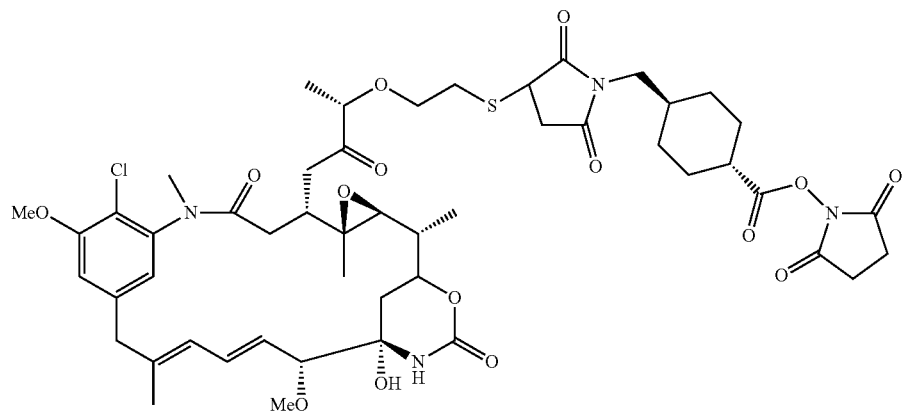
CE-037
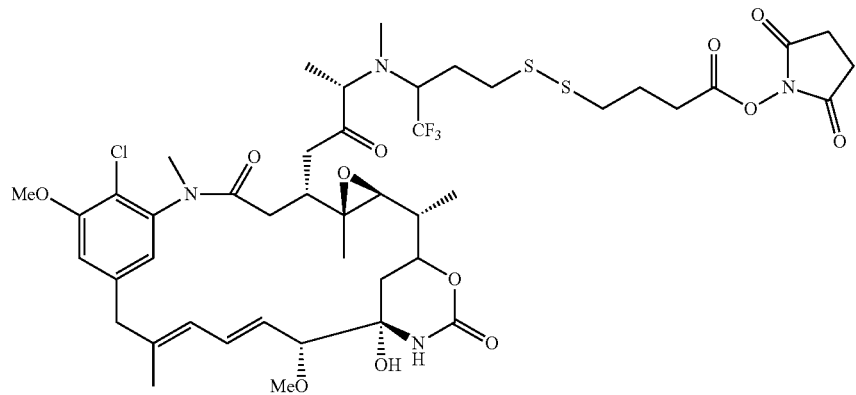
CE-007

-continued
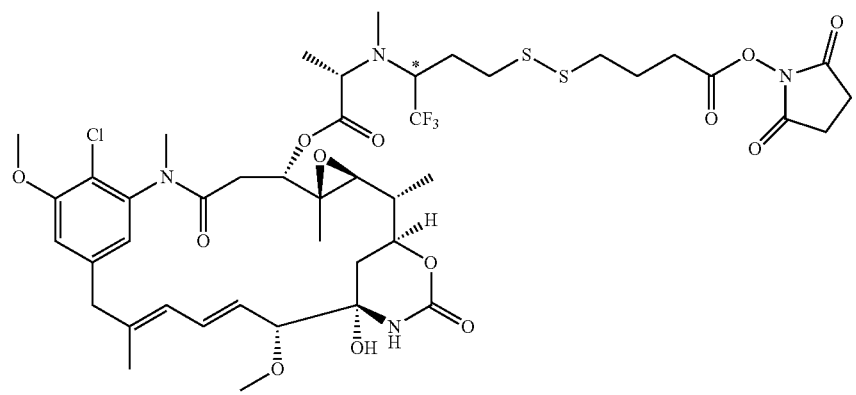
CE-041
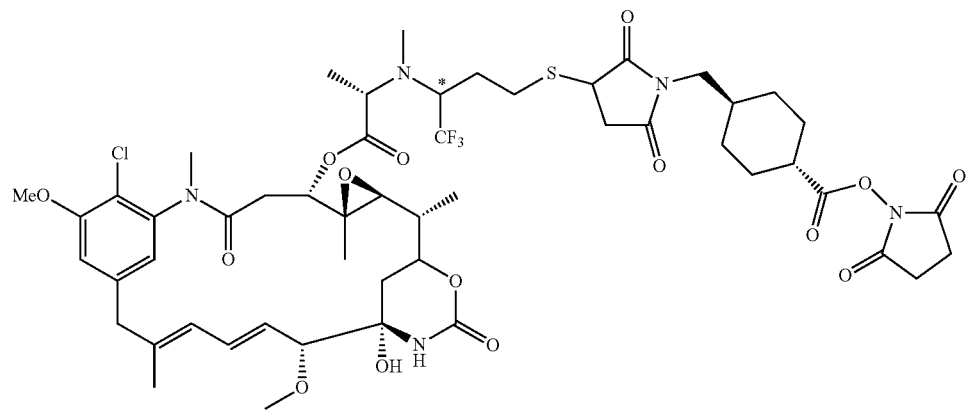
CE-038
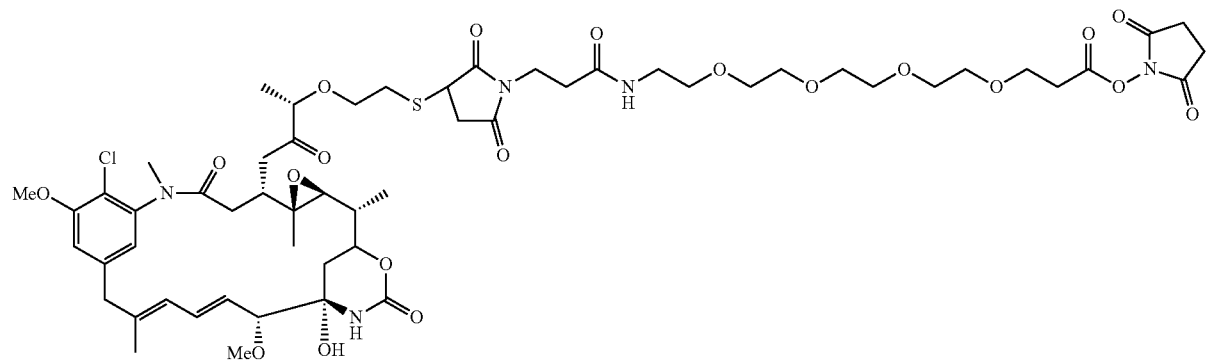
CE-039
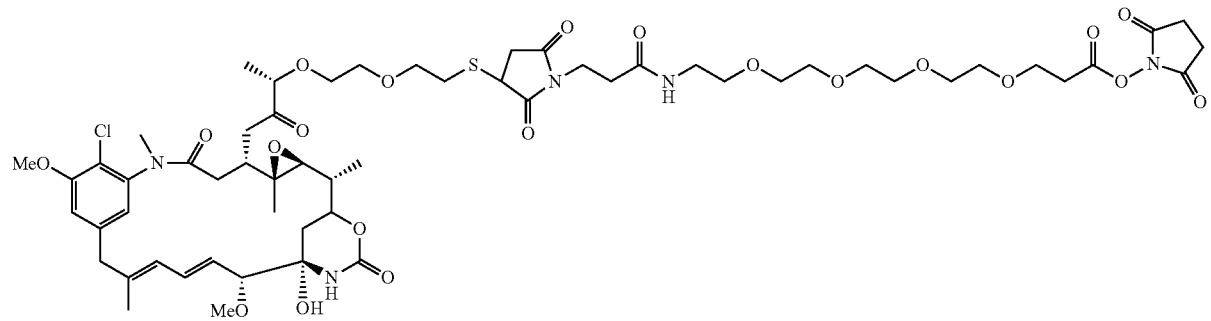
CE-040

CE-043
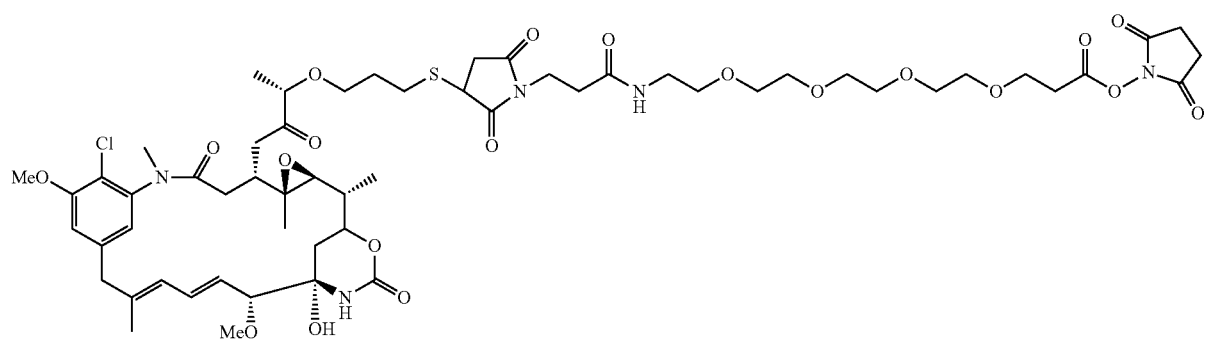
CE-048
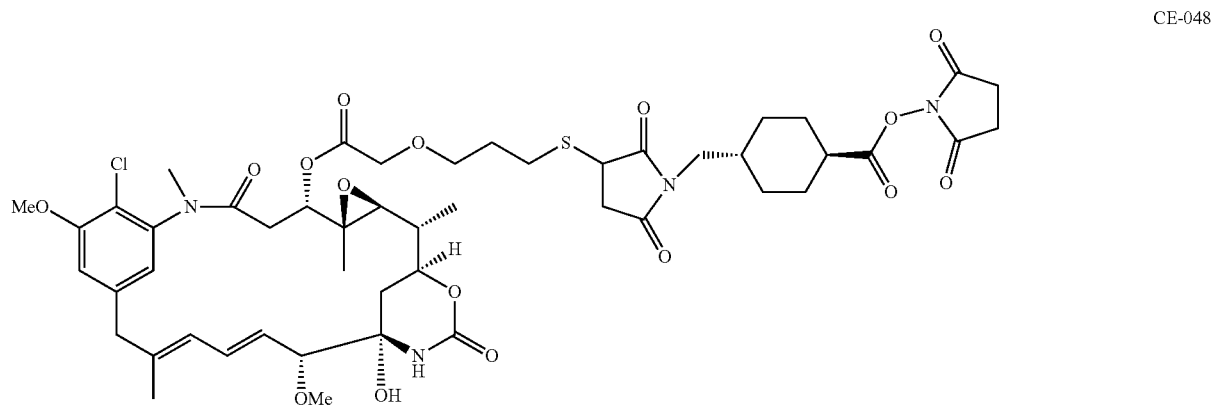
CE-049
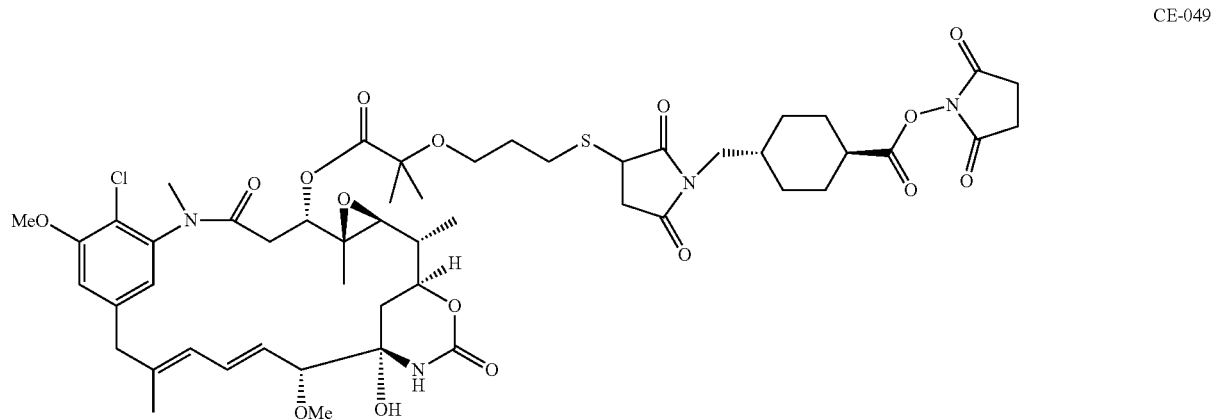
CE-051
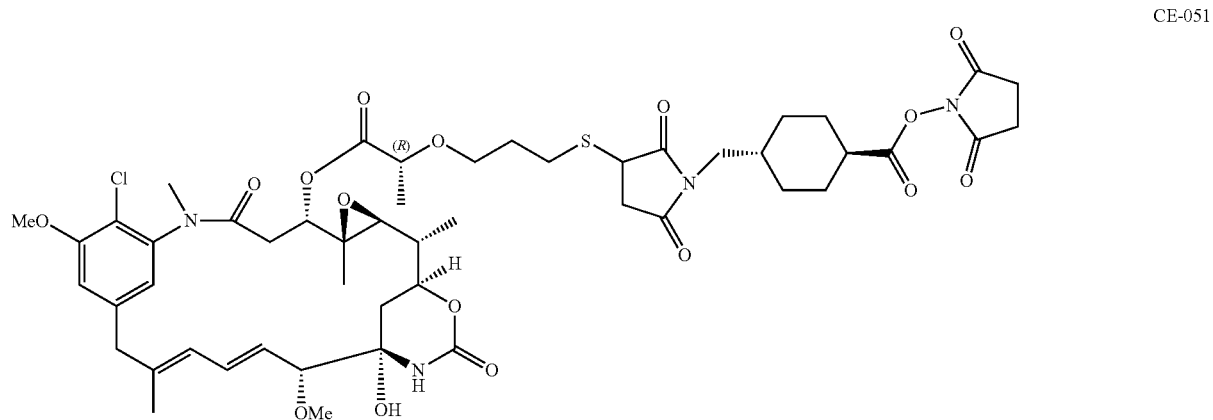

-continued
CE-052
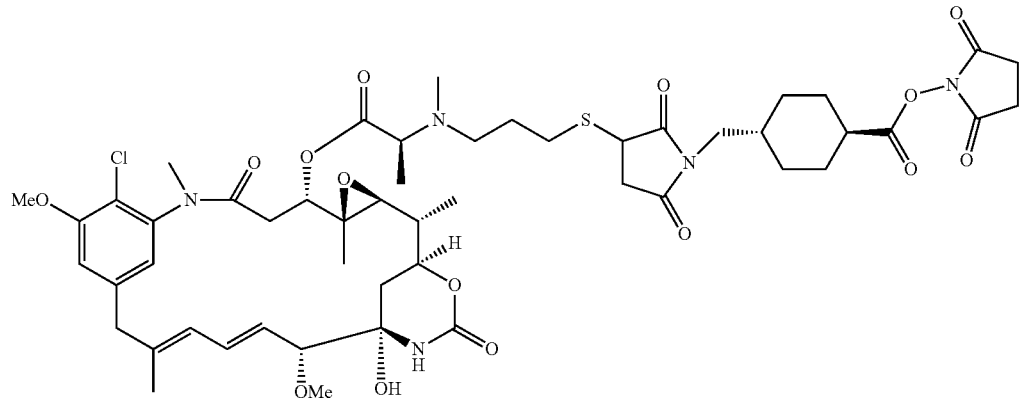
XDCE-M-001
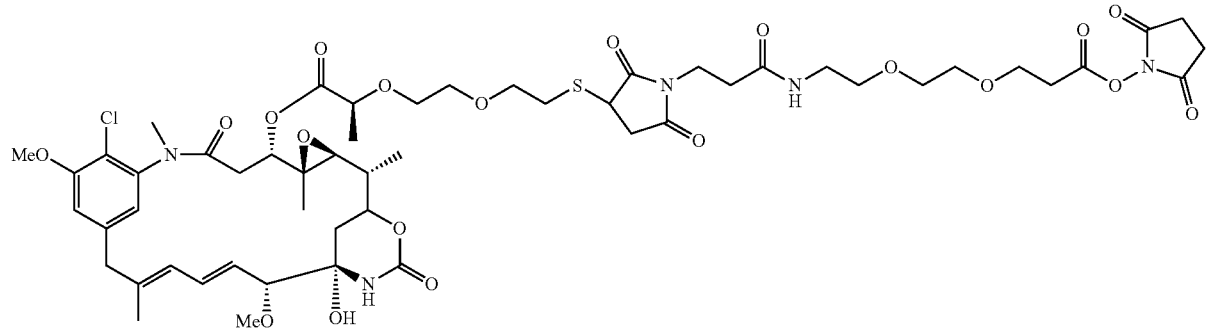
XDCE-M-002
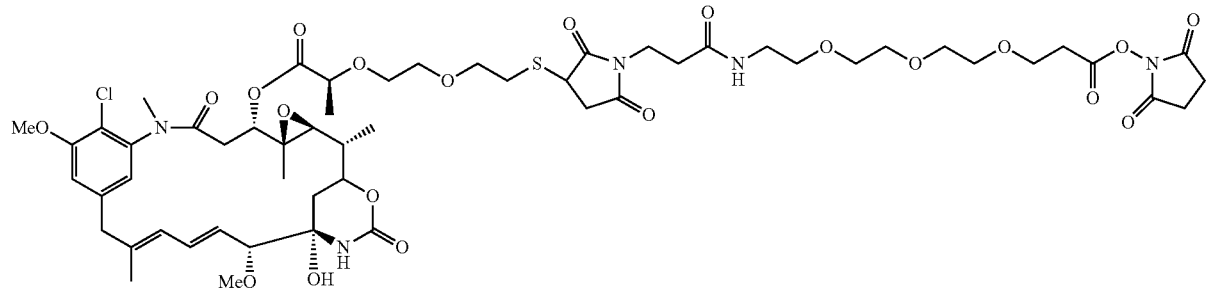
CE-045
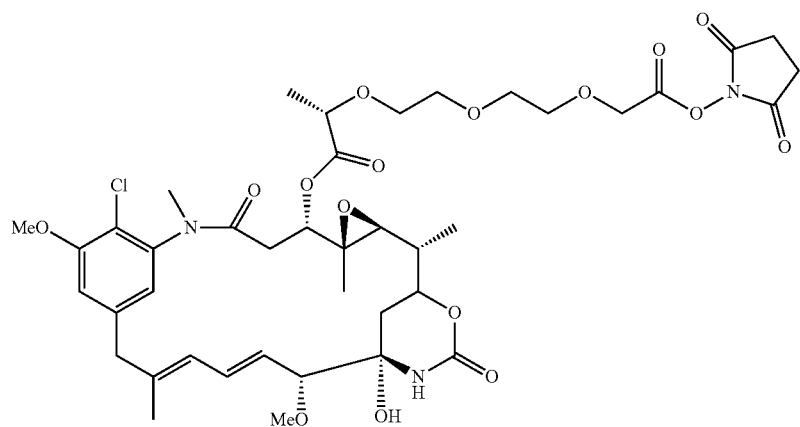

-continued
CE-047
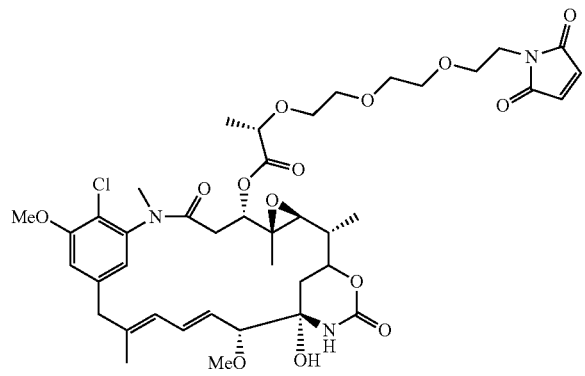
CE-050
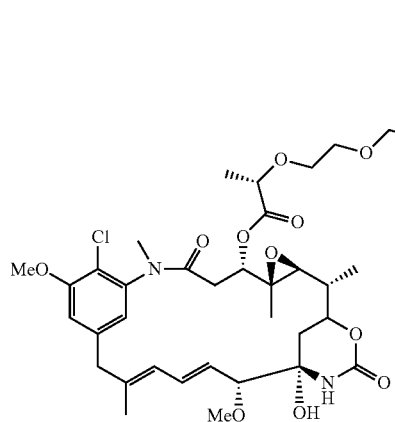
CE-046
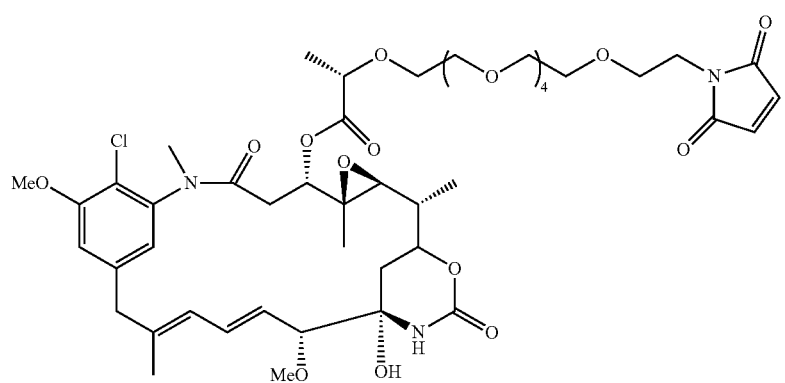
CE-052a
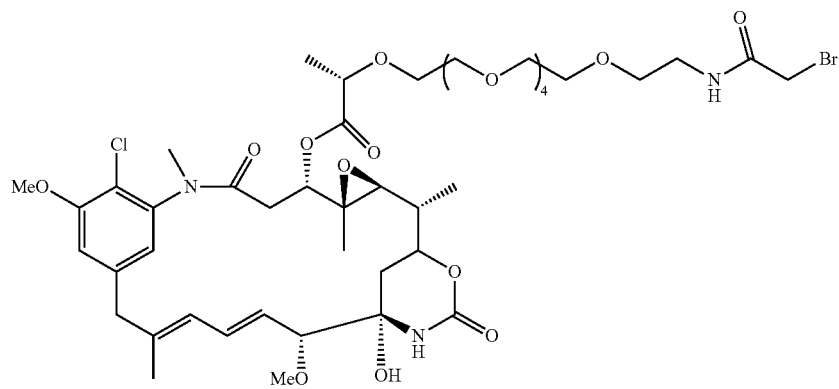
CE-063
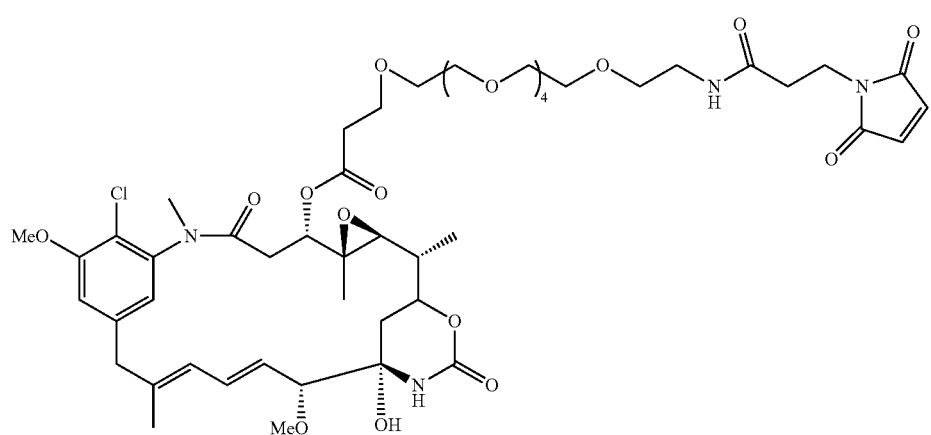

-continued
CE-048
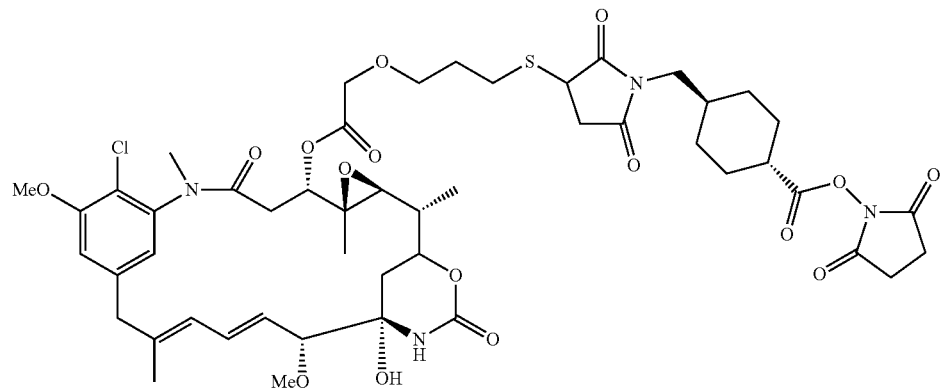
CE-049
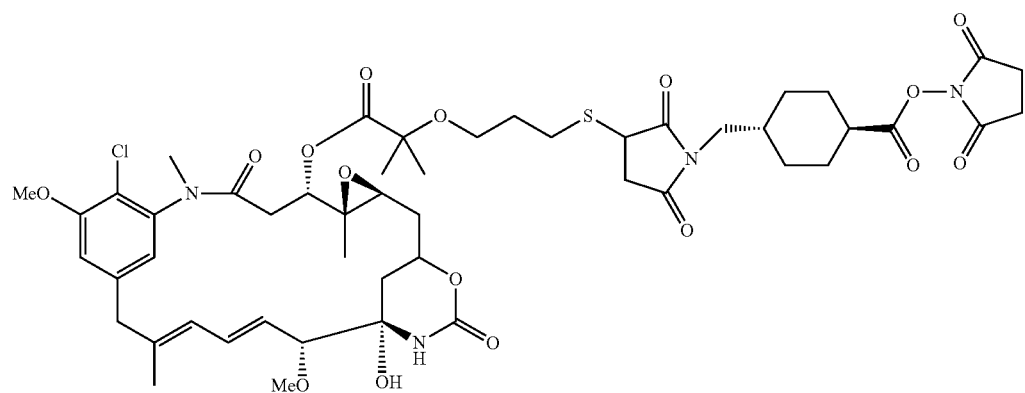
CE-051
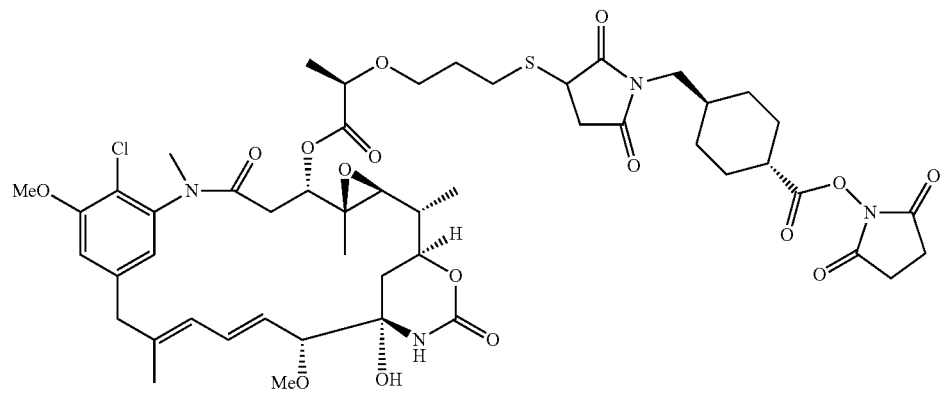
CE-053
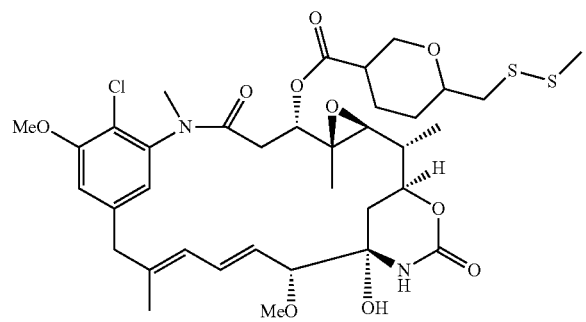
CE-054/CE-055
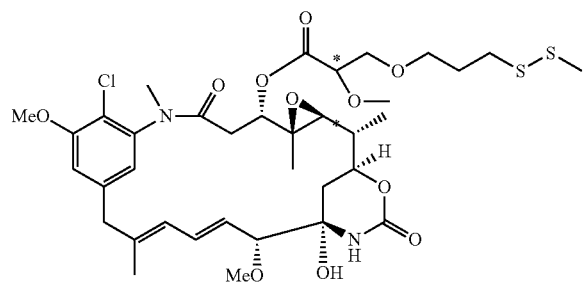

-continued
CE-056
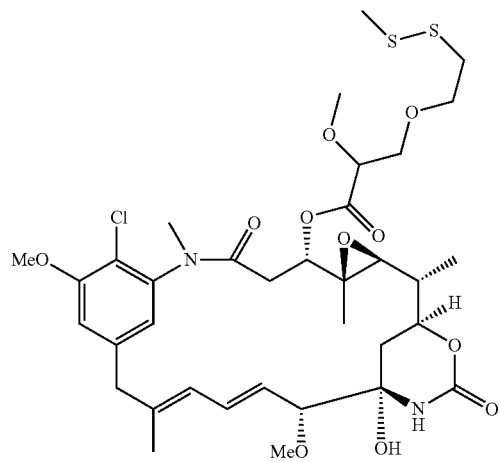
CE-057
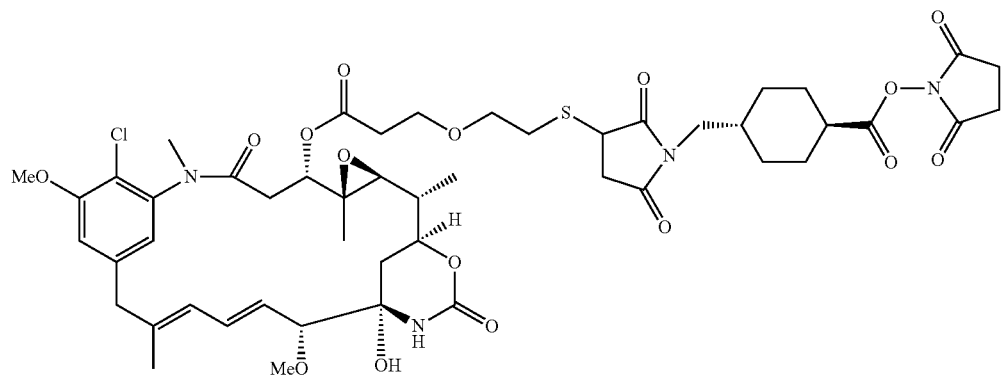
CE-052a
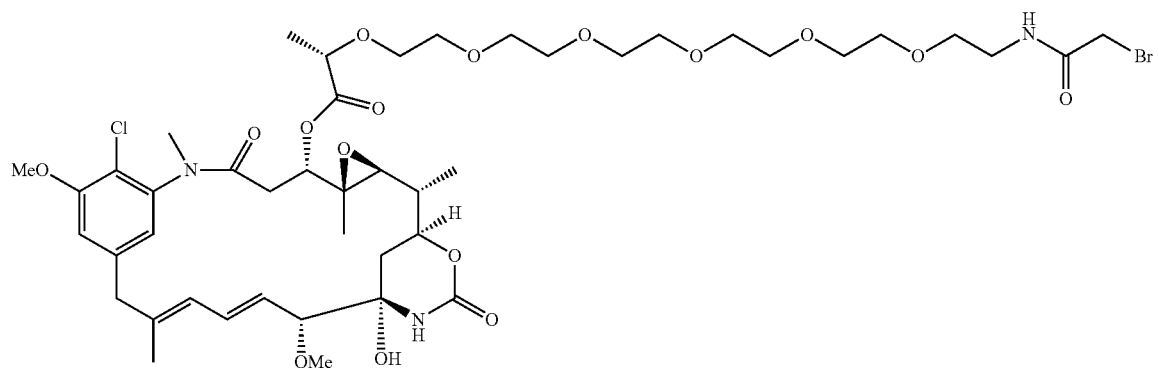
10-16
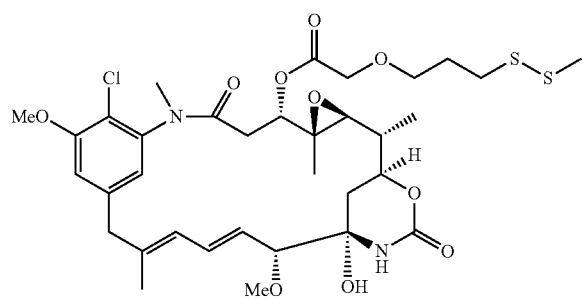
11-16
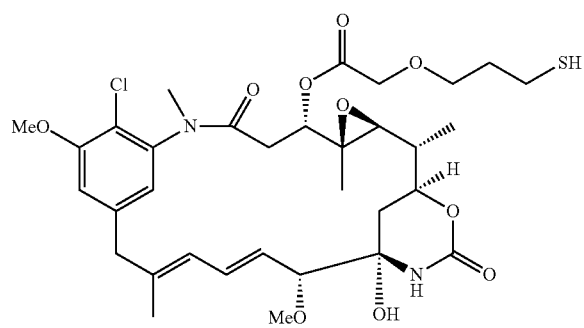

-continued 8-17
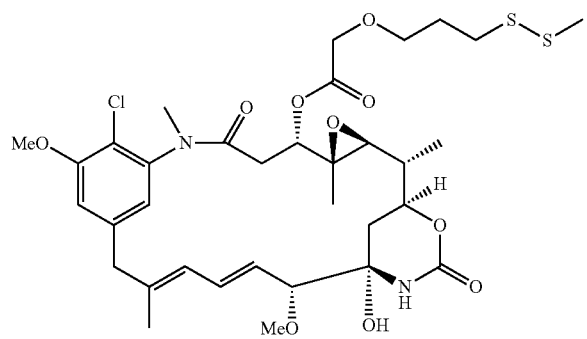

9-17
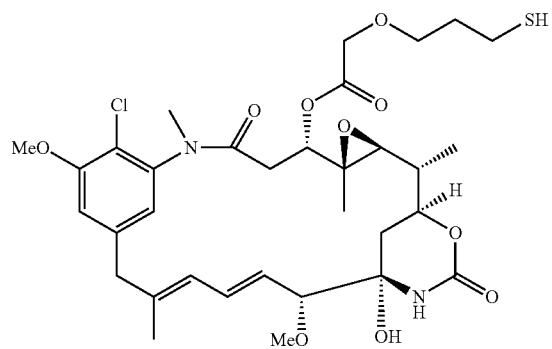

8-18
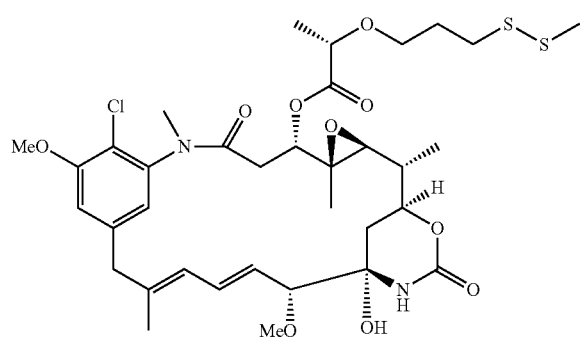

9-18
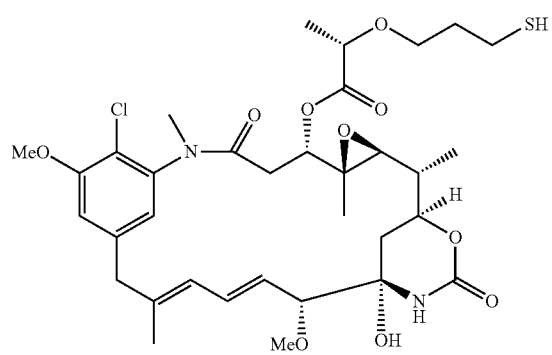

7-22
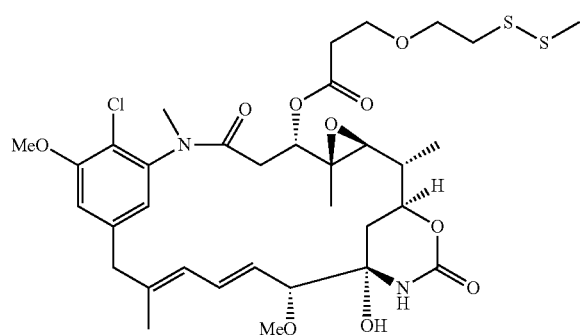

8-22
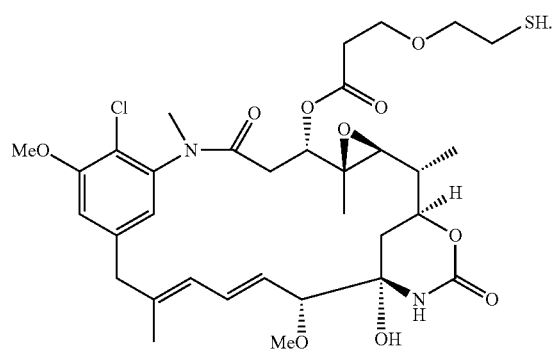

In the present invention, a carbon atom marked with *, represents a chiral or an achiral carbon atom, the configuration of which can be R, S or racemate.

The present invention also provides a process for preparing the antibody drug conjugate represented by formula IB, comprising in an organic solvent, under the condition of pH 6-8, conjugating an intermediate (a toxin with a linker) IA with a monoclonal antibody (such as Herceptin) to deliver the antibody drug conjugate represented by formula IB;

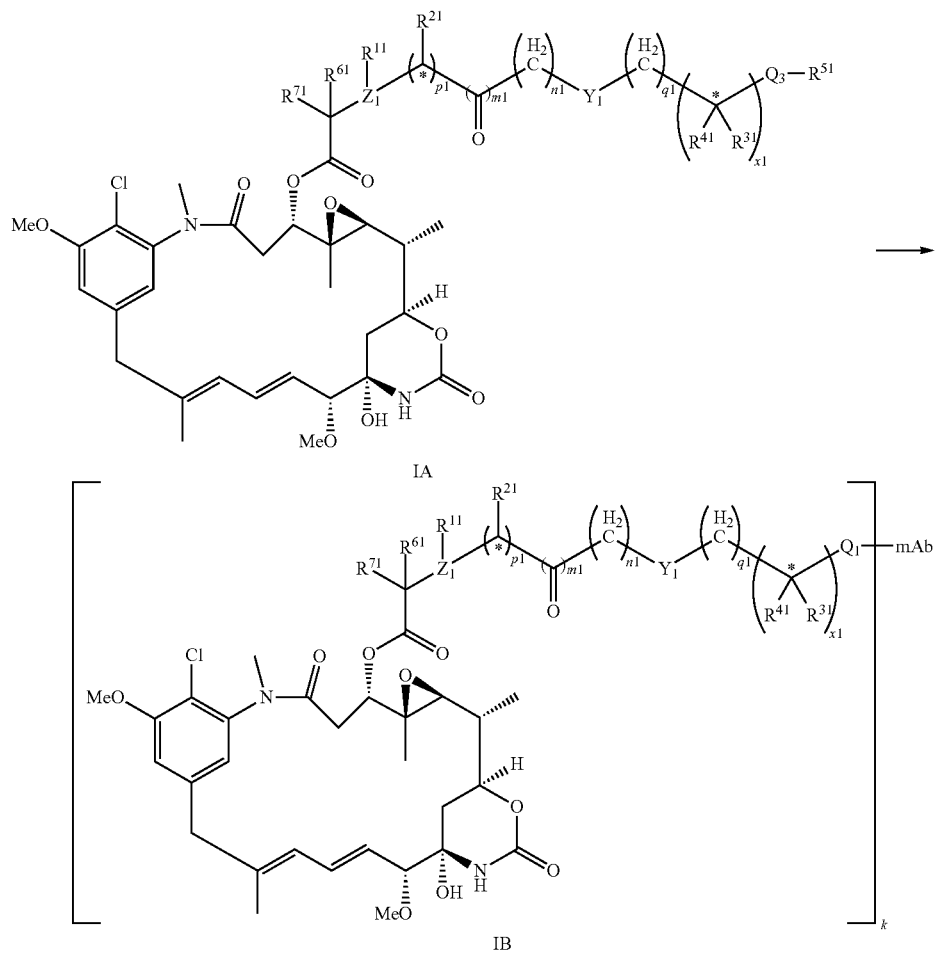

IA

IB

In the compounds represented by formula IA and IB, the definition of each letter and group are the same as above.

The methods and conditions used for the process for preparing the antibody drug conjugate represented by formula IB can be that commonly used for this kind of conjugating reactions in the art, specifically can refer to Gail D. Lewis Phillips, et al., *Cancer. Res.*, 2008, 68, 9280 and Teemu T. Junttila, et al., *Breast. Cancer. Res. Treat.*, 2011, 128, 347, which are incorporated into this application by their entities.

The present invention preferably employs the following methods and conditions:

In the process for preparing the antibody drug conjugate represented by formula IB, the organic solvent is preferably selected from the group consisting of amides solvent, sulfoxides solvent and ethers solvent. The amides solvent is preferably N,N-dimethylformamide (DMF) and/or N,N-dimethylacetamide (DME); the sulfoxides solvent is preferably dimethyl sulfoxide (DMSO). The ethers solvent is preferably tetrahydrofuran.

In the process for preparing the antibody drug conjugate represented by formula IB, the mass-to-volume ratio of the intermediate (a toxin with a linker) IA to the organic solvent is preferably 0.1 mg/mL-100 mg/mL.

In the process for preparing the antibody drug conjugate represented by formula IB, the molar ratio of the intermediate IA to the monoclonal antibody (such as Herceptin) is preferably 1-10 (e.g. 6), more preferably 1-5.

In the process for preparing the antibody drug conjugate represented by formula IB, pH 6-8 can be adjusted by a buffer; the buffer is usually a low salt buffer, preferably a phosphate buffer, such as a buffer containing potassium phosphate and monopotassium phosphate; or a boric acid buffer, such as the buffer containing boric acid and sodium borate. In the process for preparing the antibody drug conjugate represented by formula Ib, the conjugating is preferably at 4° C.-37° C. (preferably at ambient temperature).

In the process for preparing the antibody drug conjugate represented by formula IB, the progress of the conjugating may be monitored by using conventional methods in the art (e.g. TLC, HPLC or NMR), generally the reaction finishes when the intermediate IA is completely consumed.

The process for preparing the antibody drug conjugate represented by formula IB is preferably carried out under inert gas atmosphere, and when the process for preparing the antibody drug conjugate represented by formula IB is carried out under inert gas atmosphere, the inert gas is preferably nitrogen gas.

The process for preparing the antibody drug conjugate represented by formula IB preferably comprises in a pH 6-8 (e.g. 7.5) buffer, dialyzing a monoclonal antibody (such as Herceptin), followed by adding the intermediate IA and an organic solvent to carry out the conjugating.

The present invention also provides a process for preparing the antibody drug conjugate represented by formula Ib or Ib1, comprising in an organic solvent, conjugating the intermediate (a toxin with a linker) Ia or Ia1 with a monoclonal antibody (such as Herceptin) at pH 6-8 to deliver the antibody drug conjugate represented by formula Ib or Ib1;

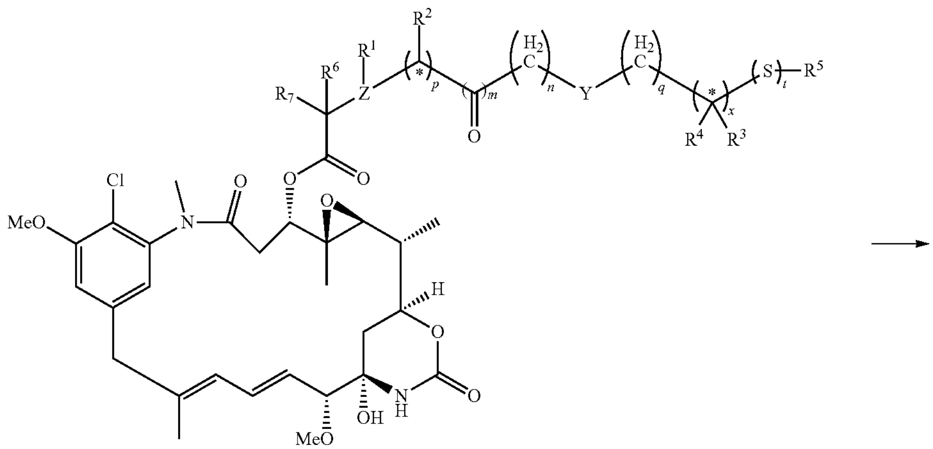

Ia

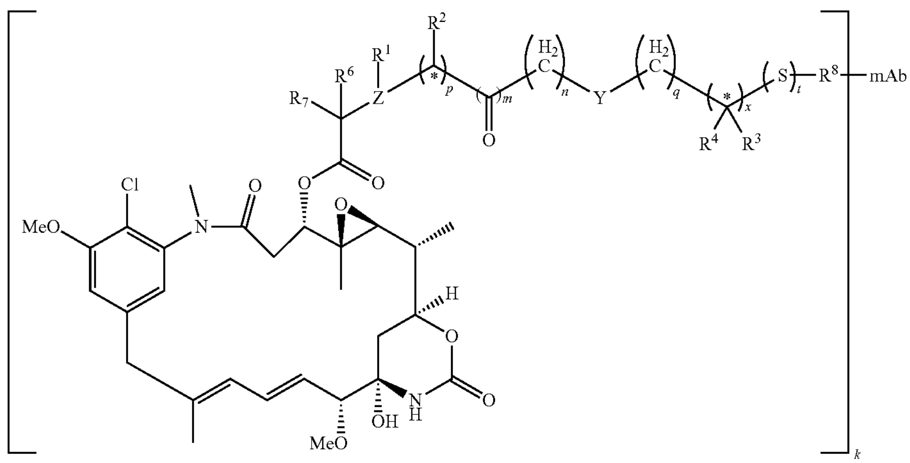

Ib

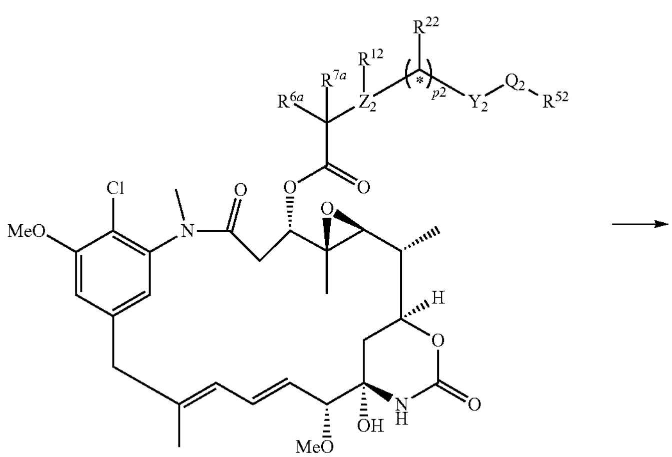

Ia1

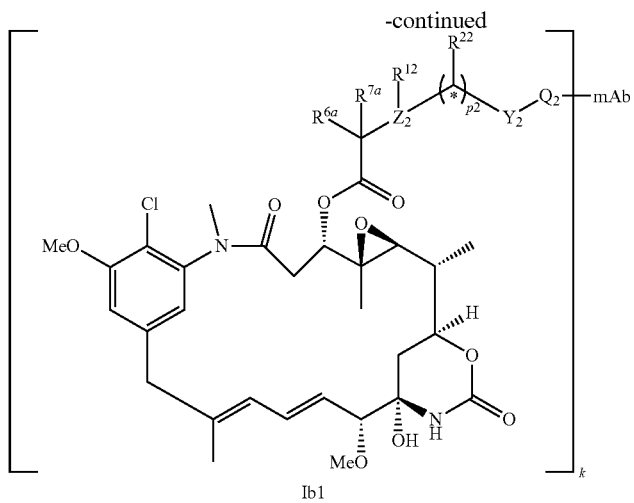

Ib1

In the compounds represented by formula Ia, Ia1, Ib and Ib1, the definition of each letter and group are the same as above.

The present invention also provides a use of the antibody drug conjugate represented by formula IB and/or the intermediate (a toxin with a linker) represented by formula IA in manufacturing a medicament for the treatment and/or prevention of cancers. The present invention also provides a use of the compound selected from the group consisting of Ib, Ib1, Ia and Ia1 in manufacturing a medicament for the treatment and/or prevention of cancers.

The cancers can be any conventional cancers in the art, including but not limited to breast cancer, lymphoma, lung cancer, liver cancer, colon cancer, head and neck cancer, bladder cancer, kidney cancer, esophageal cancer, gallbladder cancer, ovarian cancer, pancreatic cancer, gastric cancer, cervical cancer, cancerous goiter, prostate cancer, skin cancer including squamous cell carcinoma; leukocytosis, acute lymphocytic leukemia, acute lymphoblastic leukemia, B cell lymphoma, T cell lymphoma, Hodgkin lymphoma, non-Hodgkin lymphoma and hairy cell lymphoma, Burkitt's lymphoma, acute and chronic myelocytic leukemia, myelodysplastic syndrome, promyelocytic leukemia, fibrosarcoma, rhabdomyoma sarcomatosun, astrocytoma, neuroblastoma, glioma, neurilemmoma, melanoma, seminoma, teratocarcinoma, osteosarcoma, atrophoderma pigmentosum, keratinous xanthoma, thyroid follicular carcinoma and Kaposi's sarcoma.

The tumor cells of the cancer include but not limited to Her2 positive human BT474 breast tumor cells, Her2 low-expressing human MCF-7 breast tumor cells, MCF-7 Her2-derived human breast tumor MCF7-Her2 stable cell line.

The present invention further provides a pharmaceutical composition comprising the antibody drug conjugate represented by formula IB and/or the intermediate represented by formula IA, as well as one or more than one pharmaceutically acceptable excipients.

The present invention further provides a pharmaceutical composition comprising an ingredient selected from the group consisting of the antibody drug conjugate represented by formula Ib, the antibody drug conjugate represented by formula Ib1, the intermediate represented by formula Ia and the intermediate represented by formula Ia1, as well as one or more than one pharmaceutically acceptable excipients.

In the present invention, the term "pharmaceutically acceptable excipients" refers to conventionally pharmaceutical excipients in the pharmaceutical art, including all conventionally pharmaceutical materials besides the antibody drug conjugate of the present invention, which is added for ensuring the formability, effectiveness, stability and safety of the formulation, such as a diluent (e.g. carboxymethyl starch sodium, etc.), an adhesive (e.g. povidone, etc.), a disintegrating agent (e.g. microcrystalline cellulose, etc.), a lubricant (e.g. magnesium stearate, gum arabic, etc.) as well as other adjuvants. The antibody drug conjugate of the present invention can be prepared to a pharmaceutical formulation with the above-mentioned excipient as required according to the conventional method in the art; the pharmaceutical formulation can be any conventional administration, such as tablet, powder, pill, capsule, granule, oral liquid, suspension or dropping pill.

In the present invention, May represents Me OHH

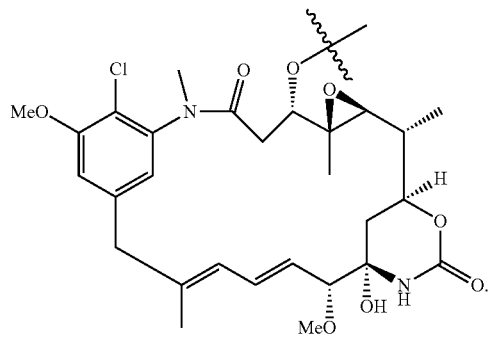 [SMILES: *O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In the present invention, the term "alkyl" intends to encompass a saturated linear or branched-chain aliphatic hydrocarbyl with specified carbon atoms, e.g. a $C_1$-$C_4$ alkyl intends to encompass a group with linear or branched-chain structure having 1, 2, 3 or 4 carbon atoms. For example, a $C_1$-$C_4$ alkyl concretely includes a methyl, an ethyl, a n-propyl, an iso-propyl, a n-butyl, a tert-butyl and an iso-butyl etc.

In the present invention, the term "alkoxy" represents a group derived from an alkyl attached to an oxygen atom, i.e. RO—, R is an alkyl.

In the present invention, the $C_{x1-y1}$ alkyl (both x1 and y1 are integer) with indicated carbon atoms, such as $C_1$-$C_4$ alkyl, represents unsubstituted $C_1$-$C_4$ alkyl.

In the present invention, the term "halogen" represents fluorine, chorine, bromine, iodine or astatine.

In the present invention, the term "cyano" represents

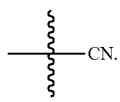

In the present invention, TBDPS represents tert-butyldiphenylsilyl.

The above various preferred conditions can be combined randomly without departing from common knowledge in the art to obtain various preferred embodiments of the present invention.

The reagents and starting materials used in the present invention are all commercially available. The room temperature described in the present invention refers to ambient temperature ranging from 10° C.-35° C.

The positive effects achieved by the present invention are that a series of novel antibody drug conjugates stable to acid and peptidase cathepsin are designed and synthesized in the present invention, the linkage of which are stable ether bond, thereby improving the water-solubility and stability obviously. The activity assays in vivo and in vitro show high cytotoxicity of the conjugates of the present invention, some of which have cytotoxicity better than or close to T-DM1.

Furthermore, the synthetic procedure of the antibody drug conjugate of the present invention is simple and has much higher yield than that of T-DM1, which leads to convenient structural modifications for improving the physical and chemical properties and biological activity of the conjugates. The conjugates of the present invention have promising market prospects.

DETAILED DESCRIPTION OF THE PREFERRED EMBODIMENT

Figure 1:
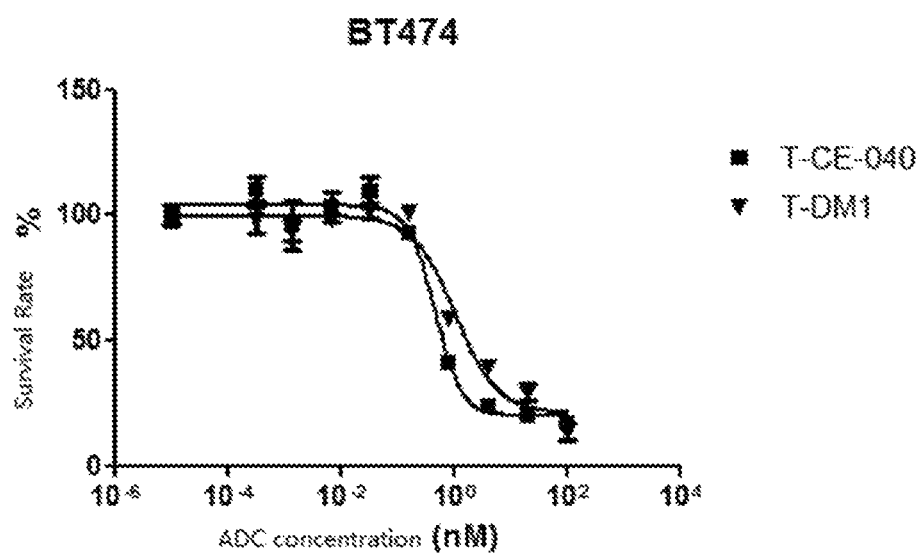
FIG. 1 is a growth inhibition curve graph of T-CE-040 and T-DM1 against BT474.

Embodiment 1 the Synthetic Routes for CE-016/017, CE-023/024, CE-005

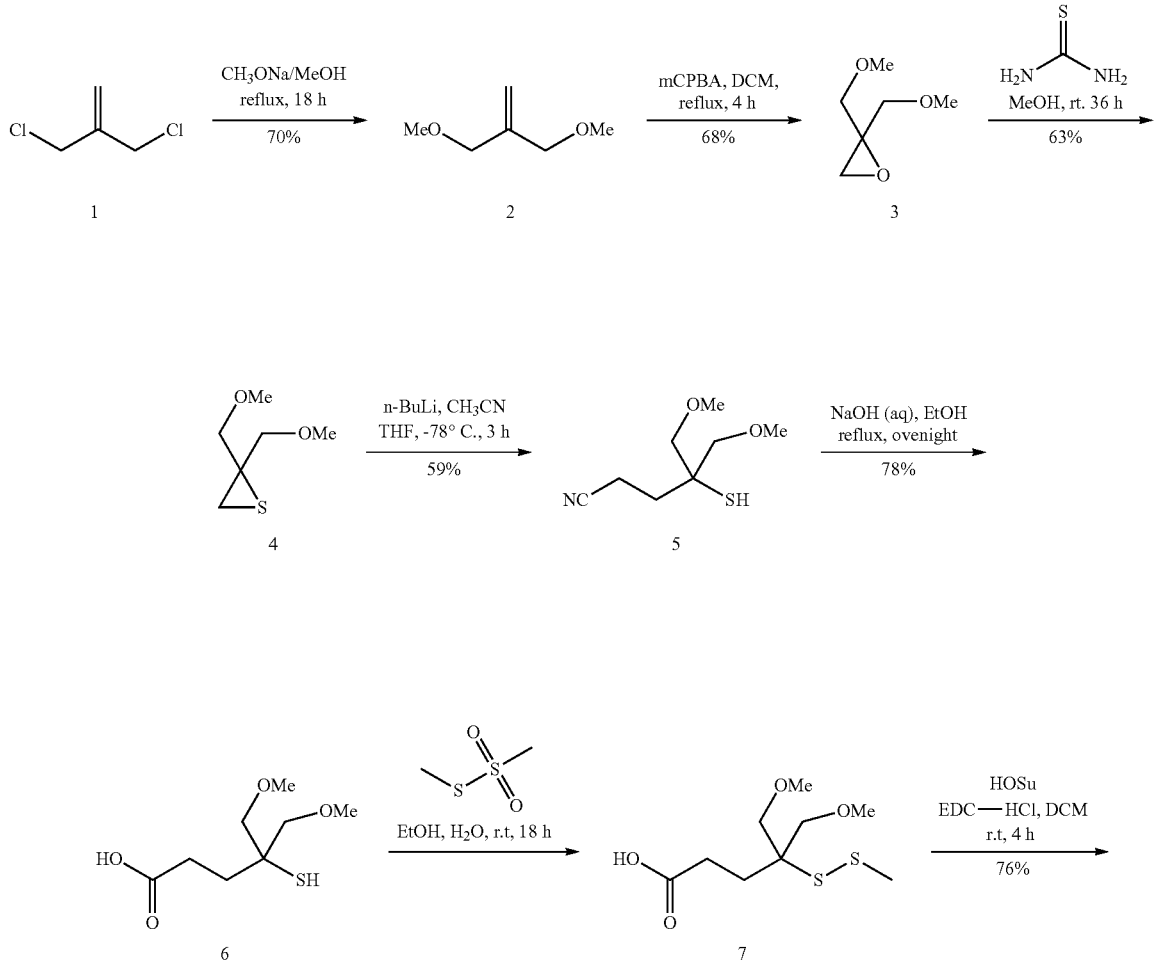

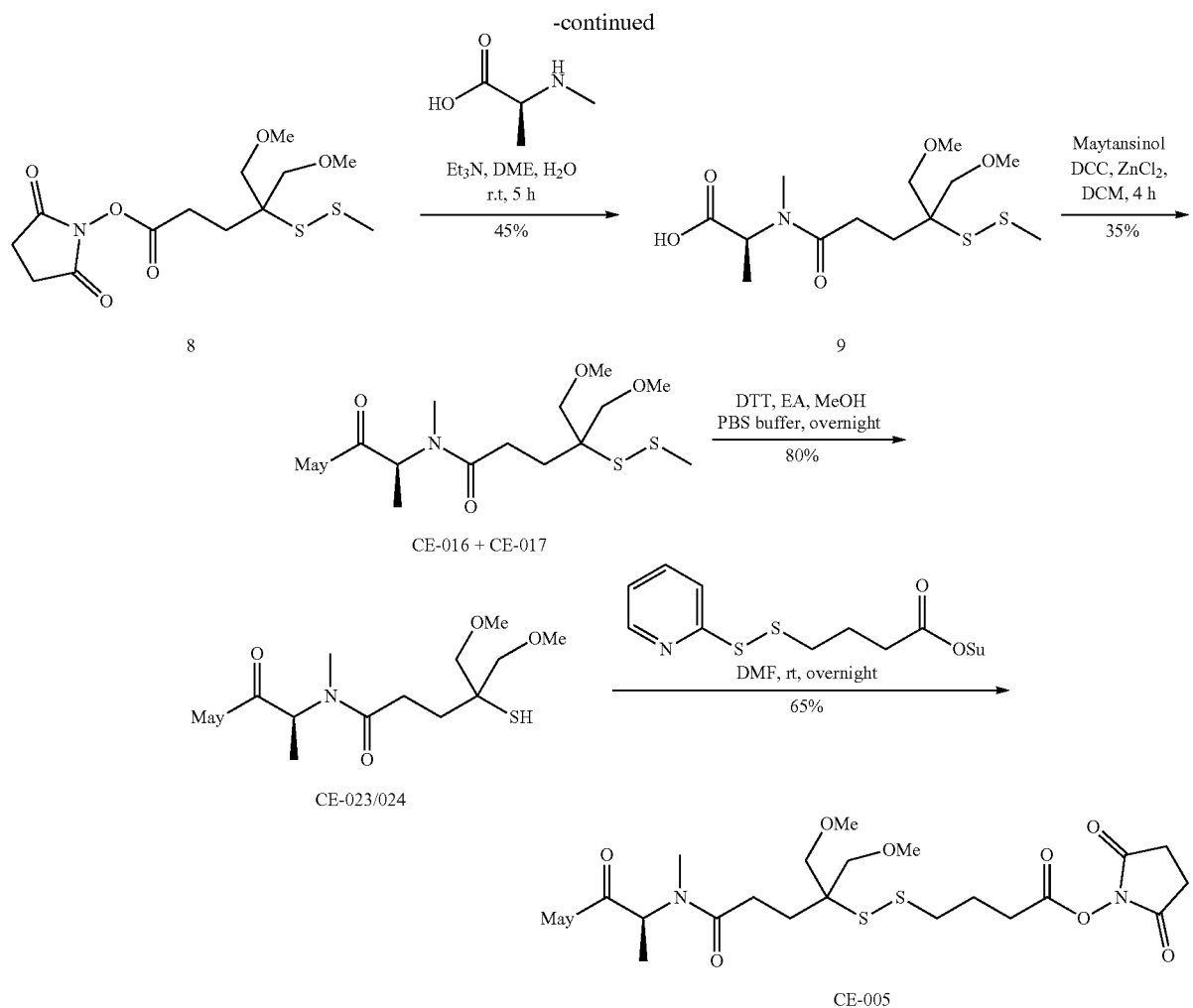

Experimental Procedure

Synthesis of Compound 2

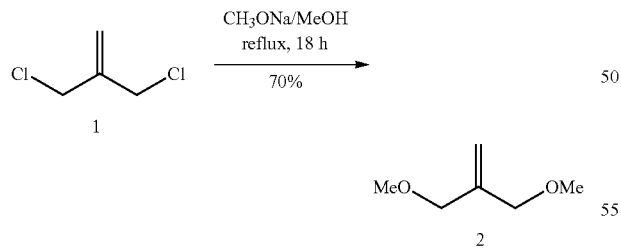

3-Chloro-2-(chloromethyl)prop-1-ene (25 g, 0.2 mol) was weighed and dissolved in 200 mL absolute methanol, sodium methoxide (21.6 g, 0.4 mol) was added in batches. The reaction mixture was heated to reflux and stirred overnight. The reaction mixture was cooled to room temperature, filtered, 250 mL water was added into the filtrate, and the mixture was neutralized with acetic acid, then extracted with petrol ether (boiling point 30-60° C., 150 mL×3) for 3 times. The organic phases were combined, dried over anhydrous sodium sulfate, concentrated to give 15 g crude product as colorless oil, which was used directly for the next step.

Synthesis of Compound 3

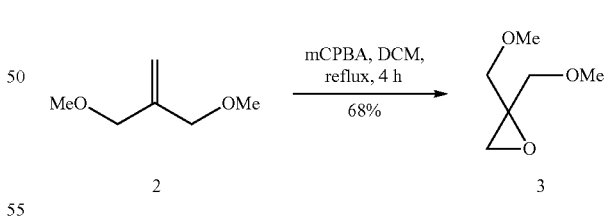

The crude product 2 (15.1 g, 0.13 mol) obtained in the previous step was dissolved in 150 mL dichloromethane, mCPBA (33.54 g, 0.195 mol) was added in batches. The reaction mixture was heated to reflux and stirred for 2 h. After TLC showed the reaction was complete, the reaction mixture was cooled to room temperature. 30 mL saturated sodium hyposulfite solution was added and the mixture was stirred for half an hour and quenched. The resultant was extracted with DCM for 3 times (100 mL×3). The organic phases were combined, dried over anhydrous sodium sulfate, and concentrated to give 12 g crude product 3 as colorless oil, which was directly used for the next reaction. $^1$H NMR (400 MHz, CDCl$_3$) δ ppm 2.57 & 2.54 (dd, J$_1$=16.4 Hz, J$_2$=11.2 Hz, 4H), 3.39 (s, 6H), 2.78 (s, 2H).

Synthesis of Compound 4

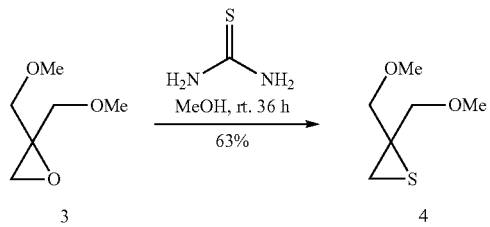

The crude product 3 (13.2 g, 0.1 mol) obtained in the previous step was dissolved in 100 mL absolute methanol, and thiourea (15.2 g, 0.2 mol) was added. The reaction mixture was stirred overnight at room temperature. After TLC showed that the starting material was completely consumed, methanol was removed by distillation under reduced pressure. 200 mL water was added into the residue, the mixture was then extracted with DCM for 3 times (100 mL×3). The organic phases were combined, dried over anhydrous sodium sulfate, concentrated, and the crude product was purified by silica gel column chromatography (petrol ether/EtOAc 10:1) to give 9.3 g product 4 as colorless oil, yield 63%. $^1$H NMR (400 MHz, CDCl$_3$) δ ppm 2.62 & 2.60 (dd, J$_1$=16.0 Hz, J$_2$=10.0 Hz, 4H), 3.41 (s, 6H), 2.40 (s, 2H).

Synthesis of Compound 5

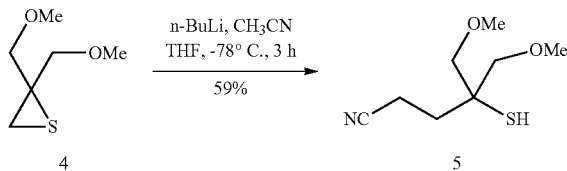 [SMILES: COCC1(COC)CS1 ; COCC(S)(CCC#N)COC]

Under nitrogen atmosphere, n-BuLi (8.8 mL, 2.5 mol/mL, 22 mmol) was added to 40 mL anhydrous THF at −78° C. CH$_3$CN (1.1 mL, 21.2 mmol) in 10 mL THF was added to the reaction mixture. The reaction mixture was stirred at −78° C. for half an hour. Compound 4 (2.96 g, 20 mmol) was dissolved in 20 mL THF, which was then added to the reaction mixture dropwise. After the addition, the reaction mixture was gradually warmed to room temperature and stirred for 3 hours. The reaction mixture was cooled to 0° C., dilute hydrochloric acid (0.5 M, 10 mL) was added dropwise to quench the reaction, the mixture was then extracted with ethyl acetate for 3 times (50 mL×3). The organic phases were combined, dried over anhydrous sodium sulfate, concentrated. The crude product was purified by silica gel column chromatography (petrol ether/EtOAc=1:1) to give 2.23 g product as light yellow oil, yield 59%. $^1$H NMR (400 MHz, CDCl$_3$) δ ppm 3.62 (d, J=9.2 Hz, 2H), 3.51 (d, J=9.2 Hz, 2H), 3.39 (s, 6H), 2.81 (t, J=7.2 Hz, 2H), 2.07 (t, J=7.2 Hz, 2H).

Synthesis of Compound 6

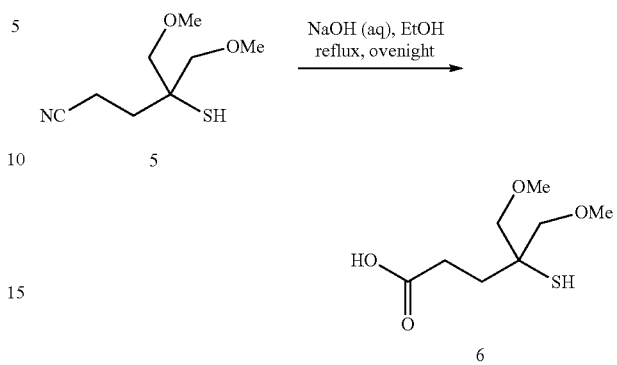

The product 5 (2.8 g, 15 mmol) obtained in the previous step was dissolved in 10 mL ethanol, the mixture was purged by argon for 3 times, sodium hydroxide solution (8 M, 4 mL, 32 mmol) was slowly added. The reaction mixture was heated to reflux under argon atmosphere and stirred overnight. The reaction mixture was cooled to room temperature, adjusted to pH=2 with dilute hydrochloric acid, then extracted with DCM for 3 times (50 mL×3). The organic phases were combined, dried over anhydrous sodium sulfate, concentrated. The crude product was purified by silica gel column chromatography (petrol ether/EtOAc=2:1) to give 2.43 g product 6 as light yellow oil, yield 78%. LCMS (ESI) m/z 209.1 (M+H)$^+$.

Synthesis of Compound 7

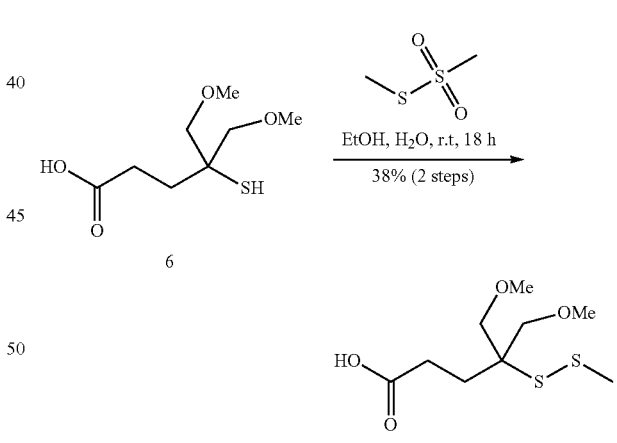

The product 6 (2.08 g, 10 mmol) obtained in the previous step was dissolved in 20 mL ethanol and 10 mL water, methyl methanethiolsulfonate (1.38 g, 11 mmol) was added. The reaction mixture was stirred at room temperature under argon atmosphere overnight. 50 mL water was added, the mixture was extracted with ethyl acetate for 3 times (50 mL×3). The organic phases were combined, washed with saturated brine for 3 times (50 mL×3), dried over anhydrous sodium sulfate, and concentrated to give crude product 7, which was used directly for the next reaction. LCMS (ESI) m/z 255.1 (M+H)$^+$.

Synthesis of Compound 8

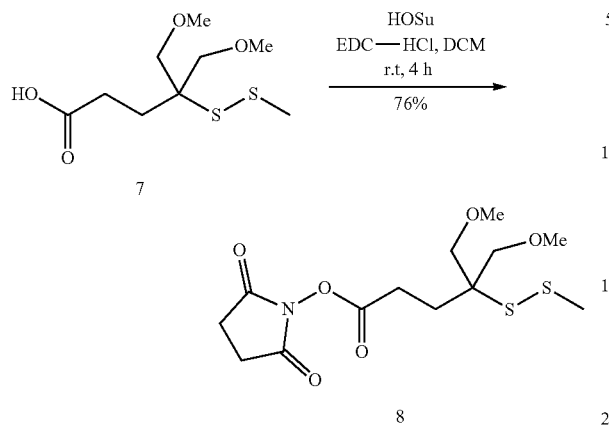

The product 7 (1 g, 4 mmol) obtained in the previous step was dissolved in 2 mL DCM, N-hydroxysuccinimide (HOSu) (0.50 g, 4.4 mmol) and 1-ethyl-(3-dimethylaminopropyl) carbodiimide hydrochloride (EDC-HCl) (0.84 g, 4.4 mmol) were added. The reaction mixture was stirred for 4 hours at room temperature. 50 mL water was added, and the mixture was extracted with ethyl acetate for 3 times (50 mL×3). The organic phases were combined, washed with saturated brine for 3 times (50 mL×3), dried over anhydrous sodium sulfate, and concentrated. The crude product was purified by silica gel column chromatography (petrol ether/EtOAc=1:3) to give 1.3 g product 8 as yellow oil, yield 76%. LCMS (ESI) m/z 352.1 $(M+H)^+$.

Synthesis of Compound 9

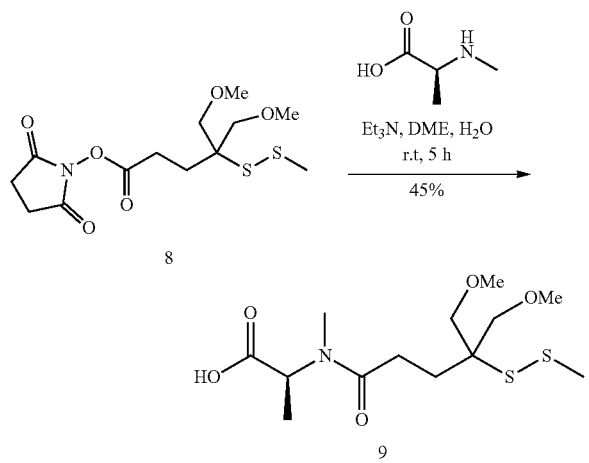

N-methyl-L-alanine (618 mg, 6.0 mmol) was dissolved in 15 mL 1,2-dimethoxyethane and 15 mL water. $Et_3N$ (1.7 mL g, 12 mmol) was added and the mixture was stirred vigorously. The product 8 (2.1 g, 6 mmol) obtained in the previous step was dissolved in 15 mL 1,2-dimethoxyethane, which was added into the reaction mixture dropwise over about 5 min. The reaction mixture was stirred at room temperature for 2 h, and the organic solvent was removed under reduced pressure. 10 mL water was added, then the mixture was adjusted to pH=2 with 1 M dilute hydrochloric acid, extracted with ethyl acetate for 3 times (50 mL×3). The organic phases were combined, washed with saturated brine for 3 times (50 mL×3), dried over anhydrous sodium sulfate, and concentrated. The crude product was purified by silica gel column chromatography (petrol ether/EtOAc=1:1) to give 920 mg product as yellow oil, yield 45%. LCMS (ESI) m/z 340.1 $(M+H)^+$.

Synthesis of Compound CE-016 and CE-017

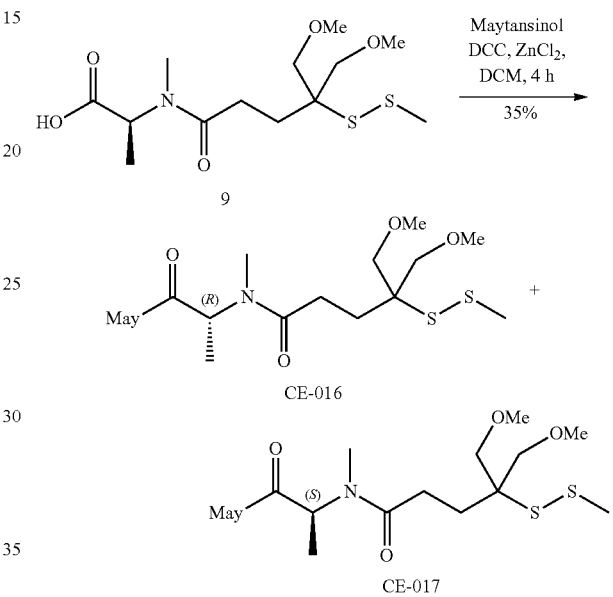

The product 9 (122 mg, 0.36 mmol) obtained in the previous step and dicyclohexylcarbodiimide (DCC) (0.15 g, 0.72 mmol) were added into a dried Schlenk tube, the mixture was purged by argon for 3 times, followed by adding 1 mL DCM and stirred. Maytansinol (63 mg, 0.12 mmol) in 4 mL dried DCM was added, followed by adding zinc chloride/ether solution (1 M, 0.72 mL, 0.72 mmol). The reaction mixture was stirred at room temperature for 2 hours, 0.3 mL was slowly added to quench the reaction. After 15 mL ethyl acetate was added, the mixture was filtrated and then rinsed with ethyl acetate. The filtrate was dried over anhydrous sodium sulfate, and concentrated. The crude product was purified by silica gel column chromatography (DCM/MeOH=40:1) to give two isomers CE-016 (25 mg, P1) and CE-017 (37 mg, P2) as white solid, yield 24%+35%. LCMS (ESI) m/z 867.8 $(M+H)^+$.

HPLC (15 min): CE-016, Rt=10.680; CE-017, Rt=10.621 (Rt: Retention time)

Mobile Phase: A: water (0.01% TFA) B: CAN (acetonitrile) (0.01% TFA), % was volume percentage Gradient: 0 min 5% B, 3 min 5% B, 10 min 95% B, 15 min 95/oB Flow Rate: 1.2 mL/min Column: Eclipse XDB-C18, 4.6*150 mm, 5 um Oven Temperature: 40° C.

CE-016: $^1$H NMR (400 MHz, $CDCl_3$) δ ppm 6.85 (s, 1H), 6.81 (s, 1H), 6.44 & 6.42 (dd, $J_1$=15.2 Hz, $J_2$=11.2 Hz, 1H), 6.31 (d, J=11.2 Hz, 1H), 6.23 (s, 1H), 5.90 & 5.87 (dd, $J_1$=15.2 Hz, $J_2$=9.2 Hz, 1H), 5.23 (q, J=7.2 Hz, 1H), 4.91 (s, 1H), 4.86 & 484 (dd, $J_1$=11.6 Hz, $J_2$=2.8 Hz, 1H), 4.32 (t, J=12.0 Hz, 1H), 3.99 (s, 3H), 3.55-3.40 (m, 5H), 3.37 (s, 6H), 3.34 (s, 3H), 3.19 (d, J=12.8 Hz, 1H), 3.17 (s, 3H), 3.04 (s, 3H), 2.86 (d, J=9.6 Hz, 1H), 2.65 & 2.62 (dd, $J_1$=14.4 Hz, $J_2$=12.0 Hz, 1H), 2.50 (t, J=8.0 Hz, 1H), 2.40 (s, 3H), 2.24-2.18 (m, 1H), 2.06-1.92 (m, 2H), 1.72 (d, J=13.6 Hz, 1H), 1.68 (s, 3H), 1.48 (d, J=7.6 Hz, 3H), 1.50-1.42 (m, 1H), 1.30 (s, 3H), 1.28 (s, 3H), 0.85 (s, 3H).

CE-017: $^1$H NMR (400 MHz, CDCl$_3$) δ ppm 6.82 (s, 1H), 6.75 (d, J=11.2 Hz, 1H), 6.64 (s, 1H), 6.44 & 6.42 (dd, $J_1$=15.2 Hz, $J_2$=11.2 Hz, 1H), 6.21 (s, 1H), 5.70 & 5.68 (dd, $J_1$=15.6 Hz, $J_2$=8.8 Hz, 1H), 5.41 (q, J=6.8 Hz, 1H), 4.80 & 4.77 (dd, $J_1$=12.0 Hz, $J_2$=3.2 Hz, 1H), 4.28 (t, J=11.2 Hz, 1H), 3.98 (s, 3H), 3.65 (d, J=12.8 Hz, 1H), 3.50 (d, J=8.8 Hz, 1H), 3.43 (t, J=8.8 Hz, 2H), 3.40-3.30 (m, 2H), 3.35 (s, 3H), 3.26 (s, 3H), 3.23 (s, 6H), 3.10 (d, J=12.0 Hz, 1H), 3.03 (d, J=9.2 Hz, 1H), 2.84 (s, 3H), 2.64-2.51 (m, 2H), 2.64-2.51 (m, 2H), 2.44-2.35 (m, 1H), 2.30 (s, 3H), 2.24-2.16 (m, 1H), 2.10-1.89 (m, 2H), 1.72 (d, J=13.6 Hz, 1H), 1.64 (s, 3H), 1.50-1.42 (m, 1H), 1.30 (s, 3H), 1.28 (s, 3H), 0.85 (s, 3H).

Synthesis of Compound CE-024

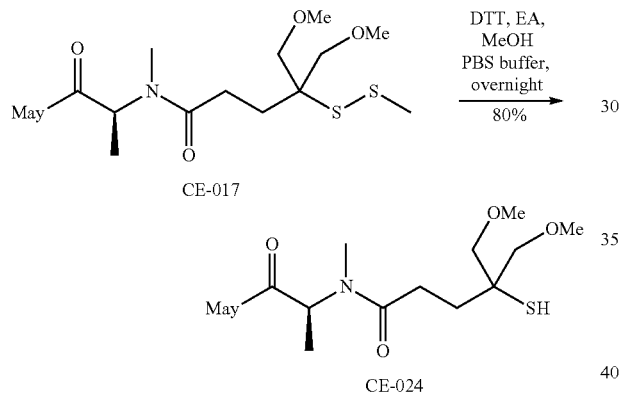

was stirred under nitrogen atmosphere for 2 hours. 3.4 mL pH=6 potassium phosphate buffer was added to quench the reaction. The mixture was extracted with ethyl acetate for 3 times (20 mL×3). The organic phases were combined, washed with saturated brine for 3 times (20 mL×3), dried over anhydrous sodium sulfate, and concentrated. The crude product was purified by prep-HPLC (CH$_3$CN in H$_2$O-0.05% TFA from 5% to 95%) to give 22 mg CE-024 as white solid, yield 80%. LCMS (ESI) m/z 840.1 (M+H)$^+$.

Synthesis of Compound CE-023

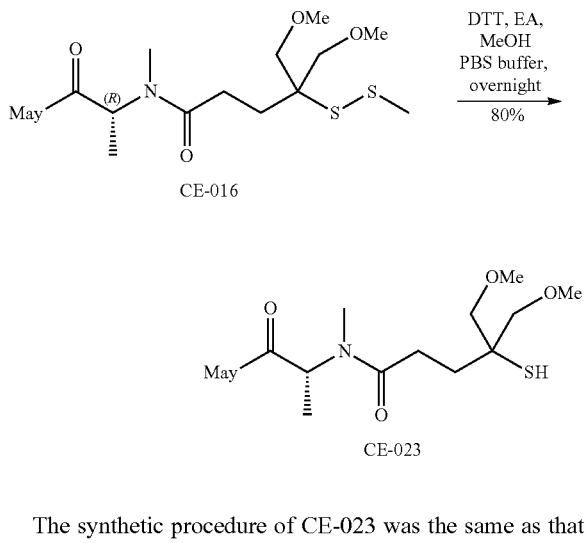

The synthetic procedure of CE-023 was the same as that of CE-024, with employing CE-016 as a starting material.

Synthesis of Compound CE-005

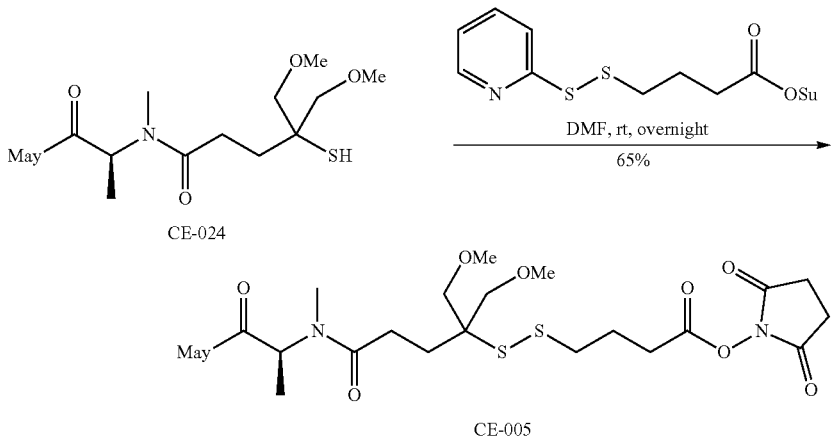

CE-017 (30 mg, 0.034 mmol) was dissolved in 0.5 mL ethyl acetate, dithiothreitol (DTT) (13 mg, 0.084 mmol) in 0.9 mL methanol was added, followed by adding 2 mL pH=7.5 potassium phosphate buffer. The reaction mixture CE-024 (18 mg, 0.02 mmol) was dissolved in 2 mL DMF, SM1 (14 mg, 0.04 mmol) was added. The reaction mixture was stirred at room temperature for 12 hours, and filtered, the filtrate was directly purified by prep-HPLC (CH$_3$CN in H₂O-0.05% TFA from 5% to 95%) to give 13.7 mg CE-005 as white solid, yield 65%.
LCMS (ESI) m/z 1076.8 (M+Na)⁺. ¹H NMR (400 MHz, CDCl₃) δ ppm 6.85 (s, 1H), 6.74 (d, J=9.4 Hz, 1H), 6.63 (s, 1H), 6.44 & 6.42 (dd, J₁=15.2 Hz, J₂=11.2 Hz, 1H), 6.29 (s, 1H), 5.70 & 5.68 (dd, J₁=15.6 Hz, J₂=8.8 Hz, 1H), 5.42 (q, J=6.8 Hz, 1H), 4.80 & 4.77 (dd, J₁=12.0 Hz, J₂=3.2 Hz, 1H), 4.28 (t, J=11.2 Hz, 1H), 3.98 (s, 3H), 3.65 (d, J=12.8 Hz, 1H), 3.50 (d, J=7.2 Hz, 1H), 3.41 (t, J=8.8 Hz, 2H), 3.40-3.30 (m, 2H), 3.35 (s, 3H), 3.25 (s, 3H), 3.23 (s, 3H), 3.22 (s, 3H), 3.11 (d, J=12.0 Hz, 1H), 3.03 (d, J=9.2 Hz, 1H), 2.84 (s, 3H), 2.64-2.51 (m, 2H), 2.68 (q, J=7.2 Hz, 4H), 2.63-2.50 (m, 2H), 2.44-2.35 (m, 1H), 2.19 & 2.16 (dd, J₁=14.4 Hz, J₂=3.2 Hz, 1H), 2.08-1.99 (m, 3H), 1.96-1.89 (m, 1H), 1.72 (d, J=13.6 Hz, 1H), 1.64 (s, 3H), 1.50-1.42 (m, 2H), 1.30 (s, 3H), 1.29 (s, 3H), 1.28 (s, 3H), 0.80 (s, 3H).
Embodiment 2 the Synthetic Routes for CE-011, CE-038, CE-041
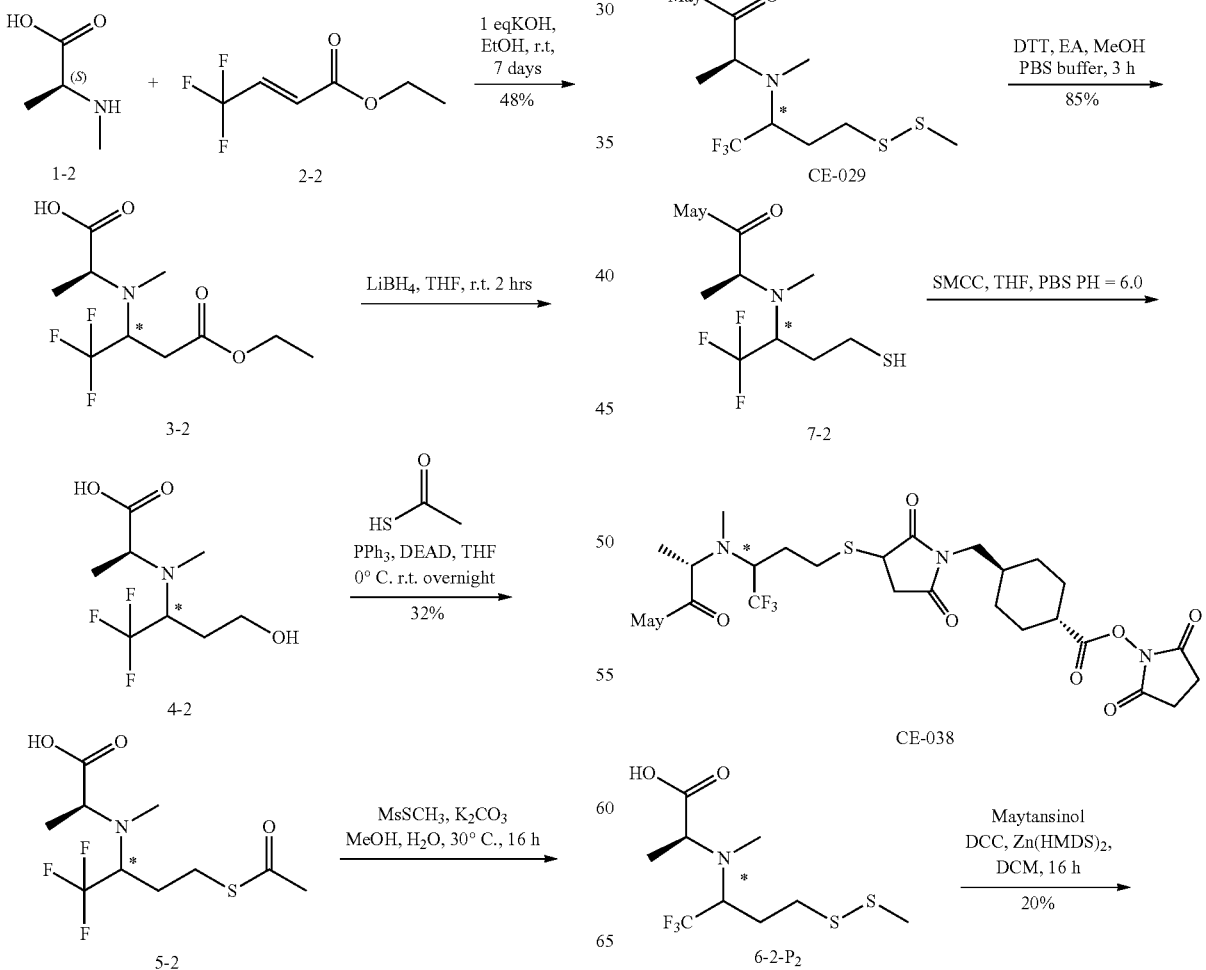
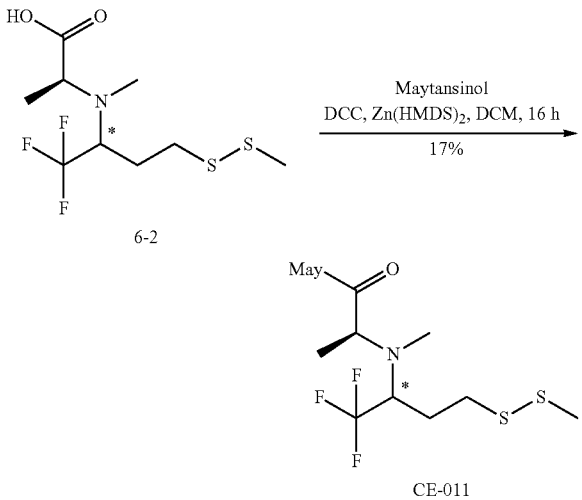
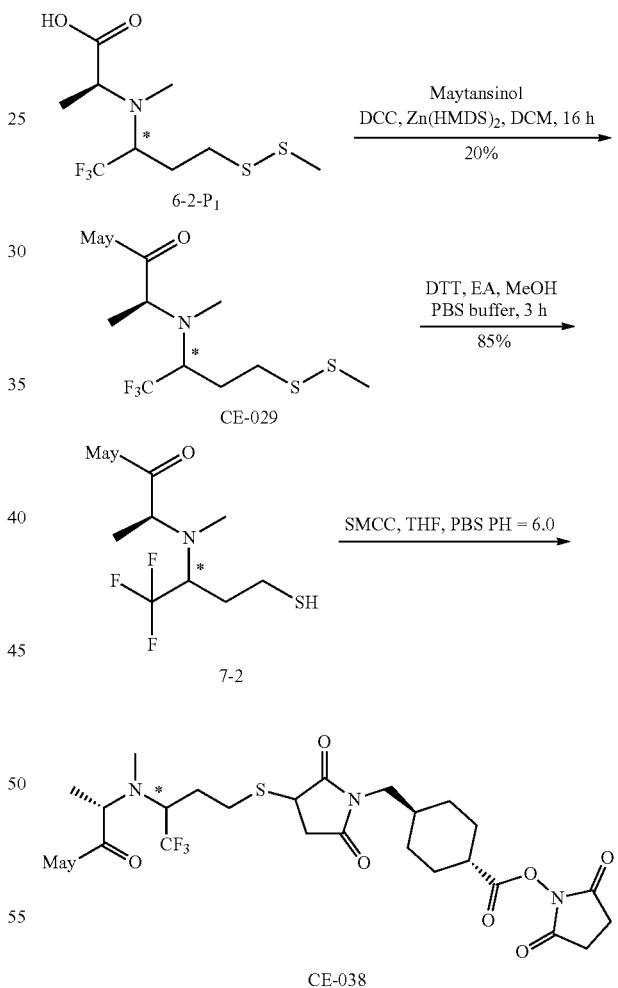
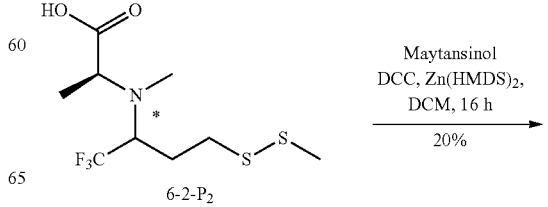

centrated under reduced pressure. 500 mL EtOAc was added, and filtrated, and the mixture was washed with 100 mL EtOAc, the filtrate was concentrated to give 12.5 g crude product, yield 48%. LCMS (ESI) m/z 272.1 (M+H)⁺.

Synthesis of Compound 4-2

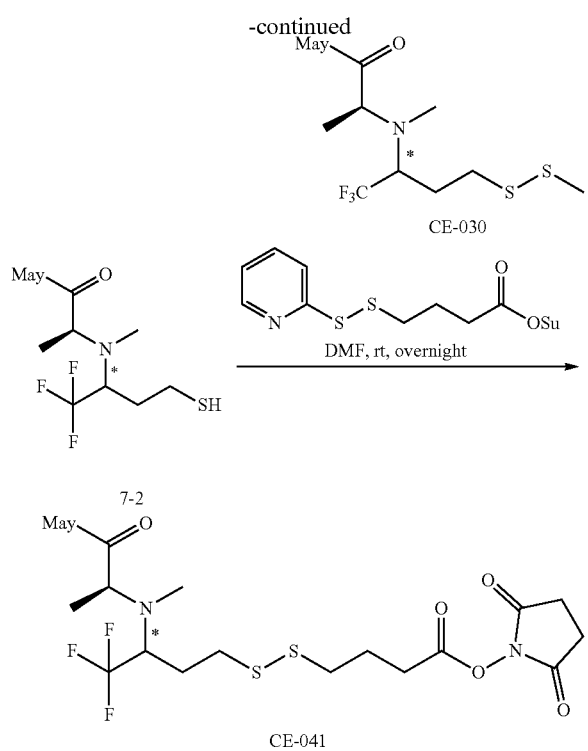

Synthesis of Compound 3-2

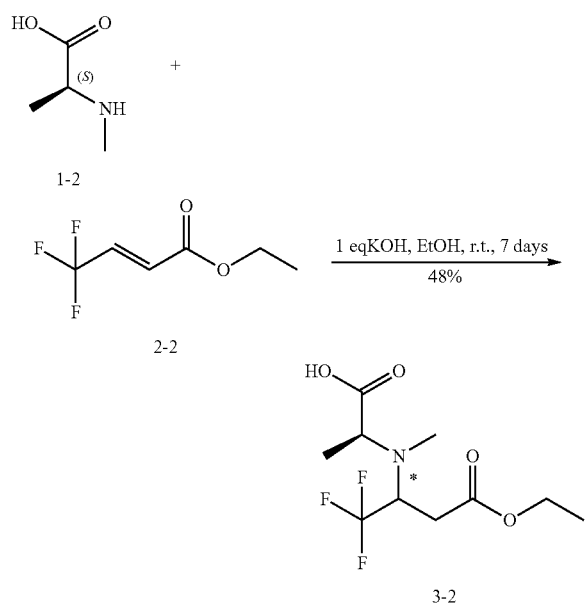

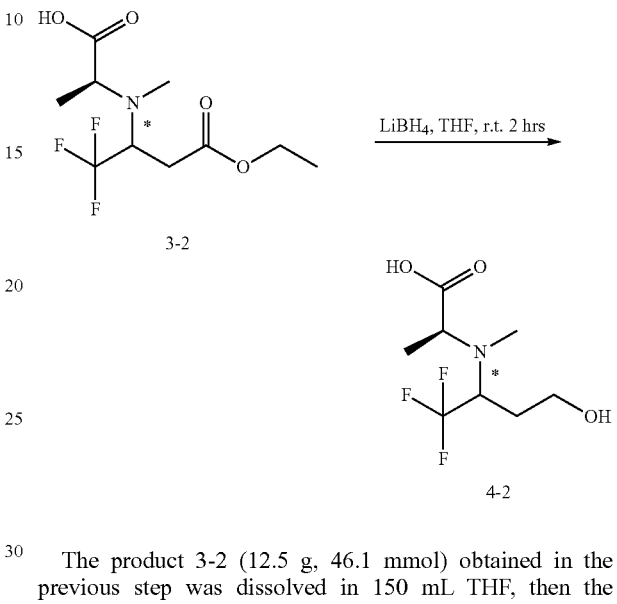

The product 3-2 (12.5 g, 46.1 mmol) obtained in the previous step was dissolved in 150 mL THF, then the mixture was cooled to 0° C., LiBH₄ (2.0 g, 90.9 mmol) was added in batches. The reaction mixture was stirred at room temperature for 3 hours, then cooled in an ice bath, 10 mL methanol was added dropwise till no bubbles emerged, then the mixture was further stirred for 2 hours. 300 mL EtOAc and 300 mL saturated ammonium chloride solution were added, the organic phase was separated, dried over anhydrous sodium sulfate, and concentrated to give 8.3 g crude product 4-2 as light yellow oil. LCMS (ESI) m/z 230.0 (M+H)⁺.

Synthesis of Compound 5-2

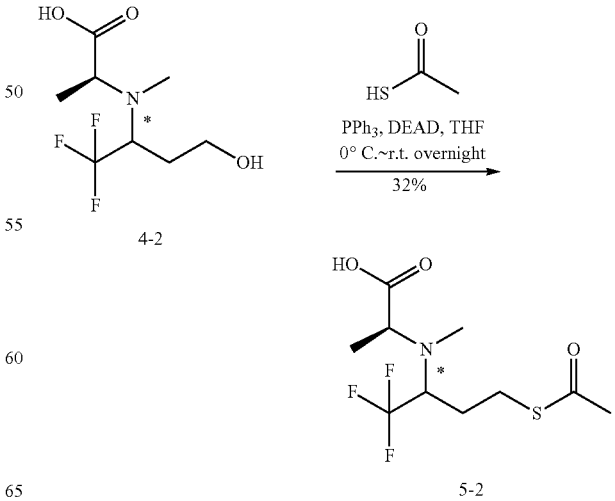

KOH (5.5 g, 0.098 mol) was added into a suspension of N-methyl-L-alanine 1-2 (10 g, 0.097 mol) in 500 mL ethanol. The reaction mixture was stirred at room temperature for 1 hour till KOH was completely dissolved. Ethyl 4,4,4-trifluoro crotonate 2-2 (20 g, 0.119 mmol) was added. The reaction mixture was heated to 35° C. and stirred for 7 days. The reaction mixture was cooled to 0° C., 10 mL concentrated hydrochloric acid was added dropwise, the mixture was stirred at room temperature for 1 hour, con- PPh₃ (12 g, 45.8 mmol) was dissolved in 200 mL THF under nitrogen atmosphere, the mixture was cooled in an ice bath and stirred. Diethyl azodicarboxylate (DEAD) (8.0 g, 45.8 mmol) was added, the mixture was further stirred for 5 minutes. A solution of compound 4-2 (8.3 g, 36.2 mmol) in 50 mL THF and thioacetic acid (4.13 g, 54.3 mmol) were added successively. The reaction mixture was warmed to room temperature and stirred overnight. 300 mL EtOAc and 200 mL saturated ammonium chloride solution were added. The organic phase was separated, and concentrated. The crude product was purified by silica gel column chromatography (PE/EtOAc 3:1 by volume) to give 3.3 g product 5-2 as light yellow oil, yield 32%. LCMS (ESI) m/z 288.0 (M+H)⁺.

Synthesis of Compound 6-2

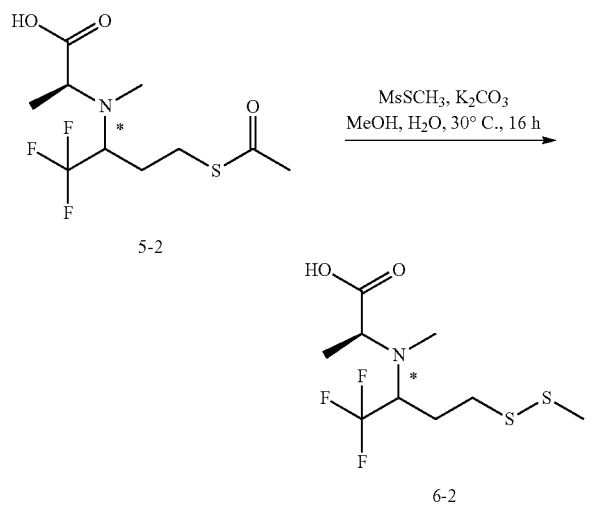

The product 5-2 (3.3 g, 11.4 mmoL) obtained in the previous step was dissolved in a mixed solution of 60 mL methanol and 30 mL water under nitrogen atmosphere, K₂CO₃ (4 g, 28.9 mmol) was added. The reaction mixture was stirred at room temperature under nitrogen atmosphere for 2 hours. Methyl methanethiosulfonate (3.0 g, 23.8 mmol) was then added. The reaction mixture was stirred at room temperature under nitrogen atmosphere for 2 hours. 200 mL water and 200 mL DCM were added and the organic phase was separated, the aqueous phase was adjusted to pH 4-5 with 1 M dilute hydrochloric acid, extracted with EtOAc (150 mL×3), the organic phases were combined, washed with saturated brine (100 mL), dried over anhydrous magnesium sulfate, concentrated to give 2.0 g crude product as light yellow oil, which was then separated by chiral prep-HPLC (AD-H, 4.6×250 mm, 5 um, flow rate: CO₂+MeOH=2.7+0.3) to deliver two isomers 6-2-P1 and 6-2-P2. LCMS (ESI) m/z 292.1 (M+H)⁺.

6-2-P1: Rt=1.72, 70%; 900 mg, ¹H NMR (400 MHz, CDCl₃) δ ppm 3.65 (q, J=7.2 Hz, 1H), 3.51 (q, J=7.2 Hz, 1H), 2.92-2.74 (m, 2H), 2.51 (s, 3H), 2.42 (s, 3H), 2.11-2.05 (m, 2H), 1.41 (d, J=7.2 Hz, 3H).

6-2-P2: Rt=2.38, 30%; 200 mg, ¹H NMR (400 MHz, CDCl₃) δ ppm 3.65 (q, J=7.2 Hz, 1H), 3.43 (q, J=7.2 Hz, 1H), 2.89-2.75 (m, 2H), 2.46 (s, 3H), 2.41 (s, 3H), 2.13-2.08 (m, 2H), 1.43 (d, J=7.2 Hz, 3H).

Synthesis of Compound CE-011

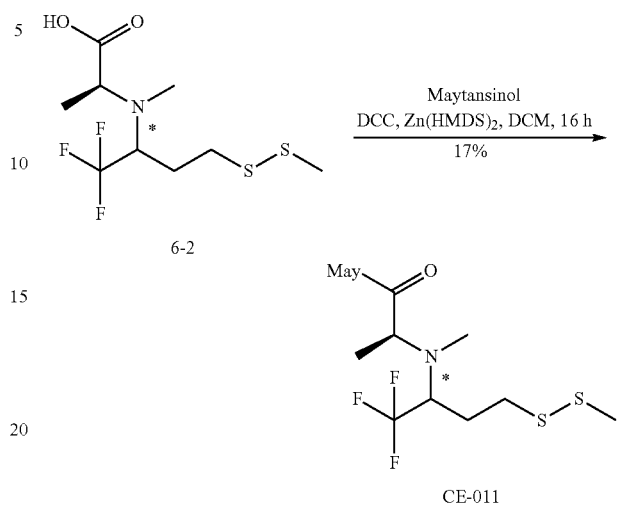

The product 6-2 (160 mg, 0.549 mmol) obtained in the previous step was dissolved in 5 mL dry DCM, dicyclohexylcarbodiimide (DCC) (80 mg, 0.388 mmol) was added, then the mixture was stirred at room temperature for 30 minutes and filtered.

Maytansinol (41 mg, 0.0726 mmol) was dissolved in 3 mL dry DMF under argon atmosphere, Zn(HDMS)₂ (0.5 mL, 0.74 mmol) was added, then the mixture was stirred at room temperature. The above-mentioned filtrate was added to the reaction mixture, the resultant mixture was stirred at room temperature for 2 hours, 20 mL saturated sodium bicarbonate solution and 30 mL EtOAc were added. The organic phase was separated and washed with 20 mL saturated brine, dried over anhydrous sodium sulfate, and concentrated. The crude product was purified by prep-HPLC to give 10 mg product CE-011 as white solid, yield 17%. LCMS (ESI) m/z 838.2 (M+H)⁺.

Synthesis of Compound CE-029

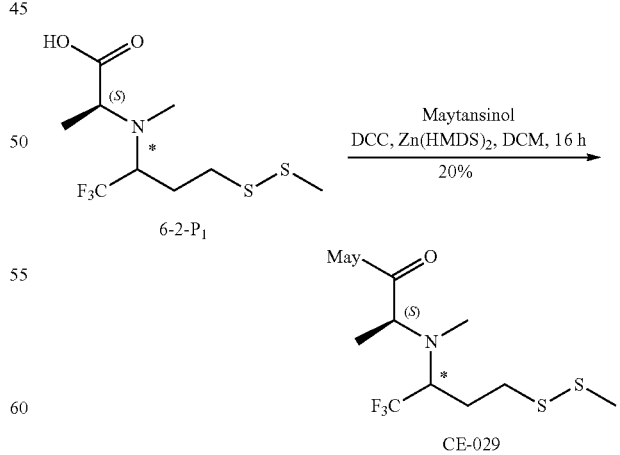

The synthetic procedure of CE-029 was the same as that of CE-011, with employing 6-2-P₁ as starting material.

¹H NMR (400 MHz, CDCl₃) δ ppm 6.84 (s, 2H), 6.42 & 6.38 (dd, J₁=15.6 Hz, J₂=8.0 Hz, 1H), 6.35 (s, 1H), 6.14 (d, J=11.6 Hz, 1H), 5.49 & 5.46 (dd, J$_1$=15.6 Hz, J$_2$=6.4 Hz, 1H), 5.35 (t, J=4.8 Hz, 1H), 4.92& 4.91 (dd, J$_1$=12.0 Hz, J$_2$=2.8 Hz, 1H), 4.28 (t, J=12.8 Hz, 1H), 3.99 (s, 3H), 3.59 (q, J=6.8 Hz, 2H), 3.50 (s, 1H), 3.49 (d, J=6.4 Hz, 1H), 3.37 (s, 3H), 3.22 (d, J=12.8 Hz, 1H), 3.13 (s, 3H), 2.89-2.84 (m, 1H), 2.81 (d, J=8.8 Hz, 1H), 2.57 (t, J=12.0 Hz, 1H), 2.44-2.42 (m, 3H), 2.36 (s, 3H), 2.29-2.27 (m, 2H), 2.08-1.99 (m, 3H), 1.68 (s, 3H), 1.58-1.65 (m, 2H), 1.45 (d, J=6.8 Hz, 3H), 1.30 (d, J=7.2 Hz, 3H), 0.84 (s, 3H).

Synthesis of Compound CE-030

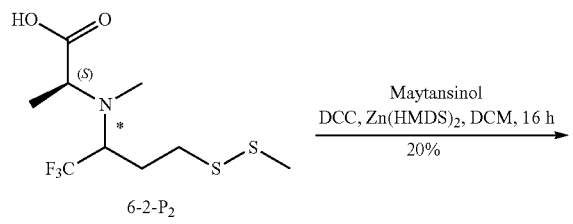

The synthetic procedure of CE-030 was the same as that of CE-011, with employing 6-2-P$_2$ as starting material.

$^1$H NMR (400 MHz, CDCl$_3$) δ ppm 6.83 (s, 1H), 6.74 (s, 1H), 6.44 (d, J=11.2 Hz, 1H), 6.40 (t, J=6.4 Hz, 1H), 6.15 (d, J=10.4 Hz, 1H), 5.49 & 5.48 (dd, J$_1$=13.6 Hz, J$_2$=8.8 Hz, 1H), 4.88 & 4.87 (dd, J$_1$=12.0 Hz, J$_2$=2.8 Hz, 1H), 4.28 (t, J=12.8 Hz, 1H), 3.99 (s, 3H), 3.61 (q, J=6.8 Hz, 1H), 3.51 (d, J=9.2 Hz, 2H), 3.35 (s, 3H), 3.22 (d, J=12.8 Hz, 1H), 3.16 (s, 3H), 2.93-2.84 (m, 2H), 2.77 (d, J=8.8 Hz, 1H), 2.53 (t, J=12.0 Hz, 1H), 2.44 (s, 3H), 2.43 (s, 3H), 2.36-2.10 (m, 1H), 2.29-2.27 (m, 2H), 2.08-1.99 (m, 3H), 1.68 (s, 3H), 1.58-1.65 (m, 2H), 1.45 (d, J=6.8 Hz, 3H), 1.30 (d, J=7.2 Hz, 3H), 0.84 (s, 3H).

Synthesis of Compound 7-2

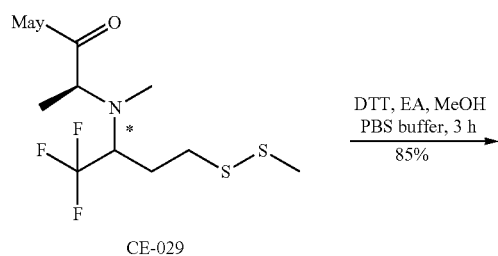

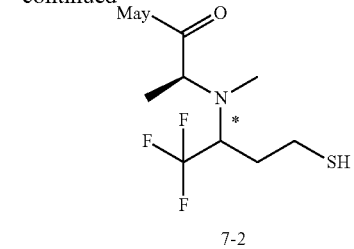

CE-029 (12 mg, 0.015 mmol) was dissolved in a mixed solution of 1 mL EtOAc and 1 mL methanol, dithiothreitol (DTT) (18 mg, 0.117 mmol) in 0.5 mL pH=7.5 potassium phosphate buffer was added. The reaction mixture was stirred under nitrogen atmosphere for 3 hours. 1 mL pH=6.0 potassium phosphate buffer was added to quench the reaction. The mixture was then extracted with EtOAc for 3 times (10 mL×3), the organic phases were combined, washed with saturated brine (5 mL) for 3 times, dried over anhydrous sodium sulfate, and concentrated. The crude product was purified by prep-HPLC (CH$_3$CN in H$_2$O-0.05% TFA from 5% to 95%) to give 10 mg product 7-2 as white solid, yield 85%. LCMS (ESI) m/z792.2 (M+H)$^+$.

Synthesis of Compound CE-038

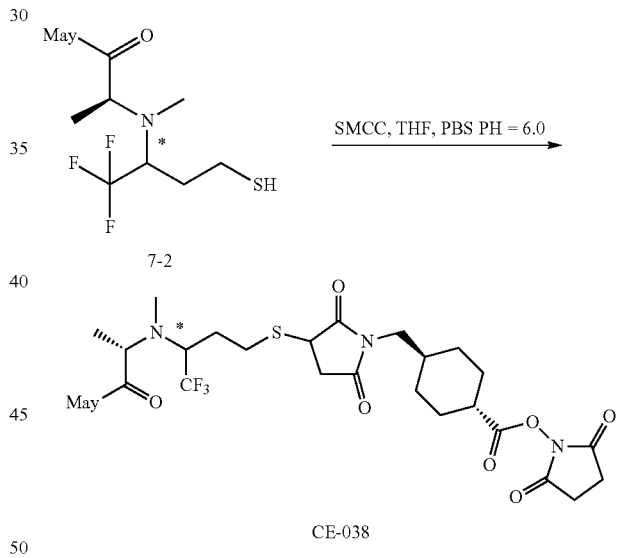

The product 7-2 (10 mg, 0.012 mmol) obtained in the previous step was dissolved in 1.5 mL THF under nitrogen atmosphere, 1.5 mL pH=6.0 potassium phosphate buffer and 4-(N-maleimidomethyl)cyclohexanecarboxylic acid N-hydroxysuccinimide ester (20 mg, 0.06 mmol, SMCC) were added. The reaction mixture was stirred at room temperature under nitrogen atmosphere overnight. The reaction mixture was filtered and the filtrate was purified by prep-HPLC to give 11.5 mg product CE-038 as white solid, yield 85%.

LCMS (ESI) m/z 1125.9 (M+H)$^+$. 1H NMR (400 MHz, CDCl$_3$) δ ppm 6.84 (s, 1H), 6.80 (s, 1H), 6.56 (d, J=8.8 Hz, 1H), 6.44 & 6.42 (dd, J$_1$=11.6 Hz, J$_2$=8.8 Hz, 1H), 6.15 (d, J=8.8 Hz, 1H), 5.52 & 5.50 (dd, J$_1$=11.2 Hz, J$_2$=6.4 Hz, 1H), 4.88-4.84 (m, 1H), 4.29 (t, J=8.4 Hz, 1H), 3.99 (s, 3H), 3.95 & 3.94 (dd, J$_1$=7.2 Hz, J$_2$=2.8 Hz, 1H), 3.53-3.48 (m, 4H), 3.41-3.37 (m, 2H), 3.37 (s, 3H), 3.26-3.19 (m, 2H), 3.13 (d, J=4.8 Hz, 1H), 3.13 (s, 3H), 2.85-2.77 (m, 5H), 2.59 (t, J=8.8 Hz, 2H), 2.46 (s, 3H), 2.29-2.15 (m, 8H), 1.83-1.78 (m, 3H), 1.68 (s, 3H), 1.63 (d, J=10.8 Hz, 1H), 1.54 (d, J=10.8 Hz, 1H), 1.45 (t, J=6.8 Hz, 3H), 1.30 (t, J=7.2 Hz, 3H), 1.30 (t, J=7.2 Hz, 3H), 1.10 (q, J=10.4 Hz, 2H), 0.84 (s, 3H).

Synthesis of Compound CE-041

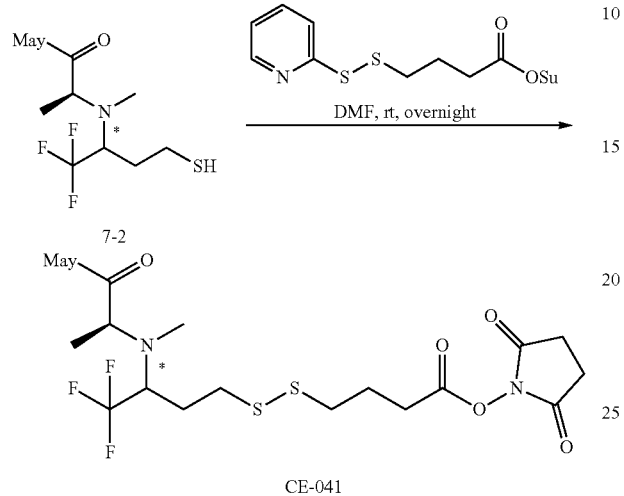

Compound 7-2 (10 mg, 0.012 mmol) was dissolved in 2 mL DMF, CE-L-019 4-(2-dithiopyridyl)butyic acid N-hydroxysuccinimide ester (6.8 mg, 0.018 mmol) was then added. The reaction mixture was stirred at room temperature under nitrogen atmosphere overnight, then filtered, the filtrate was directly purified by prep-HPLC (CH$_3$CN in H$_2$O-0.05% TFA from 5% to 95%) to give 9.6 mg product CE-041 as white solid, yield 80%.

LCMS (ESI) m/z 1007.3 (M+H)+. $^1$H NMR (400 MHz, CDCl$_3$) δ ppm 6.84 (s, 2H), 6.80 (s, 1H), 6.43 (dd, J$_1$=12.4 Hz, J$_2$=8.8 Hz, 1H), 6.15 (d, J=8.8 Hz, 1H), 5.52 & 5.51 (dd, J$_1$=12.8 Hz, J$_2$=6.8 Hz, 1H), 4.90 (d, J=9.6 Hz, 1H), 4.31 (t, J=8.8 Hz, 1H), 3.99 (s, 3H), 3.61 (q, J=5.6 Hz, 2H), 3.50 (d, J=7.2 Hz, 2H), 3.37 (s, 3H), 3.22 (d, J=12.8 Hz, 1H), 3.13 (s, 3H), 2.85-2.77 (m, 12H), 2.59 (t, J=8.8 Hz, 2H), 2.42 (s, 3H), 2.29 (d, J=8.4 Hz, 1H), 2.19-2.16 (m, 2H), 2.00-2.08 (m, 2H), 1.69 (s, 3H), 1.64 (d, J=10.8 Hz, 1H), 1.45 (d, J=6.8 Hz, 3H), 1.30 (d, J=7.2 Hz, 3H), 0.84 (s, 3H).

Embodiment 3 the Synthetic Routes for CE-012, 013, 014, 015, 032, 004

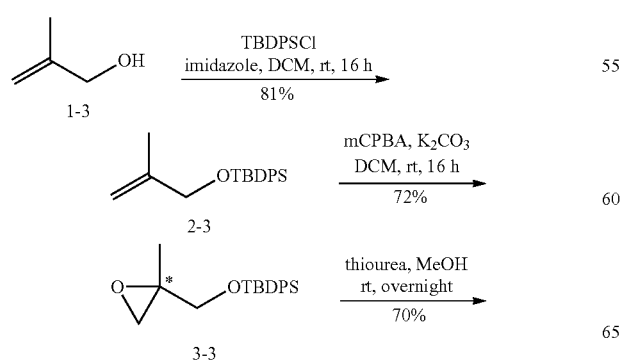

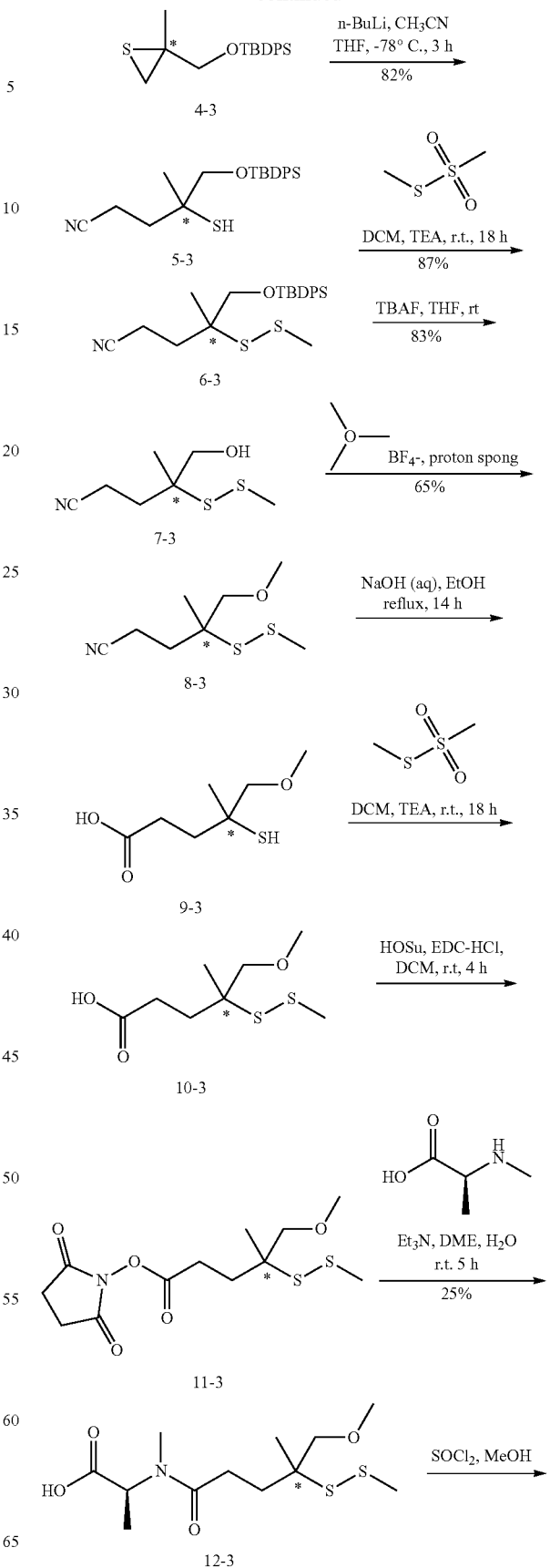

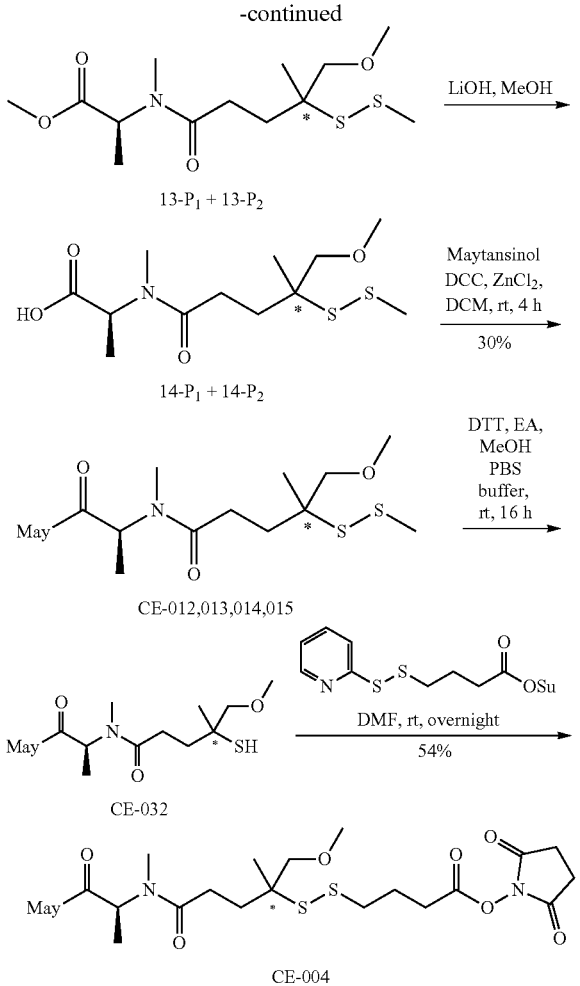

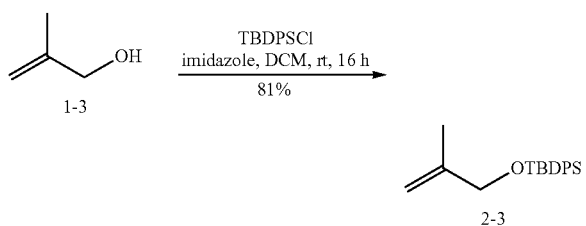

Synthesis of Compound 2-3

2-Methyl-2-propen-1-ol 1-3 (10 g, 139 mmol) and imidazole (18.9 g, 278 mmol) were dissolved in 200 mL DCM successively, the mixture was cooled to 0° C. in an ice bath, tert-butyldiphenylchlorosilane (57 g, 208 mmol) was added in batches. The reaction mixture was warmed to room temperature and stirred for 2 hours. 100 mL water was added to quench the reaction, and the mixture was then extracted with DCM for 3 times (100 mL×3). The organic phases were combined, washed with saturated brine for 3 times (50 mL×3), dried over anhydrous sodium sulfate and concentrated. The crude product was purified by silica gel column chromatography (PE/EtOAc=10:1) to give 35 g product 2-3 as light yellow solid, yield 81%.

$^1$H NMR (400 MHz, CDCl$_3$) δ ppm 7.70-7.68 (m, 4H), 7.42-7.35 (m, 6H), 5.13 (s, 1H), 4.85 (d, J=6.4 Hz, 1H), 4.07 (s, 2H), 1.68 (s, 3H), 1.07 (s, 9H).

Synthesis of Compound 3-3

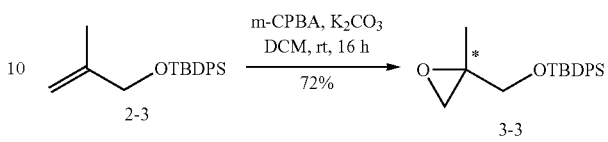

The crude product 2-3 (30 g, 96 mmol) obtained in the previous step was dissolved in 600 mL DCM, K$_2$CO$_3$ (24.9 g, 144 mmol) was added, the mixture was stirred at room temperature for 1 hour. m-CPBA (26.4 g, 192 mmol) was added in batches. The reaction mixture was stirred at room temperature overnight. 150 mL saturated sodium thiosulfate solution was added and the mixture was stirred for 0.5 hour and then quenched. The mixture was extracted with DCM for 3 times (100 mL×3). The organic phases were combined, washed with saturated brine for 3 times (100 mL×3), dried over anhydrous sodium sulfate, and concentrated. The crude product was purified by silica gel column chromatography (PE/EtOAc=10:1) to give 22.8 g product 3-3, yield 72%.

$^1$H NMR (400 MHz, CDCl$_3$) δ ppm 7.68 (d, J=6.0 Hz, 4H), 7.42-7.36 (m, 6H), 3.66 (s, 2H), 2.71 (d, J=4.8 Hz, 1H), 2.58 (d, J=4.8 Hz, 1H), 1.37 (s, 3H), 1.06 (s, 9H).

Synthesis of Compound 4-3

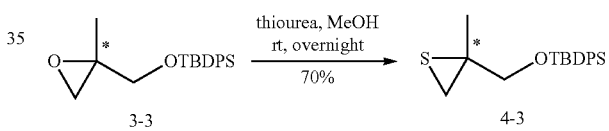

The crude product 3-3 (20 g, 62 mmol) obtained in the previous step was dissolved in 200 mL anhydrous methanol, thiourea (48 g, 124 mmol) was added. The reaction mixture was heated to reflux and stirred for 1 hour. After TLC showed that the starting material was completely consumed, the reaction mixture was cooled to room temperature, and methanol was removed by distillation under reduced pressure. 200 mL water was added to the residue, the mixture was then extracted with EtOAc for 3 times (100 mL×3). The organic phases were combined, washed with saturated brine for 3 times (100 mL×3), dried over anhydrous sodium sulfate and concentrated. The crude product was purified by silica gel column chromatography (PE:EtOAc 10:1) to give 14.8 g product as colorless oil, yield 70%.

$^1$H NMR (400 MHz, CDCl$_3$) δ ppm 7.67-7.64 (m, 4H), 7.43-7.34 (m, 6H), 3.88 (d, J=10.4 Hz, 1H), 3.57 (d, J=10.4 Hz, 1H), 2.30 (d, J=18.4 Hz, 2H), 1.68 (s, 3H), 1.07 (s, 9H).

Synthesis of Compound 5-3

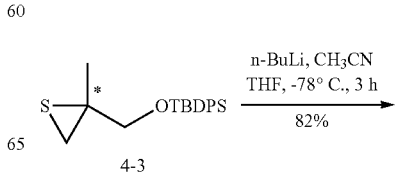

-continued

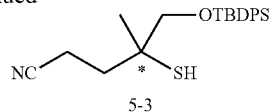

n-BuLi (2.5 M, 13 mL 32.1 mmol) was added to 100 mL anhydrous THF at −78° C. under nitrogen atmosphere. CH₃CN (1.6 mL, 30.7 mmol) in 10 mL anhydrous THF was added to the reaction mixture. The reaction mixture was stirred at −78° C. for half an hour. Compound 4-3 (10 g, 29.2 mmol) was dissolved in 20 mL THF, which was then added into the reaction mixture dropwise. After the addition, the reaction mixture was gradually warmed to room temperature and stirred for 3 hours. The mixture was cooled to 0° C., dilute hydrochloric acid (0.5 M, 20 mL) was added dropwise to quench the reaction. The mixture was then extracted with ethyl acetate for 3 times (100 mL×3). The organic phases were combined, washed with saturated brine for 3 times (100 mL×3), dried over anhydrous sodium sulfate, and concentrated. The crude product was purified by silica gel column chromatography (petrol ether/EtOAc=1:1) to give the product 9.2 g as light yellow oil, yield 82%. LCMS (ESI) m/z 384.2 (M+H)⁺.

Synthesis of Compound 6-3

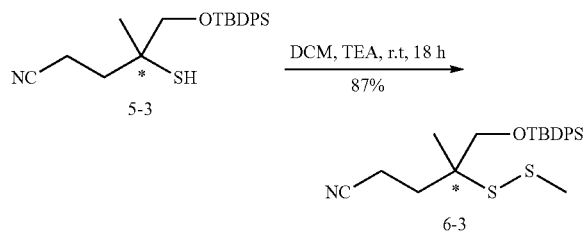

The product 5-3 (3 g, 7.8 mmol) obtained in the previous step was dissolved in 30 mL DCM, methyl methanethiosulfonate (1.2 mL, 11.7 mmoL) and Et₃N (1.6 mL, 11.7 mmol) were added. The reaction mixture was stirred at room temperature overnight under nitrogen atmosphere. 30 mL 1 M dilute hydrochloric acid and 100 mL DCM were added, the organic phase was separated, dried over anhydrous sodium sulfate, and concentrated. The crude product was purified by silica gel column chromatography (PE/EtOAc=10:1) to give 2.93 g product 6-3 as light yellow solid, yield 87%.

LCMS (ESI) m/z 451.9 (M+H)⁺. ¹HNMR (400 MHz, CDCl₃) δ 7.65-7.62 (m, 4H), 7.45-7.38 (m, 6H), 3.57 (s, 2H), 2.43-2.37 (m, 2H), 2.25 (s, 3H), 2.14-2.03 (m, 2H), 1.27 (s, 3H), 1.08 (s, 9H).

Synthesis of Compound 7-3

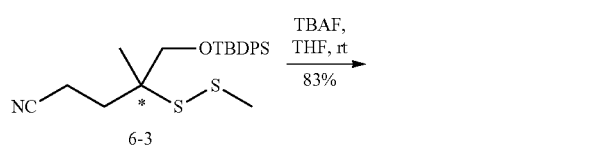

-continued

The product 6-3 (3.2 g, 7.45 mmoL) obtained in the previous step was dissolve in 30 mL THF, tetrabutylammonium fluoride (22 mL, 22 mmol, 1 M in THF) was added. The reaction mixture was stirred at room temperature overnight. 300 mL 1 N dilute hydrochloric acid was added slowly to quench the reaction, 200 mL EtOAc was added, the organic phase was separated and dried over anhydrous sodium sulfate, and concentrated. The crude product was purified by silica gel column chromatography (PE/EtOAc=2:1) to give 1.18 g product 7-3 as colorless oil, yield 83%.

LCMS (ESI) m/z 192.1 (M+H)⁺. ¹HNMR (400 MHz, CDCl₃) δ 3.57 (s, 3H), 2.59-2.42 (m, 2H), 2.43 (s, 3H), 2.10-1.94 (m, 2H), 1.30 (s, 3H).

Synthesis of Compound 8-3

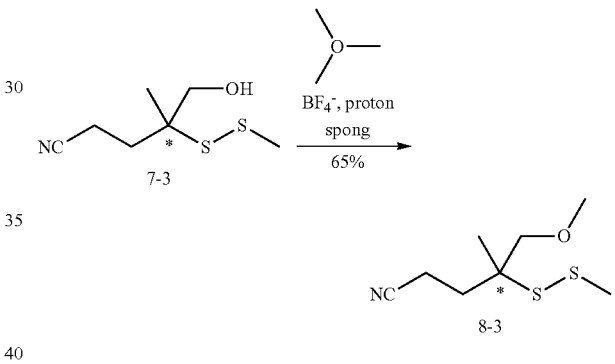

The product 7-3 (1.18 g, 6.17 mmoL) obtained in the previous step was dissolved in 100 mL DCM, trimethyloxonium tetrafluoroborate (1.83 g, 12.35 mmoL) and 1,8-bis(methylamino)naphtalene (2.7 g, 12.35 mmol) were added. The reaction mixture was stirred at room temperature overnight, and then filtered, washed with 30 mL DCM, the filtrate was washed with 150 mL 1 M dilute hydrochloric acid. The organic phase was separated, dried over anhydrous sodium sulfate, and concentrated. The crude product was purified by silica gel column chromatography (PE/EtOAc=8:1) to give 820 mg compound 8-3 as yellow oil, yield 65%.

LCMS (ESI) m/z 205.9 (M+H)⁺. ¹HNMR (400 MHz, CDCl₃) δ 3.37-3.31 (m, 5H), 2.56-2.42 (m, 2H), 2.41 (s, 3H), 2.08-2.03 (m, 2H), 1.30 (s, 3H).

Synthesis of Compound 9-3

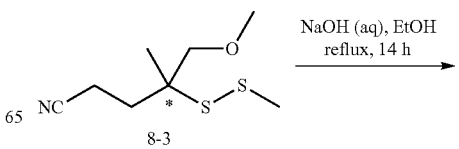

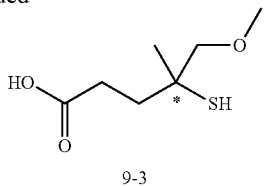

9-3

The product 8-3 (760 mg, 3.7 mmol) obtained in the previous step was dissolved in 8 mL ethanol, the mixture was purged by argon for 3 times, sodium hydroxide solution (8 M, 4 mL, 32 mmol) was slowly added. The reaction mixture was heated to reflux under argon atmosphere and stirred overnight. The reaction mixture was cooled to room temperature, adjusted to pH=2 with dilute hydrochloric acid, and then extracted with DCM for 3 times (50 mL×3). The organic phases were combined, dried over anhydrous sodium sulfate, concentrated to give the crude product 700 mg as yellow oil, which was used directly for the next step. $^1$HNMR (400 MHz, CDCl$_3$) δ 3.37-3.31 (m, 5H), 2.61-2.13 (m, 2H), 2.03-1.91 (m, 2H), 1.30 (s, 3H).

Synthesis of Compound 10-3

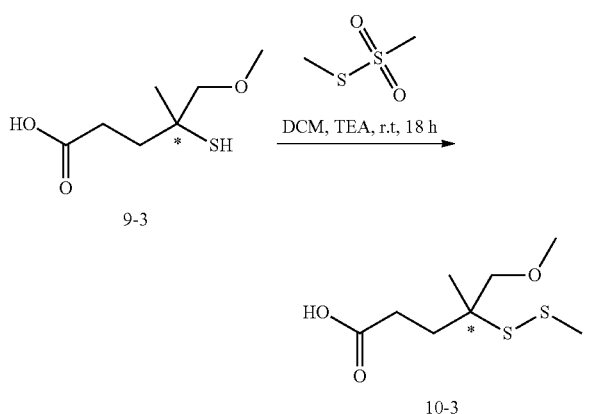

10-3

The product 9-3 (700 mg, 3.9 mmol) obtained in the previous step was dissolved in 10 mL DCM, methyl methanethiosulfonate (0.5 mL, 14 mmoL) and Et$_3$N (0.6 mL, 4.3 mmol) were added. The reaction mixture was stirred at room temperature overnight under nitrogen atmosphere. 15 mL 1 M dilute hydrochloric acid and 50 mL DCM were added, the organic phase was separated, dried over anhydrous sodium sulfate, and concentrated to give 1.2 g crude product 10-3 as yellow oil, which was used directly for the next step. LCMS (ESI) m/z 225.1 (M+H)$^+$.

Synthesis of compound 11-3

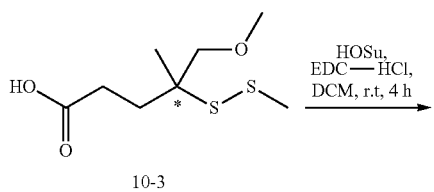

10-3

11-3

The product 10-3 (1.2 g, 5.35 mmol) obtained in the previous step and HOSu (700 mg, 6.08 mmoL) were dissolved in 20 mL DCM, EDC-HCl (1.2 g, 6.28 mmol) was added. The reaction mixture was stirred at room temperature for 2 hours. 30 mL water was added to the mixture, the mixture was then extracted with EtOAc for 3 times (50 mL×3). The organic phases were combined, washed with saturated brine (50 mL), dried over anhydrous sodium sulfate, and concentrated. The crude product was purified by silica gel column chromatography (PE/EtOAc=1:3) to give 1.7 g product as yellow oil, which was used directly for the next step. LCMS (ESI) m/z 339.0 (M+H)$^+$.

Synthesis of Compound 12-3

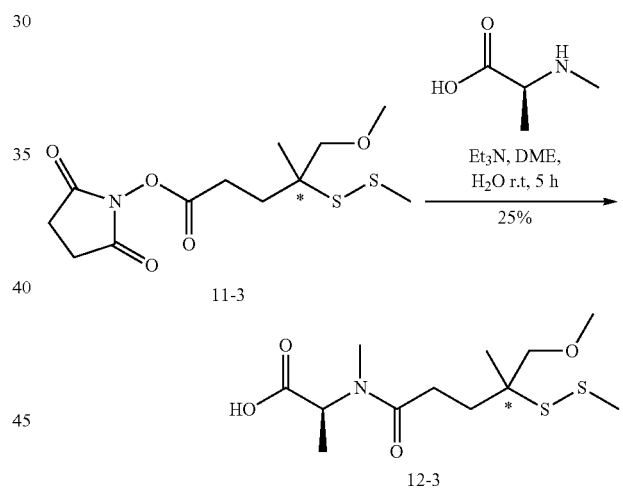

11-3

12-3

N-methyl-L-alanine (560 mg, 5.28 mmol) was dissolved in 20 mL 1,2-dimethoxyethane and 20 mL water. Et$_3$N (1.5 mL, 10.56 mmol) was added and the mixture was stirred vigorously. The product 12-3 (1.7 g, 5.29 mmol) obtained in the previous step was dissolved in 20 mL 1,2-dimethoxyethane, which was added to the reaction mixture dropwise over about 5 min. The reaction mixture was stirred at room temperature for 3 hrs, and the organic solvent was removed under reduced pressure. 10 mL water was added, then the mixture was adjusted to pH=3 with 1 M dilute hydrochloric acid, extracted with ethyl acetate for 3 times (50 mL×3). The organic phases were combined, washed with saturated brine for 3 times (50 mL×3), dried over anhydrous sodium sulfate, and concentrated. The crude product was purified by silica gel column chromatography (petrol ether/EtOAc/AcOH=50:50:0.5) to give 460 mg product as yellow oil, yield 25%. LCMS (ESI) m/z310.0 (M+H)$^+$.

Synthesis of Compound 13-3-P$_1$, 13-3-P$_2$

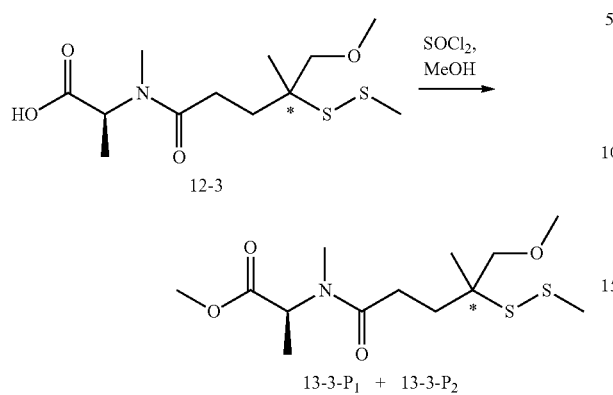

The product 12-3 (360 mg, 1.165 mmol) obtained in the previous step was dissolved in 10 mL methanol, 0.5 mL thionyl chloride was added dropwise slowly. The reaction mixture was stirred at room temperature for 2 hours, concentrated under reduced pressure. 50 mL EtOAc was added, 20 mL saturated sodium bicarbonate solution was added slowly, the organic phase was separated, dried over anhydrous sodium sulfate, and concentrated. The crude product was purified by chiral prep-HPLC (AD-H, 4.6×250 mm, CO$_2$+MeOH=2.55+0.45, P$_1$: Rt=2.19; P$_2$: Rt=2.77) to give 119 mg product 13-3-P$_1$ and 130 mg product 13-3-P$_2$. LCMS (ESI) m/z 324.1 (M+H)$^+$.

Synthesis of Compound 14-3-P$_2$

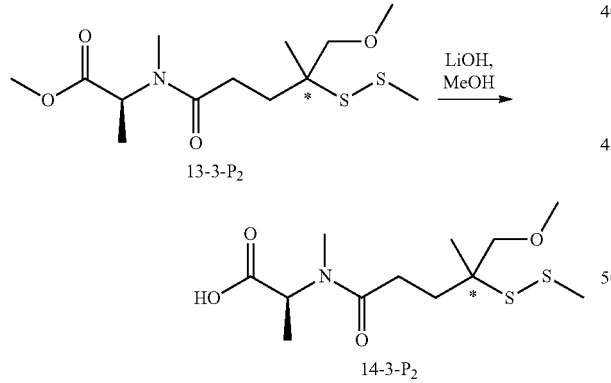

The product 13-3-P$_2$ (119 mg, 0.0368 mmoL) obtained in the previous step was dissolved in a mixed solution of 5 mL methanol and 5 mL water, LiOH (50 mg, 2.08 mmol) was added. The reaction mixture was stirred at room temperature for 1.5 hours. The reaction mixture was acidified with 1 M dilute hydrochloric acid to pH=3, then extracted with EtOAc for 3 times (50 mL×3), the organic phases were combined, washed with saturated brine (30 mL), dried over anhydrous sodium sulfate, and concentrated to give 106 mg product 14-3-P$_2$ as colorless oil, yield 94%. LCMS (ESI) m/z 310.0 (M+H)$^+$.

Synthesis of Compound 14-3-P$_1$

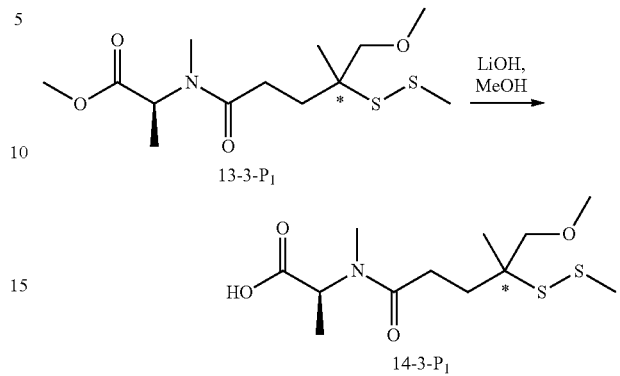

The synthetic procedure of 14-3-P$_1$ was the same as that of 14-3-P$_2$, with employing 13-3-P$_1$ as starting material.

Synthesis of Compound CE-012, 013

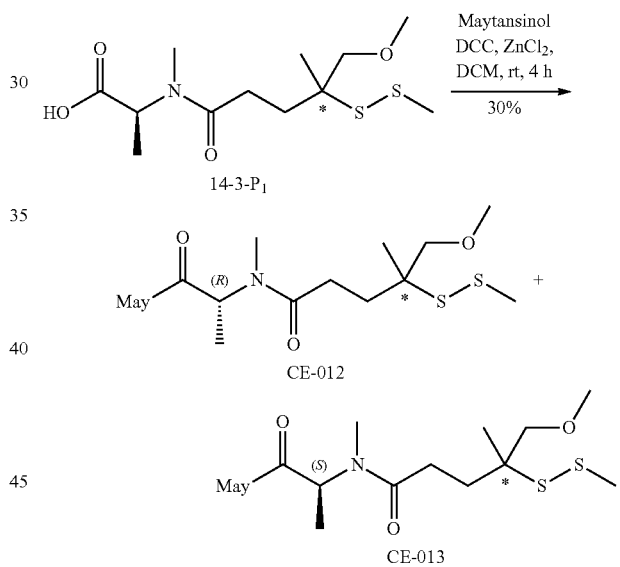

The product 14-3-P$_1$ (106 mg, 0.343 mmol) obtained in the previous step and DCC (290 mg, 1.40 mmol) were added to a dried Schlenk tube, the mixture was purged by argon for 3 times, 2 mL DCM was added and stirred. Maytansinol (96.5 mg, 0.171 mmol) in 8 mL dried DCM was added, followed by adding zinc chloride/ether solution (1 M, 1 mL, 1 mmol). The reaction mixture was stirred at room temperature for 2 hours, 1 mL saturated sodium bicarbonate solution was slowly added to quench the reaction. After 30 mL ethyl acetate was added, the mixture was filtrated and then rinsed with ethyl acetate. The filtrate was dried over anhydrous sodium sulfate, and concentrated. The crude product was purified by silica gel column chromatography (DCM/MeOH=50:1-40:1) to give two isomers CE-012 (45 mg, P$_1$) and CE-013 (40 mg, P$_2$) as white solid, yield 31%+28%. LCMS (ESI) m/z 838.8 (M+H)$^+$.

HPLC (15 min): CE-012, Rt=8.063; CE-013, Rt=8.142

Mobile Phase: A: Water (0.01% TFA) B: CAN (0.01% TFA)
Gradient: 0 min 5% B, 7 min 95% B, 15 min 95% B
Flow Rate: 1.0 mL/min
Column: Xbridge C18, 4.6*150 mm, 3.5 um
Oven Temperature: 40° C.

CE-012: $^1$H NMR (400 MHz, CDCl$_3$) δ ppm 6.85 (s, 1H), 6.79 (s, 1H), 6.44 & 6.41 (dd, J$_1$=15.2 Hz, J$_2$=10.8 Hz, 1H), 6.26 (d, J=10.8 Hz, 1H), 6.25 (s, 1H), 5.86 & 5.83 (dd, J$_1$=15.2 Hz, J$_2$=9.2 Hz, 1H), 5.17 (q, J=7.2 Hz, 1H), 5.00 (s, 1H), 4.94 & 4.91 (dd, J$_1$=12.0 Hz, J$_2$=3.2 Hz, 1H), 4.33 (t, J=10.4 Hz, 1H), 3.99 (s, 3H), 3.52 (d, J=13.2 Hz, 1H), 3.43 (d, J=8.8 Hz, 1H), 3.38 (s, 3H), 3.35 (s, 3H), 3.20 (d, J=12.8 Hz, 1H), 3.17 (s, 3H), 3.04 (s, 3H), 2.82 (d, J=9.2 Hz, 1H), 2.66 & 2.63 (dd, J$_1$=14.8 Hz, J$_2$=12.0 Hz, 1H), 2.51-2.46 (m, 2H), 2.41 (s, 3H), 2.24-2.18 (m, 1H), 2.04-1.88 (m, 2H), 1.76 (d, J=13.6 Hz, 1H), 1.69 (s, 3H), 1.55 (s, 2H), 1.49 (d, J=7.2 Hz, 3H), 1.30-1.35 (m, 1H), 1.30 (s, 3H), 1.28 (s, 3H), 0.86 (s, 3H).

CE-013: $^1$H NMR (400 MHz, CDCl$_3$) δ ppm 6.82 (s, 1H), 6.74 (d, J=10.8 Hz, 1H), 6.63 (s, 1H), 6.44 & 6.41 (dd, J$_1$=15.2 Hz, J$_2$=10.8 Hz, 1H), 6.21 (s, 1H), 5.70 & 5.66 (dd, J$_1$=15.2 Hz, J$_2$=9.2 Hz, 1H), 5.40 (q, J=7.2 Hz, 1H), 4.79 & 4.78 (dd, J$_1$=12.0 Hz, J$_2$=3.2 Hz, 1H), 4.28 (t, J=12.0 Hz, 1H), 3.98 (s, 3H), 3.65 (d, J=12.4 Hz, 1H), 3.50 (d, J=8.8 Hz, 1H), 3.35 (s, 3H), 3.29 (d, J=2.8 Hz, 2H), 3.26 (s, 3H), 3.23 (s, 3H), 3.11 (d, J=12.8 Hz, 1H), 3.03 (d, J=10.0 Hz, 1H), 2.85 (s, 3H), 2.62 & 2.59 (dd, J$_1$=14.8 Hz, J$_2$=12.0 Hz, 1H), 2.52-2.38 (m, 2H), 2.30 (s, 3H), 2.19 & 2.16 (dd, J$_1$=14.4 Hz, J$_2$=3.5 Hz, 1H), 2.06-1.88 (m, 2H), 1.64 (s, 3H), 1.55 (s, 2H), 1.50-1.42 (m, 1H), 1.20-1.30 (n, 1H), 1.30 (d, J=2.8 Hz, 3H), 1.28 (d, J=2.8 Hz, 3H), 1.22 (s, 3H), 0.80 (s, 3H).

Synthesis of Compound CE-014, 015

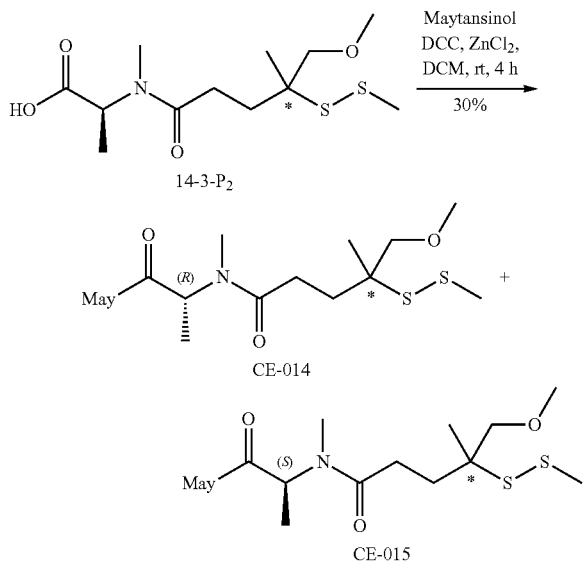

The synthetic procedures of CE-014, CE-015 were the same as those of CE-012, CE-013, with employing 14-P$_2$ as starting material.

CE-014: $^1$H NMR (400 MHz, CDCl$_3$) δ ppm 6.85 (s, 1H), 6.81 (s, 1H), 6.43 & 6.40 (dd, J$_1$=15.2 Hz, J$_2$=11.2 Hz, 1H), 6.28 (d, J=10.8 Hz, 1H), 6.24 (s, 1H), 5.88 & 5.85 (dd, J$_1$=15.2 Hz, J$_2$=9.6 Hz, 1H), 5.19 (q, J=7.6 Hz, 1H), 4.99 (s, 1H), 4.91 & 4.88 (dd, J$_1$=12.0 Hz, J$_2$=3.2 Hz, 1H), 4.32 (t, J=10.4 Hz, 1H), 4.00 (s, 3H), 3.52 (d, J=13.2 Hz, 1H), 3.43 (d, J=9.2 Hz, 1H), 3.39 (s, 3H), 3.38 (s, 3H), 3.35 (s, 3H), 3.20 (d, J=12.8 Hz, 1H), 3.17 (s, 3H), 3.04 (s, 3H), 2.84 (d, J=9.2 Hz, 1H), 2.66 & 2.63 (dd, J$_1$=14.8 Hz, J$_2$=12.0 Hz, 1H), 2.57-2.45 (m, 2H), 2.41 (s, 3H), 2.24-2.18 (m, 1H), 2.04-1.88 (m, 2H), 1.74 (d, J=13.6 Hz, 1H), 1.69 (s, 3H), 1.49 (d, J=7.2 Hz, 3H), 1.38-1.30 (m, 1H), 1.30 (s, 3H), 1.28 (s, 3H), 0.86 (s, 3H).

CE-015: $^1$H NMR (400 MHz, CDCl$_3$) δ ppm 6.82 (s, 1H), 6.74 (d, J=10.8 Hz, 1H), 6.64 (s, 1H), 6.44 & 6.41 (dd, J$_1$=15.2 Hz, J$_2$=10.8 Hz, 1H), 6.23 (s, 1H), 5.71 & 5.67 (dd, J$_1$=15.2 Hz, J$_2$=9.2 Hz, 1H), 5.41 (q, J=7.2 Hz, 1H), 4.80 & 4.77 (dd, J$_1$=12.0 Hz, J$_2$=3.2 Hz, 1H), 4.28 (t, J=12.0 Hz, 1H), 3.98 (s, 3H), 3.65 (d, J=12.4 Hz, 1H), 3.50 (d, J=8.8 Hz, 1H), 3.35 (s, 3H), 3.30 (d, J=2.8 Hz, 2H), 3.26 (s, 3H), 3.22 (s, 3H), 3.11 (d, J=12.8 Hz, 1H), 3.03 (d, J=10.0 Hz, 1H), 2.85 (s, 3H), 2.64-2.50 (m, 2H), 2.36-2.28 (m, 1H), 2.33 (s, 3H), 2.19 & 2.16 (dd, J$_1$=14.4 Hz, J$_2$=3.5 Hz, 1H), 2.06-1.88 (m, 2H), 1.64 (s, 3H), 1.55 (s, 2H), 1.50-1.42 (m, 1H), 1.35-1.25 (m, 1H), 1.30 (d, J=2.8 Hz, 3H), 1.28 (d, J=2.8 Hz, 3H), 1.19 (s, 3H), 0.80 (s, 3H).

Synthesis of Compound CE-032

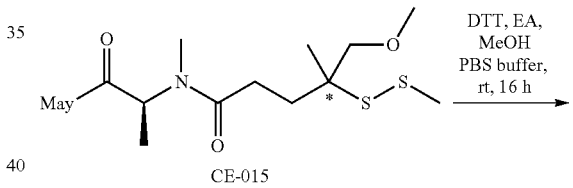

CE-015 (40 mg, 0.047 mmol) was dissolved in 0.6 mL EtOAc, dithiothreitol (DTT) (18 mg, 0.12 mmol) in 1.2 mL methanol was added, 2.7 mL pH=7.5 potassium phosphate buffer was added. The reaction mixture was stirred under nitrogen atmosphere for 2 hours. 10.2 mL pH=6.0 potassium phosphate buffer was added to quench the reaction. The reaction mixture was extracted with EtOAc for 3 times (20 mL×3), the organic phases were combined, washed with saturated brine for 3 times (20 mL×3), dried over anhydrous sodium sulfate, and concentrated. The crude product was purified by prep-HPLC (CH$_3$CN in H$_2$O-0.05% TFA from 5% to 95%) to give 22 mg product CE-032 as white solid, yield 80%. LCMS (ESI) m/z 808.2 (M+H)$^+$.

Synthesis of Compound CE-004

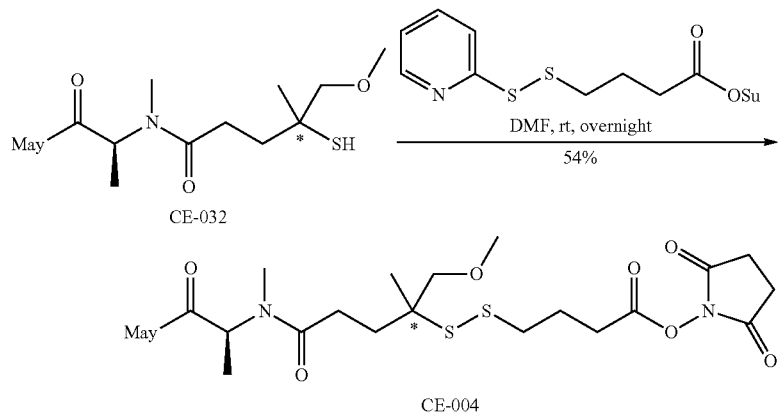

CE-032 (30 mg, 0.037 mmol) was dissolved in 4 mL DMF, SM1 (24 mg, 0.074 mmol) was added. The reaction mixture was stirred at room temperature overnight, ane then filtered, the filtrate was directly purified by prep-HPLC (CH$_3$CN in H$_2$O-0.05% TFA from 5% to 95%) to give 20.4 mg product CE-004 as white solid, yield 54%. LCMS (ESI) m/z 1024.2 (M+H)$^+$.

$^1$H NMR (400 MHz, CDCl$_3$) δ ppm 6.84 (s, 1H), 6.73 (d, J=11.2 Hz, 1H), 6.63 (s, 1H), 6.44 & 6.42 (dd, J$_1$=15.2 Hz, J$_2$=11.2 Hz, 1H), 6.29 (s, 1H), 5.70 & 5.68 (dd, J$_1$=15.2 Hz, J$_2$=9.2 Hz, 1H), 5.41 (q, J=6.8 Hz, 1H), 4.78 & 4.78 (dd, J$_1$=11.6 Hz, J$_2$=2.8 Hz, 1H), 4.28 (q, J=10.4 Hz, 1H), 3.98 (s, 3H), 3.65 (d, J=13.2 Hz, 1H), 3.50 (d, J=8.8 Hz, 1H), 3.36 (s, 3H), 3.28 (d, J=3.2 Hz, 2H), 3.25 (s, 3H), 3.22 (s, 3H), 3.12 (d, J=8.4 Hz, 1H), 3.03 (d, J=10.0 Hz, 1H), 2.84 (s, 6H), 2.70 (q, J=7.6 Hz, 4H), 2.64-2.49 (m, 2H), 2.36-2.28 (m, 1H), 2.18 & 2.17 (dd, J$_1$=14.4 Hz, J$_2$=2.8 Hz, 1H), 2.10-1.98 (m, 4H), 1.94-1.86 (m, 1H), 1.64 (s, 3H), 1.58 (d, J=13.2 Hz, 1H), 1.50-1.42 (m, 1H), 1.30 (s, 3H), 1.28 (s, 3H), 1.30-1.24 (m, 1H), 1.19 (s, 3H), 0.80 (s, 3H).

Embodiment 4 the Synthetic Routes for CE-018 and CE-019

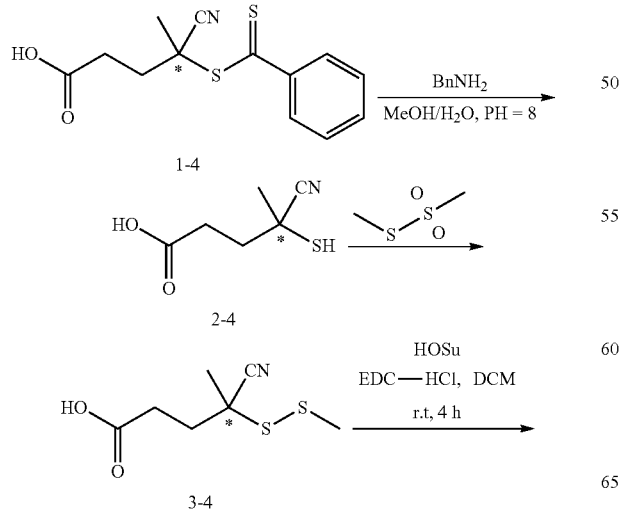

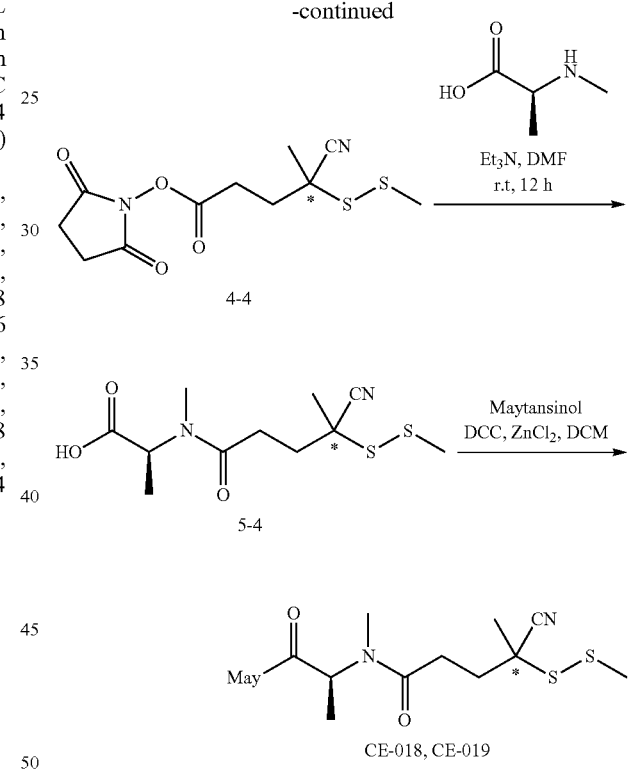

Experimental Procedure

Synthesis of Compound 3-4

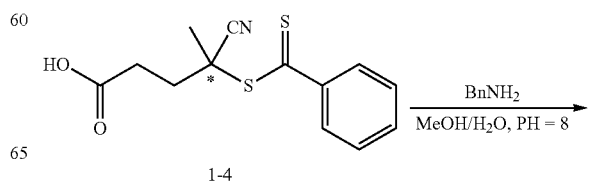

95

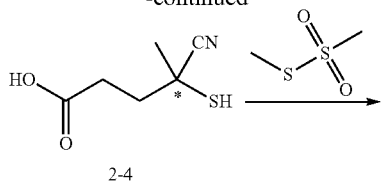

Compound 1-4 (2.0 g, 7.2 mmol) was dissolved in a mixed solution of 80 mL water and 20 mL methanol, pH was adjusted to 8, and benzylamine (1.53 g, 14 mmol) was added. The reaction mixture was stirred at room temperature for 1 hour under nitrogen atmosphere. Methyl methanethiosulfonate (1.18 g, 9.4 mmol) was added, the reaction mixture was stirred overnight at room temperature under nitrogen atmosphere. Methanol was removed by distillation under reduced pressure, then the mixture was extracted with DCM (80 mL), the aqueous phase was separated, to which 2 N dilute hydrochloric acid was added to adjust pH=2, the mixture was extracted with EtOAc for 3 times (50 mL×3), the organic phases were combined, washed with water (50 mL) and saturated brine (50 mL), dried over anhydrous sodium sulfate, concentrated to give 1.1 g crude product as yellow oil, which was used directly for the next step.

LCMS (ESI) m/z 206 (M+H)$^+$. $^1$H NMR (400 MHz, CD$_3$OD) δ ppm 2.51 (s, 3H), 2.46-2.42 (m, 2H), 2.19-2.05 (m, 2H), 1.56 (s, 3H).

Synthesis of Compound 4-4

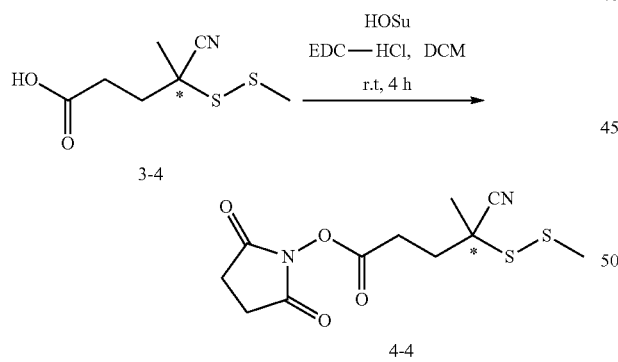

The product 3-4 (1.8 g, 8.78 mmol) obtained in the previous step and HOSu (1.51 g, 13 mmoL) were dissolved in 20 mL DCM, 1-(3-dimethylaminopropyl)-3-ethyl carbodiimide hydrochloride (EDC) (2.51 g, 13 mmol) was added. The reaction mixture was stirred at room temperature for 2 hours, then 50 mL water was added, the mixture was extracted with EtOAc for 3 times (50 mL×3). The organic phases were combined, washed with saturated brine for 3 times (50 mL×3), dried over anhydrous sodium sulfate, and concentrated to give 2.2 g product as yellow oil, which was used directly for the next step. LCMS (ESI) m/z 303.1 (M+H)$^+$.

96

Synthesis of Compound 5-4

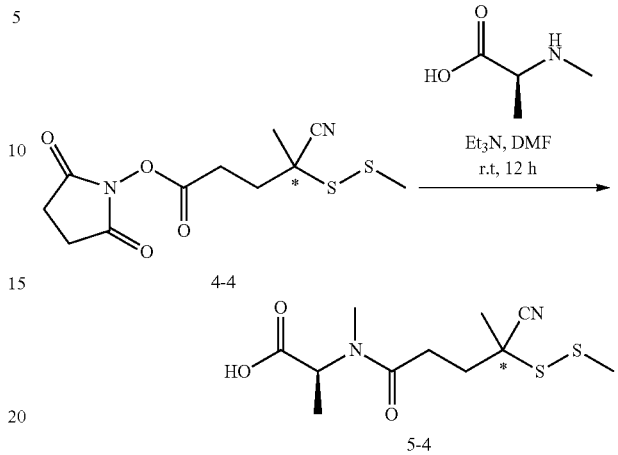

N-methyl-L-alanine (900 mg, 8.74 mmol) was dissolved in 20 mL DMF. Et$_3$N (0.5 mL, 3.5 mmol) was added, the mixture was stirred vigorously. The product 4-4 (2.2 g, 7.28 mmol) obtained in the previous step in 5 mL DMF was added dropwise over about 5 min. The reaction mixture was stirred at room temperature overnight. The reaction mixture was adjusted to pH=3 with 1 M dilute hydrochloric acid, then extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc/AcOH=50:50:0.5) to give 1.2 g product as yellow oil, yield 57%.

LCMS (ESI) m/z 291.1 (M+H)$^+$. $^1$H NMR (400 MHz, CD$_3$OD) δ ppm 5.03 (q, J=7.2 Hz, 1H), 3.05 (s, 3H), 2.72-2.68 (m, 2H), 2.63 (s, 3H), 2.36-2.15 (m, 2H), 1.71 (s, 3H), 1.43 (d, J=7.2 Hz, 3H).

Synthesis of Compound 6-4

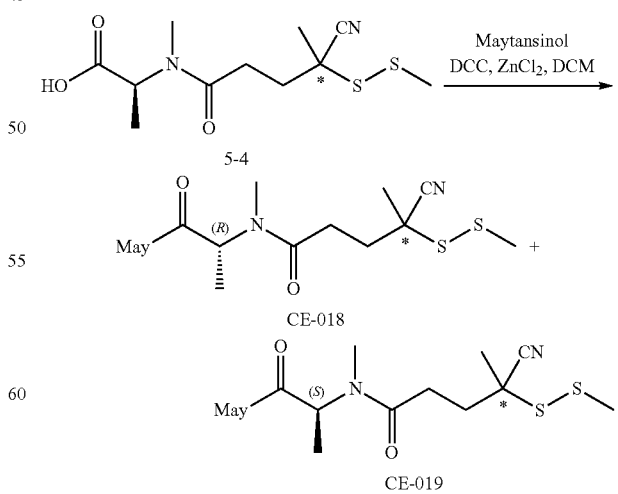

The product 5-4 (130 mg, 0.45 mmol) obtained in the previous step and DCC (130 mg, 0.45 mmol) were added to a dried Schlenk tube, the mixture was purged by argon for 3 times, 1 mL DCM was added and stirred. Maytansinol (84.0 mg, 0.15 mmol) in 5 mL dried DCM was added, followed by adding zinc chloride/ether solution (1 M, 1 mL, 1 mmol). The reaction mixture was stirred at room temperature for 2 hours, 5 mL saturated sodium bicarbonate solution was slowly added to quench the reaction. After 30 mL ethyl acetate was added, the organic phase was separated, dried over anhydrous sodium sulfate, and concentrated. The crude product was purified by preparative silica gel plate (DCM/MeOH=20:1) to give two isomers CE-018 (15 mg, $P_1$) and CE-019 (15 mg, $P_2$) as white solid, yield 120/+12%. LCMS (ESI) m/z 837.2 (M+H)$^+$.

HPLC (15 min): CE-018, Rt=7.812; CE-019, Rt=7.656

Mobile Phase: A: Water (0.010% TFA) B: CAN (0.01% TFA)

Gradient: 0 min 5% B, 7 min 95% B, 15 min 95% B

Flow Rate: 1.0 mL/min

Column: Xbridge C18, 4.6*150 mm, 3.5 um

Oven Temperature: 40° C.

CE-018: $^1$H NMR (400 MHz, CDCl$_3$) δ ppm 6.85 (s, 1H), 6.79 (s, 1H), 6.45 & 6.43 (dd, $J_1$=15.2 Hz, $J_2$=10.8 Hz, 1H), 6.37 (s, 1H), 6.24 (d, J=10.8 Hz, 1H), 5.83 & 5.81 (dd, $J_1$=15.2 Hz, $J_2$=9.2 Hz, 1H), 5.23-5.18 (m, 1H), 4.95 (d, J=10.0 Hz, 1H), 4.29 (t, J=10.4 Hz, 1H), 3.99 (s, 3H), 3.52 (d, J=12.8 Hz, 1H), 3.45 (d, J=9.2 Hz, 1H), 3.35 (s, 3H), 3.20 (d, J=12.8 Hz, 1H), 3.18 (s, 3H), 3.05 (d, J=5.6 Hz, 3H), 2.81 (d, J=10.0 Hz, 1H), 2.69-2.58 (m, 2H), 2.63 (s, 3H), 2.36-2.15 (m, 2H), 2.09-2.02 (m, 2H), 1.74 (d, J=14.4 Hz, 3H), 1.76-1.69 (m, 1H), 1.69 (s, 3H), 1.52 (d, J=7.2 Hz, 3H), 1.49-1.40 (m, 1H), 1.35-1.30 (m, 1H), 1.28 (d, J=6.4 Hz, 3H), 0.86 (s, 3H).

CE-019: $^1$H NMR (400 MHz, CDCl$_3$) δ ppm 6.83 (s, 1H), 6.72 & 6.69 (dd, $J_1$=15.6 Hz, $J_2$=2.8 Hz, 1H), 6.61 (s, 1H), 6.45 & 6.42 (dd, $J_1$=15.6 Hz, $J_2$=10.8 Hz, 1H), 6.27 (s, 1H), 5.69-5.62 (m, 1H), 5.45-5.36 (m, 1H), 4.78 (d, J=10.8 Hz, 1H), 4.28 (t, J=10.8 Hz, 1H), 3.99 (s, 3H), 3.63 & 3.61 (dd, $J_1$=12.4 Hz, $J_2$=9.2 Hz, 1H), 3.51 (d, J=9.2 Hz, 1H), 3.36 (s, 3H), 3.23 (d, J=9.2 Hz, 3H), 3.15 (t, J=11.6 Hz, 3H), 3.03 (d, J=5.6 Hz, 3H), 2.88 (s, 3H), 2.69-2.58 (m, 2H), 2.55 (d, J=22.0 Hz, 3H), 2.40-2.05 (m, 2H), 1.76-1.69 (m, 1H), 1.64 (s, 3H), 1.58 (d, J=8.0 Hz, 1H), 1.60-1.40 (m, 1H), 1.32-1.28 (m, 7H), 0.80 (s, 3H).

Embodiment 5 Synthetic Routes for CE-021 and CE-022

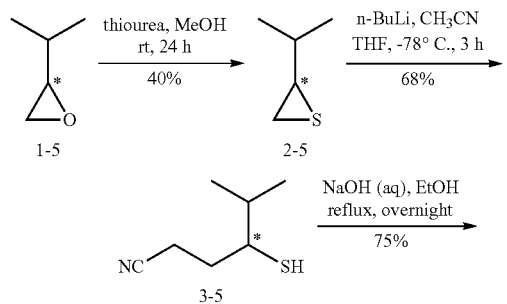

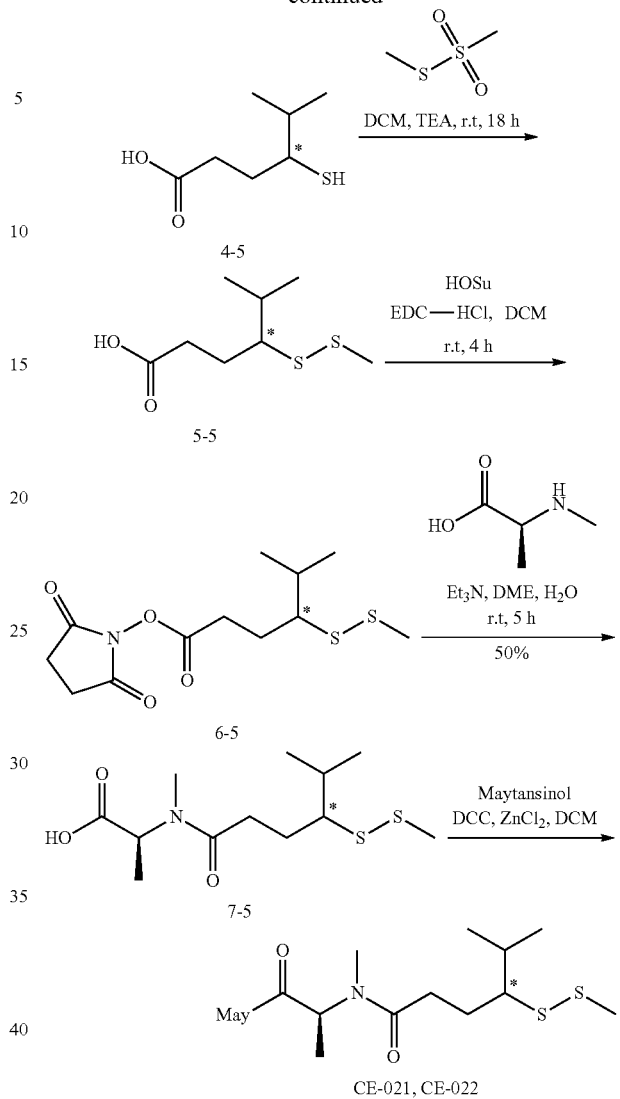

Experimental Procedure

Synthesis of Compound 2-5

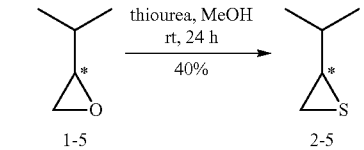

The starting material 1-5 (10 g, 116 mmol) was dissolved in 50 mL absolute methanol, and thiourea (18 g, 232 mmol) was added. The reaction mixture was heated to 50° C. and stirred for 24 hours, TLC showed that the starting material was completely consumed. The reaction mixture was cooled to room temperature, 100 mL water was added, and the resultant mixture was extracted with petrol ether (boiling point 30-60° C.) for 3 times (50 mL×3). The organic phases were combined, washed with saturated brine for 3 times (50 mL×3), dried over anhydrous sodium sulfate, and concentrated, the crude product was purified by silica gel column chromatography (boiling point 30-60° C. PE) to give 4.7 g product 2-5 as colorless oil, yield 40%. $^1$H NMR (400 MHz, CDCl$_3$) δ ppm 2.71 (m, J=10.0 Hz, 1H), 2.47 (d, J=6.4 Hz, 1H), 2.18 (d, J=6.0 Hz, 1H), 1.38-1.24 (m, 1H), 1.09 (t, J=10.0 Hz, 6H).

Synthesis of Compound 3-5

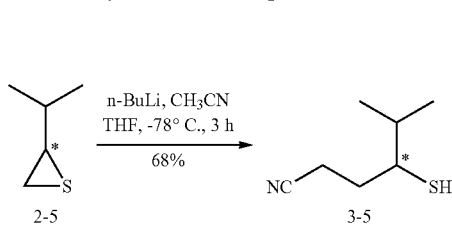

Under nitrogen atmosphere, n-BuLi (2.5 M, 17.6 mL, 43.2 mmol) was added to 150 mL anhydrous THF at −78° C. CH$_3$CN (1.8 g, 44.8 mmol) in 10 mL anhydrous THF was added. The reaction mixture was stirred at −78° C. for half an hour. Compound 2-5 (4 g, 39.2 mmol) was dissolved in 20 mL THF, which was then added to the reaction mixture dropwise. After the addition, the reaction mixture was gradually warmed to room temperature and stirred for 3 hours. The mixture was cooled to 0° C., dilute hydrochloric acid (0.5 M, 20 mL) was added dropwise to quench the reaction, and the resultant mixture was extracted with ethyl acetate for 3 times (100 mL×3). The organic phases were combined, washed with saturated brine for 3 times (100 mL×3), dried over anhydrous sodium sulfate, and concentrated to give 3.8 g crude product as light yellow oil, which was used directly for the next step, yield 68%. LCMS (ESI) m/z 144.1 (M+H)$^+$.

Synthesis of Compound 4-5

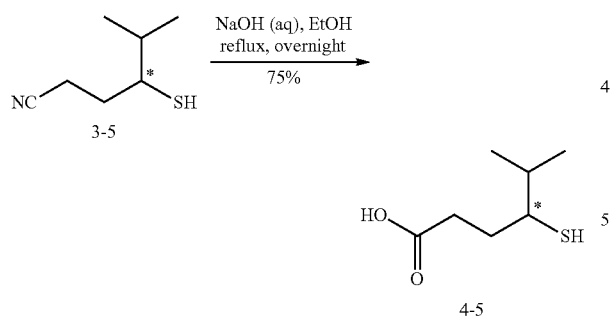

The product 3-5 (2.86 g, 20 mmol) obtained in the previous step was dissolved in 20 mL ethanol, the mixture was purged by argon for 3 times, sodium hydroxide solution (8 M, 10 mL, 80 mmol) was slowly added. The reaction mixture was heated to reflux under argon atmosphere and stirred overnight. The reaction mixture was cooled to room temperature, adjusted to pH=2 with dilute hydrochloric acid, and then extracted with DCM for 3 times (50 mL×3). The organic phases were combined, dried over anhydrous sodium sulfate, and concentrated. The crude product was purified by silica gel column chromatography (petrol ether/EtOAc=2:1) to give 2.4 g product 4-5 as light yellow oil, yield 75%. LCMS (ESI) m/z163.1 (M+H)$^+$. $^1$H NMR (400 MHz, d$^6$-DMSO) δ ppm 12.07 (br, 1H), 3.35 (br, 1H), 2.73-2.66 (m, 1H), 2.49-2.28 (m, 2H), 2.04-2.00 (m, 1H), 1.93-1.77 (m, 1H), 1.60-1.50 (m, 1H), 0.92 (d, J=6.8 Hz, 3H), 0.86 (d, J=6.8 Hz, 3H).

Synthesis of Compound 5-5

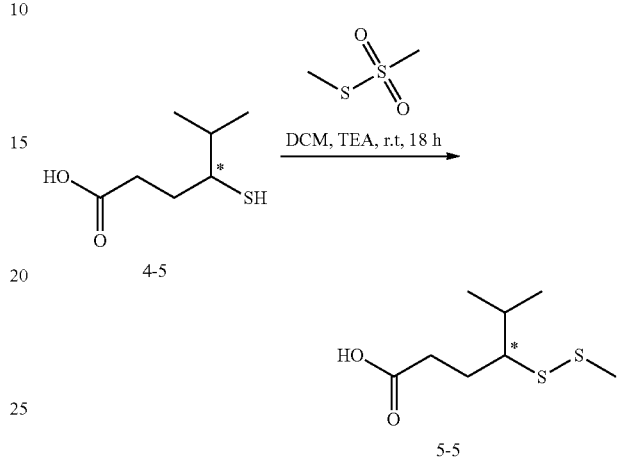

The product 4-5 (810 mg, 5 mmol) obtained in the previous step was dissolved in 15 mL DCM under argon atmosphere, methyl methanethiosulfonate (0.65 mL, 18 mmoL) and Et$_3$N (0.8 mL) were added. The reaction mixture was stirred overnight at room temperature under argon atmosphere. 40 mL 1 M dilute hydrochloric acid was added, the mixture was extracted with EtOAc for 3 times (50 mL×3), the organic phases were combined, washed with saturated brine (50 mL), dried over anhydrous sodium sulfate, and concentrated to give 780 mg crude product 5-5, which was used directly for the next step. LCMS (ESI) m/z 209.1 (M+H)$^+$.

Synthesis of Compound 6-5

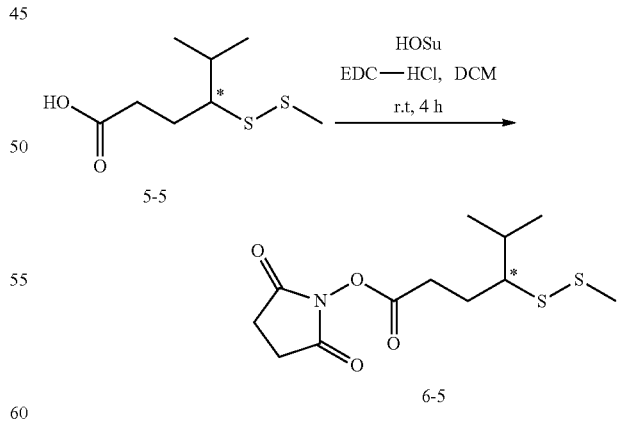

The product 5-5 (730 mg, 3.5 mmol) obtained in the previous step and HOSu (445 mg, 3.85 mmoL) were dissolved in 20 mL DCM, EDC (800 mg, 4.2 mmol) was added. The reaction mixture was stirred at room temperature for 2 hours. 30 mL water and 50 mL EtOAc were added, and then the organic phase was separated, washed with saturated brine for 3 times (50 mL×3), dried over anhydrous sodium sulfate, concentrated to give 578 mg crude product 6-5 as yellow oil, which was used directly for the next step. LCMS (ESI) m/z 306.1 (M+H)⁺.

Synthesis of Compound 7-5

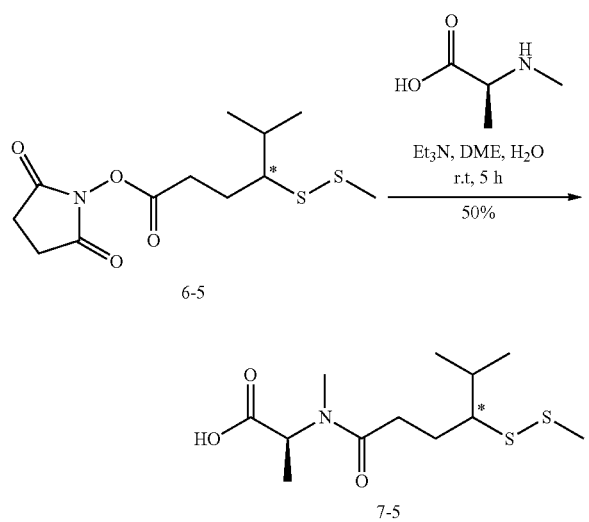

N-methyl-L-alanine (190 mg, 1.8 mmol) was dissolved in 10 mL 1,2-dimethoxyethane and 10 mL water. Et₃N (0.5 mL, 3.6 mmol) was added and the mixture was stirred vigorously. The product 6-5 (550 mg, 1.8 mmol) obtained in the previous step was dissolved in 5 mL 1,2-dimethoxyethane, which was added to the reaction mixture dropwise over about 5 min. The reaction mixture was stirred at room temperature for 3 hours, the organic solvent was removed under reduced pressure. 10 mL water was added, then the mixture was adjusted to pH=3 with 1 M dilute hydrochloric acid, extracted with ethyl acetate for 3 times (50 mL×3). The organic phases were combined, washed with saturated brine for 3 times (50 mL×3), dried over anhydrous sodium sulfate, and concentrated. The crude product was purified by silica gel column chromatography (petrol ether/EtOAc/AcOH=50:50:0.5) to give 260 mg product as yellow oil, yield 50%. LCMS (ESI) m/z 293.1 (M+H)⁺. 02071 Synthesis of compound CE-021 and CE-022

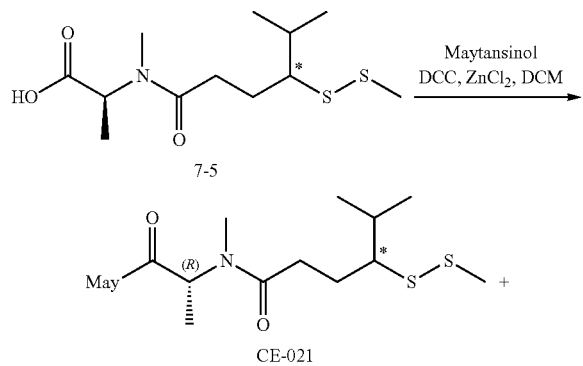

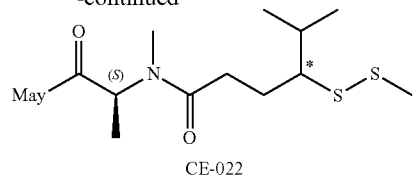

The product 7-5 (40 mg, 0.138 mmol) obtained in the previous step and DCC (76 mg, 0.368 mmol) were added into a dried Schlenk tube, the mixture was purged by argon for 3 times, 1 mL DCM was added and stirred. Maytansinol (26 mg, 0.046 mmol) in 4 mL dried DCM was added, followed by adding zinc chloride/ether solution (1 M, 0.3 mL, 0.3 mmol). The reaction mixture was stirred at room temperature for 2 hours, 0.5 mL was slowly added to quench the reaction. After 20 mL ethyl acetate was added, the mixture was filtered, washed with EtOAc. The filtrate was dried over anhydrous sodium sulfate, and concentrated. The crude product was purified by silica gel column chromatography (DCM/MeOH=50:1-40:1) to give two isomers CE-021 (6 mg, P₁) and CE-022 (12 mg, P₂) as white solid, yield 18.50/%+36.7%. LCMS (ESI) m/z 840.9 (M+H)⁺.

HPLC (15 min): CE-021, Rt=11.197; CE-022, Rt=11.292&11.345

Mobile Phase: A: water (0.01% TFA) B: CAN (0.01% TFA)

Gradient: 0 min 5% B, 3 min 5% B, 10 min 95% B, 15 min 95% B

Flow Rate: 1.2 mL/min

Column: Eclipse XDB-C18, 4.6×150 mm, 5 um

Oven Temperature: 40° C.

CE-021: ¹H NMR (400 MHz, CDCl₃) δ ppm 6.85 (s, 1H), 6.79 (s, 1H), 6.44 (t, J=12.8 Hz, 1H), 6.29 (d, J=6.8 Hz, 1H), 6.24 (t, d, J=6.8 Hz, 1H), 5.88-5.80 (m, 1H), 5.18-5.08 (m, 1H), 4.98-4.90 (m, 1H), 4.32 (t, J=10.4 Hz, 1H), 3.99 (s, 3H), 3.51 (d, J=12.8 Hz, 1H), 3.44 (d, J=8.8 Hz, 1H), 3.34 (s, 3H), 3.20 (d, J=12.8 Hz, 1H), 3.17 (s, 3H), 3.05 (d, J=5.6 Hz, 3H), 2.82 (t, J=10.0 Hz, 1H), 2.69-2.57 (m, 4H), 2.41 (s, 3H), 2.23-2.20 (m, 1H), 2.09-2.02 (m, 2H), 1.76-1.69 (m, 1H), 1.69 (s, 3H), 1.50 (d, J=7.2 Hz, 3H), 1.49-1.40 (m, 1H), 1.30 (s, 3H), 1.28 (s, 3H), 1.03 (d, J=6.0 Hz, 6H), 0.86 (s, 3H).

CE-022: ¹H NMR (400 MHz, CDCl₃) δ ppm 6.82 (s, 1H), 6.76 & 6.75 (dd, J₁=11.2 Hz, J₂=6.4 Hz, 1H), 6.64 (d, J=4.0 Hz, 1H), 6.44 & 6.41 (dd, J₁=14.8 Hz, J₂=11.2 Hz, 1H), 6.22 (s, 1H), 5.72-5.63 (m, 1H), 5.43-5.37 (m, 1H), 4.81-4.76 (m, 1H), 4.28 (t, J=11.2 Hz, 1H), 3.99 (s, 3H), 3.67 & 3.65 (dd, J₁=12.4 Hz, J₂=8.0 Hz, 1H), 3.50 (d, J=10.4 Hz, 1H), 3.35 (s, 3H), 3.30 (d, J=7.2 Hz, 1H), 3.23 (s, 3H), 3.11 (d, J=13.2 Hz, 1H), 3.04 (d, J=10.0 Hz, 1H), 2.85 (s, 3H), 2.70-2.33 (m, 4H), 2.30 (d, J=6.4 Hz, 3H), 2.23-2.16 (m, 1H), 2.04-1.89 (m, 2H), 1.71-1.65 (m, 1H), 1.64 (s, 3H), 1.60-1.55 (m, 2H), 1.51-1.43 (m, 1H), 1.30 (d, J=6.8 Hz, 3H), 1.27 (s, 3H), 0.99-0.88 (m, 6H), 0.80 (s, 3H).

Compound CE-002 can be prepared according to the process for preparing compound CE-005 in embodiment 1, with replacing the intermediate CE-017 with CE-022 in the following reaction.

Embodiment 6 Synthetic Route for CE-033
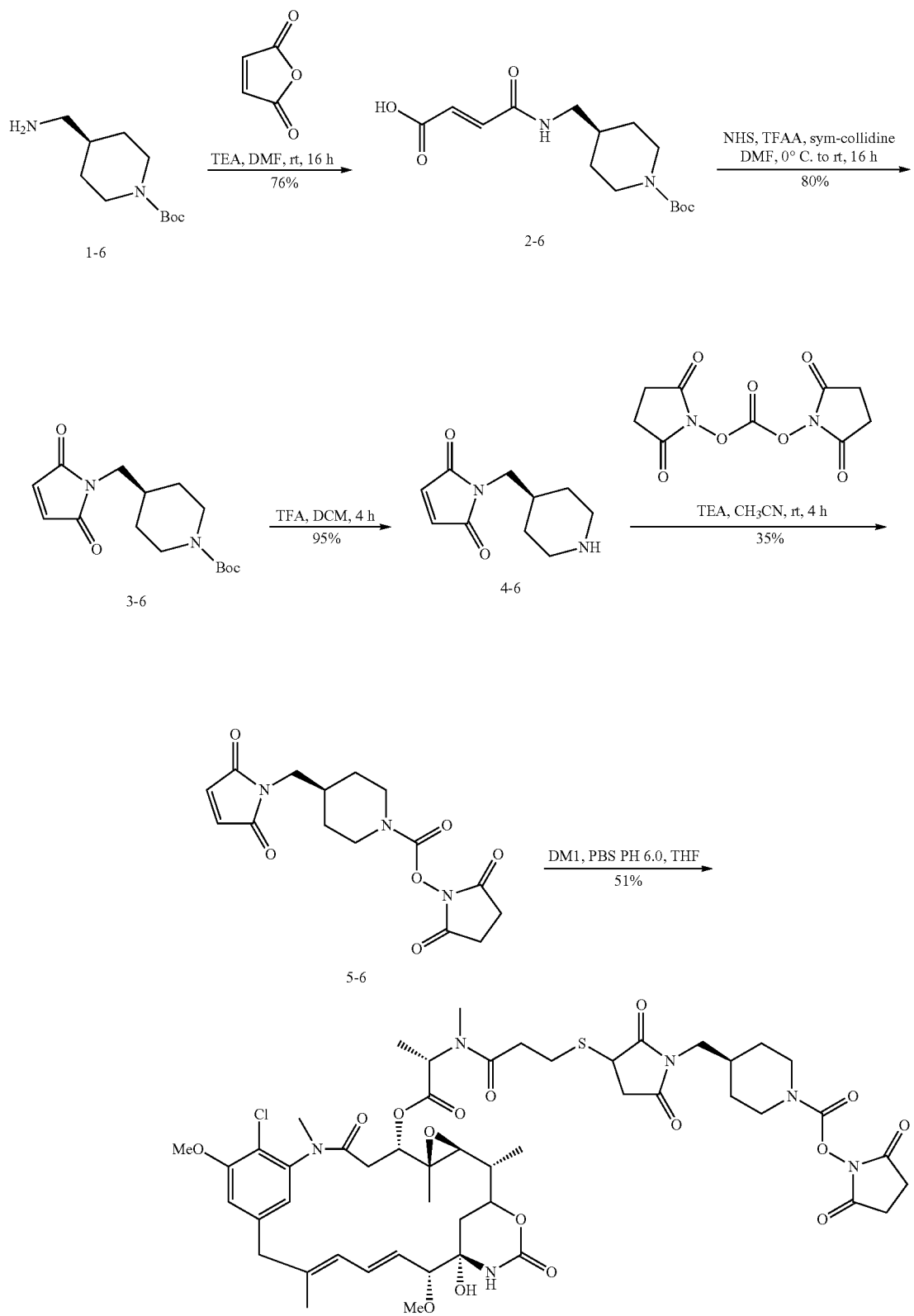
CE-033

Experimental Procedure

Synthesis of Compound 2-6

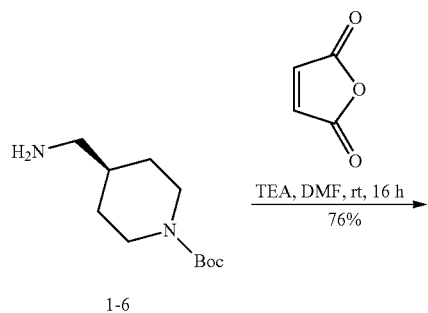

Compound 1-6 (2.0 g, 9.4 mmol) was dissolved in 20 mL DMF, Et₃N (1.9 g, 18.8 mmol) and maleic anhydride (1.8 g, 18.8 mmol) were added. The reaction mixture was stirred at room temperature overnight. 50 mL water was added to the reaction mixture, the resultant mixture was extracted with EtOAc for 3 times (50 mL×3), and the organic phases were combined, washed with saturated brine for 3 times (50 mL×3), dried over anhydrous sodium sulfate, and concentrated. The crude product was purified by prep-HPLC (CH₃CN in H₂O-0.05% TFA from 5% to 95%) to give 1 g product 2-6 as yellow oil, yield 76%. LCMS (ESI) m/z 312.2 (M+H)⁺.

Synthesis of Compound 3-6

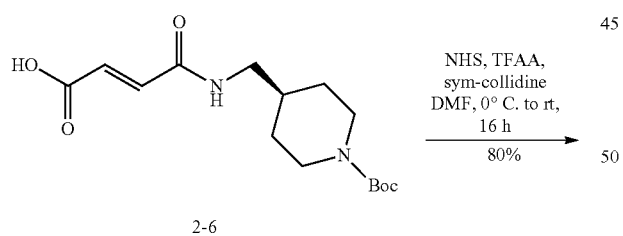

N-Hydroxysuccinimide (1.5 g, 12.8 mmol) was dissolved in 15 mL DMF, cooled to 0° C., trifluoroacetic anhydride (1.8 mL, 12.8 mmol) was added and the mixture was stirred for 10 min.

The product 2-6 (1.0 g, 3.2 mmol) obtained in the previous step was dissolved in 15 mL DMF, the mixture was cooled to 0° C. and stirred, 2,4,6-trimethylpipyridine (774.4 mg, 6.4 mmol) was added. The reaction mixture was warmed to room temperature and stirred overnight. 20 mL 1 N dilute hydrochloric acid was added to quench the reaction, then the mixture was extracted with DCM for 3 times (30 mL×3). The organic phases were combined, washed with 1 N dilute hydrochloric acid for 3 times (20 mL×3), dried over anhydrous sodium sulfate, and concentrated. The crude product was purified by prep-HPLC (CH₃CN in H₂O-0.05% TFA from 5% to 950%) to give 752 mg product 3-6 as white solid, yield 80%. LCMS (ESI) m/z 295.1 (M+H)⁺.

Synthesis of Compound 4-6

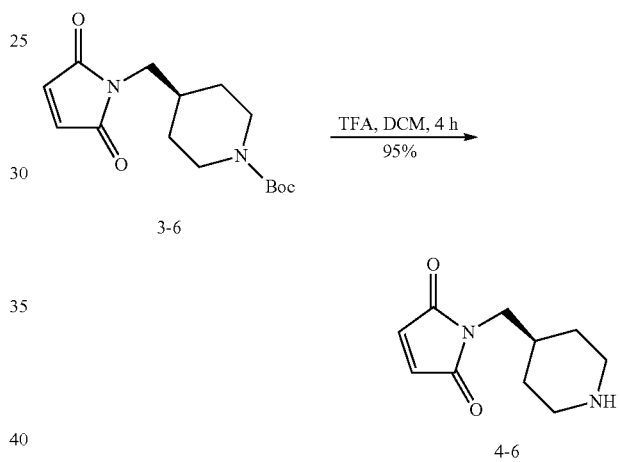

The product 3-6 (700 mg, 2.4 mmol) obtained in the previous step was dissolved in 10 mL DCM, then 3 mL TFA was added. The reaction mixture was stirred at room temperature for 4 hours, concentrated to give 442 mg crude product as yellow oil, yield 95%, which was used directly for the next step. LCMS (ESI) m/z 195.2 (M+H)⁺.

Synthesis of Compound 5-6

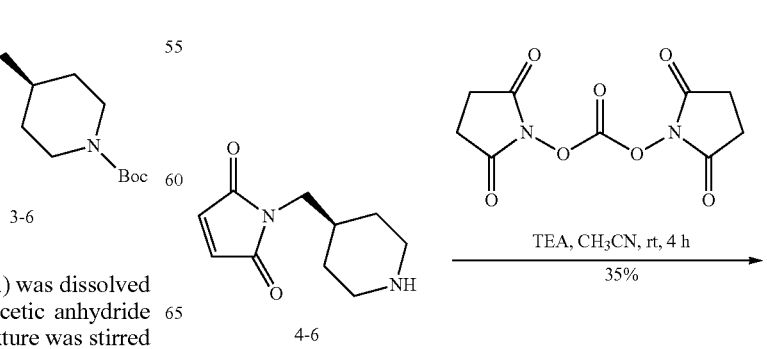

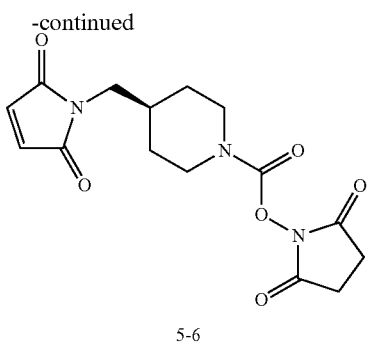

5-6

The product 4-6 (300 mg, 1.6 mmol) obtained in the previous step was dissolved in 40 mL MeCN, Et₃N (315 mg, 3.2 mmol) and N,N'-disuccinimidyl carbonate (798 mg, 3.2 mmol) were added. The reaction mixture was stirred overnight at room temperature, concentrated. The crude product was purified by prep-HPLC (CH₃CN in H₂O-0.05% TFA from 5% to 95%) to give 188 mg product 5-6 as white solid, yield 35%. LCMS (ESI) m/z 336.2 (M+H)⁺.

Synthesis of Compound CE-033

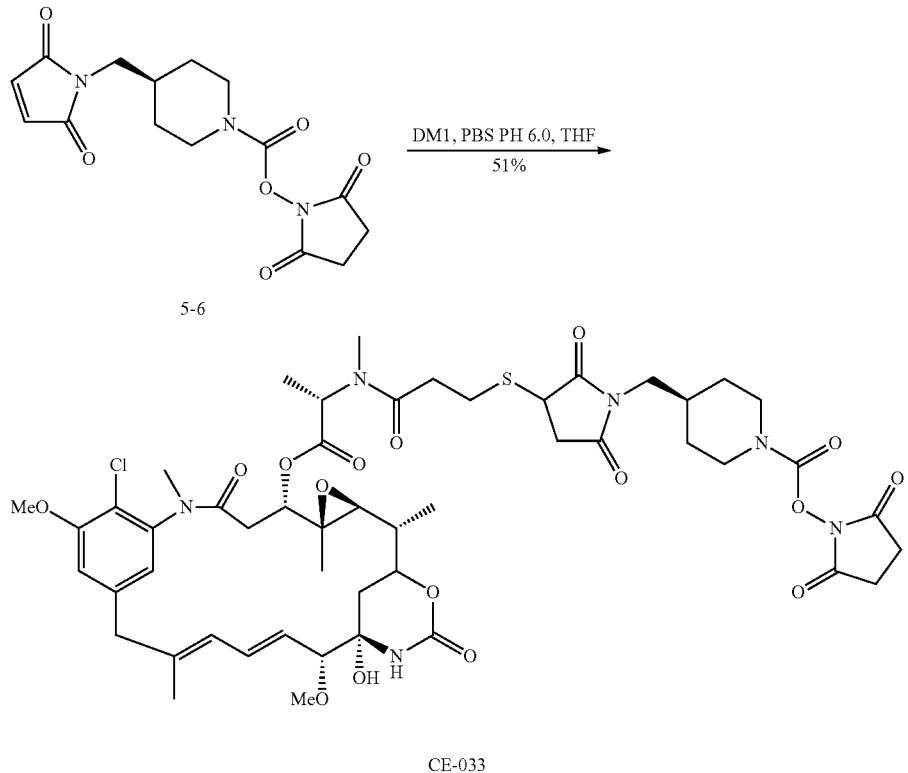

CE-033

DM1 (N2'-deacetyl-N2'-(3-mercapto-1-oxopropyl)maytansine) (37 mg, 0.05 mmol) was dissolved in 2 mL THF under argon atmosphere, 2 mL pH=6.0 potassium phosphate buffer and the product 5-6 (20 mg, 0.06 mmol) obtained in the previous step were added. The reaction mixture was stirred overnight at room temperature under argon atmosphere, filtered and the filtrate was directly purified by preparative to give 28 mg product CE-033 as white solid, yield 51%. LCMS (ESI) m/z 1094.8 (M+Na)⁺.

¹H NMR (400 MHz, CDCl₃) δ ppm 12.30 (br, 1H), 6.84 (s, 1H), 6.68 (t, J=7.2 Hz, 1H), 6.64 (d, J=7.2 Hz, 1H), 6.42 (t, J=12.8 Hz, 1H), 6.24 (s, 1H), 5.70-5.61 (m, 1H), 5.37 (q, J=6.8 Hz, 1H), 4.79 (d, J=12.0 Hz, 1H), 4.28 (t, J=10.4 Hz, 1H), 4.21-4.05 (m, 2H), 3.99 (s, 3H), 3.76-3.64 (m, 3H), 3.49 (d, J=8.8 Hz, 1H), 3.42 (d, J=7.2 Hz, 1H), 3.35 (d, J=2.4 Hz, 3H), 3.32 (d, J=6.4 Hz, 1H), 3.20 (d, J=2.8 Hz, 3H), 3.19-3.08 (m, 6H), 3.02 (d, J=9.6 Hz, 1H), 3.01-2.93 (m, 2H), 2.85 (d, J=2.8 Hz, 3H), 2.82 (s, 3H), 2.68-2.56 (m, 2H), 2.43-2.33 (m, 1H), 2.18 (d, J=14.4 Hz, 1H), 1.95-1.85 (m, 1H), 1.70 (s, 3H), 1.59-1.55 (m, 1H), 1.50-1.43 (m, 1H), 1.35-1.23 (m, 10H), 0.80 (s, 3H).

Embodiment 7 the Synthetic Routes for CE-028, 034

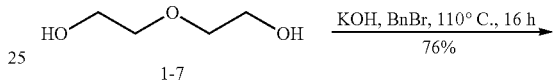

1-7

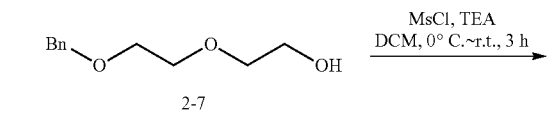

2-7

109

-continued

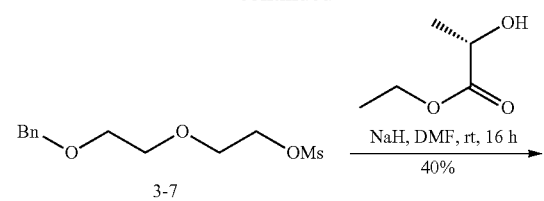
3-7

NaH, DMF, rt, 16 h
40%

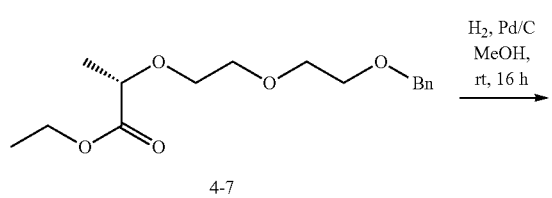
4-7

H₂, Pd/C
MeOH,
rt, 16 h

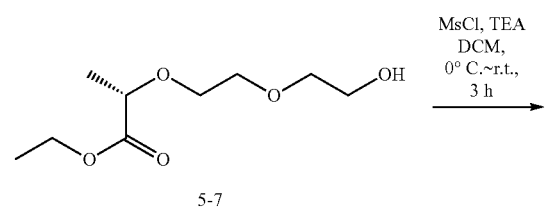
5-7

MsCl, TEA
DCM,
0° C.~r.t.,
3 h

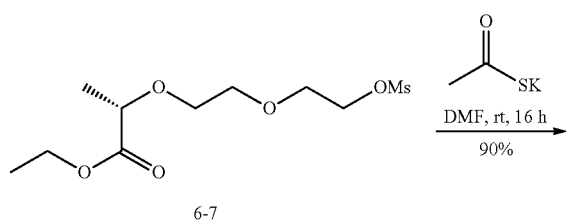
6-7

<image style="acetylthio potassium" />
DMF, rt, 16 h
90%

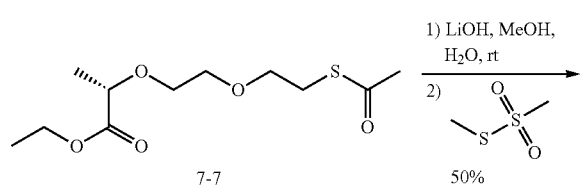
7-7

1) LiOH, MeOH, H₂O, rt
2) methyl methanethiosulfonate
50%

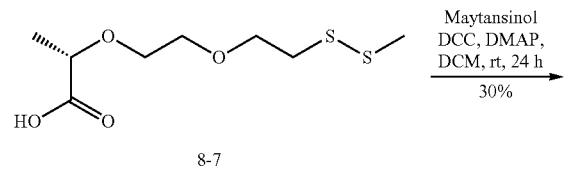
8-7

Maytansinol
DCC, DMAP,
DCM, rt, 24 h
30%

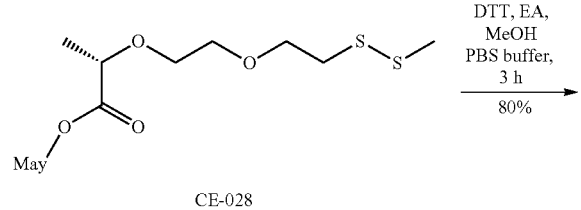
CE-028

DTT, EA,
MeOH
PBS buffer,
3 h
80%

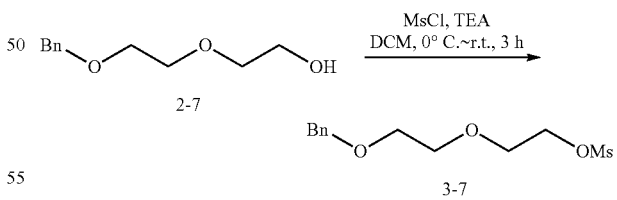
9-7

SMCC
PBS PH 6.0,
THF, 16 h
85%

110

-continued

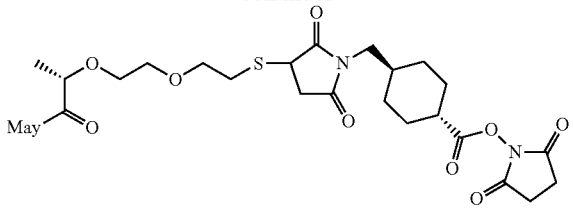
CE-034

Experimental Procedure

Synthesis of Compound 2-7

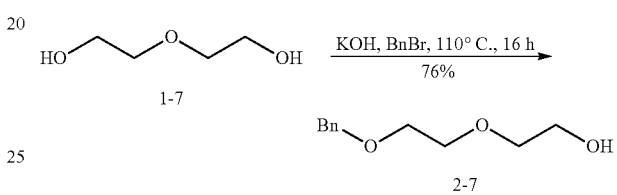
1-7

KOH, BnBr, 110° C., 16 h
76%

Bn~O~~~O~~OH
2-7

Compound 1-7 (64 g, 0.6 mol) was added to a 250 mL eggplant shaped bottle, KOH (11.2 g, 0.2 mol) was added while stirring. The suspension was heated to 90° C., and stirred till KOH was completely dissolved. BnBr (34 g, 23.6 mL, 0.2 mol) was added dropwise slowly. The reaction mixture was heated to 110° C. and stirred overnight. The reaction mixture was cooled to room temperature, 800 mL water was added, the resultant mixture was extracted with EtOAc for 3 times (150 mL×3). The organic phases were combined, washed with water for 3 times (150 mL×3) and saturated brine (150 mL), dried over anhydrous sodium sulfate, and concentrated. The crude product was purified by silica gel column chromatography (PE/EtOAc 10:1-3:1) to give 30 g product 2-7 as colorless oil, yield 76%. LCMS (ESI) m/z 197.1 (M+H)⁺

Synthesis of Compound 3-7

Bn~O~~~O~~OH
2-7

MsCl, TEA
DCM, 0° C.~r.t., 3 h

Bn~O~~~O~~OMs
3-7

The product 2-7 (19.6 g, 0.1 mol) obtained in the previous step and Et₃N (16.6 mL, 0.12 mol) were dissolved in 150 mL DCM, the mixture was cooled to 0° C., methanesulfonyl chloride (8.5 mL, 0.11 mol) was added dropwise. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give 27 g crude product 3-7 as yellow oil, which was used directly for the next step.

Synthesis of Compound 4-7

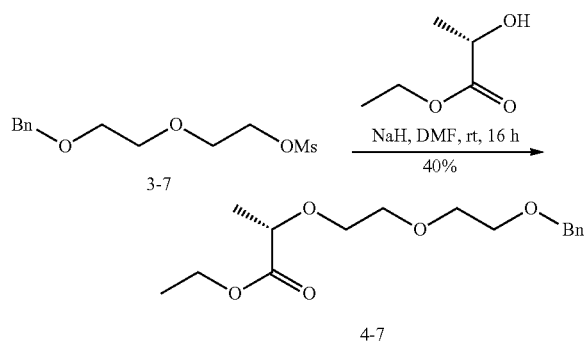

The product 3-7 (27.4 g, 0.1 mol) obtained in the previous step and L-ethyl lactate (23.6 g, 0.2 mol) were dissolved in 150 mL DMF, the mixture was cooled to 0° C., NaH (8 g, 60%, suspended in mineral oil, 0.2 mol) was added in batches slowly. The reaction mixture was warmed to room temperature and stirred overnight. The reaction mixture was cooled to 0° C., 20 mL saturated ammonium chloride solution was added dropwise slowly to quench the reaction, 150 mL water was added, the mixture was extracted with EtOAc for 3 times (100 mL×3), the organic phases were combined, washed with water for 3 times (100 mL×3) and saturated brine (100 mL), dried over anhydrous sodium sulfate, and concentrated. The crude product was purified by silica gel column chromatography (PE/EtOAc=10:1-2:1) to give 12 g product 4-7 as light yellow oil, yield 40%. LCMS (ESI) m/z 297.1 (M+H)+.

Synthesis of Compound 5-7

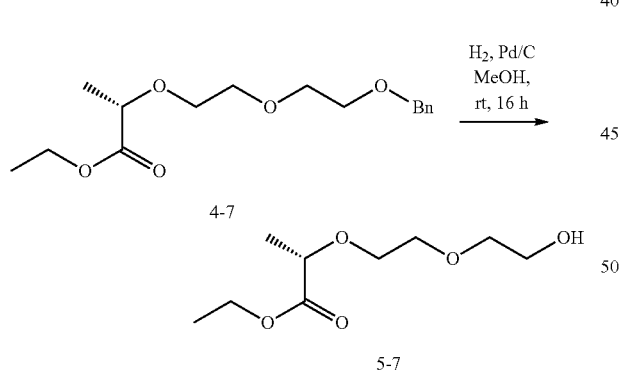

The product 4-7 (12 g, 40 mmol) obtained in the previous step was dissolved in 50 mL methanol, the mixture was purged by nitrogen for 3 times, 200 mg 10% Pd/C dry powder was added. The reaction mixture was purged by hydrogen gas for 3 times, stirred overnight at room temperature under hydrogen gas atmosphere. The reaction mixture was then purged by nitrogen gas for 3 times, 50 mL DCM was added, the resultant was filtered, washed with DCM, the filtrate was concentrated to give 8.0 g crude product as light yellow oil, which was used directly for the next step. LCMS (ESI) m/z 207.1 (M+H)+, 230.1 (M+Na)+.

Synthesis of compound 6-7

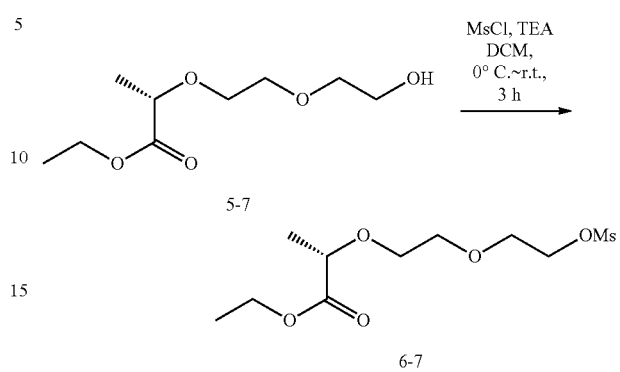

The product 5-7 (10.3 g, 50 mmol) obtained in the previous step and Et₃N (8.3 mL, 60 mmol) were dissolved in 80 mL DCM, the mixture was cooled to 0° C., methanesulfonyl chloride (4.4 mL, 55 mmol) was added dropwise. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give crude product as light yellow oil, which was used directly for the next step.

Synthesis of Compound 7-7

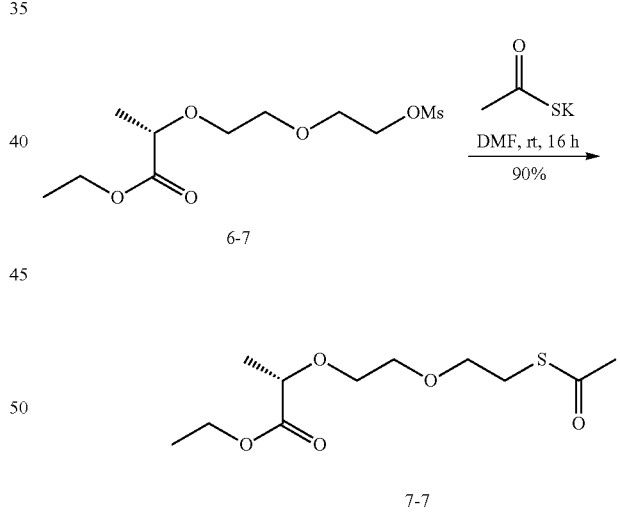

The crude product 6-7 (2 g, 7.0 mmol) obtained in the previous step was dissolved in 20 mL DMF, potassium thioacetate (1.6 g, 14 mmol) was added. The reaction mixture was stirred overnight at room temperature, 30 mL water was added, and the resultant mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography to give 1.66 g product 7-7 as brown oil, yield 90%. LCMS (ESI) m/z 265.1 (M+H)+.

Synthesis of Compound 8-7

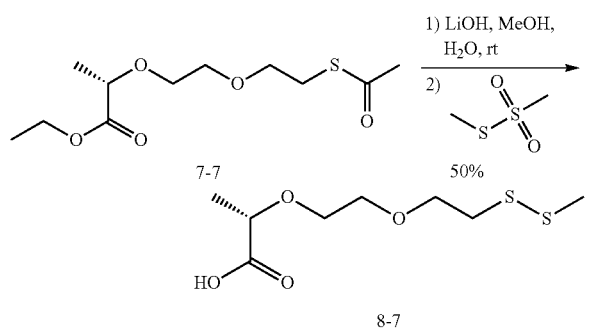

Under nitrogen atmosphere, the product 7-7 (1.66 g, 6.3 mmol) obtained in the previous step was dissolved in a mixed solution of 20 mL methanol and 10 mL water, LiOH (0.76 g, 31.5 mmol) was added. The reaction mixture was stirred at room temperature for 2 hours under nitrogen gas atmosphere, methyl methanethiosulfonate (0.95 g, 7.6 mmol) was added. The reaction mixture was further stirred overnight at room temperature, 50 mL water was added, and then the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 0.91 g product 8-7 as light yellow oil, yield 60%. LCMS (ESI) m/z 241.0 (M+H)$^+$, 263.0 (M+Na)$^+$.

Synthesis of Compound CE-028

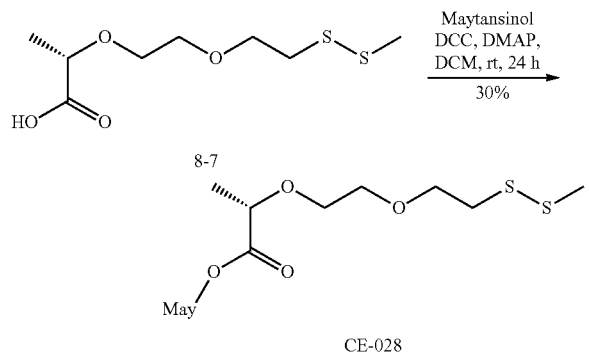

The product 8-7 (80 mg, 0.34 mmol) obtained in the previous step, DCC (148 mg, 0.72 mmol) and DMAP (29 mg, 0.24 mmol) were added to a dry Schlenk tube, the mixture was purged by argon gas for 3 times, 1 mL DCM was added and stirred. Maytansinol (63 mg, 0.12 mmol) in 4 mL dry DCM was added. The reaction mixture was stirred for 2 hours at room temperature, 0.3 mL water was added slowly to quench the reaction, and 15 mL EtOAc was added, the mixture was filtered and washed with EtOAc. The filtrate was dried over anhydrous sodium sulfate, and concentrated. The crude product was purified by prep-HPLC to give 28 mg product CE-028 as white solid, yield 30%. LCMS (ESI) m/z 787.2 (M+H)$^+$ $^1$H NMR (400 MHz, CDCl$_3$) δ ppm 6.83 (d, J=10.8 Hz, 2H), 6.44 & 6.42 (dd, J$_1$=15.2 Hz, J$_2$=10.8 Hz, 1H), 6.22 (s, 1H), 6.19 (d, J=11.2 Hz, 1H), 5.57 & 5.55 (dd, J$_1$=14.8 Hz, J$_2$=8.4 Hz, 1H), 4.93 (d, J=12.0 Hz, 1H), 4.27 (t, J=10.8 Hz, 1H), 4.18 (q, J=6.8 Hz, 1H), 3.99 (s, 3H), 3.78 (t, J=6.4 Hz, 3H), 3.69-3.64 (m, 1H), 3.67 (s, 3H), 3.51 (t, J=9.2 Hz, 2H), 3.36 (s, 3H), 3.20 (d, J=12.8 Hz, 1H), 3.15 (s, 3H), 2.92 (d, J=6.4 Hz, 3H), 2.58 (t, J=14.0 Hz, 1H), 2.43 (s, 3H), 2.30-2.25 (m, 1H), 2.01 (q, J=6.8 Hz, 1H), 1.69 (s, 3H), 1.52 (d, J=7.2 Hz, 3H), 1.53-1.50 (m, 1H), 1.29 (d, J=7.2 Hz, 3H), 0.83 (s, 3H).

Synthesis of Compound 9-7

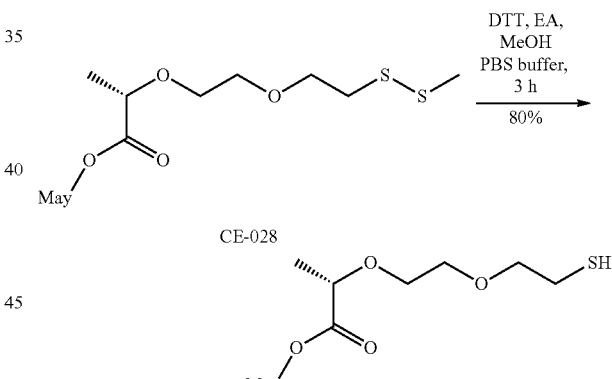

CE-028 (12 mg, 0.015 mmol) was dissolved in a mixed solution of 0.5 mL EtOAc and 0.5 mL methanol, dithiothreitol (DTT) (18 mg, 0.117 mmol) in 0.5 mL pH=7.5 potassium phosphate buffer was added. The reaction mixture was stirred for 3 hours under nitrogen atmosphere. 1 mL pH=6 potassium phosphate buffer was added to quench the reaction, the resultant mixture was extracted with EtOAc for 3 times (5 mL×3), the organic phases were combined, washed with saturated brine (5 mL), dried over anhydrous sodium sulfate, and concentrated. The crude product was purified by prep-HPLC (CH$_3$CN in H$_2$O-0.05% TFA from 5% to 95%) to give 8.9 mg product 9-7 as white solid, yield 80%. LCMS (ESI) m/z 741.3 (M+H)$^+$.

Synthesis of Compound CE-034

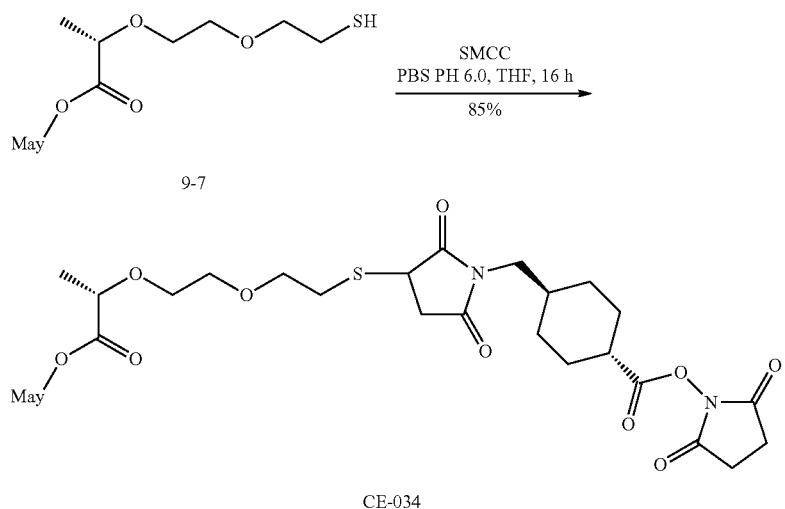

The product 9-7 (8.9 mg, 0.012 mmol) obtained in the previous step was dissolved in 1.5 mL THF, 1.5 mL pH=6 potassium phosphate buffer and 4-(N-maleimidomethyl)cyclohexane-1-carboxylic acid N-hydroxysuccinimide ester (20 mg, 0.06 mmol) were added, the mixture was stirred overnight at room temperature under nitrogen gas atmosphere. The reaction mixture was stirred, and directly purified by prep-HPLC to give 11 mg product CE-034 as white solid, yield 85%. LCMS (ESI) m/z 1075.4 (M+H)$^+$.

$^1$H NMR (400 MHz, CDCl$_3$) δ ppm 6.82 (d, J=17.2 Hz, 2H), 6.42 (d, J=15.2 Hz, 2H), 6.19 (d, J=14.4 Hz, 1H), 5.56 & 5.54 (dd, J$_1$=14.8 Hz, J$_2$=8.4 Hz, 1H), 4.91 (d, J=14.4 Hz, 1H), 4.27 (t, J=10.8 Hz, 1H), 4.15 (q, J=6.8 Hz, 1H), 3.99 (s, 3H), 3.83-3.76 (m, 3H), 3.66 (s, 3H), 3.50 (t, J=9.2 Hz, 2H), 3.40 (d, J=12.0 Hz, 2H), 3.35 (s, 3H), 3.21-3.15 (m, 3H), 3.15 (s, 3H), 2.91-2.83 (m, 3H), 2.83 (s, 3H), 2.62-2.50 (m, 3H), 2.25-2.14 (m, 3H), 1.81-1.70 (m, 4H), 1.68 (s, 3H), 1.58-1.45 (m, 6H), 1.29 (d, J=7.2 Hz, 6H), 1.08 (d, J=12.0 Hz, 2H), 0.83 (s, 3H).

Embodiment 8 Synthetic Routes for CE-027, 035

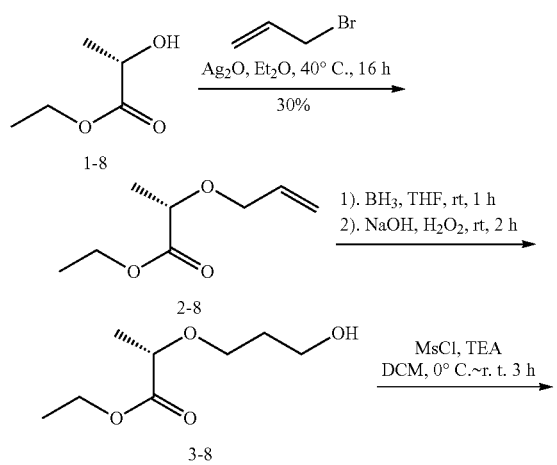

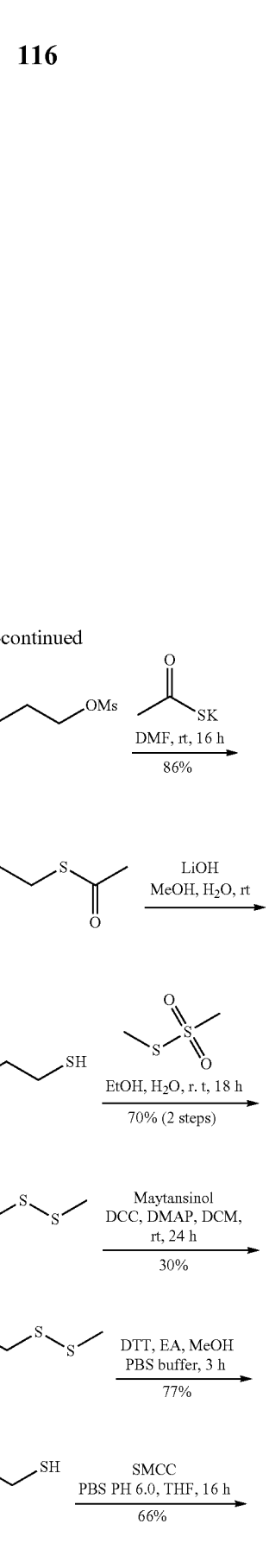

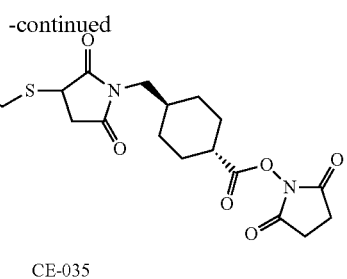

CE-035

Experimental Procedure

Synthesis of Compound 2-8

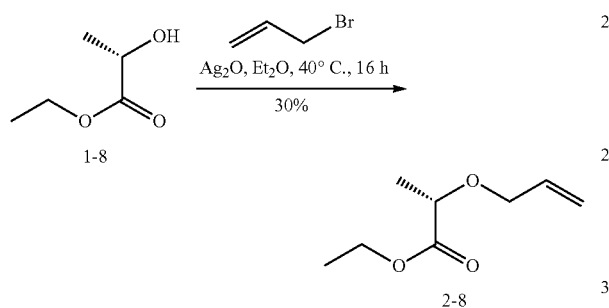

Compound 1-8 (9.7 mL, 84 mmol) and allyl bromide (9.3 mL, 108 mmol) were dissolved in 200 mL Et$_2$O, Ag$_2$O (21 g, 92.4 mmol) was added. The suspension was heated to reflux and stirred overnight. The reaction mixture was cooled to room temperature and filtered, and then washed with EtOAc, the filtrate was concentrated. The crude product was purified by silica gel column chromatography (PE/EtOAc 10:1) to give 3.9 g product 2-8 as colorless oil, yield 30%.

$^1$H NMR (400 MHz, CDCl$_3$) δ ppm 5.97-5.87 (m, 1H), 5.29 (d, J=16.8 Hz, 1H), 5.20 (d, J=10.0 Hz, 1H), 4.25-4.12 (m, 3H), 4.04-3.92 (m, 2H), 1.42 (d, J=6.8 Hz, 3H), 1.29 (t, J=7.2 Hz, 3H).

Synthesis of Compound 3-8

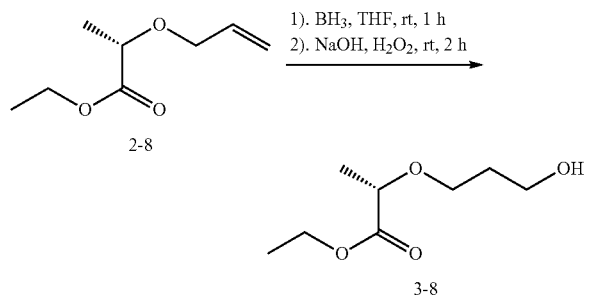

The product 2-8 (3.9 g, 24.7 mmol) obtained in the previous step was dissolved in 40 mL THF, the mixture was cooled to 0° C., BH$_3$/THF solution (1 M, 29 mL, 29 mmol) was added dropwise while stirring. The reaction mixture was warmed to room temperature and stirred for 2 hours. The reaction mixture was cooled to 0° C., sodium hydroxide solution (3 N, 10 mL, 30 mmol) was added dropwise, 15 mL 30% hydrogen peroxide solution was added slowly, and the reaction mixture was warmed to room temperature and stirred overnight. 200 mL Et$_2$O was added, then the organic phase was separated, washed with saturated brine (50 mL×3), dried over anhydrous sodium sulfate, concentrated to give 1.6 g crude product 3-8 as light yellow oil, which was used directly for the next step.

$^1$H NMR (400 MHz, CDCl$_3$) δ ppm 4.27-4.17 (m, 2H), 3.96 (q, J=7.2 Hz, 1H), 3.89-3.71 (m, 2H), 3.68-3.61 (m, 2H), 2.82 (s, 1H), 1.93-1.75 (m, 2H), 1.40 (d, J=7.2 Hz, 3H), 1.27 (t, J=6.8 Hz, 3H).

Synthesis of Compound 4-8

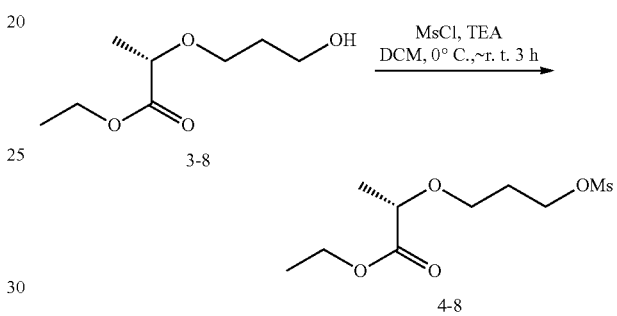

The product 3-8 (7.04 g, 40 mmol) obtained in the previous step and Et$_3$N (6.6 mL, 48 mmol) were dissolved to 50 mL DCM, the mixture was cooled to 0° C., methanesulfonyl chloride (3.5 mL, 44 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give the crude product as light yellow oil, which was used directly for the next step. LCMS (ESI) m/z 255.1 (M+H)$^+$.

Synthesis of Compound 5-8

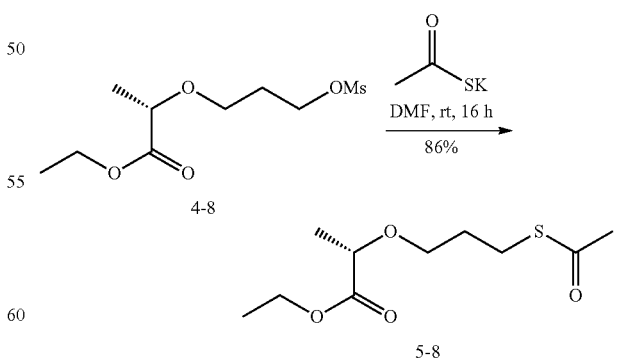

The crude product 4-8 (2.54 g, 10.0 mmol) obtained in the previous step was dissolved in 20 mL DMF, potassium thioacetate (2.3 g, 20 mmol) was added. The reaction mixture was stirred overnight at room temperature, 30 mL water was added, and the resultant mixture was extracted with EtOAc for 3 times (50 mL×3). The organic phases were combined, washed with water for 3 times (30 mL×3), washed with saturated brine (50 mL), dried over anhydrous sodium sulfate, and concentrated. The crude product was purified by silica gel column chromatography (PE/EtOAc=1:1) to give 2.0 g product 5-8 as brown oil, yield 86%. LCMS (ESI) m/z 235.2 (M+H)$^+$.

Synthesis of Compound 7-8

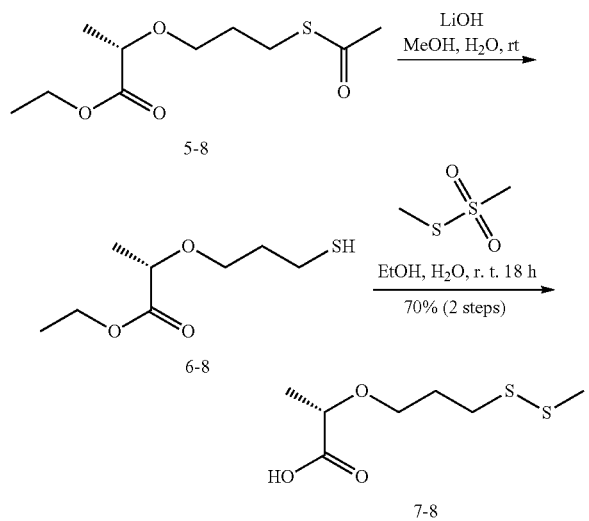

Under nitrogen atmosphere, the product 5-8 (1.87 g, 8 mmol) obtained in the previous step was dissolved in a mixed solution of 20 mL methanol and 10 mL water, LiOH (0.78 g, 32 mmol) was added. The reaction mixture was stirred for 2 hours at room temperature under nitrogen atmosphere, methyl methanethiosulfonate (1.2 g, 9.6 mmol) was added. The reaction mixture was further stirred overnight at room temperature. 50 mL water was added to the reaction mixture, the mixture was then extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 1.18 g product 7-8 as light yellow oil, yield 70%. LCMS (ESI) m/z 197.0 (M+H)$^+$, 211.1 (M+Na)$^+$. $^1$H NMR (400 MHz, CDCl$_3$) δ ppm 4.02 (q, J=7.2 Hz, 1H), 3.70-3.60 (m, 2H), 2.82 (t, J=7.2 Hz, 2H), 2.41 (s, 3H), 2.05-2.01 (m, 2H), 1.47 (d, J=6.8 Hz, 3H).

Synthesis of Compound CE-027

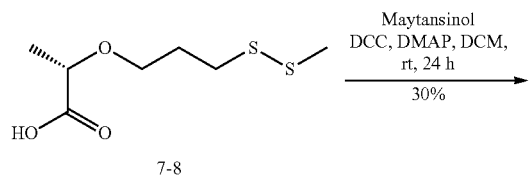

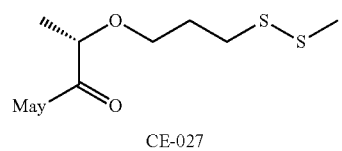

The product 7-8 (63 mg, 0.30 mmol) obtained in the previous step, DCC (124 mg, 0.6 mmol) and DMAP (24 mg, 0.2 mmol) were added to a dry Schlenk tube, the mixture was purged by argon for 3 times, 1 mL DCM was added and stirred. Maytansinol (56 mg, 0.10 mmol) was in 4 mL dry DCM was added. The reaction mixture was stirred for 2 hours at room temperature, 0.3 mL water was added slowly to quench the reaction, and 15 mL EtOAc was added, the mixture was filtered, washed with EtOAc. The filtrate was dried over anhydrous sodium sulfate, and concentrated. The crude product was purified by prep-HPLC to give 23 mg product CE-027 as white solid, yield 30%.

LCMS (ESI) m/z 757.3 (M+H)$^+$. $^1$H NMR (400 MHz, CDCl$_3$) δ ppm 6.96 (s, 1H), 6.84 (s, 1H), 6.48 & 6.44 (dd, J$_1$=21.2 Hz, J$_2$=6.8 Hz, 1H), 6.23 (s, 1H), 6.18 (d, J=6.8 Hz, 1H), 5.48 & 5.45 (dd, J$_1$=14.8 Hz, J$_2$=8.4 Hz, 1H), 4.92 (d, J=12.0 Hz, 1H), 4.25 (t, J=13.2 Hz, 1H), 4.13 (q, J=6.8 Hz, 1H), 3.99 (s, 3H), 3.65 (q, J=6.8 Hz, 1H), 3.56-3.43 (m, 3H), 3.36 (s, 3H), 3.21 (d, J=12.8 Hz, 1H), 3.17 (s, 3H), 3.06 (s, 1H), 2.87 (d, J=8.4 Hz, 1H), 2.80 (t, J=7.2 Hz, 1H), 2.58 & 2.55 (dd, J$_1$=19.2 Hz, J$_2$=8.4 Hz, 1H), 2.37 (s, 3H), 2.36-2.20 (m, 2H), 2.03-1.96 (m, 3H), 1.68 (s, 3H), 1.47 (d, J=6.8 Hz, 3H), 1.38-1.30 (m, 1H), 1.30 (d, J=7.2 Hz, 3H), 0.84 (s, 3H).

Synthesis of Compound 8-8

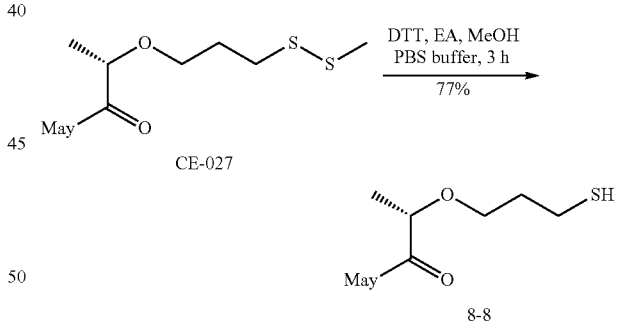

CE-027 (15 mg, 0.02 mmol) was dissolved in a mixed solution of 0.5 mL EtOAc and 0.5 mL methanol, dithiothreitol (DTT) (18 mg, 0.117 mmol) in 0.5 mL pH=7.5 potassium phosphate buffer was added. The reaction mixture was stirred for 3 hours under nitrogen atmosphere. 1 mL pH=6 potassium phosphate buffer was added to quench the reaction, the mixture was then extracted with EtOAc for 3 times (5 mL×3). The organic phases were combined, washed with saturated brine (5 mL), dried over anhydrous sodium sulfate, and concentrated. The crude product was purified by prep-HPLC (CH$_3$CN in H$_2$O-0.05% TFA from 5% to 95%) to give 11 mg product 8-8 as white solid, yield 77%. LCMS (ESI) m/z 711.3 (M+H)$^+$.

Synthesis of Compound CE-035

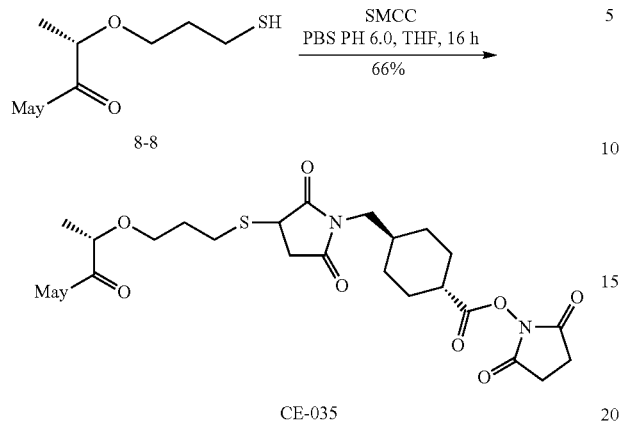

The product 8-8 (9 mg, 0.013 mmol) obtained in the previous step was dissolved in 1.5 mL THF, 1.5 mL pH=6 potassium phosphate buffer and 4-(N-maleimidomethyl) cyclohexanecarboxylic acid N-hydroxysuccinimide ester (22 mg, 0.065 mmol) were added, the mixture was stirred overnight at room temperature under nitrogen atmosphere. The reaction mixture was filtered, purified directly by prep-HPLC to give 9 mg product CE-035 as white solid, yield 66%. LCMS (ESI) m/z 1045.4 (M+H)$^+$. $^1$H NMR (400 MHz, CDCl$_3$) δ ppm 6.93 (d, J=7.6 Hz, 1H), 6.84 (s, 1H), 6.43 & 6.41 (dd, J$_1$=21.2 Hz, J$_2$=7.2 Hz, 1H), 6.30 (s, 1H), 6.20 & 6.18 (dd, J$_1$=13.2 Hz, J$_2$=6.8 Hz, 1H), 5.47 & 5.45 (dd, J$_1$=13.2 Hz, J$_2$=7.2 Hz, 1H), 4.92-4.88 (m, 1H), 4.26 (q, J=7.2 Hz, 1H), 4.12 (q, J=6.8 Hz, 1H), 3.99 (s, 3H), 3.75 (q, J=6.8 Hz, 1H), 3.66 (q, J=7.2 Hz, 1H), 3.55-3.43 (m, 3H), 3.38 (d, J=6.4 Hz, 3H), 3.36 (s, 3H), 3.23-3.16 (i, 2H), 3.18 (s, 3H), 3.10-2.94 (m, 1H), 2.90-2.83 (m, 3H), 2.83 (s, 3H), 2.57-2.53 (m, 3H), 2.27 (d, J=14.4 Hz, 1H), 2.16 (d, J=13.6 Hz, 2H), 1.98-1.90 (m, 1H), 1.80-1.78 (m, 2H), 1.68 (s, 3H), 1.56-1.51 (m, 4H), 1.47-1.42 (m, 4H), 1.28 (d, J=8.4 Hz, 3H), 1.07 (q, J=8.4 Hz, 3H), 0.83 (s, 3H).

Embodiment 9 Synthetic Route for CE-036

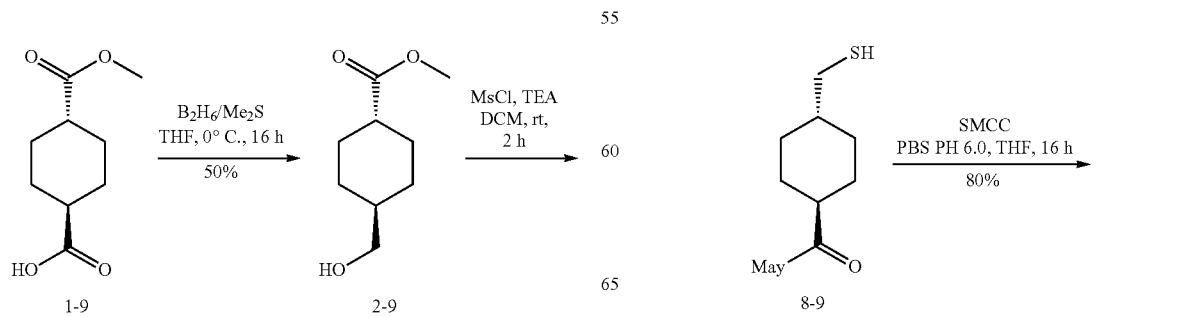

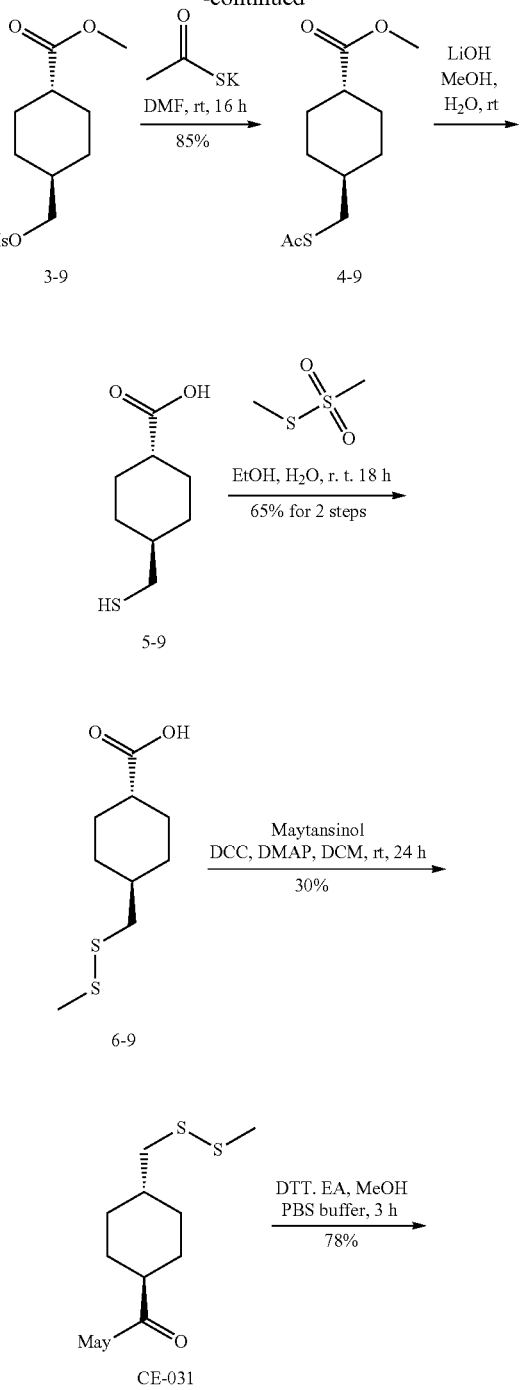

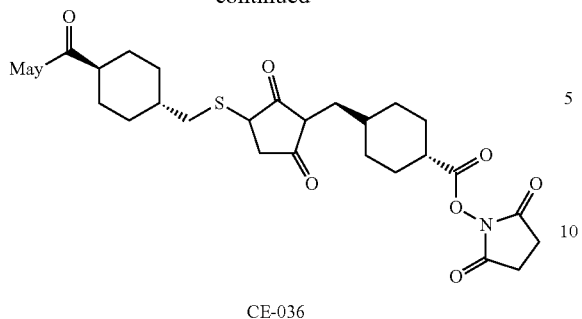

CE-036

Experimental Procedure

Synthesis of Compound 2-9

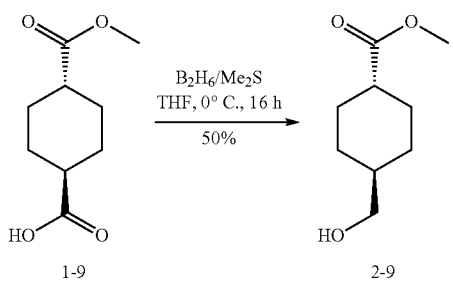

Compound 1-9 (9.30 g, 50 mmol) was dissolved in 50 mL THF, the mixture was cooled to 0° C., a solution of 1 M B$_2$H$_6$/Me$_2$S complex in THF (75 mL, 75 mmol) was added dropwise while stirring. The reaction mixture was warmed to room temperature and stirred overnight. The reaction mixture was cooled to 0° C., 50 mL methanol was added dropwise to quench the reaction, the resultant mixture was stirred for 1 hour at room temperature, concentrated under reduced pressure, the residue was purified by silica gel column chromatography (PE/EtOAc=1:1) to give 4.3 g product 2-9 as colorless oil, yield 50%. LCMS (ESI) m/z 173.1 (M+H)$^+$.

Synthesis of Compound 3-9

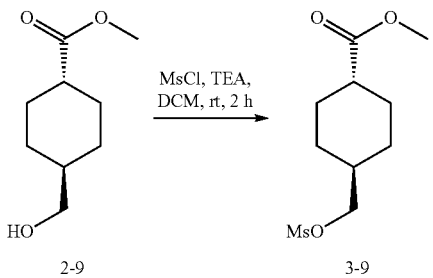 [SMILES: COC(=O)[C@H]1CC[C@H](CO)CC1 ; COC(=O)[C@H]1CC[C@H](COS(C)(=O)=O)CC1]

The product 2-9 (8.6 g, 50 mmol) obtained in the previous step and Et$_3$N (8.3 mL, 60 mmol) were dissolved in 80 mL DCM, the mixture was cooled to 0° C., methanesulfonyl chloride (MsCl) (4.3 mL, 55 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give the crude product 3-9 as light yellow oil, which was used directly for the next step. LCMS (ESI) m/z 251.1 (M+H)$^+$ Synthesis of Compound 4-9

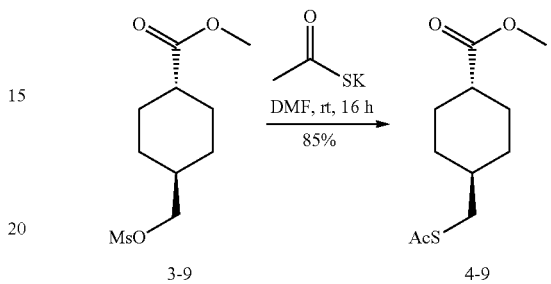

The crude product 3-9 (4 g, 16.0 mmol) obtained in the previous step was dissolved in 50 mL DMF, potassium thioacetate (3.45 g, 30 mmol) was added. The reaction mixture was stirred overnight at room temperature, 30 mL water was added, the mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography (PE/EtOAc=1:1) to give 2.9 g product 4-9 as brown oil, yield 85%. LCMS (ESI) m/z 231.1 (M+H)$^+$ Synthesis of Compound 6-9

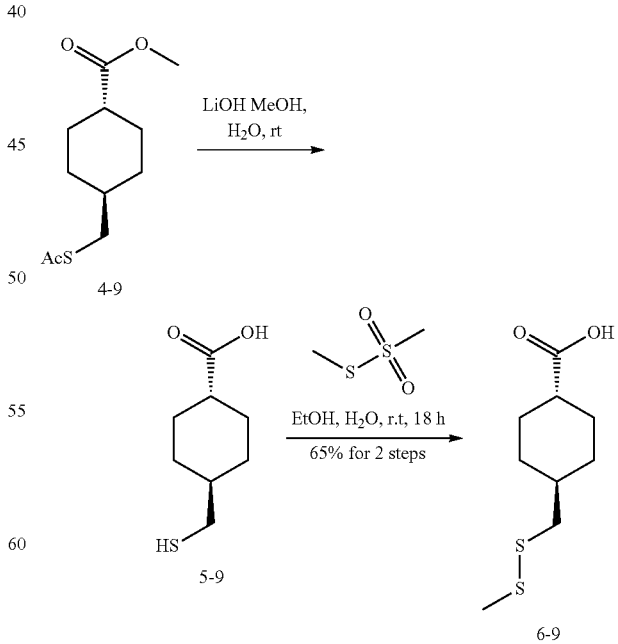

Under nitrogen atmosphere, the product 4-9 (2.3 g, 10 mmol) obtained in the previous step was dissolved in a mixed solution of 25 mL methanol and 10 mL water, LiOH (0.98 g, 40 mmol) was added. The reaction mixture was stirred for 2 hours at room temperature under nitrogen atmosphere, methyl methanethiosulfonate (1.5 g, 12 mmol) was added. The reaction mixture was further stirred overnight at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 1.43 g product 6-9 as light yellow oil, yield 65%. LCMS (ESI) m/z 221.0 (M+H)$^+$, 243.1 (M+Na)$^+$.

Synthesis of Compound CE-031

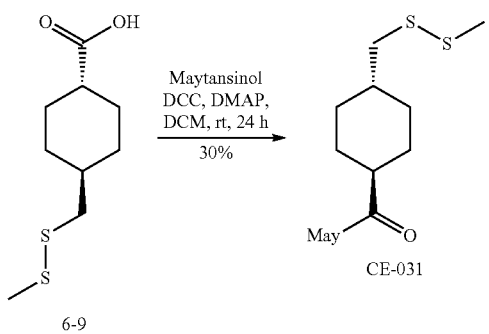

The product 6-9 (53 mg, 0.24 mmol) obtained in the previous step, DCC (99 mg, 0.48 mmol) and DMAP (19 mg, 0.16 mmol) were added to a dry Schlenk tube, the mixture was purged by argon for 3 times, 1 mL DCM was added, and stirred. Maytansinol (45 mg, 0.08 mmol) in 4 mL dry DCM was added. The reaction mixture was stirred overnight at room temperature, 0.5 mL water was added slowly to quench the reaction, and 20 mL EtOAc was added, the mixture was filtered, and washed with EtOAc. The filtrate was dried over anhydrous sodium sulfate, and concentrated. The crude product was purified by prep-HPLC to give 18 mg product CE-031 as white solid, yield 30%.

LCMS (ESI) m/z 767.3.0 (M+H)$^+$. $^1$H NMR (400 MHz, CDCl$_3$) δ ppm 6.83 (d, J=6.8 Hz, 2H), 6.46 & 6.44 (dd, J$_1$=15.6 Hz, J$_2$=10.8 Hz, 1H), 6.35 (s, 1H), 6.14 (d, J=10.8 Hz, 1H), 5.44 & 5.42 (dd, J$_1$=16.0 Hz, J$_2$=8.4 Hz, 1H), 4.86 &4.85 (dd, J$_1$=12.0 Hz, J$_2$=3.2 Hz, 1H), 4.26 (t, J=10.4 Hz, 1H), 3.99 (s, 3H), 3.51 (s, 1H), 3.48 (d, J=3.6 Hz, 1H), 3.37 (s, 3H), 3.23 (d, J=12.8 Hz, 1H), 3.15 (s, 3H), 2.90 (d, J=10.8 Hz, 1H), 2.75-2.63 (m, 2H), 2.55 (t, J=13.6 Hz, 1H), 2.42 (s, 3H), 2.34-2.02 (m, 5H), 1.84-1.65 (m, 4H), 1.70 (s, 3H), 1.54-1.44 (m, 3H), 1.47 (d, J=6.8 Hz, 3H), 1.29-1.09 (m, 3H), 0.84 (s, 3H).

Synthesis of Compound 8-9

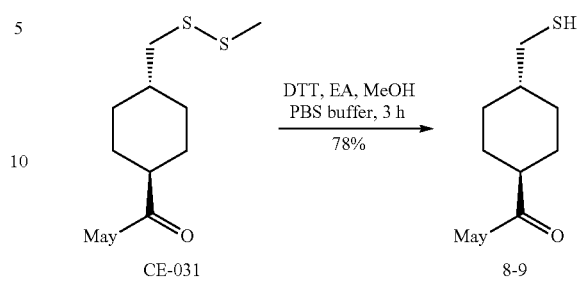

CE-031 (15 mg, 0.02 mmol) was dissolved in a mixed solution of 0.5 mL EtOAc and 0.5 mL methanol, dithiothreitol (DTT) (18 mg, 0.117 mmol) in 0.5 mL pH=7.5 potassium phosphate buffer was added. The reaction mixture was stirred for 3 hours under nitrogen atmosphere. 1 mL pH=6 potassium phosphate buffer was added to quench the reaction, the mixture was then extracted with EtOAc for 3 times (5 mL×3). The organic phases were combined, washed with saturated brine (5 mL), dried over anhydrous sodium sulfate, and concentrated. The crude product was purified by prep-HPLC (CH$_3$CN in H$_2$O-0.05% TFA from 5% to 95%) to give 11 mg product 8-9 as white solid, yield 78%. LCMS (ESI) m/z 721.3 (M+H)$^+$.

Synthesis of Compound CE-036

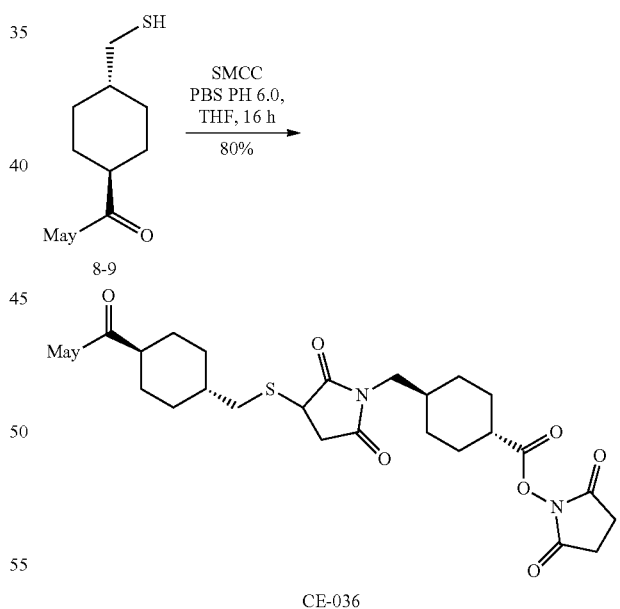

The product 8-9 (9.0 mg, 0.013 mmol) obtained in the previous step was dissolved in 1.5 mL THF, 1.5 mL pH=6 potassium phosphate buffer and 4-(N-maleimidomethyl) cyclohexanecarboxylic acid N-hydroxysuccinimide ester (22 mg, 0.065 mmol) were added, the mixture was stirred overnight at room temperature under nitrogen atmosphere. The reaction mixture was filtered, and purified directly by prep-HPLC to give 9.0 mg product CE-036 as white solid, yield 64%.

LCMS (ESI) m/z 1055.4 (M+H)⁺. ¹H NMR (400 MHz, CDCl₃) δ ppm 6.83 (d, J=16.0 Hz, 2H), 6.47-6.39 (m, 2H), 6.15 & 6.13 (dd, J₁=10.0 Hz, J₂=4.8 Hz, 1H), 5.43& 5.41 (dd, J₁=15.2 Hz, J₂=8.8 Hz, 1H), 4.86 (t, J=9.2 Hz, 1H), 4.26 (t, J=11.2 Hz, 1H), 3.99 (s, 3H), 3.69 (d, J=8.4 Hz, 1H), 3.50-3.36 (m, 4H), 3.37 (s, 3H), 3.23 (d, J=12.8 Hz, 1H), 3.14 (s, 3H), 2.90-2.77 (m, 6H), 2.58-2.51 (m, 3H), 2.29 (q, J=11.2 Hz, 1H), 2.22-1.90 (m, 10H), 1.85 (s, 3H), 1.70-1.50 (m, 8H), 1.27 (d, J=6.8 Hz, 3H), 1.20-1.00 (m, 5H), 0.83 (s, 3H).

Embodiment 10 Synthetic Routes for CE-026, 037

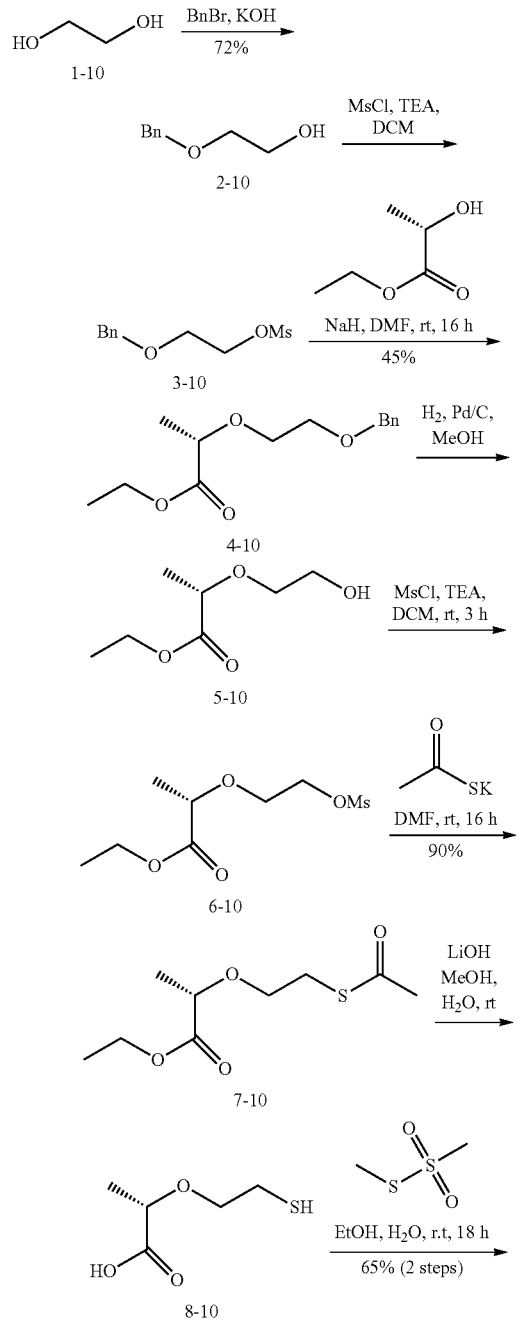

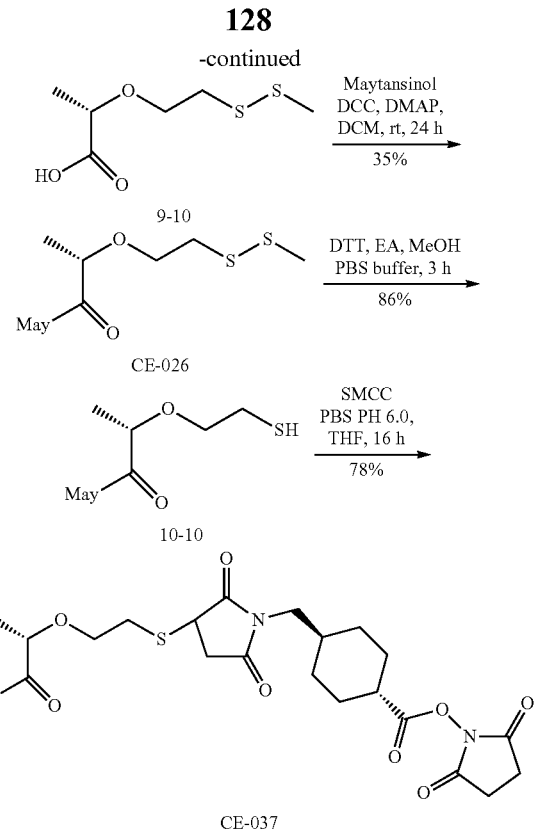

Experimental Procedure

Synthesis of compound 2-10:

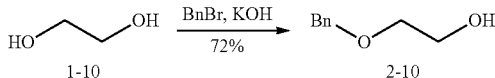

Compound 1-10 (37.2 g, 0.6 mol) was added to a 250 mL eggplant shaped bottle, KOH (11.2 g, 0.2 mol) was added while stirring. The suspension was heated to 90° C., and stirred till KOH was completely dissolved. BnBr (34 g, 23.6 mL, 0.2 mol) was added dropwise slowly. The reaction mixture was heated to 110° C. and stirred overnight. The reaction mixture was cooled to room temperature, 800 mL water was added, and the resultant mixture was extracted with EtOAc for 3 times (150 mL×3). The organic phases were combined, washed with water for 3 times (150 mL×3) and saturated brine (150 mL), dried over anhydrous sodium sulfate, and concentrated. The crude product was purified by silica gel column chromatography (PE/EtOAc 10:1-3:1) to give 22 g product 2-10 as colorless oil, yield 72%. LCMS (ESI) m/z 153.1 (M+H)⁺

Synthesis of Compound 3-10

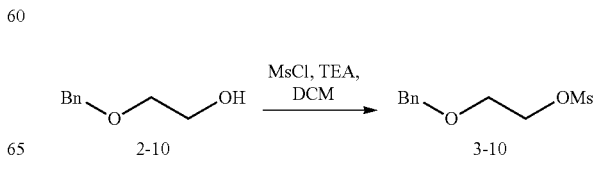

The product 2-10 (15.2 g, 0.1 mol) obtained in the previous step and Et₃N (16.6 mL, 0.12 mol) were dissolved in 150 mL DCM, the mixture was cooled to 0° C., methanesulfonyl chloride (8.5 mL, 0.11 mol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give 23 g crude product 3-10 as yellow oil, which was used directly for the next step.

Synthesis of Compound 4-10

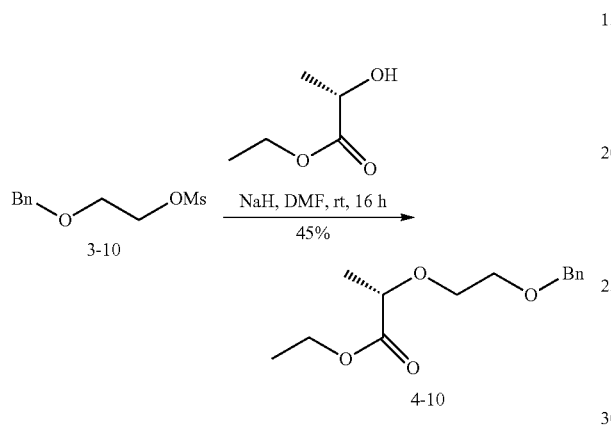

The product 3-10 (23 g, 0.1 mol) obtained in the previous step and L-ethyl lactate (23.6 g, 0.2 mol) were dissolved in 150 mL DMF, the mixture was cooled to 0° C., NaH (8 g, 60%, suspended in mineral oil, 0.2 mol) was added in batches slowly. The reaction mixture was warmed to room temperature and stirred overnight. The reaction mixture was cooled to 0° C., 20 mL saturated ammonium chloride solution was added dropwise slowly to quench the reaction, 150 mL water was added, the resultant mixture was extracted with EtOAc for 3 times (100 mL×3). The organic phases were combined, washed with water for 3 times (100 mL×3) and saturated brine (100 mL), dried over anhydrous sodium sulfate, and concentrated. The crude product was purified by silica gel column chromatography (PE/EtOAc=10:1-2:1) to give 11.3 g product 4-10 as light yellow oil, yield 45%. LCMS (ESI) m/z 253.1 (M+H)⁺.

Synthesis of Compound 5-10

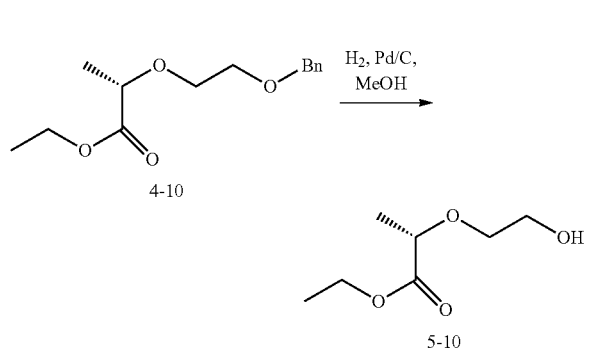

The product 4-10 (11.3 g, 45 mmol) obtained in the previous step was dissolved in 50 mL methanol, the mixture was purged by nitrogen for 3 times, 200 mg 10% Pd/C dry powder was added. The reaction mixture was purged by hydrogen for 3 times, stirred overnight at room temperature under hydrogen gas atmosphere. Then the reaction mixture was purged by nitrogen for 3 times, 50 mL DCM was added, the mixture was filtered, washed with DCM, the filtrate was concentrated to give 7.2 g crude product as light yellow oil, which was used directly for the next step. LCMS (ESI) m/z 164.1 (M+H)⁺, 186.1 (M+Na)⁺.

Synthesis of Compound 6-10

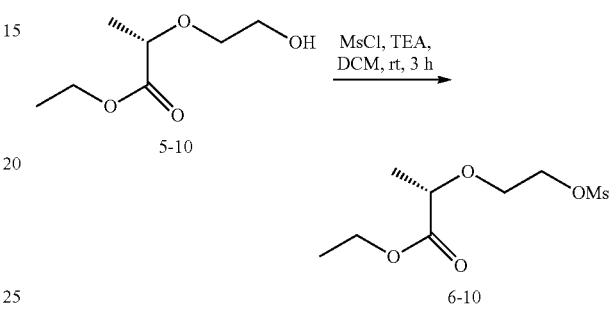

The product 5-10 (6.5 g, 40 mmol) obtained in the previous step and Et₃N (6.6 mL, 48 mmol) were dissolved in 50 mL DCM, the mixture was cooled to 0° C., methanesulfonyl chloride (3.5 mL, 44 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give the crude product as light yellow oil, which was used directly for the next step.

Synthesis of Compound 7-10

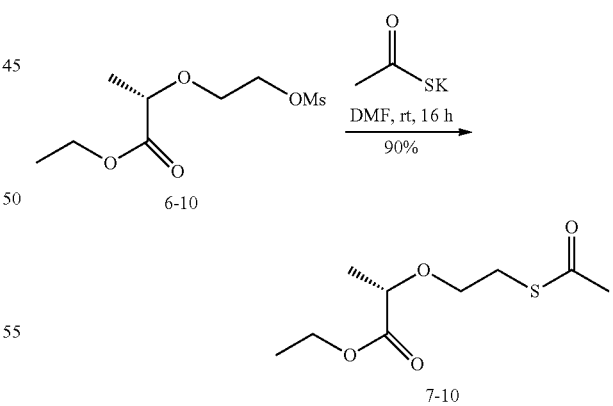

The crude product 6-10 (2 g, 7.0 mmol) obtained in the previous step was dissolved in 20 mL DMF, potassium thioacetate (1.6 g, 14 mmol) was added. The reaction mixture was stirred overnight at room temperature, 30 mL water was added, and the mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography to give 2.0 g product 7-10 as brown oil, yield 90%. LCMS (ESI) m/z 221.1 (M+H)+

Synthesis of Compound 9-10

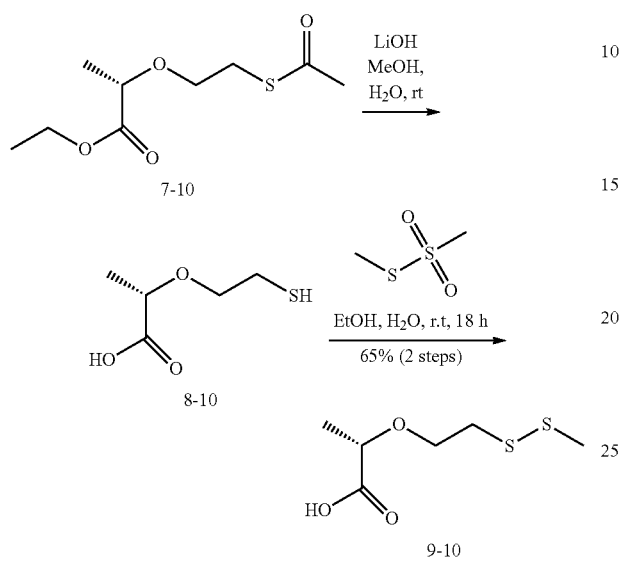

Under nitrogen atmosphere, the product 7-10 (1.76 g, 8 mmol) obtained in the previous step was dissolved in a mixed solution of 20 mL methanol and 10 mL water, LiOH (0.78 g, 32 mmol) was added. The reaction mixture was stirred for 2 hours at room temperature under nitrogen atmosphere, methyl methanethiosulfonate (1.2 g, 9.6 mmol) was added. The reaction mixture was further stirred overnight at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 1.01 g product 9-10 as light yellow oil, yield 65%. LCMS (ESI) m/z 197.0 (M+H)+, 219.0 (M+Na)+.

Synthesis of Compound CE-026

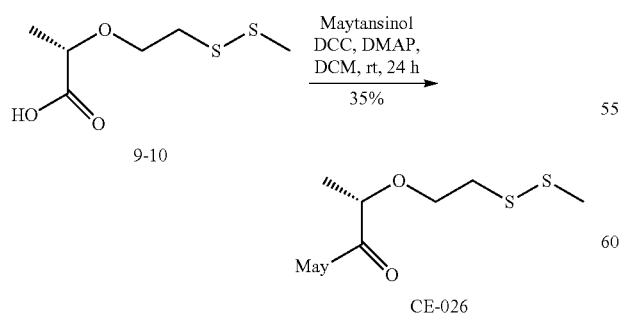

The product 9-10 (65 mg, 0.33 mmol) obtained in the previous step, DCC (136 mg, 0.66 mmol) and DMAP (27 mg, 0.22 mmol) were added to a dry Schlenk tube, the mixture was purged by argon for 3 times, 1 mL DCM was added and stirred. Maytansinol (62 mg, 0.11 mmol) in 4 mL dry DCM was added. The reaction mixture was stirred for 2 hours at room temperature, 0.3 mL water was added slowly to quench the reaction, then 15 mL EtOAc was added, the mixture was filtered, washed with EtOAc. The filtrate was dried over anhydrous sodium sulfate, and concentrated. The crude product was purified by prep-HPLC to give 29 mg product CE-026 as white solid, yield 35%.

LCMS (ESI) m/z 744.3 (M+H)+. 1H NMR (400 MHz, CDCl3) δ ppm 6.83 (d, J=8.0 Hz, 2H), 6.46 & 6.44 (dd, $J_1$=15.2 Hz, $J_2$=10.8 Hz, 1H), 6.21 (s, 1H), 6.18 (d, J=11.6 Hz, 1H), 5.55 & 5.53 (dd, $J_1$=15.2 Hz, $J_2$=9.2 Hz, 1H), 4.93 & 4.92 (dd, $J_1$=12.0 Hz, $J_2$=2.8 Hz, 1H), 4.28 (t, J=10.4 Hz, 1H), 4.10 (q, J=9.2 Hz, 1H), 3.99 (s, 3H), 3.96-3.92 (m, 1H), 3.74-3.67 (m, 1H), 3.53 (d, J=4.8 Hz, 1H), 3.50 (s, 1H), 3.36 (s, 3H), 3.29 (s, 1H), 3.19 (d, J=13.6 Hz, 1H), 3.16 (s, 3H), 3.04 (s, 1H), 2.94-2.89 (m, 3H), 2.59 (t, J=12.0 Hz, 1H), 2.44 (s, 3H), 2.25-2.21 (m, 1H), 2.05-2.00 (m, 1H), 1.70 (s, 3H), 1.54-1.44 (m, 1H), 1.52 (d, J=7.2 Hz, 3H), 1.40 (d, J=6.8 Hz, 1H), 1.30 (d, J=7.2 Hz, 3H), 1.29-1.09 (m, 2H), 0.83 (s, 3H).

Synthesis of Compound 10-10

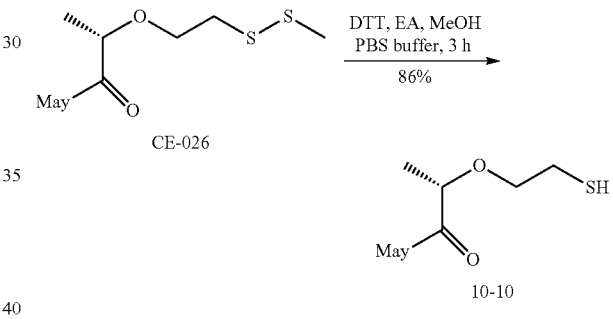

CE-026 (15 mg, 0.02 mmol) was dissolved in a mixed solution of 0.5 mL EtOAc and 0.5 mL methanol, dithiothreitol DTT (18 mg, 0.117 mmol) in 0.5 mL pH=7.5 potassium phosphate buffer was added. The reaction mixture was stirred for 3 hours under nitrogen atmosphere. 1 mL pH=6.0 potassium phosphate buffer was added to quench the reaction, the resultant mixture was then extracted with EtOAc for 3 times (5 mL×3). The organic phases were combined, washed with saturated brine (5 mL), dried over anhydrous sodium sulfate, and concentrated. The crude product was purified by prep-HPLC (CH3CN in H2O-0.05% TFA from 5% to 95%) to give 12 mg product 10-10 as white solid, yield 86%. LCMS (ESI) m/z697.3 (M+H)+.

Synthesis of Compound CE-037

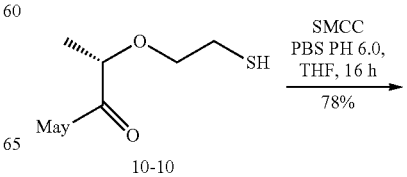

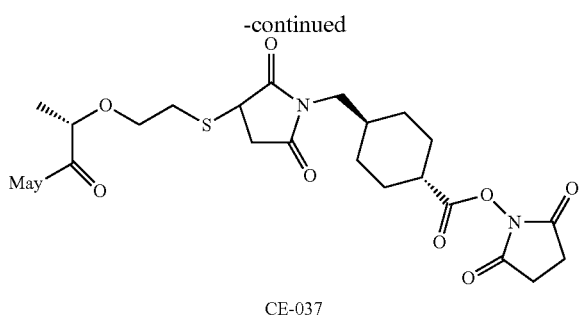

CE-037

The product 10-10 (9 mg, 0.013 mmol) obtained in the previous step was dissolved in 1.5 mL THF, 1.5 mL pH=6 potassium phosphate buffer and 4-(N-maleimidomethyl)cyclohexanecarboxylic acid N-hydroxysuccinimide ester (22 mg, 0.065 mmol) were added, the mixture was stirred overnight under nitrogen atmosphere at room temperature. The reaction mixture was filtered, purified directly by prep-HPLC to give 12 mg product CE-037 as white solid, yield 78%.

LCMS (ESI) m/z 1031.4 (M+H)$^+$. $^1$H NMR (400 MHz, CDCl$_3$) δ ppm 6.81 (d, J=8.0 Hz, 2H), 6.46 & 6.44 (dd, J$_1$=15.2 Hz, J$_2$=10.8 Hz, 1H), 6.44 (s, 1H), 6.18 (d, J=7.6 Hz, 1H), 5.59-5.51 (m, 1H), 4.97 (d, J=12.4 Hz, 1H), 4.26 (q, J=10.4 Hz, 1H), 4.13 (t, J=6.4 Hz, 1H), 3.99 (s, 3H), 3.99-3.96 (m, 2H), 3.53-3.47 (m, 2H), 3.40-3.37 (m, 2H), 3.35 (d, J=13.6 Hz, 3H), 3.35-3.30 (m, 2H), 3.21-3.15 (m, 2H), 3.13 (s, 3H), 2.92-2.82 (m, 2H), 2.82 (s, 3H), 2.60-2.58 (m, 3H), 2.25-2.15 (m, 3H), 1.70 (s, 3H), 1.70-1.60 (m, 2H), 1.54-1.44 (m, 3H), 1.52 (d, J=7.2 Hz, 3H), 1.30-1.26 (m, 6H), 1.19-1.09 (m, 2H), 0.83 (s, 3H).

Embodiment 11 Synthetic Routes for CE-039, 040, 043

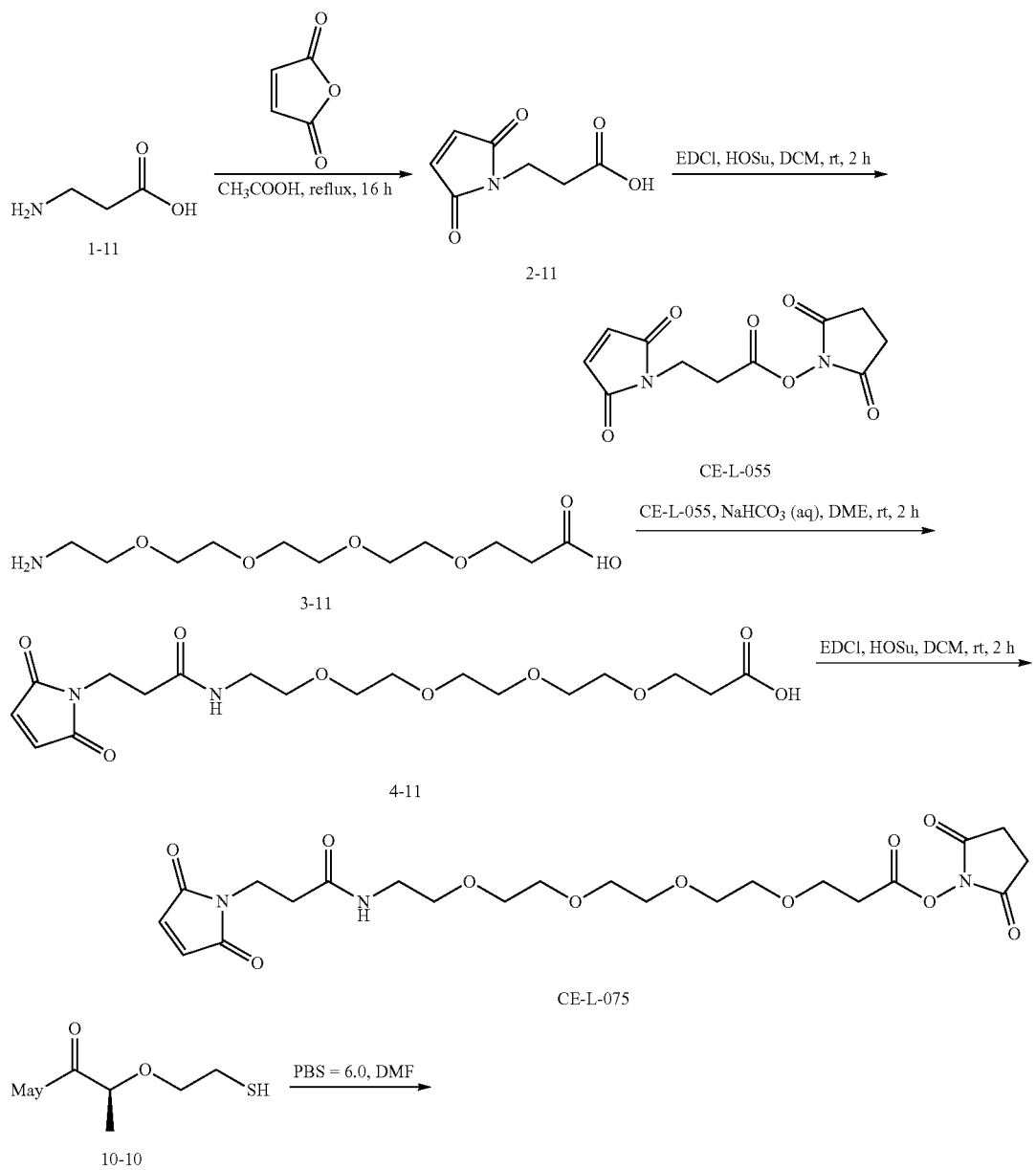

-continued

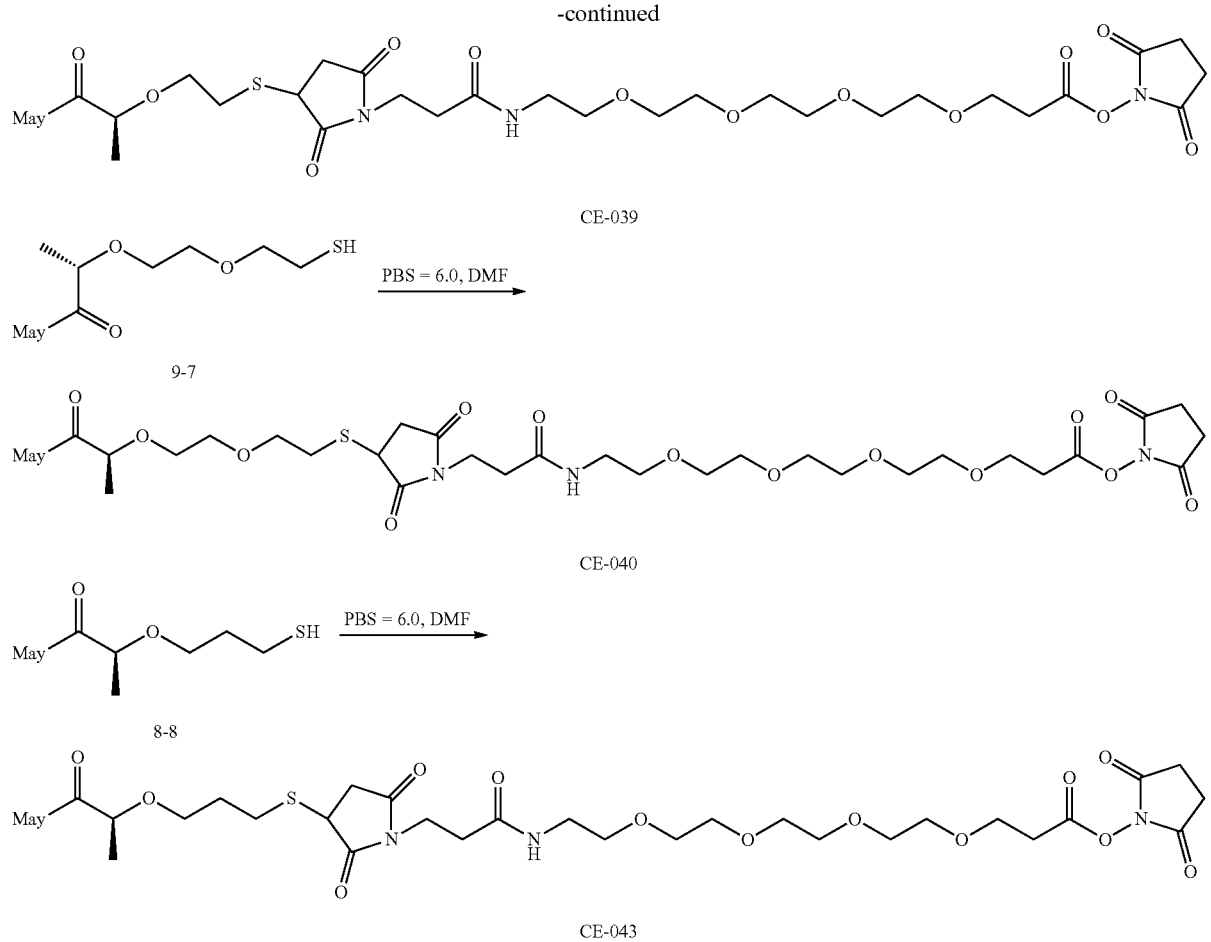

Experimental Procedure

Synthesis of Compound 2-11 reduced pressure. The residue was purified by silica gel column chromatography (DCM) to give 3.6 g product 2-11 as white solid, yield 42%. LCMS (ESI) m/z 170.1 (M+H)+.

Synthesis of Compound CE-L-055

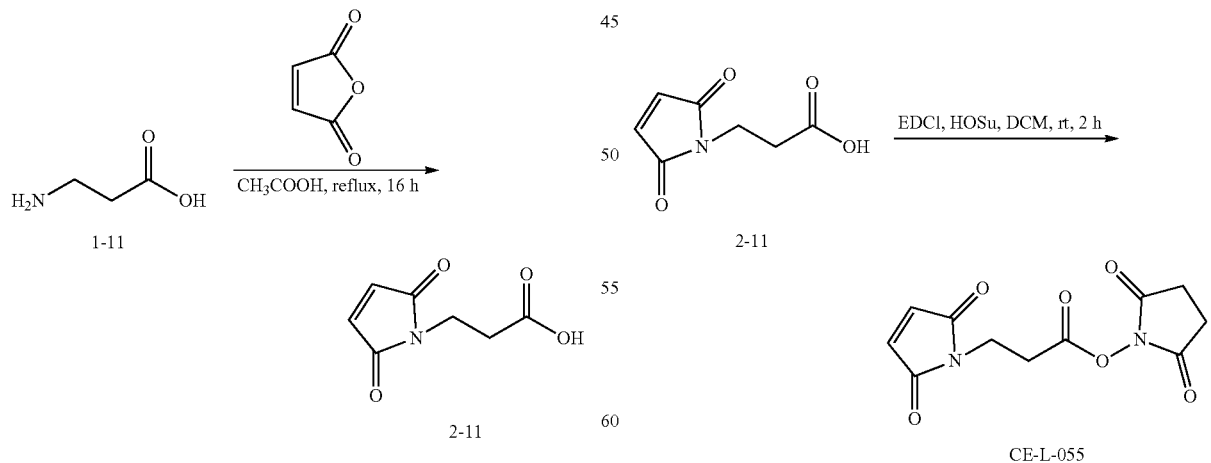

Maleic anhydride (5 g, 51 mmol, 1 eq) and (-aminopropanoic acid (4.54 g, 51 mmol, 1 eq) were dissolved in 80 mL AcOH. The reaction mixture was heated to reflux and stirred overnight under nitrogen atmosphere. The reaction mixture was cooled to room temperature, AcOH was removed under The product 2-11 (3.6 g, 21.4 mmol) obtained in the previous step and EDC-HCl (4.93 g, 25.7 mmol) were dissolved in 50 mL DCM, HOSu (2.96 g, 25.7 mol) was added. The reaction mixture was stirred for 2 hours at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:3) to give 4.55 g product as yellow oil, yield 80%. LCMS (ESI) m/z 267.1 (M+H)$^+$.

Synthesis of Compound 4-11

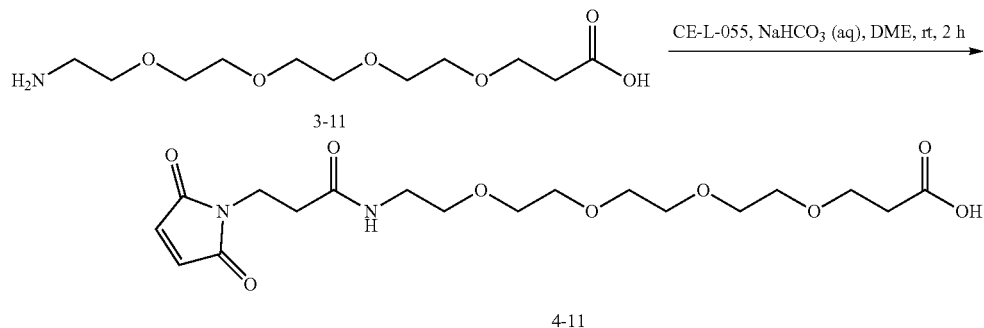

Compound 3-11 (4.55 g, 18.7 mmol) was dissolved in 10 mL water, NaHCO$_3$ (1.71 g, 20.4 mmol) was added and the mixture was stirred. CE-L-055 (4.55 g, 17 mmol) in 30 mL 1,2-dimethoxyethane was added dropwise slowly. The reaction mixture was stirred for 2 hours at room temperature. 50 mL water was added, the mixture was adjusted to pH 3-4 with 1 M dilute hydrochloric acid, and then extracted with EtOAc for 10 times (50 mL×10). The organic phases were combined, dried over anhydrous sodium sulfate, and concentrated to give the crude product, which was used directly for the next step. LCMS (ESI) m/z 417.2 (M+H)$^+$.

Synthesis of Compound CE-L-075

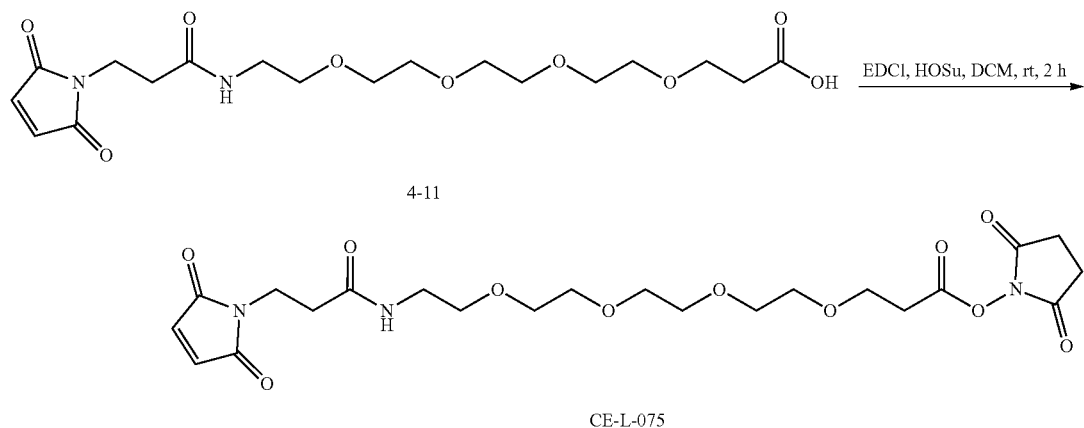

The product 4-11 (1.0 g, 2.4 mmol) obtained in the previous step and EDC·HCl (0.55 g, 2.88 mmol) were dissolved in 25 mL DCM, HOSu (0.33 g, 2.88 mmol) was added. The reaction mixture was stirred at room temperature for 2 hours. 50 mL water was added, the mixture was then extracted with EtOAc for 3 times (50 mL×3). The organic phases were combined, washed with saturated brine for 3 times (50 mL×3), dried over anhydrous sodium sulfate, and concentrated. The crude product was purified by prep-HPLC to give 330 mg product as colorless oil, yield 27%. LCMS (ESI) m/z 514.2 (M+H)$^+$.

Synthesis of Compound CE-039

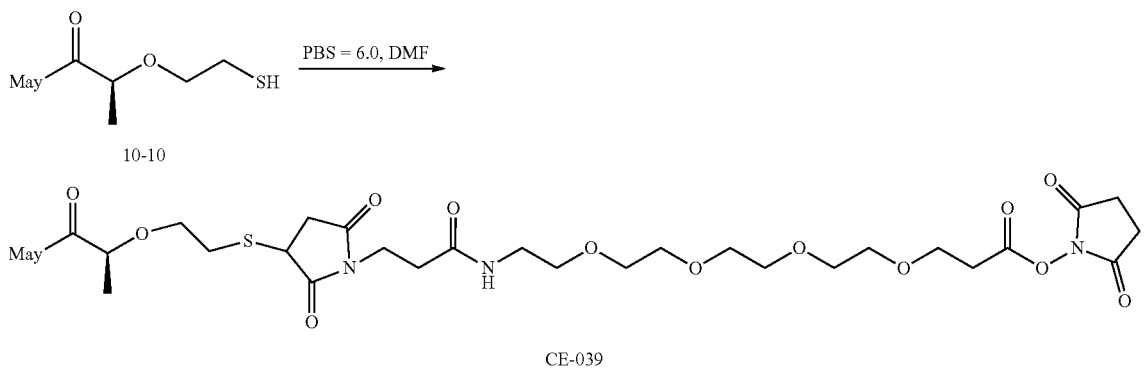

Compound 10-10 (20 mg, 0.03 mmol) was dissolved in 2 mL DMF, 0.1 mL pH=6 potassium phosphate buffer and CE-L-075 (77 mg, 0.15 mnmol) were added, the mixture was stirred overnight at room temperature under nitrogen atmosphere. The reaction mixture was filtered, purified directly by prep-HPLC to give 18 mg product CE-039 as white solid, yield 50%.

LCMS (ESI) m/z 1232.3 (M+H)$^+$, 627.8 (M/2+H)$^+$. $^1$H NMR (400 MHz, CDCl$_3$) δ ppm 7.13 (br, 1H), 6.77 (s, 1H), 6.72 (s, 1H), 6.70 (s, 1H), 6.38 & 6.36 (dd, J$_1$=12.4 Hz, J$_2$=8.8 Hz, 1H), 6.12 (d, J=9.2 Hz, 1H), 5.55-5.48 (m, 1H), 4.92 (t, J=8.4 Hz, 1H), 4.25 (q, J=7.2 Hz, 1H), 4.07 (t, J=6.8 Hz, 1H), 3.92 (s, 3H), 3.88-3.76 (m, 4H), 3.65 (s, 14H), 3.58-3.42 (m, 7H), 3.35 (s, 3H), 3.22-3.18 (m, 4H), 3.15 (s, 3H), 3.00-2.88 (m, 4H), 2.85 (s, 3H), 2.56 (t, J=7.6 Hz, 1H), 2.50 (t, J=7.2 Hz, 2H), 2.16 (d, J=12.8 Hz, 1H), 1.63 (s, 3H), 1.44 (d, J=8.4 Hz, 3H), 1.29 (d, J=8.4 Hz, 3H), 1.23-1.18 (m, 6H), 0.77 (s, 3H).

Synthesis of Compound CE-040

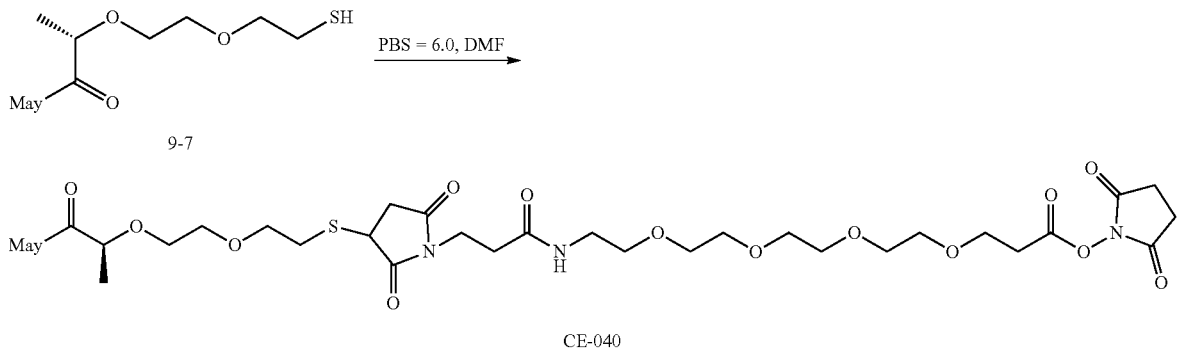

Compound 9-7 (20 mg, 0.027 mmol) was dissolved in 2 mL DMF, 0.1 mL pH=6 potassium phosphate buffer and CE-L-075 (70 mg, 0.14 mmol) were added, the mixture was stirred overnight at room temperature under nitrogen atmosphere. The reaction mixture was filtered, purified directly by prep-HPLC to give 15 mg product CE-040 as white solid, yield 44%.

LCMS (ESI) m/z 627.8 (M/2+H)$^+$. $^1$H NMR (400 MHz, CDCl$_3$) δ ppm 6.85 (s, 1H), 6.79 (s, 1H), 6.44 (t, J=12.8 Hz, 1H), 6.19 (t, J=9.2 Hz, 1H), 5.60-5.55 (m, 1H), 4.92 (t, J=8.4 Hz, 1H), 4.29 (q, J=7.6 Hz, 1H), 4.14 (t, J=6.8 Hz, 1H), 3.99 (s, 3H), 3.87-3.76 (m, 6H), 3.66 (s, 16H), 3.55-3.42 (m, 9H), 3.35 (s, 3H), 3.20 (t, J=10.8 Hz, 2H), 3.15 (s, 3H), 2.92 (t, J=6.8 Hz, 2H), 2.90-2.85 (m, 6H), 2.60-2.50 (m, 4H), 2.30-2.20 (m, 2H), 1.69 (s, 3H), 1.50 (d, J=8.4 Hz, 3H), 1.28 (d, J=8.4 Hz, 6H), 0.83 (s, 3H).

Synthesis of Compound CE-043

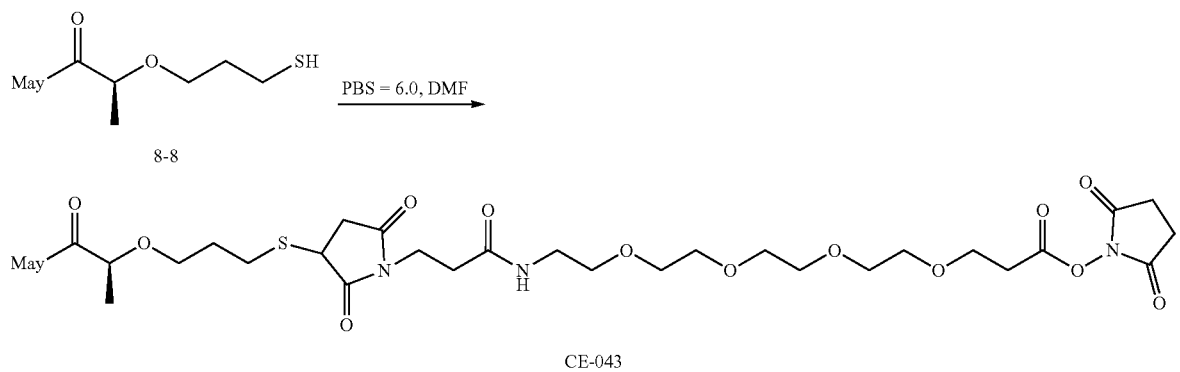

Compound 8-8 (21 mg, 0.03 mmol) was dissolved in 2 mL DMF, 0.1 mL pH=6 potassium phosphate buffer and CE-L-075 (77 mg, 0.15 mmol) were added, the mixture was stirred overnight at room temperature under nitrogen atmosphere. The reaction mixture was filtered, purified directly by prep-HPLC to give 18 mg product CE-043 as white solid, yield 49%.

LCMS (ESI) m/z 1246.4 (M+Na)$^+$, 612.8 (M/2+Na)$^+$, $^1$H NMR (400 MHz, CDCl$_3$) δ ppm 6.84 (s, 1H), 6.79 (s, 1H), 6.44 (t, J=8.8 Hz, 1H), 6.18 (d, J=8.8 Hz, 1H), 5.59-5.56 (m, 1H), 4.95 (t, J=9.2 Hz, 1H), 4.32 (q, J=7.6 Hz, 1H), 4.05 (q, J=6.8 Hz, 1H), 3.99 (s, 3H), 3.88-3.76 (m, 6H), 3.65 (s, 16H), 3.58-3.42 (m, 8H), 3.35 (s, 3H), 3.22-3.18 (m, 2H), 3.15 (s, 3H), 3.00-2.88 (m, 6H), 2.85 (s, 3H), 2.56 (t, J=7.6 Hz, 2H), 2.50 (t, J=7.2 Hz, 2H), 2.16 (d, J=12.8 Hz, 1H), 1.98-1.90 (m, 2H), 1.69 (s, 3H), 1.48 (d, J=8.4 Hz, 3H), 1.29 (d, J=8.4 Hz, 3H), 0.83 (s, 3H).

Embodiment 12 Synthetic Routes for XDCE-M-001, XDCE-M-002

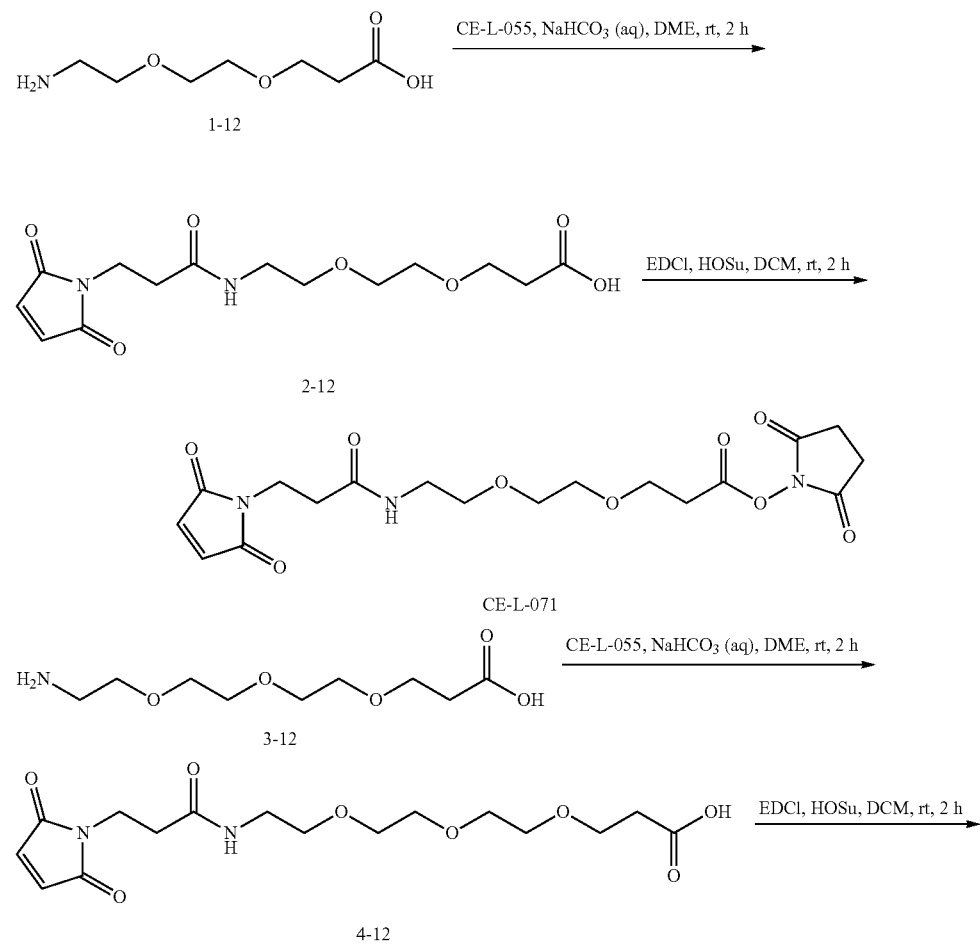

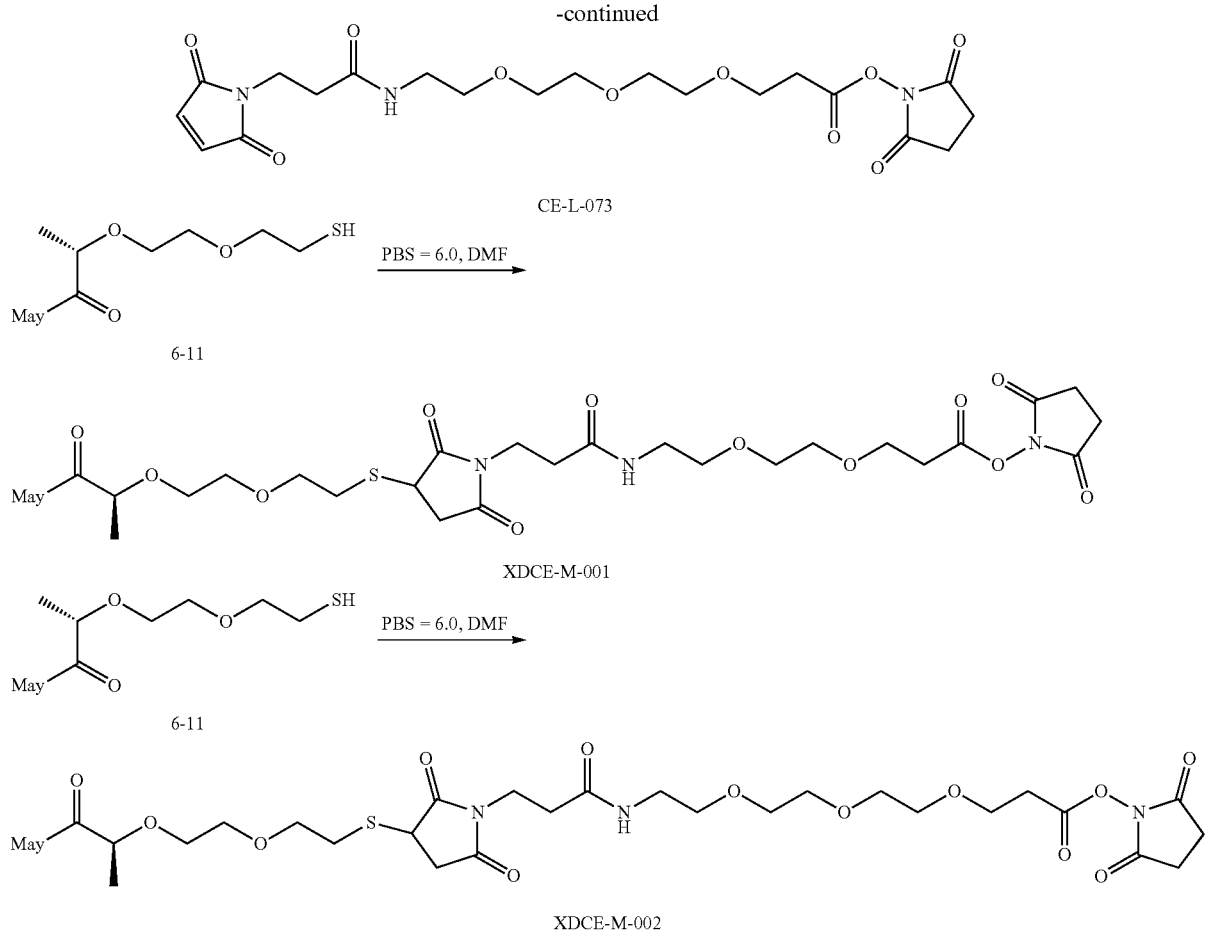

Experimental Procedure

Synthesis of Compound 2-12

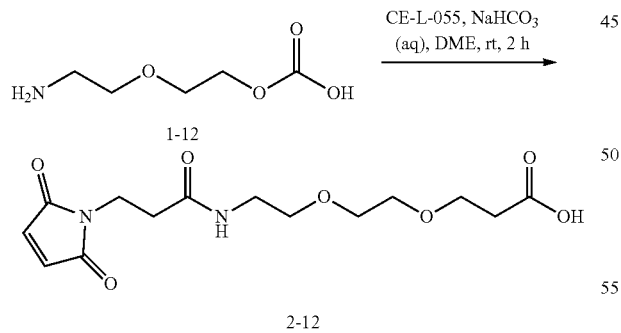

Compound 1-12 (1.77 g, 10 mmol) was dissolved in 5 mL water, NaHCO$_3$ (0.92 g, 11 mmol) was added and stirred. CE-L-055 (2.51 g, 9.5 mmol) in 15 mL 1,2-dimethoxyethane was added dropwise slowly. The reaction mixture was stirred for 2 hours at room temperature. After LCMS showed that the reaction was complete, the reaction mixture was purified directly by reversed phase column (TFA 0.05% aqueous solution) to give 1.0 g product as colorless oil, yield 48%. LCMS (ESI) m/z 329.1 (M+H)$^+$.

Synthesis of Compound CE-L-071

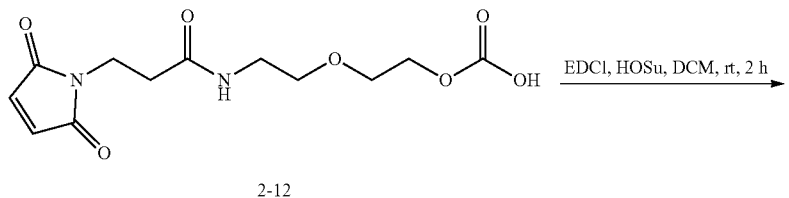

2-12

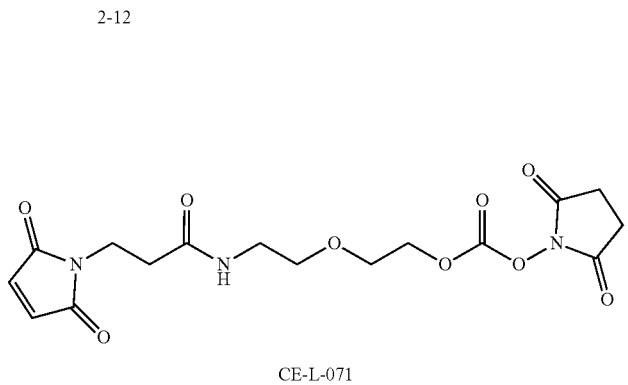

CE-L-071

The product 2-12 (1.0 g, 3.0 mmol) obtained in the previous step and EDC-HCl (0.69 g, 3.6 mmol) were dissolved in 25 mL DCM, HOSu (0.41 g, 3.6 mmol) was added. The reaction mixture was stirred at room temperature for 2 hours. After LCMS showed that the reaction was complete, the reaction mixture was concentrated. The crude product was purified by reversed phase column (TFA 0.05% aqueous solution) to give 0.32 g product as colorless oil, yield 25%. LCMS (ESI) m/z 426.3 (M+H)$^+$.

Synthesis of Compound 4-12

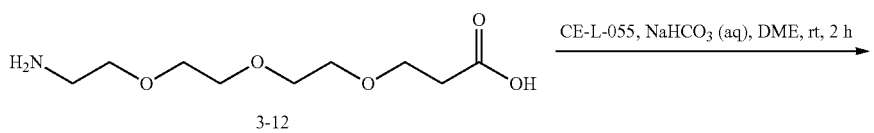

3-12

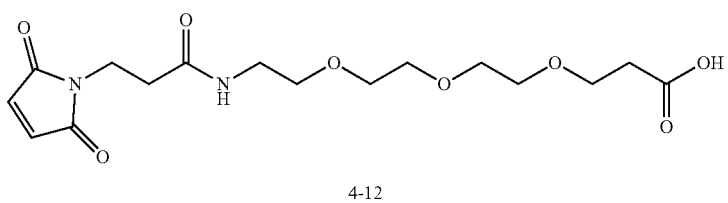

4-12

Compound 3-12 (2.21 g, 10 mmol) was dissolved in 5 mL water, NaHCO$_3$ (0.94 g, 11 mmol) was added and stirred. CE-L-055 (2.52 g, 9.5 mmol) in 15 mL 1,2-dimethoxyethane was added dropwise slowly. The reaction mixture was stirred for 2 hours at room temperature. After LCMS showed that the reaction was complete, the reaction mixture was purified directly by reversed phase column (TFA 0.05% aqueous solution) to give 1.5 g product as colorless oil, yield 42%. LCMS (ESI) m/z 373.2 (M+H)$^+$ Synthesis of Compound CE-L-073

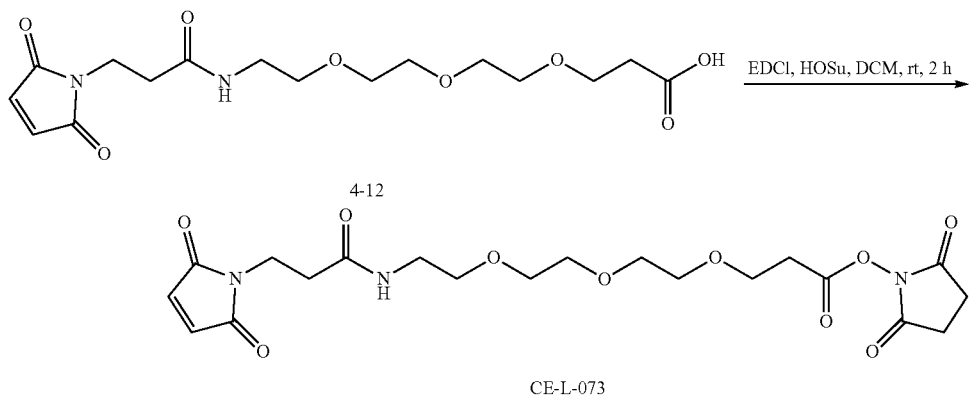

The product 4-12 (1.0 g, 2.7 mmol) obtained in the previous step and EDC-HCl (0.62 g, 3.24 mmol) were dissolved in 25 mL DCM, HOSu (0.37 g, 3.24 mmol) was added. The reaction mixture was stirred for 2 hours at room temperature. After LCMS showed that the reaction was complete, the reaction mixture was purified directly by reversed phase column (TFA 0.05% aqueous solution) to give 0.31 g product as colorless oil, yield 25%. LCMS (ESI) m/z 470.2 (M+H)$^+$ Synthesis of Compound XDCE-M-001

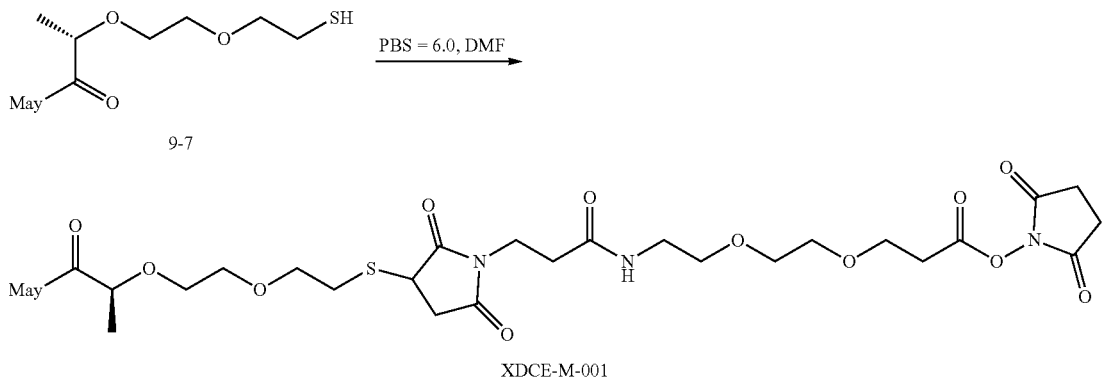

Compound 9-7 (40 mg, 0.054 mmol) was dissolved in 4 mL DMF, 0.2 mL pH=6 potassium phosphate buffer and CE-L-071 (115 mg, 0.27 mmol) were added, the mixture was stirred overnight at room temperature under nitrogen atmosphere. The reaction mixture was filtered, purified directly by prep-HPLC to give 37 mg product XDCE-M-001 as white solid, yield 59%.

LCMS (ESI) m/z 627.8 (M/2+H)$^+$. $^1$H NMR (400 MHz, CDCl$_3$) δ ppm 6.87 (br, 1H), 6.85 (s, 1H), 6.78 (s, 1H), 6.74 (br, 1H), 6.41 (t, J=13.2 Hz, 1H), 6.19 (d, J=10.8 Hz, 1H), 5.61-5.53 (m, 1H), 4.92 (d, J=11.2 Hz, 1H), 4.30 (q, J=10.4 Hz, 1H), 4.15 (q, J=7.6 Hz, 1H), 3.99 (s, 3H), 4.04-3.96 (m, 1H), 3.87-3.76 (m, 6H), 3.70-3.60 (m, 6H), 3.56-3.42 (m, 9H), 3.36 (s, 3H), 3.20 (d, J=10.8 Hz, 2H), 3.15 (s, 3H), 2.92-2.85 (m, 8H), 2.62-2.50 (m, 4H), 2.23 (d, J=14.4 Hz, 1H), 1.69 (s, 3H), 1.51-1.48 (m, 3H), 1.30-1.25 (m, 6H), 0.83 (s, 3H).

Synthesis of Compound XDCE-M-002

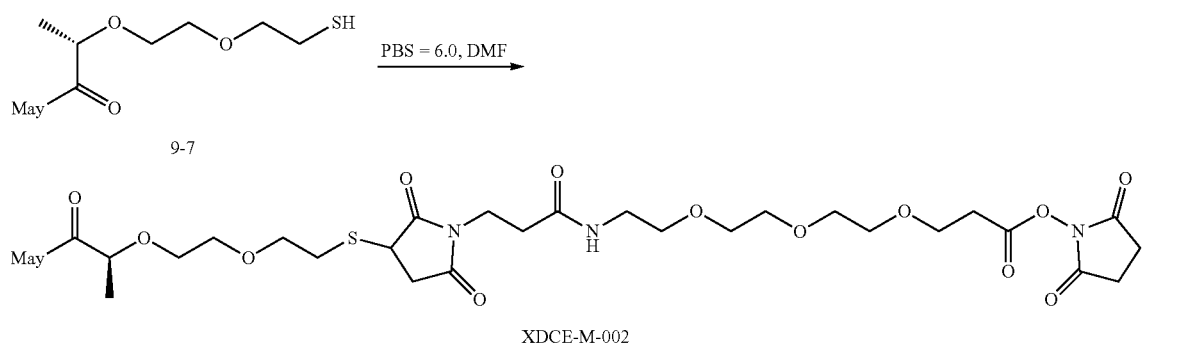

Compound 9-7 (40 mg, 0.054 mmol) was dissolved in 4 mL DMF, 0.2 mL pH=6 potassium phosphate buffer and CE-L-073 (127 mg, 0.27 mmol) were added, the mixture was stirred overnight at room temperature under nitrogen atmosphere. The reaction mixture was purified directly by prep-HPLC to give 34 mg product XDCE-M-002 as white solid, yield 52%.

LCMS (ESI) m/z 627.8 (M/2+H)$^+$. $^1$H NMR (400 MHz, CDCl$_3$) δ ppm 7.08 (br, 1H), 6.86-6.81 (m, 1H), 6.84 (s, 1H), 6.79 (s, 1H), 6.44 (dd, J$_1$=15.2 Hz, J$_2$=10.8 Hz, 1H), 6.19 (d, J=10.8 Hz, 1H), 5.60-5.55 (m, 1H), 4.92 (t, J=10.8 Hz, 1H), 4.29 (q, J=7.6 Hz, 1H), 4.13 (t, J=6.8 Hz, 1H), 4.05-3.95 (m, 1H), 3.99 (s, 3H), 3.87-3.76 (m, 6H), 3.70-3.60 (m, 10H), 3.56-3.42 (m, 10H), 3.36 (s, 3H), 3.20 (d, J=10.8 Hz, 2H), 3.15 (s, 3H), 2.92-2.85 (m, 8H), 2.62-2.50 (m, 4H), 2.23 (d, J=14.4 Hz, 1H), 1.69 (s, 3H), 1.51-1.48 (m, 3H), 1.30-1.25 (m, 6H), 0.83 (s, 3H).

Embodiment 13 Synthetic Route for CE-045

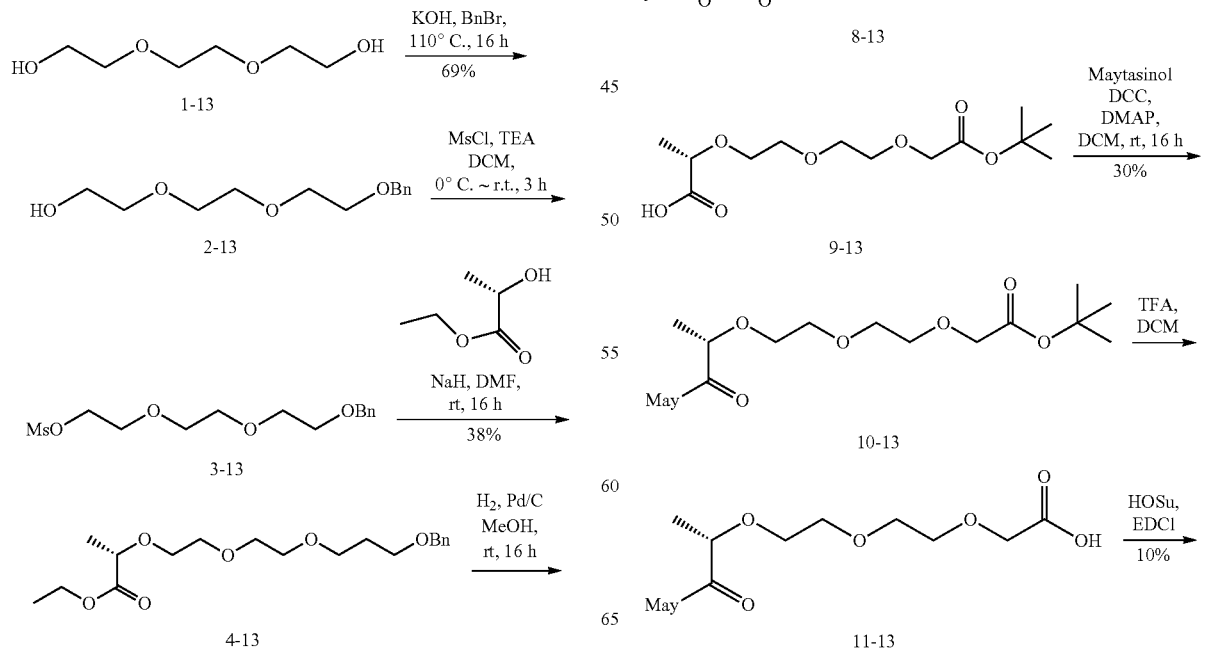

-continued

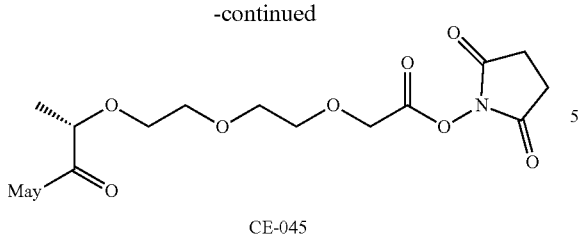

CE-045

Experimental Procedure

Synthesis of Compound 2-13

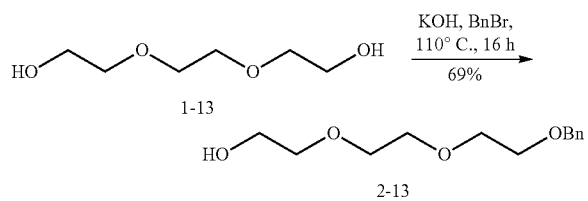

Compound 1-13 (135 g, 0.9 mol) was added to a 500 mL eggplant shaped bottle, KOH (16.8 g, 0.3 mol) was added while stirring. The suspension was heated to 90° C., and stirred till KOH was completely dissolved. BnBr (35.6 mL, 0.3 mol) was added dropwise slowly. The reaction mixture was heated to 110° C. and stirred overnight. The reaction mixture was cooled to room temperature, 1000 mL water was added, then extracted with EtOAc for 3 times (200 mL×3). The organic phases were combined, washed with water for 3 times (150 mL×3) and saturated brine (150 mL), dried over anhydrous sodium sulfate, and concentrated. The crude product was purified by silica gel column chromatography (PE/EtOAc 10:1-1:1) to give 50 g product 2-13 as colorless oil, yield 69%. LCMS (ESI) m/z 240.3 (M+H)$^+$.

Synthesis of Compound 3-13

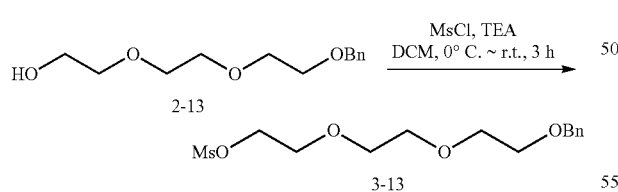

The product 2-13 (24 g, 0.1 mol) obtained in the previous step and Et$_3$N (16.6 mL, 0.12 mol) were dissolved in 150 mL DCM, the mixture was cooled to 0° C., methanesulfonyl chloride (8.5 mL, 0.11 mol) was added dropwise. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give 30 g crude product 3-13 as yellow oil, which was used directly for the next step.

Synthesis of Compound 4-13

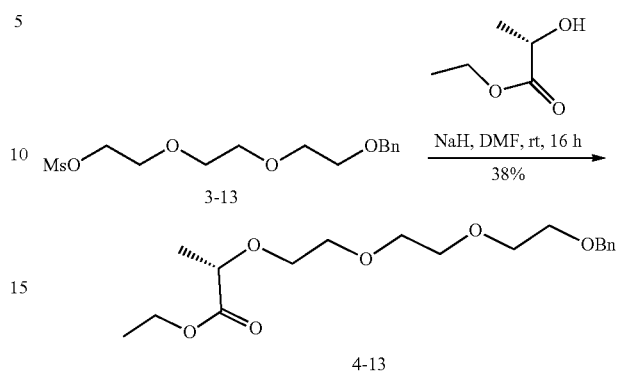

The product 3-13 (15.9 g, 0.05 mol) obtained in the previous step and L-ethyl lactate (11.8 g, 0.1 mol) were dissolved in 80 mL DMF, the mixture was cooled to 0° C., NaH (4 g, 60%, suspended in mineral oil, 0.1 mol) was added in batches slowly. The reaction mixture was warmed to room temperature and stirred overnight. The reaction mixture was cooled to 0° C., 20 mL saturated ammonium chloride solution was added dropwise slowly to quench the reaction, 150 mL water was added, the mixture was extracted with EtOAc for 3 times (100 mL×3), the organic phases were combined, washed with water for 3 times (50 mL×3) and saturated brine (50 mL), dried over anhydrous sodium sulfate, and concentrated. The crude product was purified by silica gel column chromatography (PE/EtOAc=10:1-2:1) to give 6.5 g product 4-13 as light yellow oil, yield 38%. LCMS (ESI) m/z 341.7 (M+H)$^+$ Synthesis of Compound 5-13

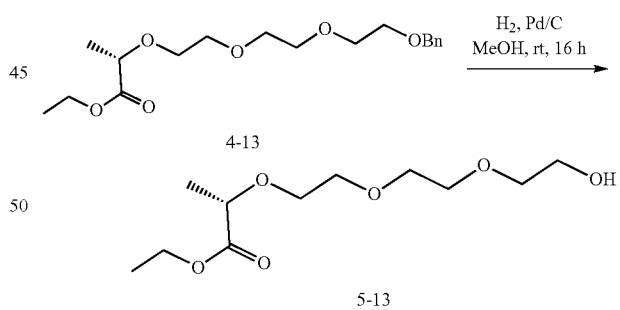

The product 4-13 (13.6 g, 40 mmol) obtained in the previous step was dissolved in 50 mL methanol, the mixture was purged by nitrogen for 3 times, 200 mg 10% Pd/C dry powder was added. The reaction mixture was purged by hydrogen gas for 3 times, the mixture was stirred overnight at room temperature under hydrogen atmosphere. The reaction mixture was then purged by nitrogen for 3 times, 50 mL DCM was added, filtered, washed with DCM, the filtrate was concentrated to give 10.0 g crude product as light yellow oil, which was used directly for the next step. LCMS (ESI) m/z 251.1 (M+H)$^+$.

Synthesis of Compound 6-13

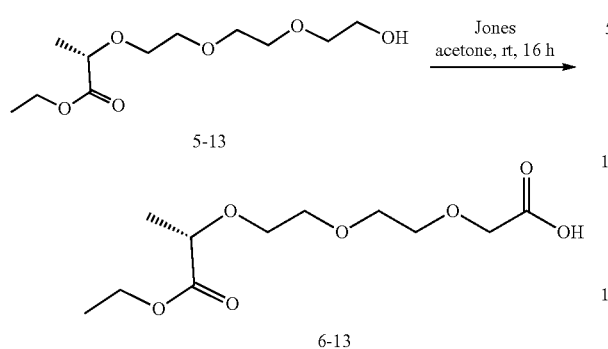

The product 5-13 (2.5 g, 10 mmol) obtained in the previous step was dissolved in 30 mL acetone, the mixture was cooled in an ice bath to 0° C., Jones reagent (3 g, 30 mmol) was added dropwise slowly over about 10 min. The reaction mixture was warmed to room temperature and stirred overnight, 2 mL 2-propanol was added to quench the reaction, acetone was removed under reduced pressure, and the residue was extracted with DCM for 3 times (50 mL×3). The organic phases were combined, dried over anhydrous sodium sulfate, and concentrated to give the crude product as light yellow oil, which was used directly for the next step. LCMS (ESI) m/z 265.7 (M+H)$^+$.

Synthesis of Compound 8-13

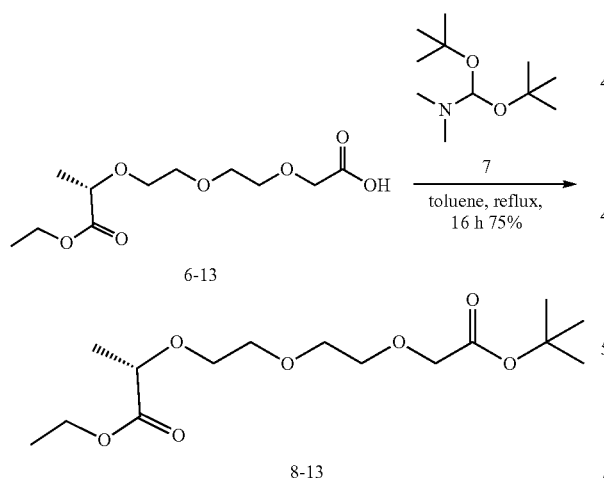

Under nitrogen atmosphere, the product 6-13 (264 mg, 1 mmol) obtained in the previous step was dissolved in 10 mL toluene, the reaction mixture was heated to reflux, 7 (264 mg, 1 mmol) was added dropwise slowly, the reaction mixture was stirred at reflux overnight. The reaction mixture was cooled to room temperature, concentrated under reduced pressure. The crude product was purified by silica gel column chromatography (PE/EtOAc=2:1) to give 240 mg product 8-13 as colorless oil, yield 75%. LCMS (ESI) m/z 321.7 (M+H)$^+$, $^1$H NMR (400 MHz, CDCl$_3$) δ ppm 4.21 (q, J=6.8 Hz, 2H), 4.03 (s, 2H), 3.76-3.67 (m, 8H), 3.61-3.58 (m, 1H), 1.48 (s, 9H), 1.41 (d, J=5.6 Hz, 3H), 1.29 (t, J=6.0 Hz, 3H).

Synthesis of Compound 9-13

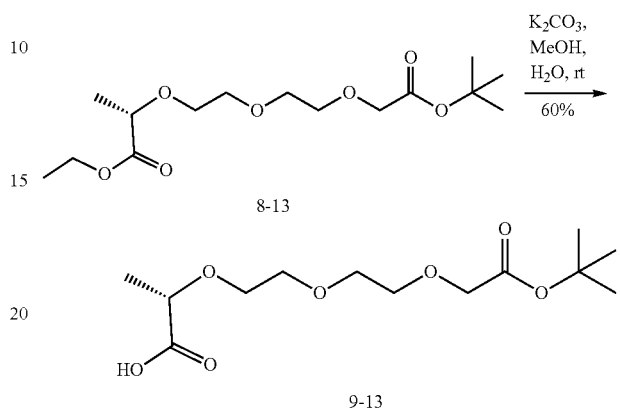

The product 8-13 (1.83 g, 5.7 mmol) obtained in the previous step was dissolved in 50 mL methanol and 20 mL water, K$_2$CO$_3$ (4 g, 28.7 mmol) was added. The reaction mixture was stirred for 3 hours at room temperature. After the starting material was completely consumed, methanol was removed under reduced pressure, 50 mL water was added, 1N HCl was added dropwise slowly to adjust pH to 4-5, then the mixture was extracted with EtOAc for 3 times (50 mL×3). The organic phases were combined, washed with saturated brine (50 mL), dried over anhydrous sodium sulfate, concentrated. The crude product was purified by silica gel column chromatography (PE/EtOAc=1:1) to give 1.0 g product 9-13 as light yellow oil, yield 60%. LCMS (ESI) m/z 293.1 (M+H)$^+$.

Synthesis of Compound 10-13

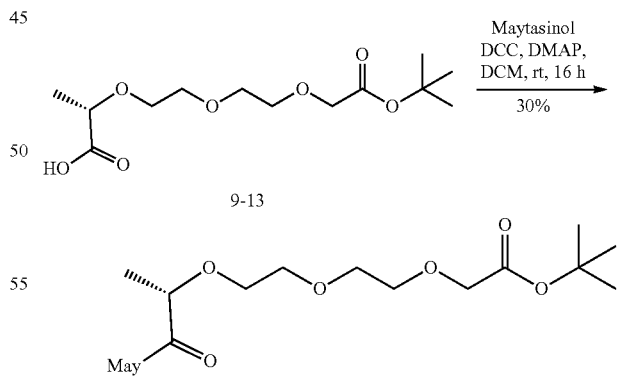

The product 9-13 (105 mg, 0.36 mmol) obtained in the previous step, DCC (148 mg, 0.72 mmol) and DMAP (29 mg, 0.24 mmol) were added into a dry Schlenk tube, the mixture was purged by argon for 3 times, 1 mL DCM was added and stirred. Maytansinol (63 mg, 0.12 mmol) in 2 mL dry DCM was added. The reaction mixture was stirred for 2 hours at room temperature, 0.3 mL water was added slowly to quench the reaction, then 15 mL EtOAc was added, filtered, and washed with EtOAc. The filtrate was dried over anhydrous sodium sulfate, and concentrated. The crude product was purified by prep-HPLC to give 28 mg product 10-13 as white solid, yield 30%. LCMS (ESI) m/z 838.2 (M+H)$^+$.

Synthesis of Compound 11-13

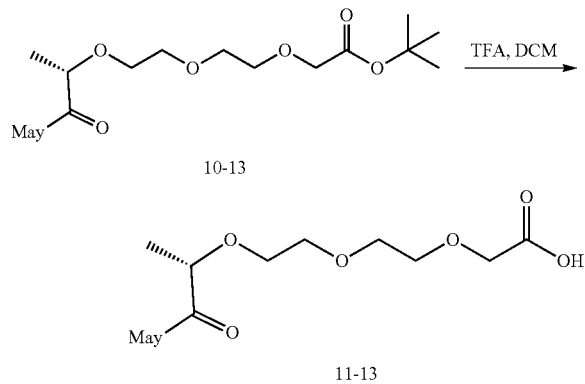

The product 10-13 (28 mg, 0.03 mmol) obtained in the previous step was dissolved in 28 mL DCM, TFA (4.2 mL) was added. The reaction mixture was stirred for 2 hours at room temperature. After the starting material was completely consumed, the mixture was concentrated under reduced pressure to give 18.3 mg crude product 11-13 as light yellow oil, which was used directly for the next step.

Synthesis of Compound CE-045

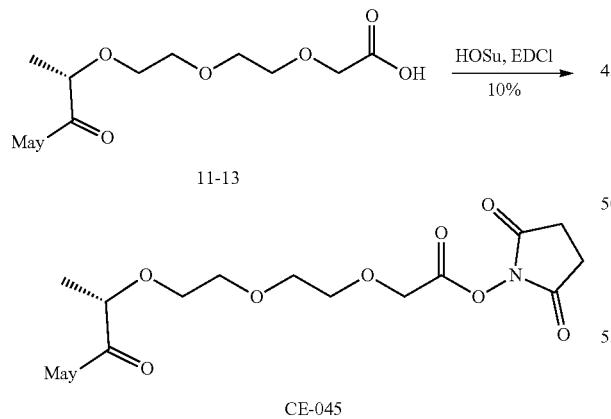

The product 11-13 (18.3 mg, 0.023 mmol) obtained in the previous step was dissolved in 2 mL DMF, HOSu (13.2 mg, 0.11 mmol) and EDCI (21 mg, 0.11 mmol) was added. The reaction mixture was stirred for 2 hours at room temperature, then purified directly by prep-HPLC to give 2 mg product CE-045 as white solid, yield 10%. LCMS (ESI) m/z 880.3 (M+H)$^+$.

Embodiment 14 Synthetic Routes for CE-047, CE-050

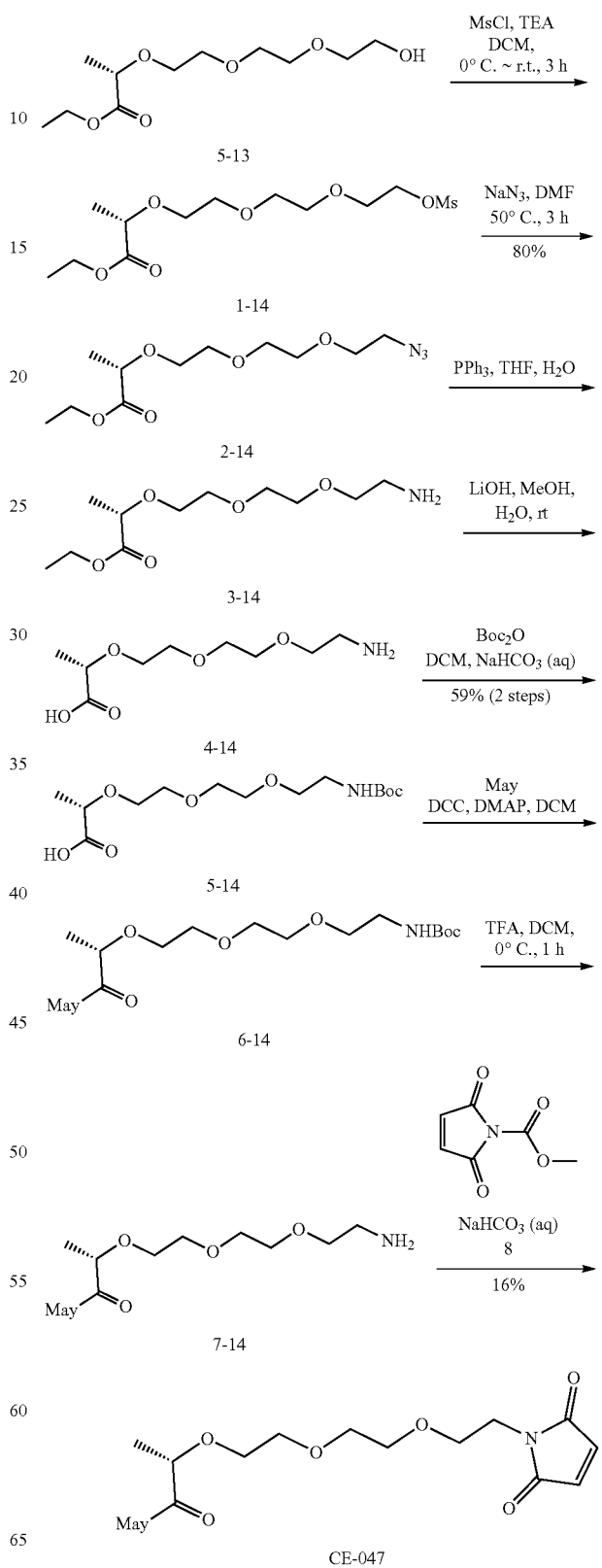

157

-continued

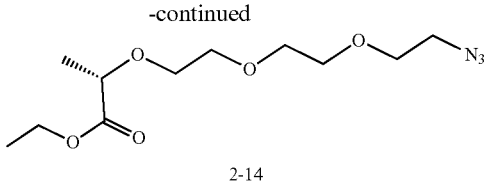

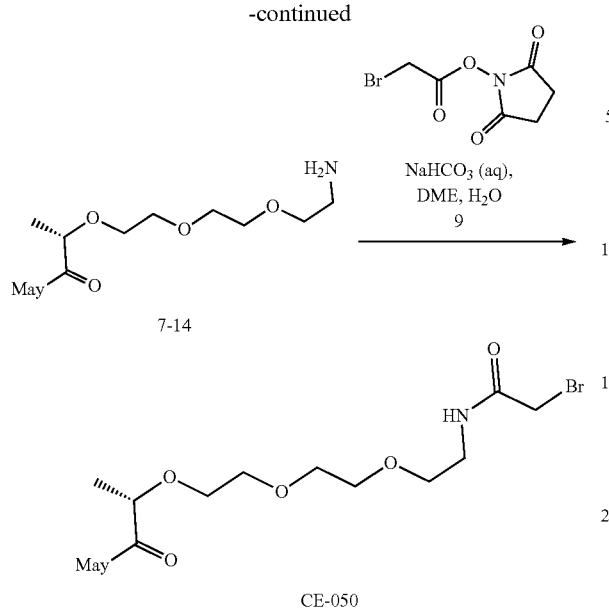

Experimental Procedure

Synthesis of Compound 1-14

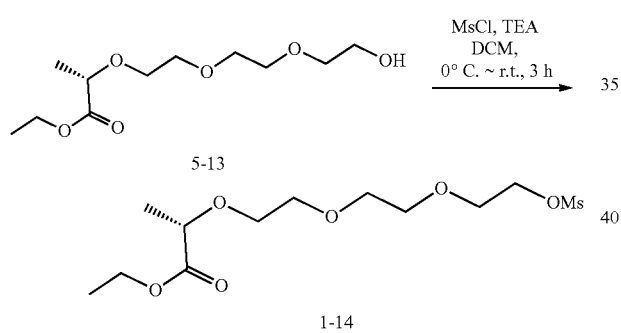

5-13 (2.5 g, 10 mmol) obtained in the previous step and Et₃N (1.7 mL, 12 mmol) were dissolved in 30 mL DCM, the mixture was cooled to 0° C., methanesulfonyl chloride (0.85 mL, 11 mmol) was added dropwise. The reaction mixture was warmed to room temperature and stirred for 2 hours. 30 mL water was added to quench the reaction, the organic phase was separated, washed with saturated brine for 3 times (30 mL×3), dried over anhydrous sodium sulfate, and concentrated to give 3.2 g crude product 1-14 as light yellow oil, which was used directly for the next step.

Synthesis of Compound 2-14

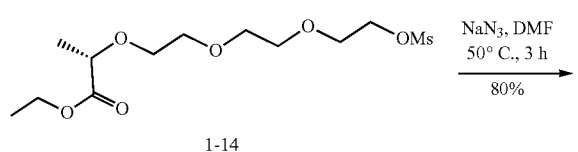

158

-continued

The product 1-14 (3.2 g, 10 mmol) obtained in the previous step was dissolved in 20 mL DMF, NaN₃ (715 mg, 11 mmol) was added. The reaction mixture was heated to 50° C. and stirred overnight. The reaction mixture was cooled to room temperature and 50 mL water was added to quench the reaction, then extracted with EtOAc for 3 times (30 mL×3). The organic phases were combined, washed with saturated brine for 3 times (30 mL×3), dried over anhydrous sodium sulfate, and concentrated to give the crude product which was purified by silica gel column chromatography (PE/EtOAc=2:1) to give 2.2 g product 2-14 as light yellow oil, yield 80%.

Synthesis of Compound 3-14

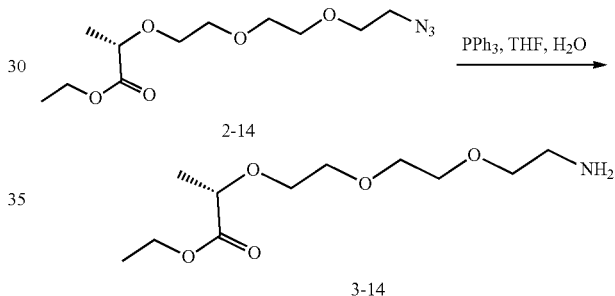

The product 2-14 (2.2 g, 8 mmol) obtained in the previous step was dissolved in 40 mL THF and 5 mL water, PPh₃ (2.62 g, 10 mmol) was added. The reaction mixture was stirred overnight at room temperature. THF was removed under reduced pressure, 20 mL 1 N dilute hydrochloric acid was added, washed with EtOAc for 3 times (20 mL×3), the aqueous phase was freezed-drying to give 1.6 g crude product 3-14 as light yellow oil. LCMS (ESI) m/z 250.7 (M+H)⁺.

Synthesis of Compound 5-14

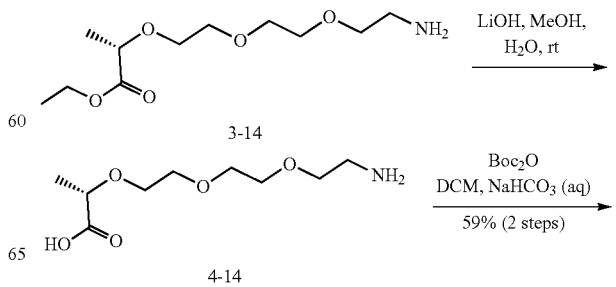

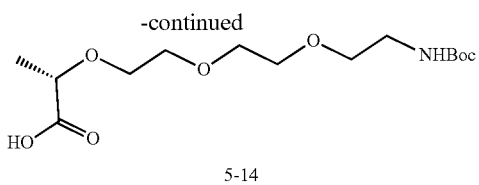

5-14

The product 3-14 (1.25 g, 5 mmol) obtained in the previous step was dissolved in 20 mL methanol and 5 mL water, lithium hydroxide monohydrate (840 mg, 20 mmol) was added. The reaction mixture was stirred for 3 hours at room temperature. After the starting material was completely consumed, methanol was removed under reduced pressure, saturated sodium bicarbonate solution 5 mL and 30 mL were added, the mixture was cooled in an ice bath to 0° C., Boc$_2$O (1.3 g, 6 mmol) was added, then the mixture was warmed to room temperature and stirred for 2 hours. The reaction mixture was washed with water for 2 times (20 mL×2), the aqueous phases were combined, 0.5 M KHSO$_4$ solution was added to quench the reaction and adjust pH to 3-4, the mixture was extracted with DCM for 3 times (20 mL×3), the organic phases were combined, dried over anhydrous sodium sulfate, and concentrated, the residue was purified by silica gel column chromatography (DCM/methanol=30:1) to give 950 mg product 5-14 as light yellow oil, yield 59%. LCMS (ESI) m/z 322.3 (M+H)$^+$.

Synthesis of Compound 6-14

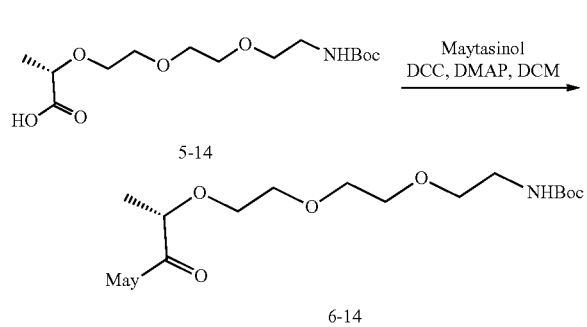

The product 5-14 (77 mg, 0.24 mmol) obtained in the previous step, DCC (132 mg, 0.64 mmol) and DMAP (20 mg, 0.16 mmol) were added to a dry Schlenk tube, the mixture was purged by argon for 3 times, 1 mL DCM was added and stirred. Maytansinol (45 mg, 0.08 mmol) in 3 mL dry DCM was added. The reaction mixture was stirred overnight at room temperature, 0.3 mL water was added slowly to quench the reaction and the mixture was stirred for 15 min, then 15 mL EtOAc was added, the mixture was filtered, washed with EtOAc. The filtrate was dried over anhydrous sodium sulfate, and concentrated. The crude product was purified by prep-HPLC to give 32 mg product 6-14 as light yellow solid, yield 46%. LCMS (ESI) m/z 868.7 (M+H)$^+$.

Synthesis of Compound 7-14

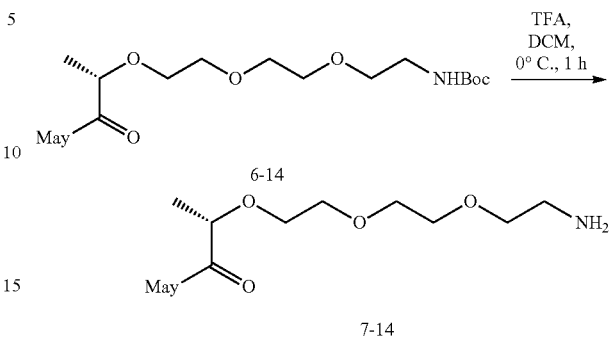

The product 6-14 (17 mg, 0.02 mmol) obtained in the previous step was dissolved in 4 mL dry DCM, the mixture was cooled in an ice bath to 0° C., 0.4 mL TFA was added dropwise slowly, then the mixture was gradually warmed to room temperature and stirred for 1 hours, after LCMS showed that the starting material was completely consumed, DCM and TFA was reduced under reduced pressure at ambient temperature to give 15 mg crude product 7-14 as yellow solid, which was used directly for the next step. LCMS (ESI) m/z 768.7 (M+H)$^+$.

Synthesis of Compound CE-047

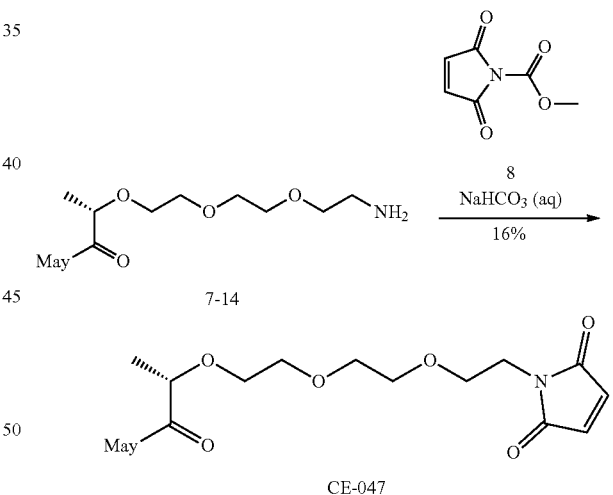

The crude product 7-14 (15 mg, 0.02 mmol) obtained in the previous step was suspended in 2 mL saturated sodium bicarbonate solution, compound 8 (15.5 mg, 0.1 mmol) was added, the reaction mixture was stirred overnight at room temperature, then extracted with DCM for 3 times (20 mL×3). The organic phases were combined, washed with saturated brine for 3 times (20 mL×3), dried over anhydrous sodium sulfate, and concentrated to give crude product. The crude product was purified by prep-HPLC to give 2.7 mg product CE-047 as light yellow solid, yield 16%. LCMS (ESI) m/z 848.7 (M+H)$^+$.

$^1$H NMR (400 MHz, MeOD) δ ppm 7.06 (s, 1H), 6.81 (s, 1H), 6.55 & 6.53 (dd, J$_1$=12.4 Hz, J$_2$=8.8 Hz, 1H), 6.38 (d, J=8.8 Hz, 1H), 6.21-6.15 (m, 2H), 5.51&5.49 (dd, $J_1$=12.4 Hz, $J_2$=7.2 Hz, 1H), 4.73 (d, J=8.0 Hz, 1H), 4.15-4.18 (m, 2H), 3.88 (s, 3H), 3.72-3.64 (m, 1H), 3.62-3.53 (m, 10H), 3.49-3.46 (m, 2H), 3.41 (t, J=4.8 Hz, 2H), 3.26 (s, 3H), 3.04 (s, 3H), 2.69 (d, J=8.0 Hz, 1H), 2.56 (t, J=10.0 Hz, 1H), 2.11 (d, J=10.0 Hz, 1H), 1.64 (s, 3H), 1.50-1.42 (m, 2H), 1.40 (d, J=5.6 Hz, 3H), 1.14 (d, J=5.6 Hz, 3H), 0.78 (s, 3H).

Synthesis of Compound CE-050

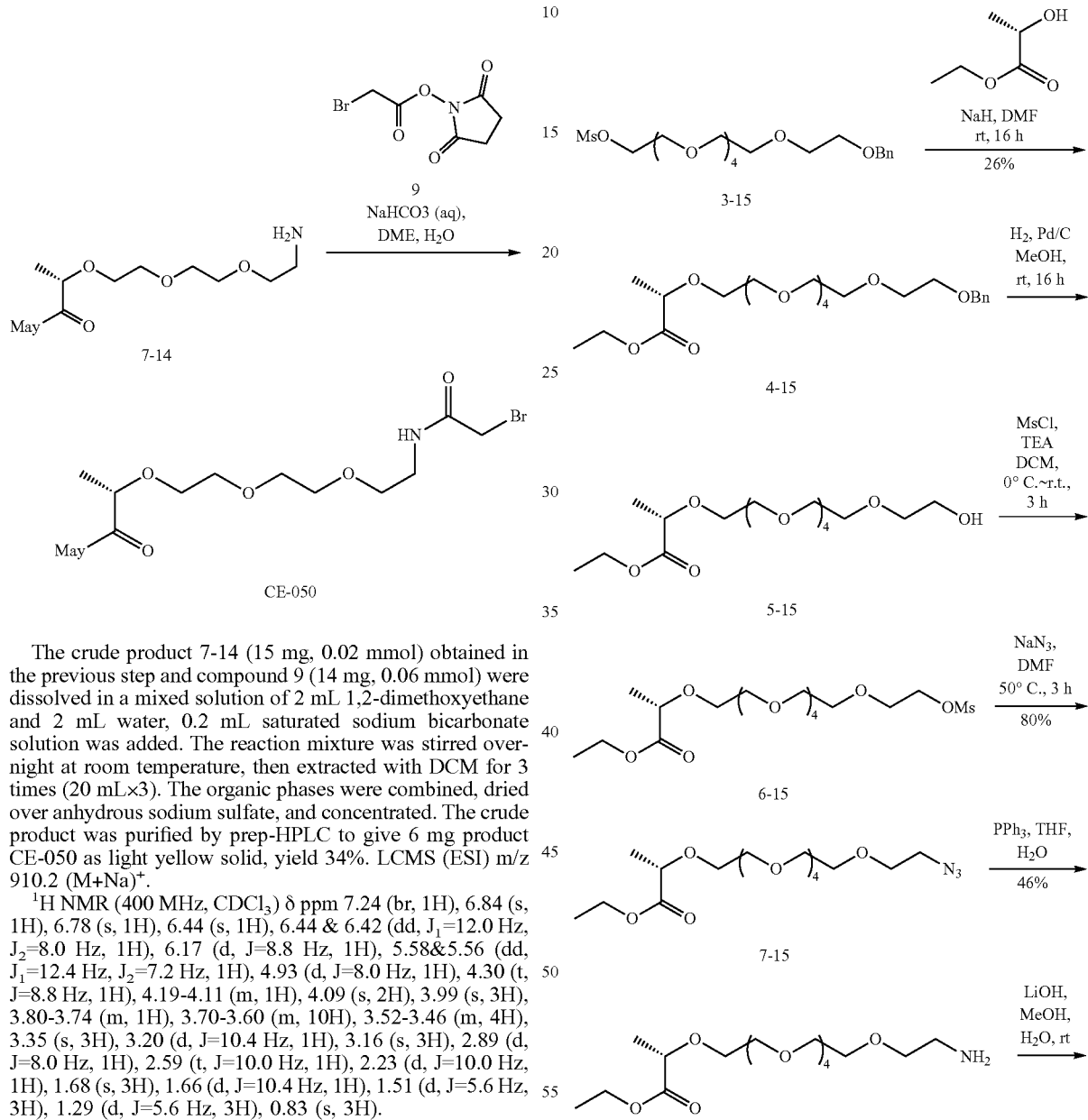

The crude product 7-14 (15 mg, 0.02 mmol) obtained in the previous step and compound 9 (14 mg, 0.06 mmol) were dissolved in a mixed solution of 2 mL 1,2-dimethoxyethane and 2 mL water, 0.2 mL saturated sodium bicarbonate solution was added. The reaction mixture was stirred overnight at room temperature, then extracted with DCM for 3 times (20 mL×3). The organic phases were combined, dried over anhydrous sodium sulfate, and concentrated. The crude product was purified by prep-HPLC to give 6 mg product CE-050 as light yellow solid, yield 34%. LCMS (ESI) m/z 910.2 (M+Na)$^+$.

$^1$H NMR (400 MHz, CDCl$_3$) δ ppm 7.24 (br, 1H), 6.84 (s, 1H), 6.78 (s, 1H), 6.44 (s, 1H), 6.44 & 6.42 (dd, $J_1$=12.0 Hz, $J_2$=8.0 Hz, 1H), 6.17 (d, J=8.8 Hz, 1H), 5.58&5.56 (dd, $J_1$=12.4 Hz, $J_2$=7.2 Hz, 1H), 4.93 (d, J=8.0 Hz, 1H), 4.30 (t, J=8.8 Hz, 1H), 4.19-4.11 (m, 1H), 4.09 (s, 2H), 3.99 (s, 3H), 3.80-3.74 (m, 1H), 3.70-3.60 (m, 10H), 3.52-3.46 (m, 4H), 3.35 (s, 3H), 3.20 (d, J=10.4 Hz, 1H), 3.16 (s, 3H), 2.89 (d, J=8.0 Hz, 1H), 2.59 (t, J=10.0 Hz, 1H), 2.23 (d, J=10.0 Hz, 1H), 1.68 (s, 3H), 1.66 (d, J=10.4 Hz, 1H), 1.51 (d, J=5.6 Hz, 3H), 1.29 (d, J=5.6 Hz, 3H), 0.83 (s, 3H).

Embodiment 15 Synthetic Routes for CE-046, CE-052a

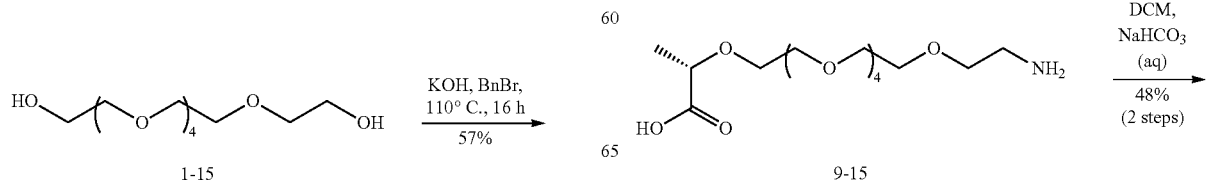

163
-continued

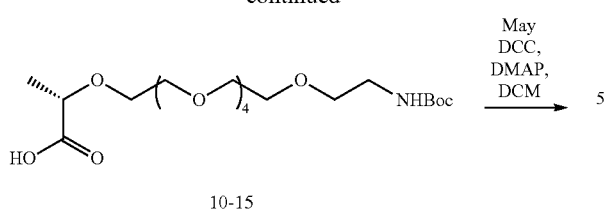
10-15

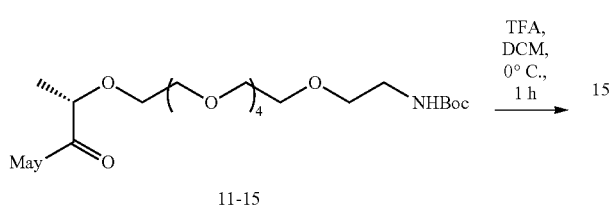
11-15

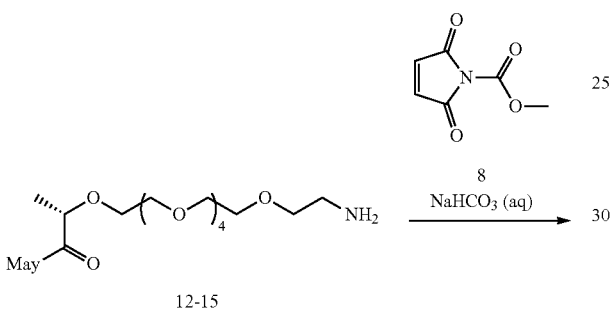
12-15

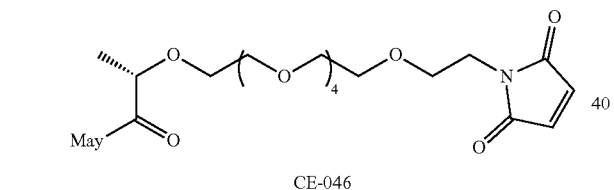
CE-046

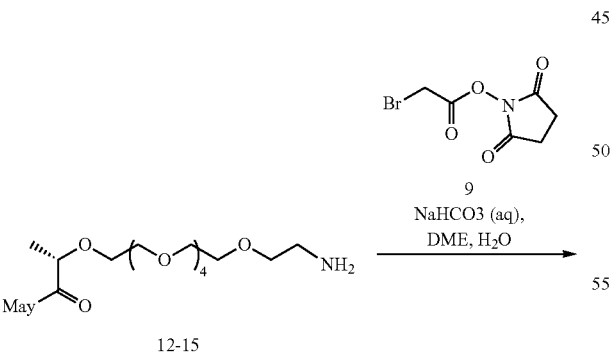
12-15

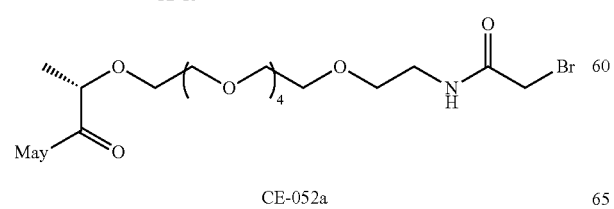
CE-052a

164
Experimental Procedure

Synthesis of Compound 2-15

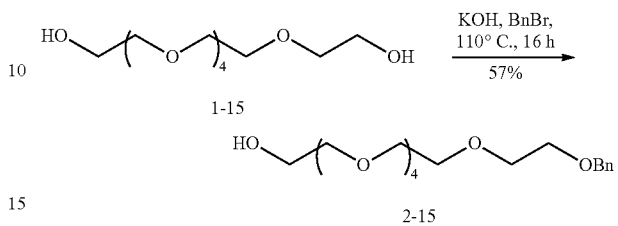
1-15

2-15

Compound 1-15 (70.5 g, 0.25 mol) was added to a 250 mL eggplant shaped bottle, KOH (5.6 g, 0.1 mol) was added while stirring. The suspension was heated to 90° C., and stirred till KOH was completely dissolved. BnBr (17 g, 11.8 mL, 0.1 mol) was added dropwise slowly. The reaction mixture was heated to 110° C. and stirred overnight. The reaction mixture was cooled to room temperature, 800 mL water was added, the resultant mixture was extracted with EtOAc for 3 times (150 mL×3). The organic phases were combined, washed with water for 3 times (150 mL×3) and saturated brine (150 mL), dried over anhydrous sodium sulfate, and concentrated. The crude product was purified by silica gel column chromatography (PE/EtOAc 10:1-1:1) to give 21 g product 2-15 as colorless oil, yield 57%. LCMS (ESI) m/z 373.3 (M+H)$^+$.

Synthesis of Compound 3-15

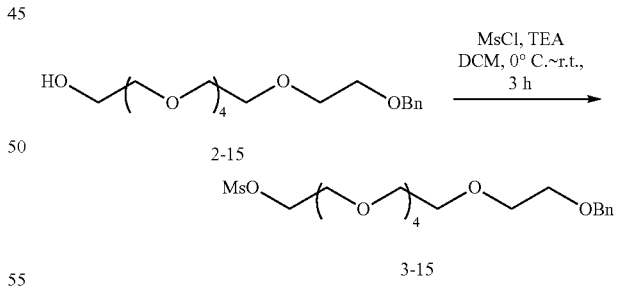
2-15

3-15

The product 2-15 (14.9 g, 0.04 mol) obtained in the previous step and Et$_3$N (6.64 mL, 0.048 mol) were dissolved in 80 mL DCM, the mixture was cooled to 0° C., methanesulfonyl chloride (3.4 mL, 0.044 mol) was added dropwise. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give 18 g crude product 3-15 as yellow oil, which was used directly for the next step.

Synthesis of Compound 4-15

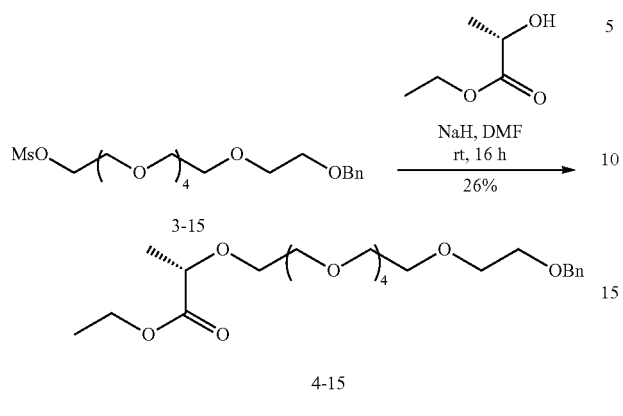

4-15

The product 3-15 (18 g, 0.04 mol) obtained in the previous step and L-ethyl lactate (9.44 g, 0.08 mol) were dissolved in 100 mL DMF, the mixture was cooled to 0° C., NaH (3.2 g, 60%, suspended in mineral oil, 0.08 mol) was added in batches slowly. The reaction mixture was warmed to room temperature and stirred for 4 hours. The reaction mixture was cooled to 0° C., 10 mL saturated ammonium chloride solution was added dropwise slowly to quench the reaction, 100 mL water was added, the mixture was extracted with EtOAc for 3 times (100 mL×3). The organic phases were combined, washed with water for 3 times (100 mL×3) and saturated brine (100 mL), dried over anhydrous sodium sulfate, and concentrated. The crude product was purified by silica gel column chromatography (PE/EtOAc=10:1-1:1) to give 5 g product 4-15 as light yellow oil, yield 26%. LCMS (ESI) m/z 473.1 (M+H)$^+$.

Synthesis of Compound 5-15

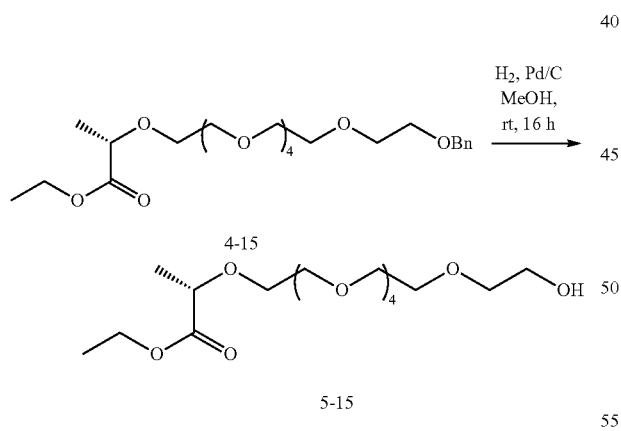

5-15

The product 4-15 (4.7 g, 10 mmol) obtained in the previous step was dissolved in 50 mL methanol, the mixture was purged by nitrogen for 3 times, 200 mg 10% Pd/C dry powder was added. The reaction mixture was purged by hydrogen gas for 3 times, stirred overnight at room temperature under hydrogen atmosphere. The reaction mixture was purged by nitrogen for 3 times, 50 mL DCM was added, the resultant mixture was filtered, washed with DCM, the filtrate was concentrated to give 3.8 g crude product as light yellow oil, which was used directly for the next step. LCMS (ESI) m/z 383.1 (M+H)$^+$.

Synthesis of Compound 6-15

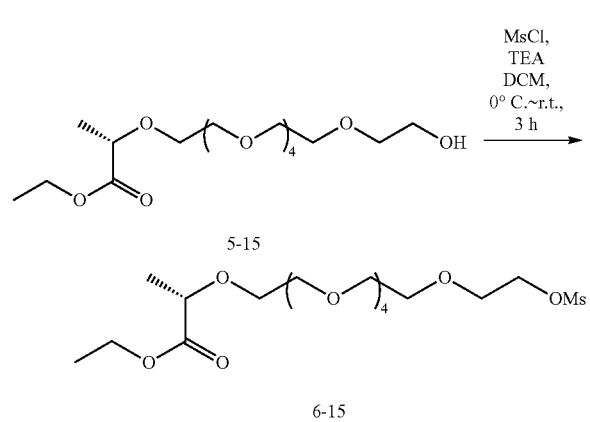

6-15

The product 5-15 (3.8 g, 10 mmol) obtained in the previous step and Et$_3$N (1.7 mL, 12 mmol) were dissolved in 30 mL DCM, the mixture was cooled to 0° C., methanesulfonyl chloride (0.9 mL, 11 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give the crude product as light yellow oil, which was used directly for the next step.

Synthesis of compound 7-15

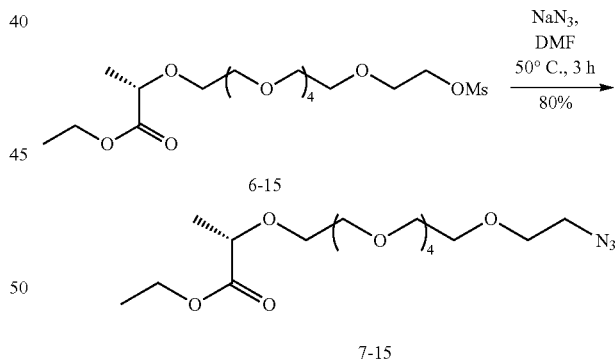

7-15

The product 6-15 (4.6 g, 10 mmol) obtained in the previous step was dissolved in 20 mL DMF, NaN$_3$ (715 mg, 11 mmol) was added. The reaction mixture was warmed to 50° C. and stirred overnight. The reaction mixture was cooled to room temperature and 50 mL water was added to quench the reaction, then the resultant mixture was extracted with EtOAc for 3 times (30 mL×3). The organic phases were combined, washed with saturated brine for 3 times (30 mL×3), dried over anhydrous sodium sulfate, and concentrated. The crude product was purified by silica gel column chromatography (PE/EtOAc=1:1) to give 3.2 g product 7-15 as light yellow oil, yield 80%.

Synthesis of Compound 8-15

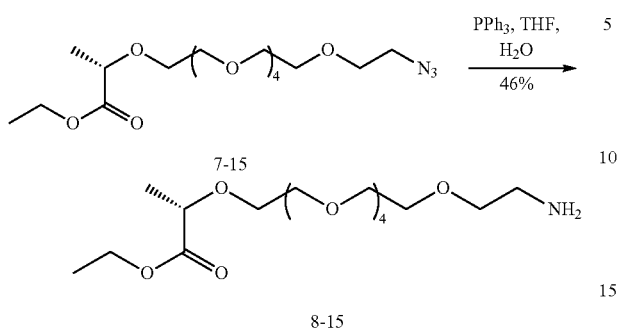

The product 7-15 (2.0 g, 5 mmol) obtained in the previous step was dissolved in 30 mL THF and 5 mL water, PPh₃ (1.57 g, 6 mmol) was added. The reaction mixture was stirred overnight at room temperature. THF was removed under reduced pressure, 20 mL 1 N dilute hydrochloric acid was added, the mixture was washed with EtOAc for 3 times (20 mL×3), and the aqueous phase was freeze-drying to give 820 mg crude product 8-15 as light yellow oil. LCMS (ESI) m/z 382.3 (M+H)⁺.

Synthesis of Compound 9-15

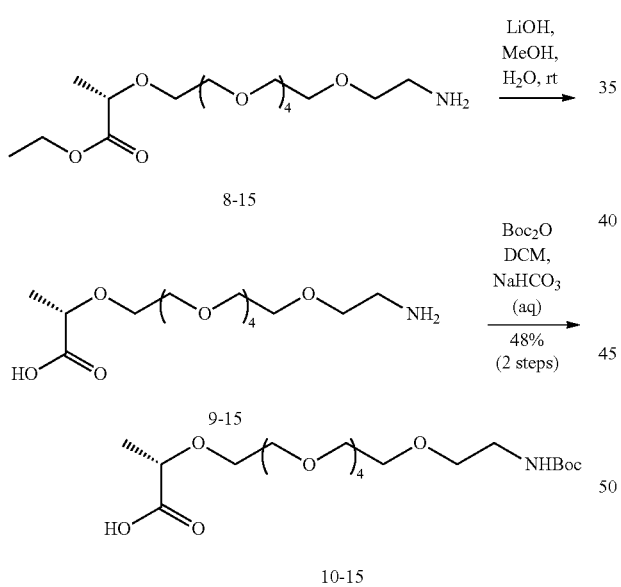

The product 8-15 (1.14 g, 3 mmol) obtained in the previous step was dissolved in 20 mL methanol and 5 mL water, lithium hydroxide monohydrate (630 mg, 15 mmol) was added. The reaction mixture was stirred for 3 hours at room temperature. After the starting material was completely consumed, methanol was removed under reduced pressure, 3 mL saturated sodium bicarbonate solution was added and cooled in an 30 mL ice bath to 0° C., Boc₂O (785 mg, 3.6 mmol) was added, then the mixture was warmed to room temperature and stirred for 2 hours. The reaction mixture was washed with water for 2 times (20 mL×2), the aqueous phases were combined, 0.5 M KHSO₄ solution was added to quench the reaction and adjust pH to 3-4, the mixture was extracted with DCM for 3 times (20 mL×3). The organic phases were combined, dried over anhydrous sodium sulfate, and concentrated, the residue was purified by silica gel column chromatography (DCM/methanol=20:1) to give 650 mg product 10-15 as light yellow oil, yield 48%. LCMS (ESI) m/z 453.9 (M+H)⁺, 475.9 (M+Na)⁺.

Synthesis of Compound 11-15: 12786-191

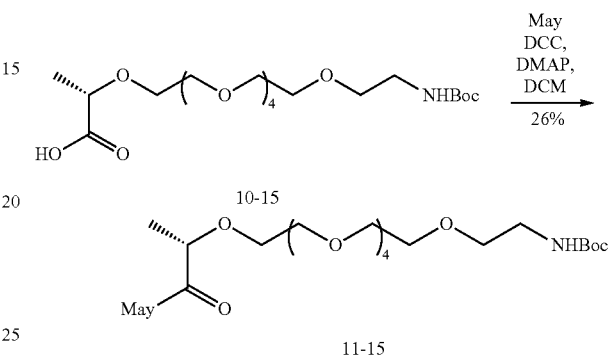

The product 10-15 (136 mg, 0.3 mmol) obtained in the previous step, DCC (165 mg, 0.8 mmol) and DMAP (24 mg, 0.2 mmol) were added to a dry Schlenk tube, the mixture was purged by argon for 3 times, 1 mL DCM was added and stirred. Maytansinol (57 mg, 0.1 mmol) in 4 mL dry DCM was added. The reaction mixture was stirred for 2 hours at room temperature, 0.3 mL water was added slowly to quench the reaction, then 15 mL EtOAc was added, the mixture was filtered, washed with EtOAc. The filtrate was dried over anhydrous sodium sulfate, and concentrated. The crude product was purified by prep-HPLC to give 26 mg product 11-15 as light yellow solid, yield 26%. LCMS (ESI) m/z 1000.7 (M+H)⁺.

Synthesis of Compound 12-15

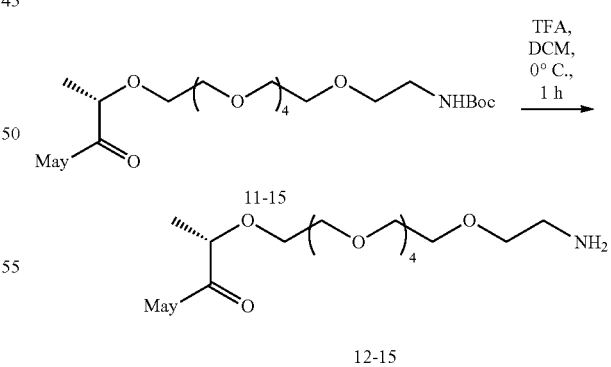

The product 11-15 (20 mg, 0.02 mmol) obtained in the previous step was dissolved in 4 mL dry DCM, the mixture was cooled in an ice bath to 0° C., 0.4 mL TFA was added dropwise slowly, the reaction mixture was gradually warmed to room temperature and stirred for 1 hour, after LCMS showed that the starting material was completely consumed, DCM and TFA were removed under reduced pressure at ambient temperature to give 14 mg crude product 12-15 as light yellow solid, which was used directly for the next step. LCMS (ESI) m/z 900.7 (M+H)⁺.

Synthesis of Compound CE-046

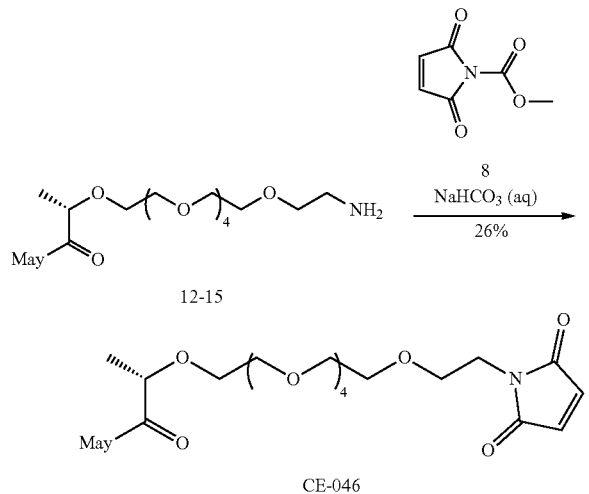

CE-046

The crude product 12-15 (12 mg, 0.015 mmol) obtained in the previous step was suspended in 2 mL saturated sodium bicarbonate solution, compound 8 (15.5 mg, 0.1 mmol) was added, the reaction mixture was stirred overnight at room temperature, then extracted with DCM for 3 times (20 mL×3). The organic phases were combined, washed with saturated brine for 3 times (20 mL×3), dried over anhydrous sodium sulfate, and concentrated to give a crude product, which was purified by prep-HPLC to give 4 mg product CE-046 as light yellow solid, yield 26%.

LCMS (ESI) m/z 980.4 (M+H)⁺.

$^1$H NMR (400 MHz, CDCl$_3$) δ ppm 6.78 (s, 1H), 6.66 (s, 1H), 6.36 & 6.33 (dd, J$_1$=12.4 Hz, J$_2$=8.8 Hz, 2H), 6.16 (d, J=10.8 Hz, 1H), 6.11 (d, J=10.2 Hz, 1H), 5.60&5.58 (dd, J$_1$=12.0 Hz, J$_2$=6.8 Hz, 1H), 5.01 (d, J=8.0 Hz, 1H), 4.40-4.30 (m, 2H), 3.93 (s, 3H), 3.77-3.68 (m, 2H), 3.62-3.53 (m, 24H), 3.43 (d, J=10.8 Hz, 2H), 3.27 (s, 3H), 3.12 (d, J=10.4 Hz, 1H), 3.09 (s, 3H), 2.64 (d, J=5.6 Hz, 1H), 2.55 (t, J=10.0 Hz, 1H), 2.15-2.10 (m, 1H), 1.93 (t, J=8.0 Hz, 1H), 1.62 (s, 3H), 1.46 (d, J=5.6 Hz, 3H), 1.18 (s, 3H), 0.79 (s, 3H).

Synthesis of Compound CE-052a

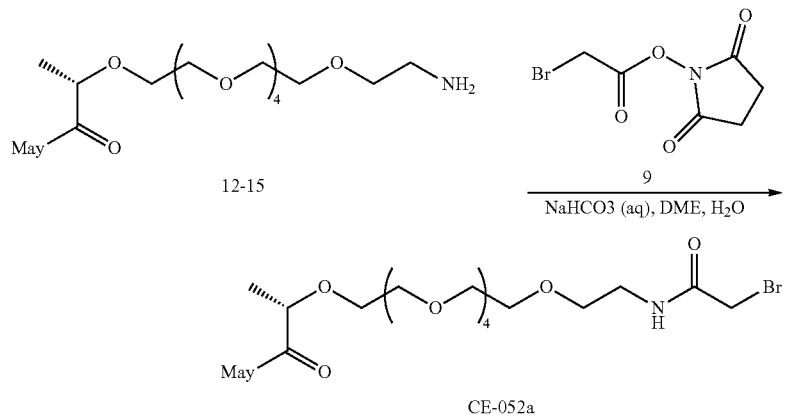

CE-052a

The crude product 12-15 (9 mg, 0.01 mmol) obtained in the previous step and compound 9 (7 mg, 0.03 mmol) were dissolved in a mixed solution of 1 mL 1,2-dimethoxyethane and 1 mL water, 0.2 mL saturated sodium bicarbonate solution was added. The reaction mixture was stirred overnight at room temperature, extracted with DCM (20 mL×3). The organic phases were combined, dried over anhydrous sodium sulfate, and concentrated. The crude product was purified by prep-HPLC to give 4.8 mg product CE-052 as light yellow solid. LCMS (ESI) m/z 1000.4 (M–H$_2$O)⁺.

$^1$H NMR (400 MHz, CDCl$_3$) δ ppm 7.37 (br, 1H), 6.85 (s, 1H), 6.78 (s, 1H), 6.68 (s, 1H), 6.44 & 6.42 (dd, J$_1$=12.0 Hz, J$_2$=9.6 Hz, 1H), 6.18 (d, J=8.4 Hz, 1H), 5.60 & 5.58 (dd, J$_1$=12.0 Hz, J$_2$=6.8 Hz, 1H), 4.95 (d, J=8.8 Hz, 1H), 4.32 (t, J=8.0 Hz, 1H), 4.19-4.11 (m, 1H), 4.08 (s, 2H), 3.99 (s, 3H), 3.85-3.74 (m, 1H), 3.70-3.60 (m, 25H), 3.51 (d, J=9.2 Hz, 2H), 3.46 (d, J=6.8 Hz, 1H), 3.35 (s, 3H), 3.20 (d, J=10.0 Hz, 1H), 3.15 (s, 3H), 2.86 (d, J=5.6 Hz, 1H), 2.60 (t, J=10.0 Hz, 1H), 2.22 (d, J=11.2 Hz, 1H), 1.68 (s, 3H), 1.67 (d, J=10.4 Hz, 1H), 1.51 (d, J=5.6 Hz, 3H), 1.28 (d, J=5.6 Hz, 3H), 0.84 (s, 3H).

Embodiment 16 Synthetic Route for CE-048

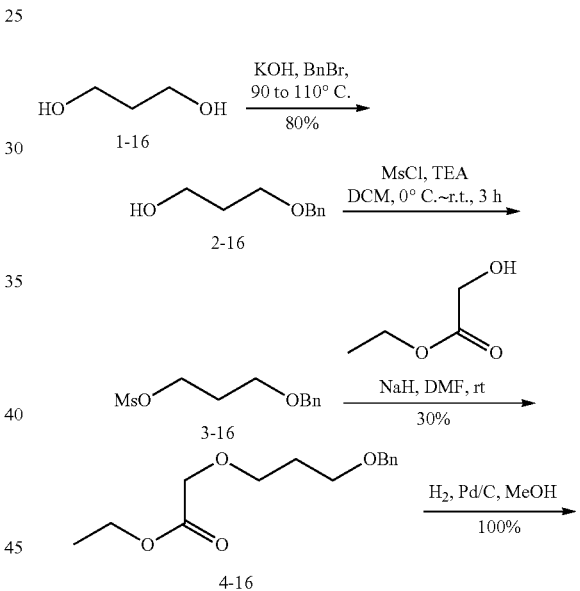

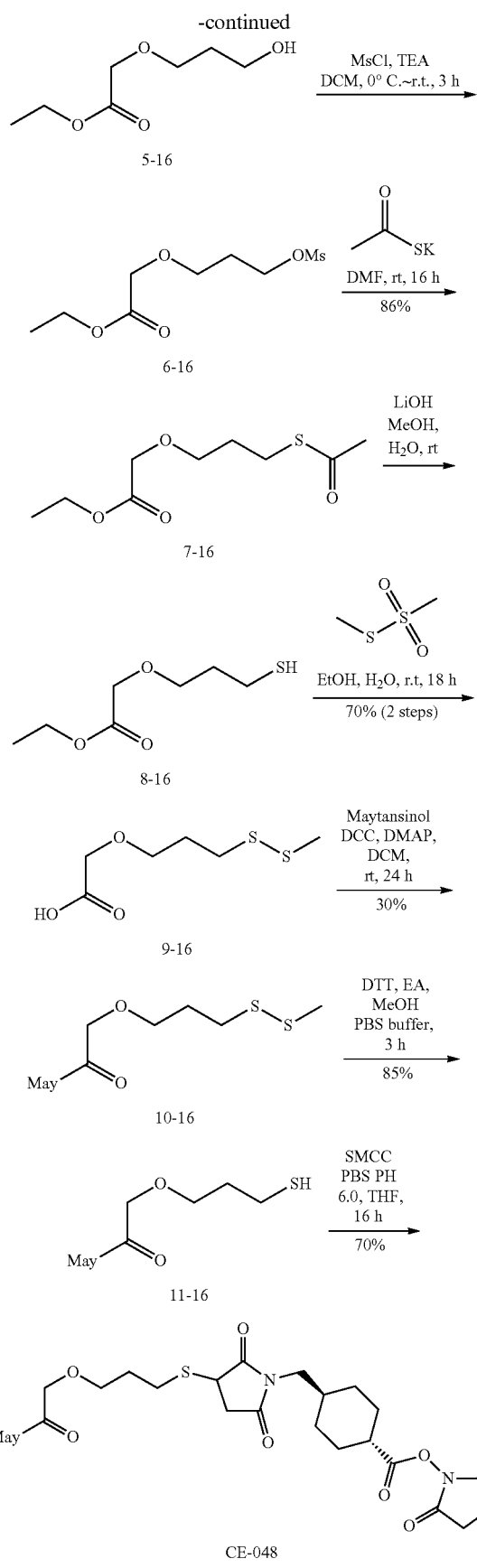

Experimental Procedure

Synthesis of Compound 2-16

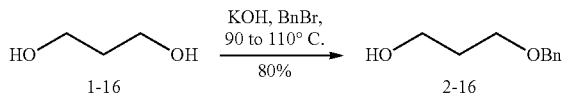 [SMILES: OCCCO ; OCCCOCc1ccccc1]

Compound 1-16 (30 g, 0.39 mol) was added to a 250 mL eggplant shaped bottle, KOH (8.1 g, 0.14 mol) was added while stirring. The suspension was heated to 90° C., and stirred till KOH was completely dissolved. BnBr (22 g, 0.13 mol) was added dropwise slowly. The reaction mixture was heated to 110° C. and stirred overnight. The reaction mixture was cooled to room temperature, 200 mL water was added, the resultant mixture was extracted with EtOAc for 3 times (100 mL×3), and the organic phases were combined, washed with water for 3 times (150 mL×3) and saturated brine (150 mL), dried over anhydrous sodium sulfate, and concentrated. The crude product was purified by silica gel column chromatography (PE/EtOAc 10:1-3:1) to give 17 g product 2-10 as colorless oil, yield 80%. LCMS (ESI) m/z167.1 (M+H)$^+$.

Synthesis of Compound 3-16

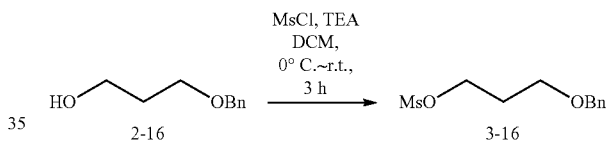

The product 2-16 (17 g, 0.1 mol) obtained in the previous step and Et$_3$N (16.6 mL, 0.12 mol) were dissolved in 150 mL DCM, the mixture was cooled to 0° C., methanesulfonyl chloride (8.5 mL, 0.11 mol) was added dropwise. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, and concentrated to give 24.4 g crude product 3-16 as yellow oil, which was used directly for the next step.

Synthesis of Compound 4-16

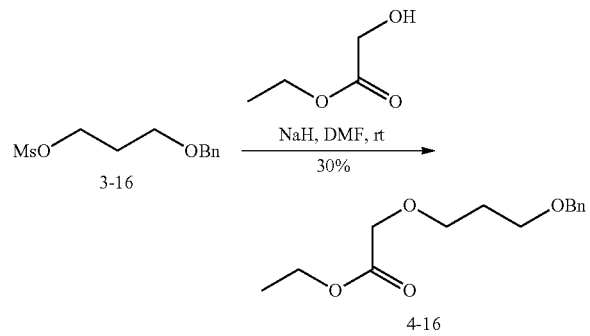

The product 3-16 (24.4 g, 0.1 mol) obtained in the previous step and L-ethyl lactate (20.8 g, 0.2 mol) were dissolved in 150 mL DMF, the mixture was cooled to 0° C., NaH (8 g, 60%, suspended in mineral oil, 0.2 mol) was added in batches slowly. The reaction mixture was warmed to room temperature and stirred overnight. The reaction mixture was cooled to 0° C., 20 mL saturated ammonium chloride solution was added dropwise slowly to quench the reaction, 150 mL water was added, the resultant mixture was extracted with EtOAc for 3 times (100 mL×3), the organic phases were combined, washed with water for 3 times (100 mL×3) and saturated brine (100 mL), dried over anhydrous sodium sulfate, and concentrated. The crude product was purified by silica gel column chromatography (PE/EtOAc=10:1-2:1) to give 7.1 g product 4-16 as light yellow oil, yield 30%. LCMS (ESI) m/z 253.1 (M+H)$^+$.

Synthesis of Compound 5-16

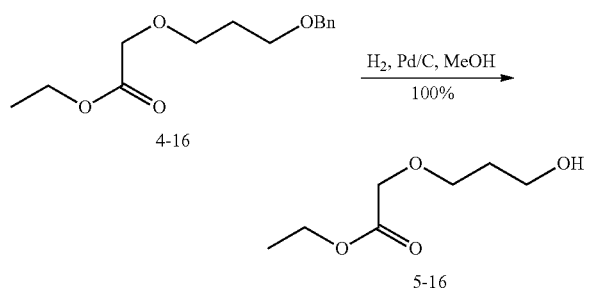

The product 4-16 (7.6 g, 30 mmol) obtained in the previous step was dissolved in 50 mL methanol, the mixture was purged by nitrogen gas for 3 times, 200 mg 10% Pd/C dry powder was added. The reaction mixture was purged by hydrogen gas for 3 times, stirred overnight at room temperature under hydrogen atmosphere. The reaction mixture was purged by nitrogen gas for 3 times, 50 mL DCM was added, the mixture was filtered, washed with DCM, the filtrate was concentrated to give 4.8 g crude product as light yellow oil, which was used directly for the next step. LCMS (ESI) m/z 163.1 (M+H)$^+$, 185.1 (M+Na)$^+$.

Synthesis of Compound 6-16

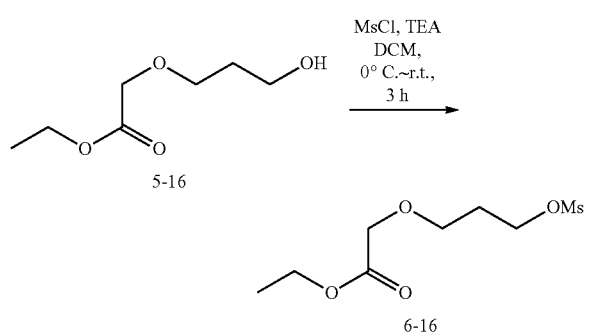

The product 5-16 (4.8 g, 30 mmol) obtained in the previous step and Et$_3$N (5.0 mL, 36 mmol) were dissolved in 50 mL DCM, the mixture was cooled to 0° C., methanesulfonyl chloride (2.64 mL, 33 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give the crude product as light yellow oil, which was used directly for the next step.

Synthesis of Compound 7-16

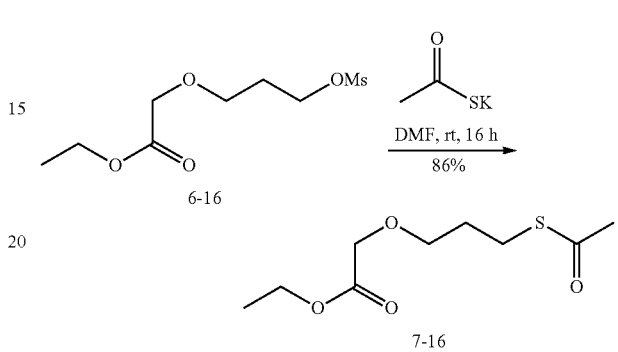

The crude product 6-16 (2 g, 8.3 mmol) obtained in the previous step was dissolved in 20 mL DMF, potassium thioacetate (1.89 g, 16.6 mmol) was added. The reaction mixture was stirred overnight at room temperature, 30 mL water was added, the resultant mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography to give 1.58 g product 7-16 as brown oil, yield 86%. LCMS (ESI) m/z 221.1 (M+H)$^+$.

Synthesis of Compound 9-16

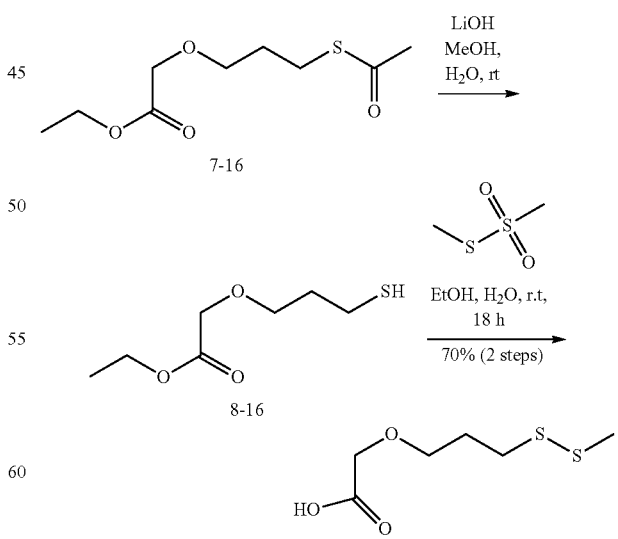

Under nitrogen atmosphere, product 7-16 (1.58 g, 7.2 mmol) obtained in the previous step was dissolved in a mixed solution of 20 mL methanol and 10 mL water, LiOH (0.87 g, 36 mmol) was added. The reaction mixture was stirred for 2 hours at room temperature under nitrogen atmosphere, methyl methanethiosulfonate (1.1 g, 8.7 mmol) was added. The reaction mixture was further stirred overnight at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 0.98 g product 9-16 as light yellow oil, yield 70%. LCMS (ESI) m/z 197.0 (M+H)+, 219.0 (M+Na)+.

Synthesis of Compound 10-16

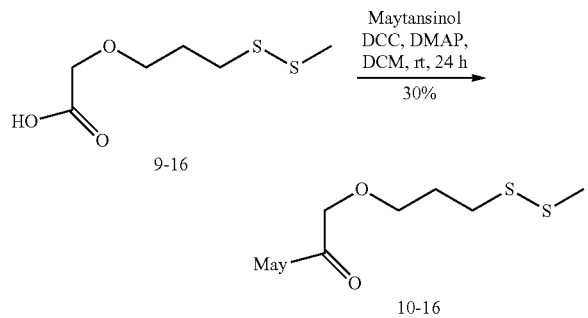

The product 9-10 (66.6 mg, 0.34 mmol) obtained in the previous step, DCC (148 mg, 0.72 mmol) and DMAP (29 mg, 0.24 mmol) were added to a dry Schlenk tube, the mixture was purged by argon for 3 times, 1 mL DCM was added and stirred. Maytansinol (65 mg, 0.12 mmol) in 2 mL dry DCM was added. The reaction mixture was stirred for 2 hours at room temperature, 0.3 mL water was added dropwise slowly to quench the reaction, 15 mL EtOAc was added, the mixture was filtered, washed with EtOAc. The filtrate was dried over anhydrous sodium sulfate and concentrated. The crude product was purified by prep-HPLC to give 25.6 mg product 10-16 as white solid, yield 30%. LCMS (ESI) m/z 743.3 (M+H)+.

Synthesis of Compound 11-16

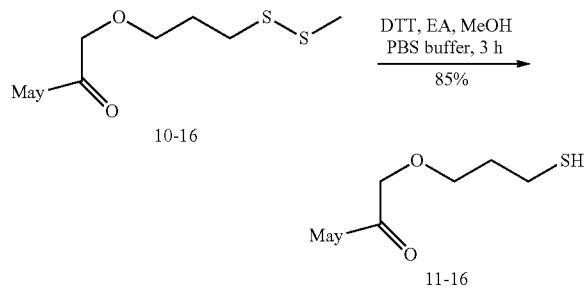

10-16 (15 mg, 0.02 mmol) was dissolved in a mixed solution of 0.5 mL EtOAc and 0.5 mL methanol, dithiothreitol (DTT) (25 mg, 0.16 mmol) in 0.5 mL pH=7.5 potassium phosphate buffer was added. The reaction mixture was stirred for 3 hours under nitrogen atmosphere. 1 mL pH=6.0 potassium phosphate buffer was added to quench the reaction, then the mixture was extracted with EtOAc for 3 times (5 mL×3). The organic phases were combined, washed with saturated brine (5 mL), dried over anhydrous sodium sulfate, and concentrated. The crude product was purified by prep-HPLC (CH3CN in H2O-0.05% TFA from 5% to 95%) to give 12 mg product 11-16 as white solid, yield 85%. LCMS (ESI) m/z 697.2 (M+H)+.

Synthesis of Compound CE-048

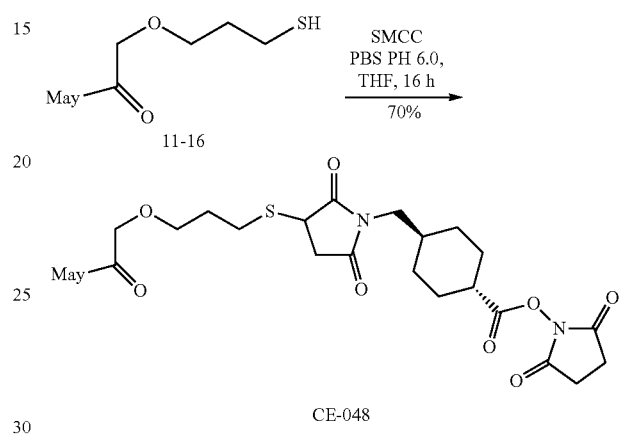

The product 11-16 (12 mg, 0.017 mmol) obtained in the previous step was dissolved in 1.5 mL THF, 1.5 mL pH=6 potassium phosphate buffer and 4-(N-maleimidomethyl) cyclohexanecarboxylic acid N-hydroxysuccinimide ester (28 mg, 0.085 mmol) were added, the mixture was stirred overnight at room temperature under nitrogen atmosphere. The reaction mixture was filtered, purified directly by prep-HPLC to give 12 mg product CE-048 as white solid, yield 70%.

LCMS (ESI) m/z 1031.3 (M+H)+

1H NMR (400 MHz, CDCl3) δ ppm 6.85 (s, 1H), 6.80 (d, J=5.6 Hz, 1H), 6.55 (s, 1H), 6.45 & 6.43 (dd, J1=12.4 Hz, J2=8.8 Hz, 1H), 6.20 (d, J=7.2 Hz, 1H), 5.59-5.53 (m, 1H), 4.92 (d, J=9.6 Hz, 1H), 4.28 (q, J=8.4 Hz, 1H), 4.19 (s, 2H), 3.99 (s, 3H), 3.80-3.74 (m, 1H), 3.72-3.68 (m, 2H), 3.52 (d, J=13.2 Hz, 1H), 3.50 (d, J=10.0 Hz, 1H), 3.39 (d, J=5.6 Hz, 2H), 3.37 (s, 3H), 3.21 (d, J=10.8 Hz, 1H), 3.17 (s, 3H), 3.18-3.13 (m, 1H), 3.06-3.00 (m, 1H), 2.93-2.86 (m, 3H), 2.82 (s, 3H), 2.61-2.52 (m, 3H), 2.25-2.15 (m, 3H), 2.01-1.93 (m, 2H), 1.82-1.73 (m, 3H), 1.68 (s, 3H), 1.61-1.46 (m, 4H), 1.30-1.26 (m, 4H), 1.08 (q, J=10.4 Hz, 2H), 0.83 (s, 3H).

Embodiment 17 Synthetic Route for CE-049

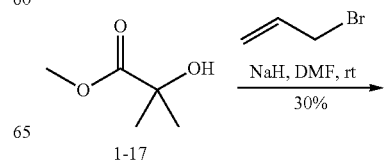

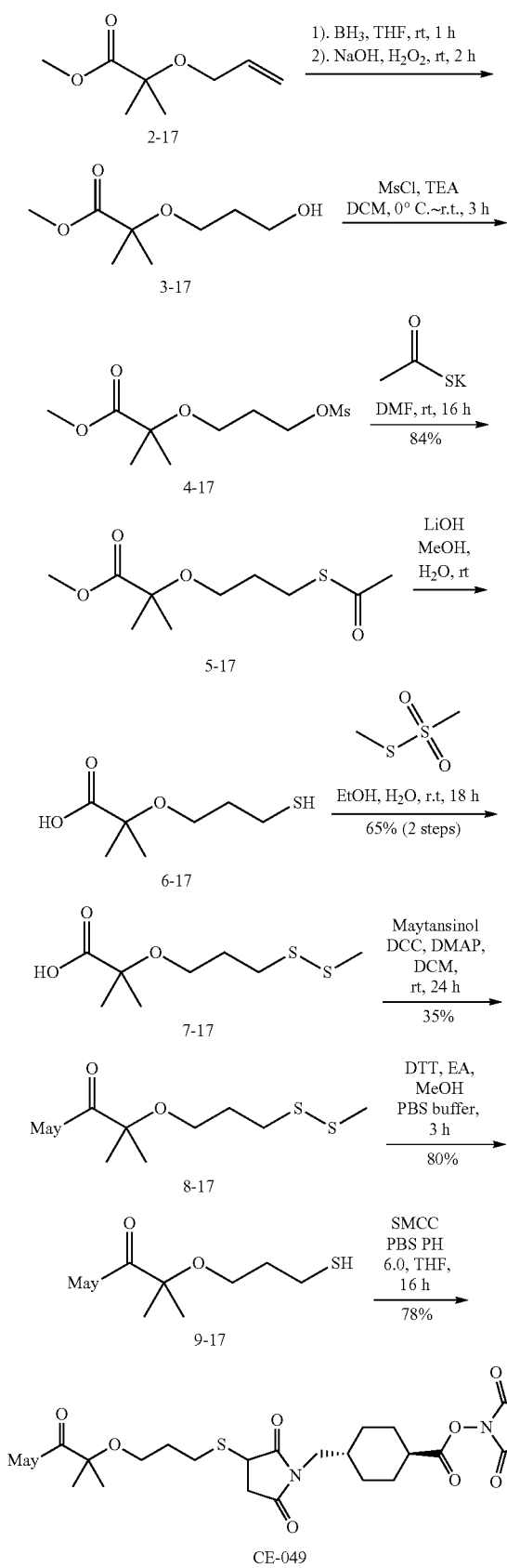

Experimental Procedure

Synthesis of Compound 2-17

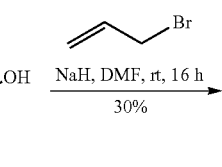 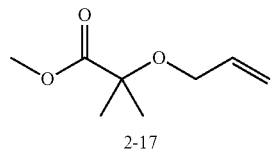

1-17 (4.5 g, 38 mmol) and allyl bromide (6.6 mL, 76 mmol) were dissolved in 50 mL DMF, the mixture was cooled to 0° C., NaH (3.04 g, 60%, suspended in mineral oil, 76 mmol) was added in batches slowly. The reaction mixture was warmed to room temperature and stirred overnight. The reaction mixture was cooled to 0° C., 20 mL saturated ammonium chloride solution was added dropwise slowly to quench the reaction, 50 mL water was added, the resultant mixture was extracted with EtOAc for 3 times (50 mL×3), the organic phases were combined, washed with water for 3 times (50 mL×3) and saturated brine (50 mL), dried over anhydrous sodium sulfate, and concentrated. The crude product was purified by silica gel column chromatography (PE/EtOAc=10:1-2:1) to give 1.95 g product 2-17 as light yellow oil, yield 30%. LCMS (ESI) m/z 159.2 (M+H)$^+$

Synthesis of Compound 3-17

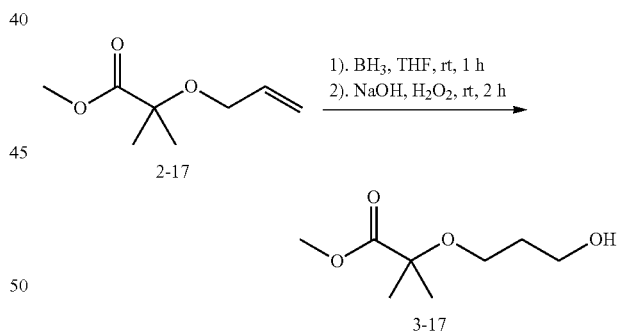

The product 2-17 (1.95 g, 8.7 mmol) obtained in the previous step was dissolved in 15 mL THF, the mixture was cooled to 0° C., BH$_3$/THF solution (1 N, 10 mL, 10 mmol) was added dropwise while stirring. The reaction mixture was warmed to room temperature and stirred for 2 hours. The reaction mixture was cooled to 0° C., sodium hydroxide solution (3 N, 3.4 mL, 10 mmol) was added dropwise, 5 mL 30% hydrogen peroxide was added slowly, and the reaction mixture was warmed to room temperature and stirred overnight. 50 mL Et$_2$O was added, the organic phase was separated, washed with saturated brine (30 mL×3), dried over anhydrous sodium sulfate, concentrated to give 1.94 g crude product 3-17 as light yellow oil, which was used directly for the nest step.

Synthesis of Compound 4-17

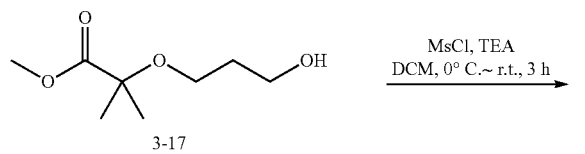

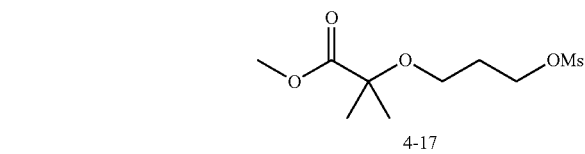

The product 3-17 (1.94 g, 10 mmol) obtained in the previous step and Et₃N (1.7 mL, 12 mmol) were dissolved in 20 mL DCM, the mixture was cooled to 0° C., methanesulfonyl chloride (0.9 mL, 11 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give 2.46 g crude product as light yellow oil, which was used directly for the next step. LCMS (ESI) m/z 255.3 (M+H)⁺.

Synthesis of Compound 5-17

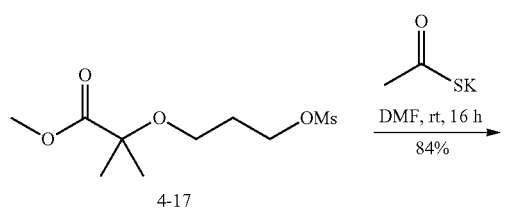

The crude product 4-17 (2.16 g, 9 mmol) obtained in the previous step was dissolved in 20 mL DMF, potassium thioacetate (2.0 g, 18 mmol) was added. The reaction mixture was stirred overnight at room temperature, 30 mL water was added, and the resultant mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography (PE/EtOAc=1:1) to give 1.7 g product 5-17 as brown oil, yield 84%. LCMS (ESI) m/z 235.3 (M+H)⁺.

Synthesis of Compound 7-17

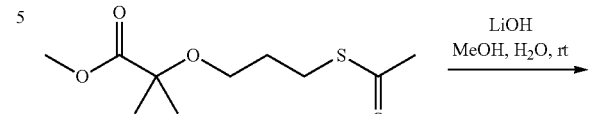

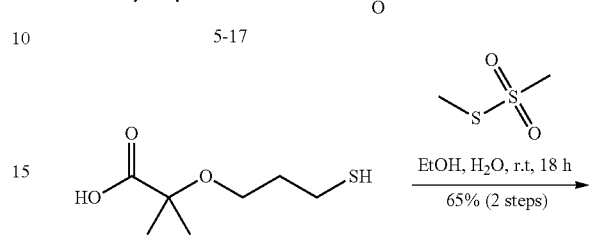

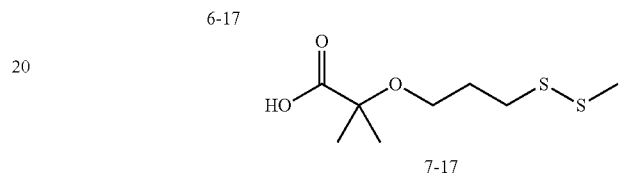

Under nitrogen atmosphere, the product 5-17 (1.87 g, 8 mmol) obtained in the previous step was dissolved in a mixed solution of 20 mL methanol and 10 mL water, LiOH (0.78 g, 32 mmol) was added. The reaction mixture was stirred for 2 hours at room temperature under nitrogen atmosphere, methyl methanethiosulfonate (1.2 g, 9.6 mmol) was added. The reaction mixture was further stirred overnight at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 1.17 g product 7-17 as light yellow oil, yield 65%.
LCMS (ESI) m/z 225.3 (M+H)⁺, 247.3 (M+Na)⁺.

Synthesis of Compound 8-17

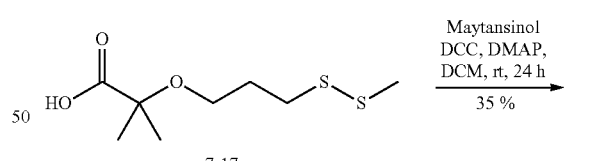

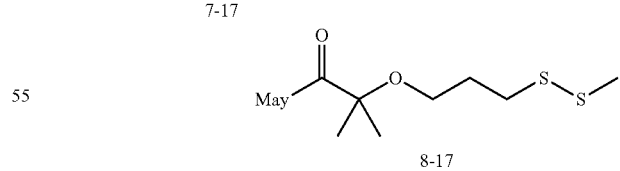

The product 7-17 (74 mg, 0.33 mmol) obtained in the previous step, DCC (136 mg, 0.66 mmol) and DMAP (27 mg, 0.22 mmol) were added to a dry Schlenk tube, the mixture was purged by argon gas for 3 times, 1 mL DCM was added and stirred. Maytansinol (62 mg, 0.11 mmol) in 2 mL dry DCM was added. The reaction mixture was stirred for 2 hours at room temperature, 0.3 mL water was added slowly to quench the reaction, and then 15 mL EtOAc was added, the mixture was filtered, washed with EtOAc. The filtrate was dried over anhydrous sodium sulfate, and concentrated. The crude product was purified by prep-HPLC to give 30 mg product 8-17 as white solid, yield 35%.

LCMS (ESI) m/z 771.3 (M+H)$^+$.

Synthesis of Compound 9-17

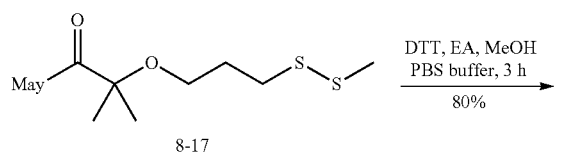

8-17 (16 mg, 0.02 mmol) was dissolved in a mixed solution of 0.5 mL EtOAc and 0.5 mL methanol, dithiothreitol (DTT) (18 mg, 0.117 mmol) in 0.5 mL pH=7.5 potassium phosphate buffer was added. The reaction mixture was stirred for 3 hours under nitrogen atmosphere. 1 mL pH=6 potassium phosphate buffer was added to quench the reaction, the mixture was then extracted with EtOAc for 3 times (5 mL×3). The organic phases were combined, washed with saturated brine (5 mL), dried over anhydrous sodium sulfate, and concentrated. The crude product was purified by prep-HPLC (CH$_3$CN in H$_2$O-0.05% TFA from 5% to 95%) to give 12 mg product 9-17 as white solid, yield 80%. LCMS (ESI) m/z 725.3 (M+H)$^+$.

Synthesis of Compound CE-049

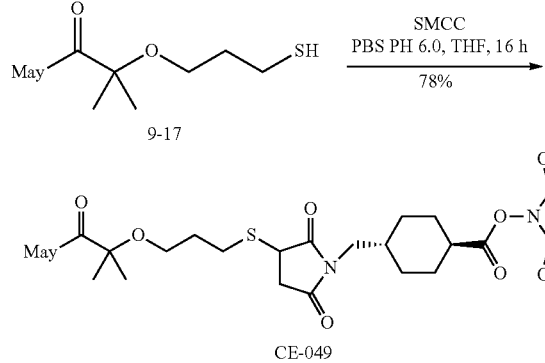

The product 9-17 (10 mg, 0.014 mmol) obtained in the previous step was dissolved in 1.5 mL THF, 1.5 mL pH=6 potassium phosphate buffer and 4-(N-maleimidomethyl) cyclohexanecarboxylic acid N-hydroxysuccinimide ester (23.4 mg, 0.07 mmol) were added, the mixture was stirred overnight at room temperature under nitrogen atmosphere. The reaction mixture was filtered, purified directly by prep-HPLC to give 11.4 mg product CE-049 as white solid, yield 78%.

LCMS (ESI) m/z 1059.3 (M+H)$^+$.

$^1$H NMR (400 MHz, CDCl$_3$) δ ppm 6.85 (s, 1H), 6.82 (d, J=5.6 Hz, 1H), 6.59 (s, 1H), 6.42 & 6.40 (dd, J$_1$=12.4 Hz, J$_2$=8.8 Hz, 1H), 6.15 (d, J=8.4 Hz, 1H), 5.55&5.53 (dd, J$_1$=12.4 Hz, J$_2$=3.6 Hz, 1H), 4.88-4.80 (m, 1H), 4.32 (q, J=8.4 Hz, 1H), 3.99 (s, 3H), 3.83-3.76 (m, 1H), 3.56-3.47 (m, 4H), 3.39 (d, J=5.6 Hz, 2H), 3.37 (s, 3H), 3.23-3.17 (m, 2H), 3.15 (s, 3H), 3.07-2.94 (m, 1H), 2.93-2.84 (m, 3H), 2.83 (s, 3H), 2.63-2.56 (m, 4H), 2.32-2.26 (m, 2H), 2.17 (d, J=9.6 Hz, 2H), 2.01-1.93 (m, 2H), 1.82-1.73 (m, 4H), 1.68 (s, 3H), 1.60-1.40 (m, 2H), 1.55 (d, J=4.0 Hz, 3H), 1.44 (s, 3H), 1.30 (d, J=4.8 Hz, 3H), 1.08 (q, J=10.0 Hz, 2H), 0.81 (s, 3H).

Embodiment 18 Synthetic Route for CE-051

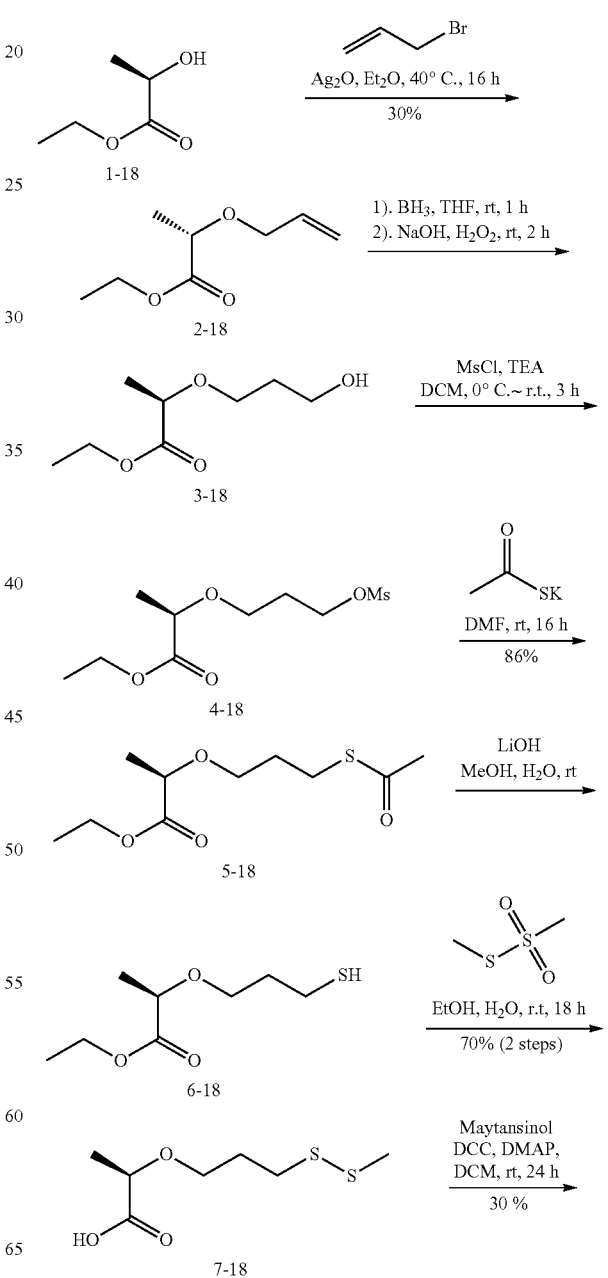

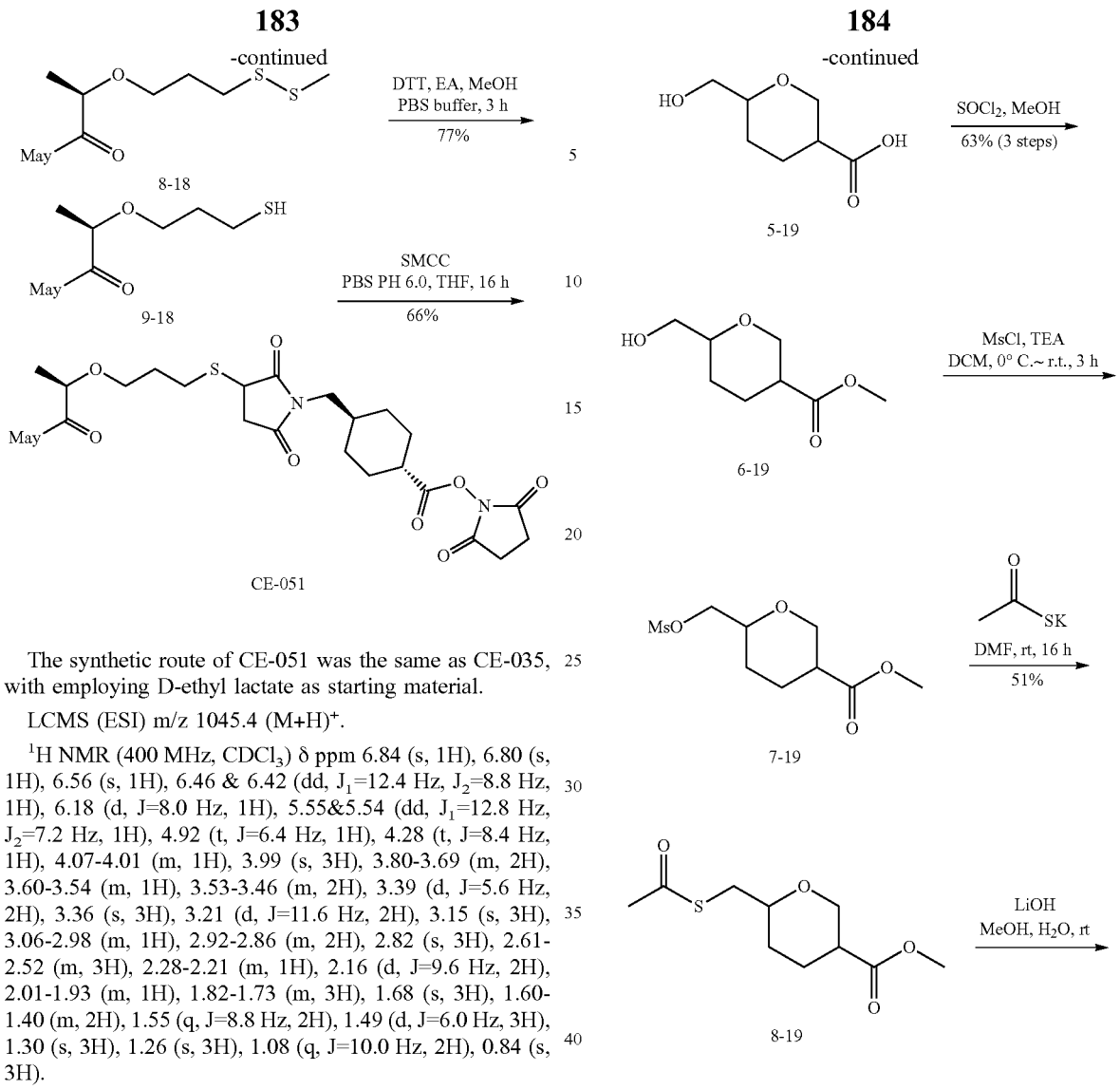
The synthetic route of CE-051 was the same as CE-035, with employing D-ethyl lactate as starting material.
LCMS (ESI) m/z 1045.4 (M+H)$^+$.
$^1$H NMR (400 MHz, CDCl$_3$) δ ppm 6.84 (s, 1H), 6.80 (s, 1H), 6.56 (s, 1H), 6.46 & 6.42 (dd, J$_1$=12.4 Hz, J$_2$=8.8 Hz, 1H), 6.18 (d, J=8.0 Hz, 1H), 5.55&5.54 (dd, J$_1$=12.8 Hz, J$_2$=7.2 Hz, 1H), 4.92 (t, J=6.4 Hz, 1H), 4.28 (t, J=8.4 Hz, 1H), 4.07-4.01 (m, 1H), 3.99 (s, 3H), 3.80-3.69 (m, 2H), 3.60-3.54 (m, 1H), 3.53-3.46 (m, 2H), 3.39 (d, J=5.6 Hz, 2H), 3.36 (s, 3H), 3.21 (d, J=11.6 Hz, 2H), 3.15 (s, 3H), 3.06-2.98 (m, 1H), 2.92-2.86 (m, 2H), 2.82 (s, 3H), 2.61-2.52 (m, 3H), 2.28-2.21 (m, 1H), 2.16 (d, J=9.6 Hz, 2H), 2.01-1.93 (m, 1H), 1.82-1.73 (m, 3H), 1.68 (s, 3H), 1.60-1.40 (m, 2H), 1.55 (q, J=8.8 Hz, 2H), 1.49 (d, J=6.0 Hz, 3H), 1.30 (s, 3H), 1.26 (s, 3H), 1.08 (q, J=10.0 Hz, 2H), 0.84 (s, 3H).
Embodiment 19 Synthetic Route for CE-053
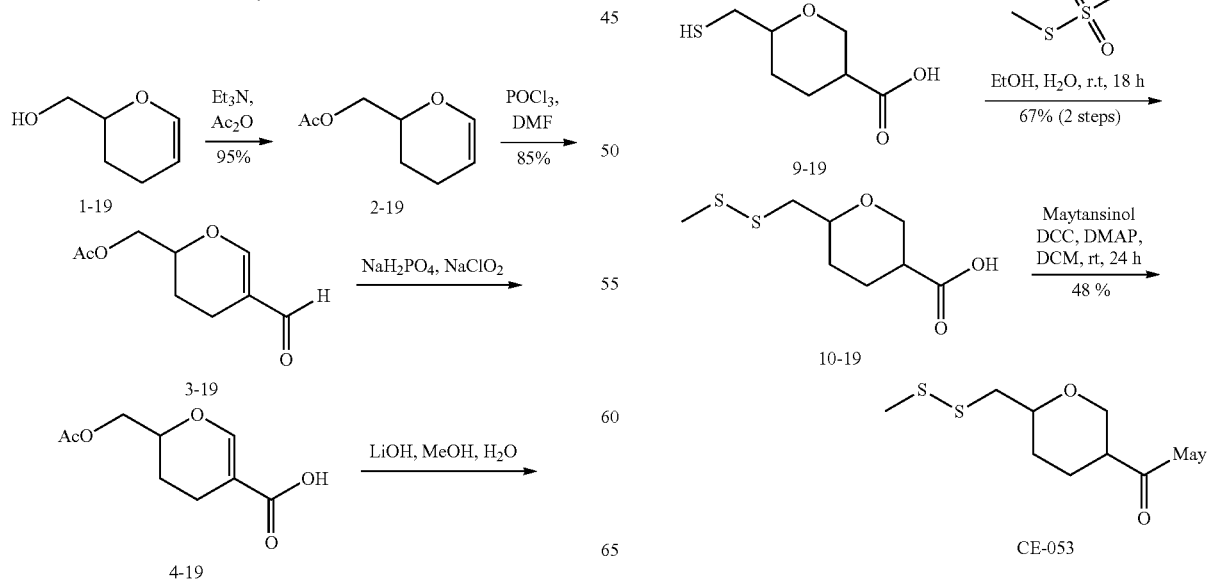

Experimental Procedure

Synthesis of Compound 2-19

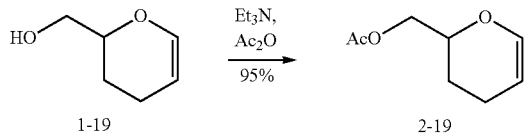 [SMILES: OCC1CCC=CO1 ; CC(=O)OCC1CCC=CO1]

Compound 1-19 (5 g, 44 mmol) was dissolved in 80 mL DCM, Et$_3$N (7.4 mL, 52.8 mol) and acetic anhydride (4.95 mL, 52.8 mol) were added successively, the mixture was stirred overnight at room temperature. After the reaction was complete, 100 mL water was added, partitioned, the aqueous phase was then extracted with DCM for 2 times (50 mL×2). The organic phases were combined, washed with saturated brine (5 mL), dried over anhydrous sodium sulfate, and concentrated. The crude product was purified by silica gel column chromatography (PE/EtOAc=5:1) to give 6.5 g product 2-19 as colorless oil, yield 95%. LCMS (ESI) m/z 157.1 (M+H)$^+$.

Synthesis of Compound 3-19

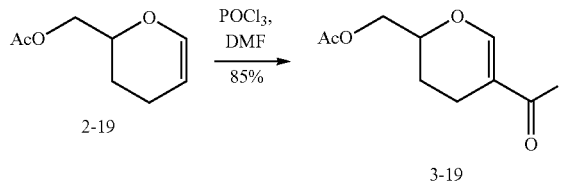

POCl$_3$ (7.7 mL, 83.4 mol) and DMF (39 mL) were added to a 25 mL flask, the mixture was stirred at ambient temperature for 30 min, then cooled in an ice-water bath to 0° C., compound 2-19 (6.5 g, 41.7 mmol) in 39 mL DMF was added to the flask dropwise slowly, the reaction mixture was warmed to room temperature and stirred overnight. 100 mL saturated sodium bicarbonate solution was added and the mixture was stirred for 10 hours, extracted with EtOAc (50 mL×3), the organic phases were combined, washed with saturated brine (50 mL), dried over anhydrous sodium sulfate, concentrated. The crude product was purified by silica gel column chromatography (PE/EtOAc=1:1) to give 6.5 g product 3-19 as colorless oil, yield 85%. LCMS (ESI) m/z 185.1 (M+H)$^+$.

Synthesis of Compound 4-19

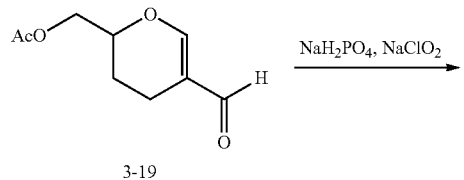

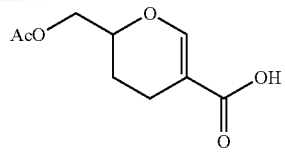

The product 3-19 (2 g, 11 mmol) obtained in the previous step was dissolved in 55 mL mixed solution of acetonitrile:tert-butanol:water=2:2:1, NaH$_2$PO$_4$ (3.96 g, 33 ml) and 30% hydrogen peroxide (1.8 mL, 55 mmol) were added, the mixture was stirred for 30 min at room temperature, then sodium hypochlorite (6 g, 66 mmol) was added, the reaction was stirred for 2 hours at ambient temperature, 50 mL water was added, 10% hydrochloric acid solution was added to adjust pH to 5-6, then the resultant mixture was extracted with DCM (50 mL×3), washed with saturated brine (30 mL), dried over anhydrous sodium sulfate, concentrated to give 1.5 g crude product as light yellow oil, which was used directly for the next step. LCMS (ESI) m/z 201.1 (M+H)$^+$

Synthesis of Compound 5-19

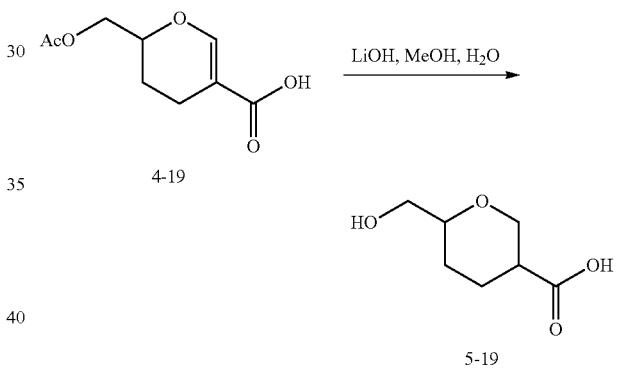

The product 4-19 (1.5 g, 7.5 mmol) obtained in the previous step was dissolved in a mixed solution of 20 mL methanol and 5 mL water, LiOH (0.36 g, 15 mmol) was added. The reaction mixture was stirred for 2 hours at room temperature, 20 mL water was added, then 1 N hydrochloric acid solution was added to adjust pH 5-6, the mixture was extracted with DCM for 3 times (50 mL×3), washed with saturated brine (30 mL), dried over anhydrous sodium sulfate, and concentrated to give 1.2 g crude product as light yellow oil, which was used directly for the next step. LCMS (ESI) m/z 161.1 (M+H)$^+$.

Synthesis of compound 6-19

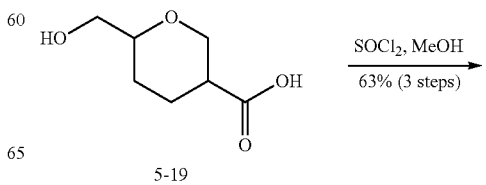

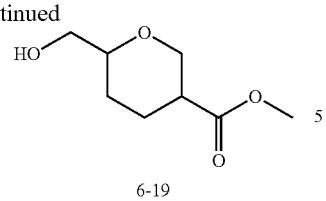

6-19

The product 5-19 (1.2 g, 7.5 mmol) obtained in the previous step was dissolved in methanol (20 mL), SOCl$_2$ (1.1 mL, 15 mmol) was added dropwise slowly under an ice-water bath, the reaction was warmed to ambient temperature and stirred overnight, 50 mL water was added to quench the reaction, the mixture was extracted with EtOAc (50 mL×3), washed with saturated brine (5 mL), dried over anhydrous sodium sulfate, and concentrated. The crude product was purified by silica gel column chromatography (PE/EtOAc=3:1) to give 1.2 g product 6-19 as colorless oil, yield 63%. LCMS (ESI) m/z 175.1 (M+H)$^+$.

Synthesis of compound 7-19

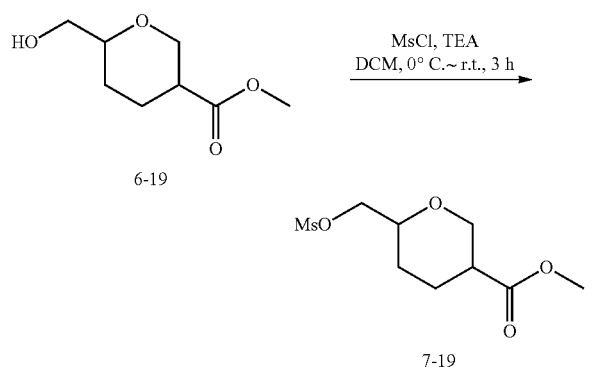

6-19

7-19

The product 6-19 (1.2 g, 6.9 mmol) obtained in the previous step and Et$_3$N (1.2 mL, 8.3 mmol) were dissolved in 20 mL DCM, the mixture was cooled to 0° C., methanesulfonyl chloride (0.68 mL, 8.3 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give 1.5 g crude product as light yellow oil, which was used directly for the next step. LCMS (ESI) m/z 253.1 (M+H)$^+$.

Synthesis of Compound 8-19

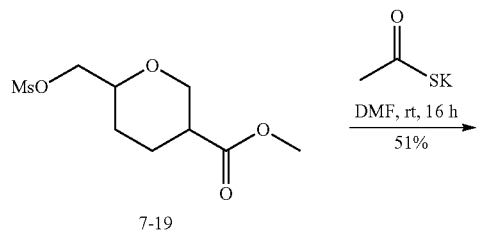

7-19

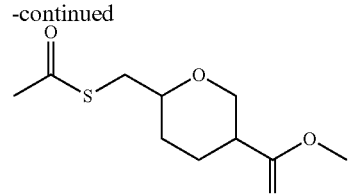

8-19

The crude product 7-19 (1.5 g, 6.3 mmol) obtained in the previous step was dissolved in 20 mL DMF, potassium thioacetate (1.12 g, 9.5 mmol) was added. The reaction mixture was stirred overnight at room temperature, 30 mL water was added, and the resultant mixture was extracted with EtOAc for 3 times (50 mL×3). The organic phases were combined, washed with water for 3 times (30 mL×3), washed with saturated brine (50 mL), dried over anhydrous sodium sulfate, and concentrated. The crude product was purified by silica gel column chromatography (PE/EtOAc=3:1) to give 700 mg product 8-19 as brown oil, yield 51%. LCMS (ESI) m/z 233.1 (M+H)$^+$ Synthesis of Compound 9-19

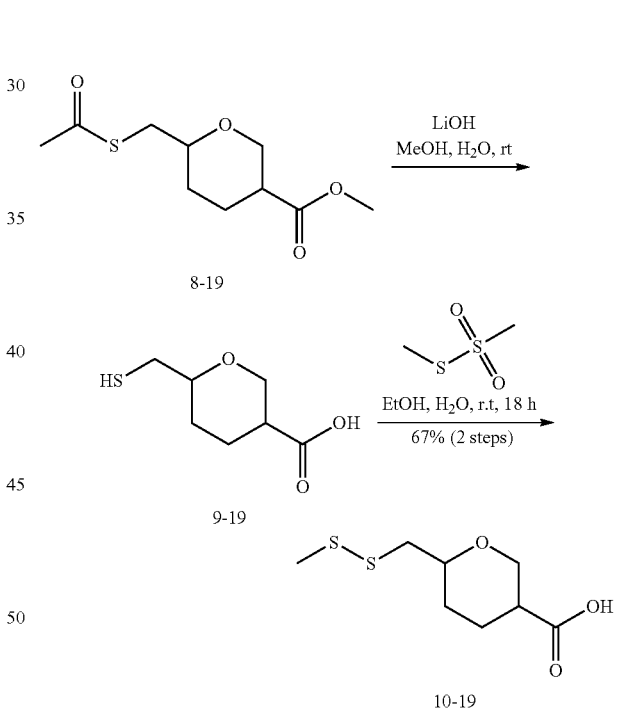

8-19

9-19

10-19

Under nitrogen atmosphere, product 8-19 (0.7 g, 3 mmol) obtained in the previous step was dissolved in a mixed solution of 20 mL methanol and 5 mL water, LiOH (0.36 g, 15 mmol) was added. The reaction mixture was stirred for 2 hours at room temperature under nitrogen atmosphere, methyl methanethiosulfonate (0.57 g, 4.5 mmol) was added. The reaction mixture was further stirred overnight at room temperature. 50 mL water was added, the mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:1) to give 0.45 g product 10-19 as light yellow oil, yield 67%. LCMS (ESI) m/z 223.1 (M+H)+.

Synthesis of Compound CE-053

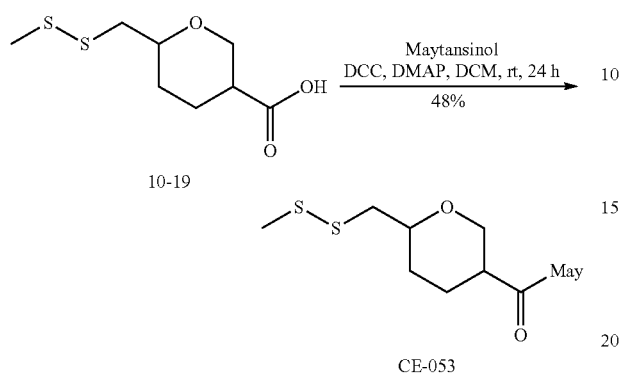

The product 10-19 (70 mg, 0.315 mmol) obtained in the previous step, DCC (130 mg, 0.63 mmol) and DMAP (25 mg, 0.21 mmol) were added to a dry Schlenk tube, the mixture was purged by argon gas for 3 times, 1 mL DCM was added and stirred. Maytansinol (60 mg, 0.105 mmol) in 2 mL dry DCM was added. The reaction mixture was stirred for 2 hours at room temperature, 0.3 mL water was added slowly to quench the reaction, 15 mL EtOAc was added, the mixture was filtered, washed with EtOAc. The filtrate was dried over anhydrous sodium sulfate, and concentrated. The crude product was purified by prep-HPLC to give 40 mg product CE-053 as white solid, yield 48%.

LCMS (ESI) m/z 768.7 (M+H)+.

$^1$H NMR (400 MHz, CDCl$_3$) δ ppm 6.84 (s, 1H), 6.79 (t, J=11.6 Hz, 1H), 6.49-6.41 (m, 1H), 6.36 (d, J=8.8 Hz, 1H), 6.24-6.13 (m, 1H), 5.59-5.38 (m, 1H), 4.91 & 4.85 (d, J=7.6 Hz, 1H), 4.31-4.16 (m, 2H), 3.99 (s, 3H), 3.65-3.45 (m, 5H), 3.37 (d, J=8.4 Hz, 2H), 3.23-3.18 (m, 2H), 3.17 (s, 3H), 3.00-2.54 (m, 6H), 2.43 (s, 3H), 2.23-2.15 (m, 2H), 1.80-1.60 (m, 2H), 1.69 (s, 3H), 1.50-1.42 (m, 2H), 1.40-1.33 (m, 1H), 1.30 (d, J=4.8 Hz, 3H), 0.81 (s, 3H).

Embodiment 20 Synthetic Routes for CE-054, 055

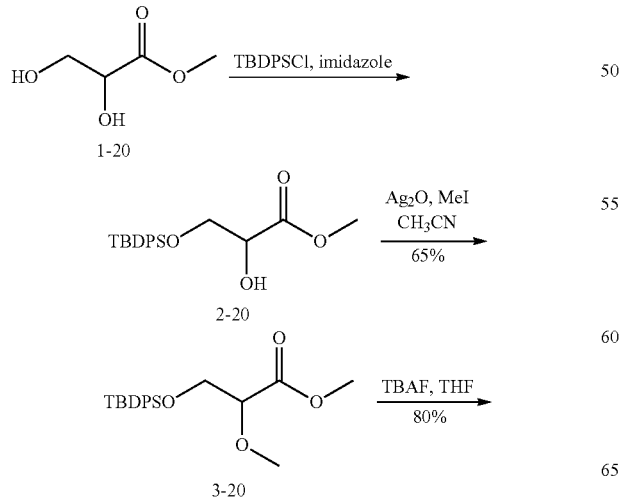

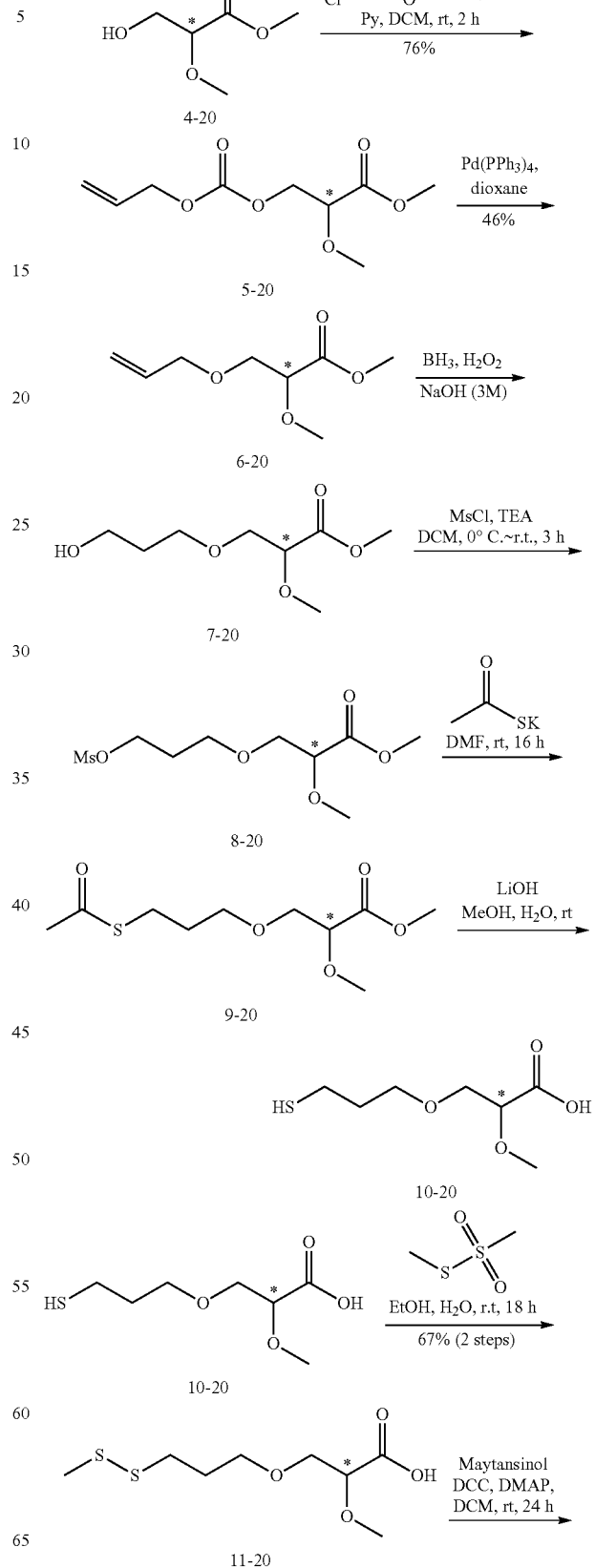

-continued

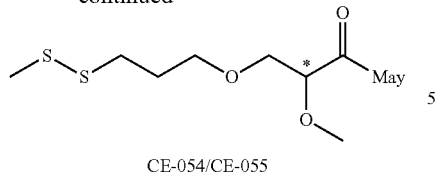

CE-054/CE-055

Experimental Procedure

Synthesis of Compound 2-20

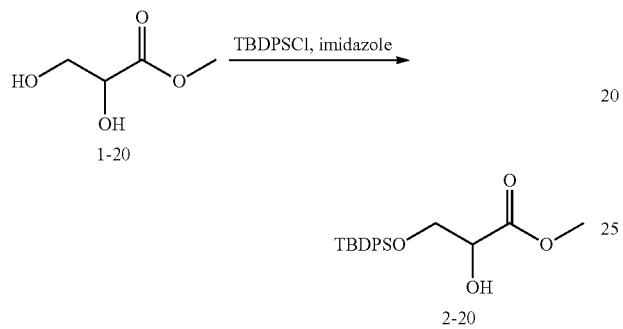

The starting material 1-20 (6 g, 50 mmol) and imidazole (4.08 g, 60 mmol) were dissolved in 80 mL THF, the mixture was cooled in an ice bath to 0° C., TBDPSCl (14 g, 51 mmol) was added in batches slowly, then the mixture was warmed to room temperature and stirred overnight. 20 mL saturated ammonium chloride solution was added to quench the reaction, the resultant mixture was then extracted with DCM, the organic phases were combined, dried over anhydrous sodium sulfate, concentrated to give 18 g crude product 2-20, which was used directly for the next step. LCMS (ESI) m/z 358.1 (M+H)$^+$.

Synthesis of Compound 3-20

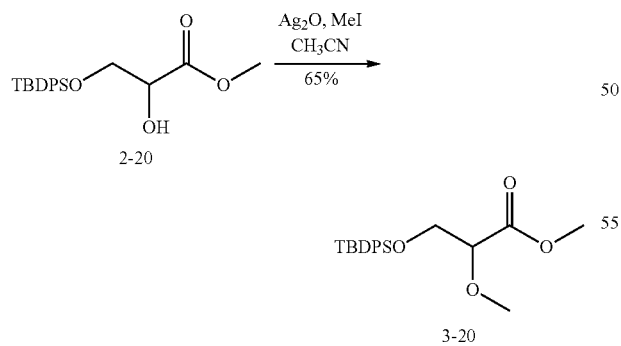

The product 2-20 (18 g, 50 mmol) obtained in the previous step was dissolved in 60 mL acetonitrile, Ag$_2$O (9.3 g, 75 mmol) was added, MeI (9.3 mL, 150 mmol) was added while stirring. The reaction mixture was stirred overnight at room temperature, filtered through diatomite, washed with DCM, the filtrate was concentrated. The residue was purified by silica gel column chromatography (PE/EtOAc=5:1) to give 12 g product 3-20 as light yellow oil, yield 65%. LCMS (ESI) m/z 372.1 (M+H)$^+$.

Synthesis of Compound 4-20

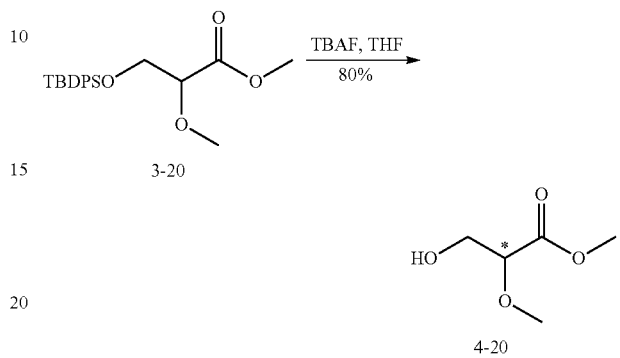

The product 3-20 (5.6 g, 15 mmol) obtained in the previous step was dissolved in 20 mL THF, TBAF (30 mL, 1 N, 30 mmol) was added. The reaction mixture was stirred overnight at room temperature, concentrated, the residue was purified by silica gel column chromatography (DCM/Methanol=20:1) to give 2 g product 4-20 as light yellow oil, yield 80%. LCMS (ESI) m/z 134.7 (M+H)$^+$. $^1$H NMR (400 MHz, CDCl$_3$) δ ppm 3.93-3.87 (m, 2H), 3.83-3.79 (m, 1H), 3.79 (s, 1H), 3.50 (s, 1H).

Synthesis of Compound 5-20

The product 4-20 (402 mg, 3 mmol) obtained in the previous step and DMAP (440 mg, 3.6 mmol) was dissolved in 15 mL DCM, the mixture was cooled in an ice bath to 0° C., allyl chloroformate (0.38 mL, 36 mmol) was added. The reaction mixture was stirred for 2 hours at room temperature, concentrated, the residue was purified by silica gel column chromatography (PE/EtOAc=5:1) to give 500 mg product 5-20 as light yellow oil, yield 76%. LCMS (ESI) m/z 219.7 (M+H)$^+$

Synthesis of Compound 6-20

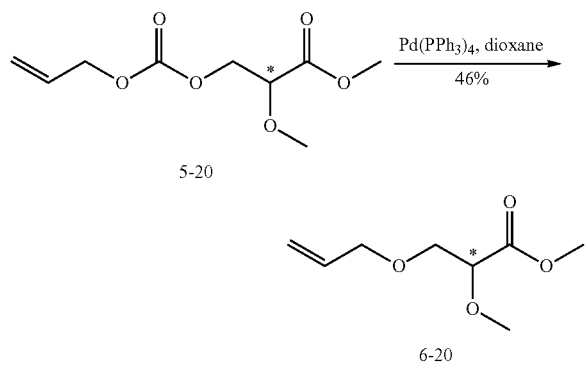

The product 5-20 (436 mg, 2 mmol) obtained in the previous step and Pd(PPh$_3$)$_4$ (12 mg, 0.01 mmol) were added to a dry Schlenk tube, the mixture was purged by argon gas for 3 times, 15 mL 1,4-dioxane was added, the mixture was heated to 100° C. and stirred for 1 hour. The reaction mixture was cooled to room temperature, concentrated, the residue was purified by silica gel column chromatography (PE/EtOAc=3:1) to give 160 mg product 6-20 as light yellow oil, yield 46%. LCMS (ESI) m/z 175.7 (M+H)$^+$.

Synthesis of Compound 7-20

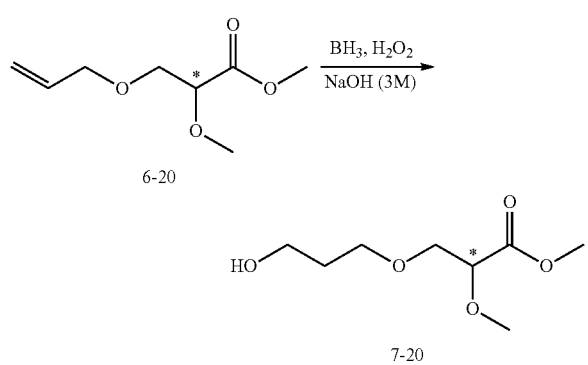

The product 6-20 (1.74 g, 10 mmol) obtained in the previous step was dissolved in 20 mL THF, the mixture was cooled to 0° C., BH$_3$/THF solution (1 M, 12 mL, 12 mmol) was added dropwise while stirring. The reaction mixture was warmed to room temperature and stirred for 2 hours. The reaction mixture was cooled to 0° C., sodium hydroxide solution (3 N, 4 mL, 12 mmol) was added dropwise, 6 mL 30% hydrogen peroxide was added slowly, and the reaction mixture was warmed to room temperature and stirred overnight. 80 mL Et$_2$O was added, the organic phase was separated, washed with saturated brine (30 mL×3), dried over anhydrous sodium sulfate, concentrated to give 1.2 g crude product 7-20 as light yellow oil, which was used directly for the next step.

Synthesis of Compound 8-20

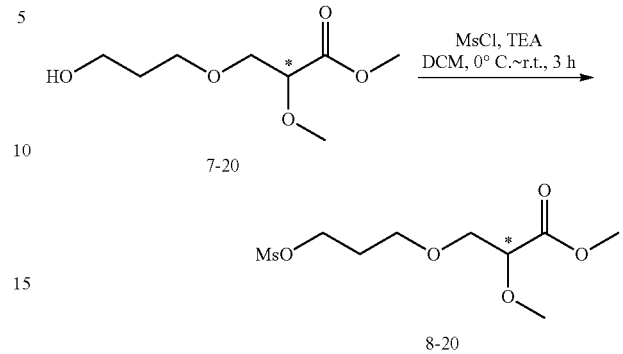

Product 7-20 (960 mg, 5 mmol) obtained in the previous step and Et$_3$N (0.83 mL, 6 mmol) were dissolved in 50 mL DCM, the mixture was cooled to 0° C., methanesulfonyl chloride (0.44 mL, 5.5 mmol) was added dropwise slowly. The reaction mixture was warmed to room temperature and stirred for 2 hours. 50 mL water was added to quench the reaction, the organic phase was separated, washed with saturated brine for 3 times (50 mL×3), dried over anhydrous sodium sulfate, concentrated to give 1.3 g crude product 8-20 as light yellow oil, which was used directly for the next step. LCMS (ESI) m/z 271.7 (M+H)$^+$.

Synthesis of compound 9-20

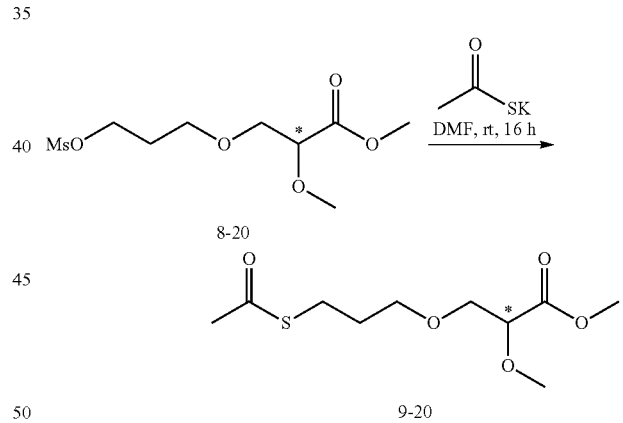

The crude product 8-20 (270 mg, 1 mmol) obtained in the previous step was dissolved in 5 mL DMF, potassium thioacetate (228 mg, 2 mmol) was added. The reaction mixture was stirred overnight at room temperature, 20 mL water was added, and the resultant mixture was extracted with EtOAc for 3 times (20 mL×3). The organic phases were combined, washed with water for 3 times (20 mL×3) and saturated brine (20 mL), dried over anhydrous sodium sulfate, and concentrated. The crude product was purified by silica gel column chromatography (PE/EtOAc=5:1) to give 170 mg product 9-20 as brown oil, yield 68%. LCMS (ESI) m/z 251.7 (M+H)$^+$, $^1$H NMR (400 MHz, CDCl$_3$) δ ppm 3.97 (t, J=3.6 Hz, 1H), 3.79 (s, 3H), 3.75-3.68 (m, 2H), 3.58-3.49 (m, 2H), 3.47 (s, 3H), 2.92 (t, J=5.6 Hz, 2H), 2.32 (s, 3H), 1.87-1.81 (m, 2H).

Synthesis of Compound 11-20

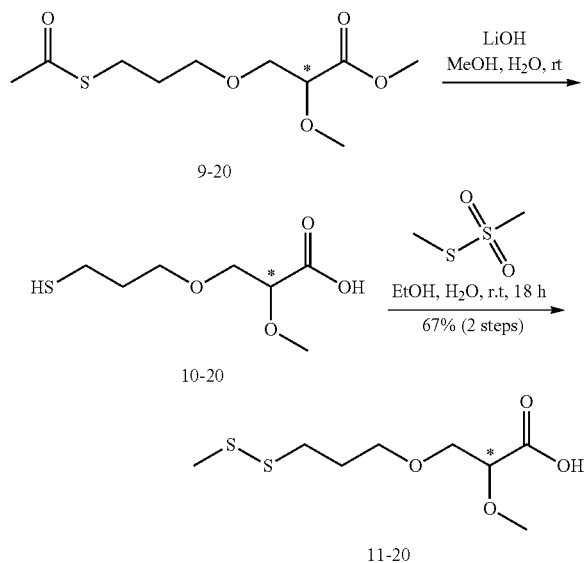

Under nitrogen atmosphere, the product 9-20 (125 mg, 0.5 mmol) obtained in the previous step was dissolved in a mixed solution of 3 mL methanol and 2 mL water, lithium hydroxide monohydrate (210 g, 5 mmol) was added. The reaction mixture was stirred for 2 hours at room temperature under nitrogen atmosphere, methyl methanethiosulfonate (126 mg, 1 mmol) was added. The reaction mixture was further stirred overnight at room temperature. 5 mL water was added, the mixture was extracted with EtOAc for 3 times (20 mL×3). The organic phases were combined, washed with saturated brine for 3 times (20 mL×3), dried over anhydrous sodium sulfate, and concentrated. The crude product was purified by silica gel column chromatography (PE/EtOAc=1:2) to give 80 mg product 11-20 as light yellow oil, yield 67%. LCMS (ESI) m/z 247.1 (M+H)+.

Synthesis of Compound CE-054, 055

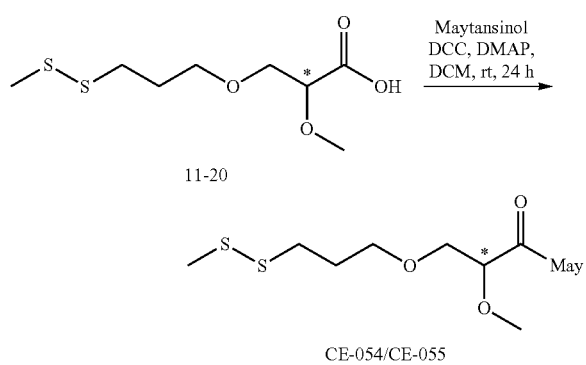

Product 11-20 (58 mg, 0.24 mmol) obtained in the previous step, DCC (132 mg, 0.64 mmol) and DMAP (20 mg, 0.16 mmol) were added to a dry Schlenk tube, the mixture was purged by argon gas for 3 times, 1 mL DCM was added and stirred. Maytansinol (46 mg, 0.08 mmol) in 4 mL dry DCM was added. The reaction mixture was stirred for 2 hours at room temperature, 0.3 mL water was added slowly to quench the reaction, then 15 mL EtOAc was added, the mixture was filtered, washed with EtOAc. The filtrate was dried over anhydrous sodium sulfate, and concentrated. The crude product was purified by prep-HPLC to give two iosomers: 25 mg CE-054 (P1) as white solid; 13 mg CE-055 (P2) as light yellow solid. LCMS (ESI) m/z 787.7 (M+H)+.

HPLC (15 min): CE-054, Rt=10.58 min; CE-055, Rt=10.75 min

Mobile Phase: A: water (0.01% TFA) B: CAN (0.01% TFA)

Gradient: 0 min 5% B, 3 min 5% B, 10 min 95% B, 15 min 95% B

Flow Rate: 1.2 mL/min

Column: Eclipse XDB-C18, 4.6×150 mm, 5 um

Oven Temperature: 40° C.

CE-054: $^1$H NMR (400 MHz, CDCl$_3$) δ ppm 6.89 (s, 1H), 6.86 (s, 1H), 6.46 & 6.44 (dd, J$_1$=12.0 Hz, J$_2$=9.2 Hz, 1H), 6.27 (s, 1H), 6.23 (d, J=8.4 Hz, 1H), 5.59 & 5.57 (dd, J$_1$=12.4 Hz, J$_2$=7.2 Hz, 1H), 4.92 (d, J=7.6 Hz, 1H), 4.27 (t, J=9.2 Hz, 1H), 4.14-4.12 (m, 1H), 3.99 (s, 3H), 3.78-3.76 (m, 1H), 3.65 (t, J=7.2 Hz, 2H), 3.52 (t, J=10.0 Hz, 1H), 3.52 (s, 3H), 3.44-3.40 (m, 1H), 3.37 (s, 3H), 3.20 (d, J=14.0 Hz, 1H), 3.19 (s, 3H), 2.89 (d, J=7.6 Hz, 1H), 2.81 (t, J=6.0 Hz, 2H), 2.60 (t, J=10.0 Hz, 1H), 2.39 (s, 3H), 2.25 & 2.23 (dd, J$_1$=8.8 Hz, J$_2$=3.2 Hz, 1H), 1.94 (d, J=9.2 Hz, 2H), 1.69 (s, 3H), 1.62 (d, J=10.4 Hz, 2H), 1.30 (d, J=4.8 Hz, 3H), 1.20-1.12 (m, 2H), 0.83 (s, 3H).

CE-055: $^1$H NMR (400 MHz, CDCl$_3$) δ ppm 7.13 (s, 1H), 6.84 (s, 1H), 6.45 & 6.43 (dd, J$_1$=12.4 Hz, J$_2$=9.2 Hz, 1H), 6.29 (s, 1H), 6.26 (d, J=9.2 Hz, 1H), 5.57 & 5.55 (dd, J$_1$=11.2 Hz, J$_2$=7.2 Hz, 1H), 4.90 (d, J=7.6 Hz, 1H), 4.37 & 4.36 (dd, J$_1$=7.2 Hz, J$_2$=3.2 Hz, 1H), 4.24 (t, J=8.8 Hz, 1H), 3.99 (s, 3H), 3.78-3.76 (m, 1H), 3.71-3.60 (m, 2H), 3.59 (d, J=11.2 Hz, 1H), 3.50 (d, J=9.2 Hz, 1H), 3.50-3.40 (m, 2H), 3.37 (s, 6H), 3.18 (d, J=14.0 Hz, 1H), 3.16 (s, 3H), 2.88 (d, J=7.6 Hz, 1H), 2.83 (t, J=5.6 Hz, 2H), 2.59 (t, J=10.0 Hz, 1H), 2.42 (s, 3H), 2.25 & 2.23 (dd, J$_1$=8.8 Hz, J$_2$=3.2 Hz, 1H), 1.94 (d, J=9.2 Hz, 2H), 1.68 (s, 3H), 1.62 (d, J=10.4 Hz, 1H), 1.29 (d, J=4.8 Hz, 3H), 1.20-1.12 (m, 2H), 0.84 (s, 3H).

Embodiment 21 Synthetic Route for CE-056

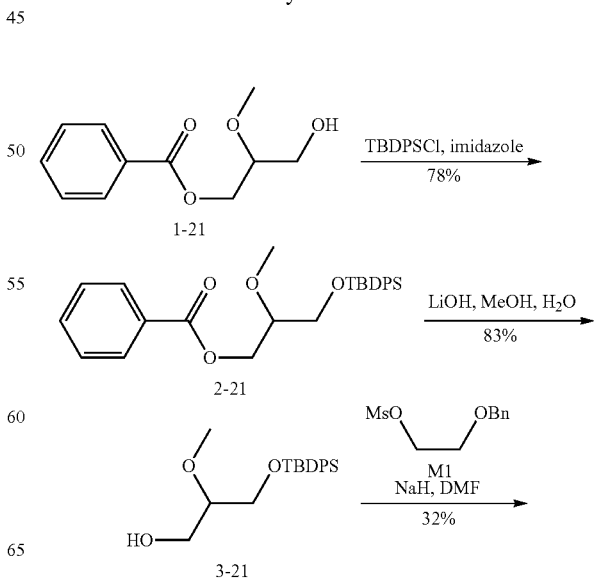

197
-continued

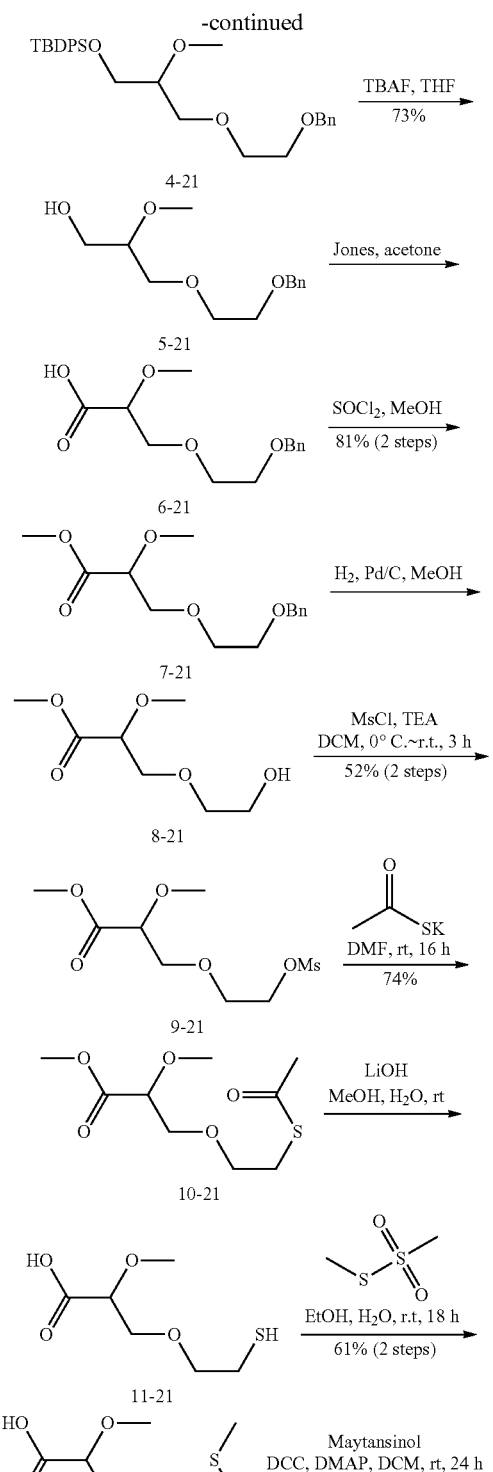

198

Experimental Procedure

Synthesis of Compound 2-21

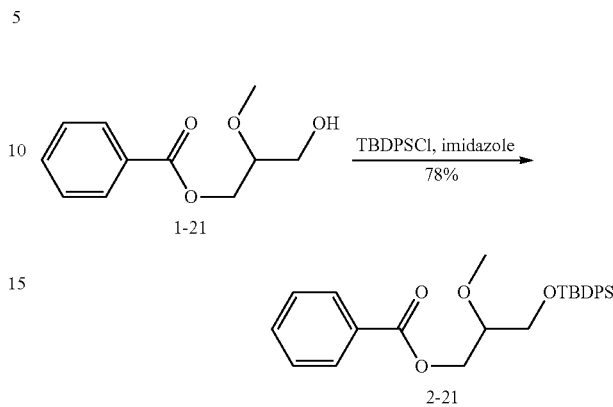

Compound 1-21 (3 g, 14.3 mmol) was dissolved in 50 mL DCM, TBDPSCl (4.32 g, 15.7 mmol) and imidazole (1.07 g, 15.7 mmol) were added, the reaction mixture was stirred for 2 hours at ambient temperature, 50 mL water was added, the mixture was extracted with DCM (50 mL×3). The organic phases were combined, washed with saturated brine for 3 times (50 mL×3), dried over anhydrous sodium sulfate, and concentrated. The crude product was purified by silica gel column chromatography (PE/EtOAc=5:1) to give 5 g product 2-21 as colorless oil, yield 78%. LCMS (ESI) m/z 449.2 (M+H)$^+$ Synthesis of Compound 3-21

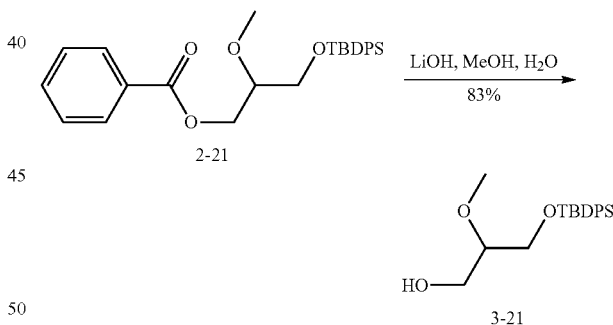

Product 2-21 (5 g, 11 mmol) obtained in the previous step was dissolved in a mixed solution of 50 mL methanol and 5 mL water, LiOH (1.32 g, 55 mmol) was added. The reaction mixture was stirred for 2 hours at room temperature under nitrogen atmosphere, methanol was removed under reduced pressure, and 50 mL water was added, the mixture was extracted with DCM (50 mL×3). The organic phases were combined, washed with saturated brine for 3 times (50 mL×3), dried over anhydrous sodium sulfate, and concentrated. The crude product was purified by silica gel column chromatography (PE/EtOAc=3:1) to give 3.2 g product 3-21 as colorless oil, yield 83%. LCMS (ESI) m/z 345.2 (M+H)$^+$.

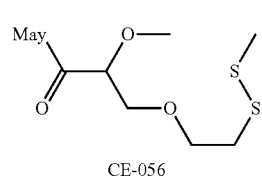

Synthesis of Compound 4-21

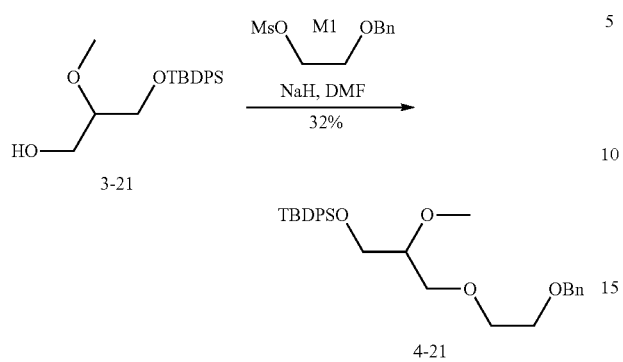

Product 3-21 (3.2 g, 9.3 mmol) obtained in the previous step and compound M1 (3.2 g, 14 mmol) were dissolved in 100 mL DMF, the mixture was cooled to 0° C., NaH (0.75 g, 60%, suspended in mineral oil, 18.6 mmol) was added in batches slowly. The reaction mixture was warmed to room temperature and stirred for 3 hours. The reaction mixture was cooled to 0° C., 20 mL saturated ammonium chloride solution was added dropwise slowly to quench the reaction, 50 mL water was added, the resultant mixture was extracted with DCM for 3 times (50 mL×3), the organic phases were combined, washed with water for 3 times (100 mL×3) and saturated brine (100 mL), dried over anhydrous sodium sulfate, and concentrated. The crude product was purified by silica gel column chromatography (PE/EtOAc=5:1) to give 1.4 g product 4-21 as light yellow oil, yield 31.5%. LCMS (ESI) m/z 479.2 (M+H)$^+$.

Synthesis of Compound 5-21

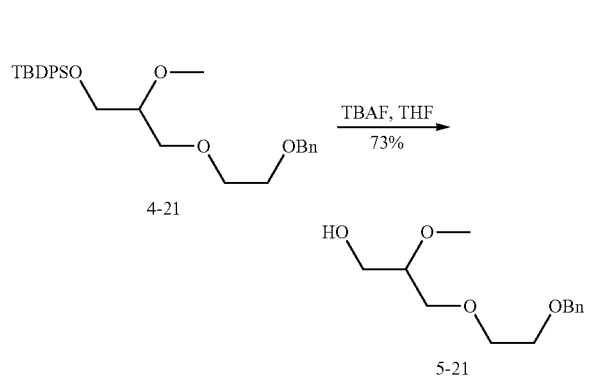

Product 4-21 (1.4 g, 3 mmol) obtained in the previous step was dissolved in 20 mL THF, TBAF/THF solution (1 N, 4.5 mL, 4.5 mmol) was added. The reaction mixture was stirred at ambient temperature for 5 hours, 50 mL water was added, the resultant mixture was extracted with EtOAc (50 mL×3), the organic phases were combined, washed with saturated brine for 3 times (50 mL×3), dried over anhydrous sodium sulfate, and concentrated. The crude product was purified by silica gel column chromatography (PE/EtOAc=3:1) to give 0.55 g product 5-21 as colorless oil, yield 73%. LCMS (ESI) m/z 241.1 (M+H)$^+$.

Synthesis of Compound 6-21

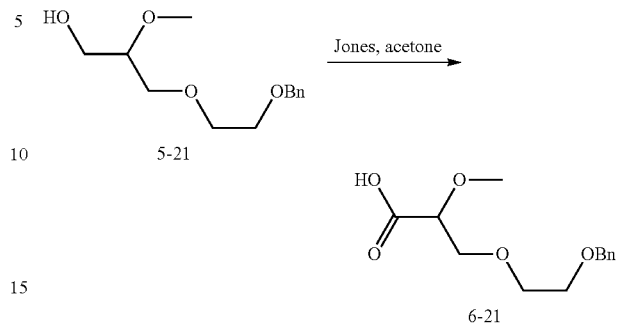

Product 5-21 (0.55 g, 2.3 mmol) obtained in the previous step was dissolved in 20 mL acetone, the mixture was cooled in an ice bath to 0° C., fresh prepared Jones reagent (0.46 g, 4.6 mmol) was added dropwise slowly over about 2 minutes. The reaction mixture was warmed to room temperature and stirred overnight, 1 mL 2-propanol was added to quench the reaction, acetone was removed under reduced pressure, 50 mL water was added, the resultant mixture was extracted with DCM for 3 times (50 mL×3), the organic phases were combined, washed with saturated brine for 3 times (50 mL×3), dried over anhydrous sodium sulfate, concentrated to give crude product as colorless oil, which was used directly for the next step. LCMS (ESI) m/z 255.1 (M+H)$^+$.

Synthesis of Compound 7-21

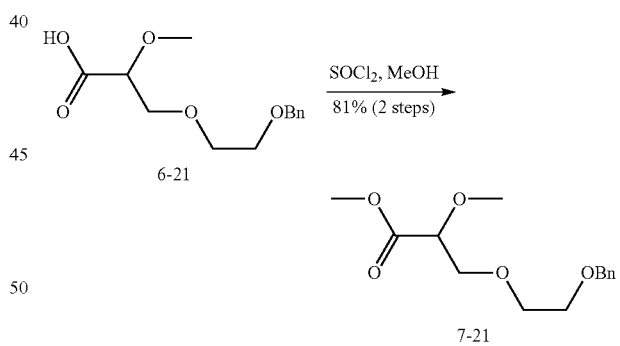

The product 6-21 (0.5 g, 2 mmol) obtained in the previous step was dissolved in methanol (20 mL), SOCl$_2$ (0.48 g, 4 mmol) was added dropwise slowly under an ice-water bath, the reaction was warmed to ambient temperature and stirred overnight, 50 mL water was added to quench the reaction, the mixture was then extracted with EtOAc (50 mL×3), washed with saturated brine (50 mL), dried over anhydrous sodium sulfate, and concentrated. The crude product was purified by silica gel column chromatography (PE/EtOAc=3:1) to give 0.5 g product 7-21 as colorless oil, yield 81%. LCMS (ESI) m/z 269.1 (M+H)$^+$.

Synthesis of Compound 8-21

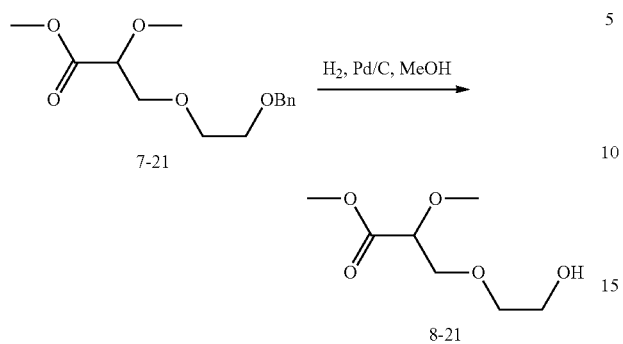

The product 7-21 (0.5 g, 1.9 mmol) obtained in the previous step was dissolved in 20 mL methanol, the mixture was purged by nitrogen gas for 3 times, 30 mg 10% Pd/C dry powder was added. The reaction mixture was purged by hydrogen gas for 3 times, stirred overnight at room temperature under hydrogen atmosphere. The reaction mixture was purged by nitrogen gas for 3 times, 20 mL DCM was added, the mixture was filtered, washed with DCM, the filtrate was concentrated to give 0.32 g crude product as light yellow oil, which was used directly for the next step. LCMS (ESI) m/z 179.1 (M+H)$^+$.

Synthesis of Compound 9-21

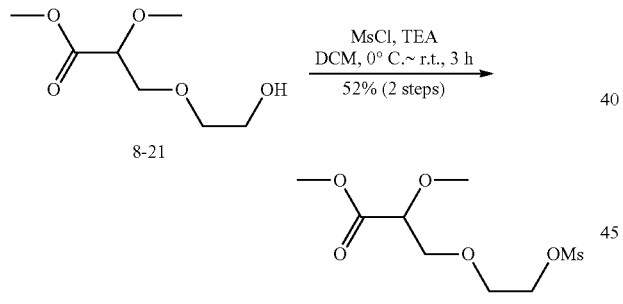

The product 8-21 (0.32 g, 1.8 mmol) obtained in the previous step and Et$_3$N (0.3 mL, 2.1 mmol) were dissolved in 20 mL DCM, the mixture was cooled to 0° C., methanesulfonyl chloride (0.17 mL, 2.1 mmol) was added dropwise slowly. The reaction mixture was warmed to room temperature and stirred for 2 hours. 20 mL Water was added to quench the reaction, the organic phase was separated, washed with saturated brine for 3 times (50 mL×3), dried over anhydrous sodium sulfate, and concentrated. The crude product was purified by silica gel column chromatography (PE/EtOAc=3:1) to give 250 mg product 9-21 as colorless oil, yield 52%. LCMS (ESI) m/z 257.1 (M+H)$^+$.

Synthesis of Compound 10-21

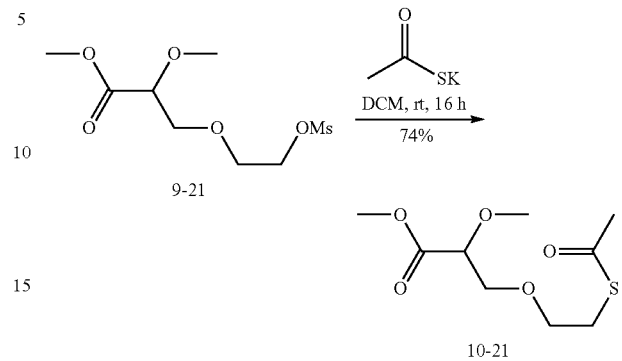

The crude product 9-21 (250 mg, 1 mmol) obtained in the previous step was dissolved in 5 mL DMF, potassium thioacetate (120 mg, 1.5 mmol) was added. The reaction mixture was stirred overnight at room temperature, 20 mL water was added, and the resultant mixture was extracted with EtOAc for 3 times (20 mL×3). The organic phases were combined, washed with water for 3 times (20 mL×3) and saturated brine (20 mL), dried over anhydrous sodium sulfate, and concentrated. The crude product was purified by silica gel column chromatography (PE/EtOAc=3:1) to give 170 mg product 10-21 as brown oil, yield 74%. LCMS (ESI) m/z 237.1 (M+H)$^+$.

Synthesis of Compound 12-21

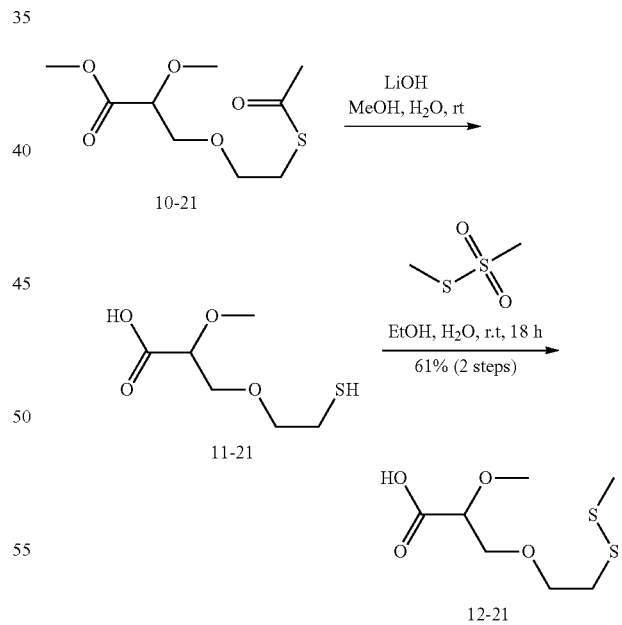

Under nitrogen atmosphere, product 10-21 (170 mg, 0.72 mmol) obtained in the previous step was dissolved in a mixed solution of 10 mL methanol and 5 mL water, LiOH (86 mg, 3.6 mmol) was added. The reaction mixture was stirred for 2 hours at room temperature under nitrogen atmosphere, methyl methanethiosulfonate (140 mg, 1.1 mmol) was added. The reaction mixture was further stirred overnight at room temperature. 20 mL Water was added, the mixture was extracted with EtOAc for 3 times (30 mL×3). The organic phases were combined, washed with saturated brine for 3 times (20 mL×3), dried over anhydrous sodium sulfate, and concentrated. The crude product was purified by silica gel column chromatography (PE/EtOAc=1:1) to give 100 mg product 12-21 as light yellow oil, yield 61%. LCMS (ESI) m/z 227.1 (M+H)+.

Synthesis of Compound CE-056

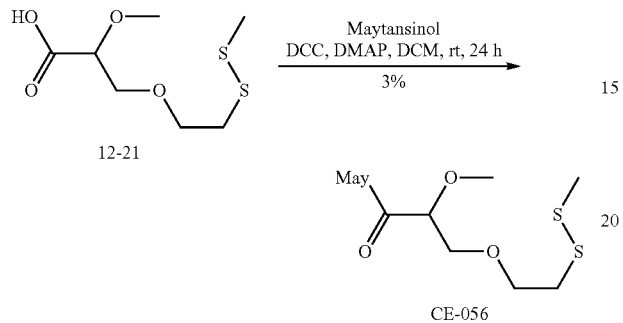

Product 12-21 (100 mg, 0.44 mmol) obtained in the previous step, DCC (173 mg, 0.84 mmol) and DMAP (34 mg, 0.28 mmol) were added to a dry Schlenk tube, the mixture was purged by argon gas for 3 times, 1 mL DCM was added and stirred. Maytansinol (79 mg, 0.14 mmol) in 2 mL dry DCM was added. The reaction mixture was stirred for 2 hours at room temperature, 0.3 mL water was added slowly to quench the reaction, and 15 mL EtOAc was added, the mixture was filtered, washed with EtOAc. The filtrate was dried over anhydrous sodium sulfate, and concentrated. The crude product was purified by prep-HPLC to give 3 mg product CE-056 as white solid, yield 3%.

LCMS (ESI) m/z 773.3 (M+H)+.

Embodiment 22 the Synthetic Route for CE-057

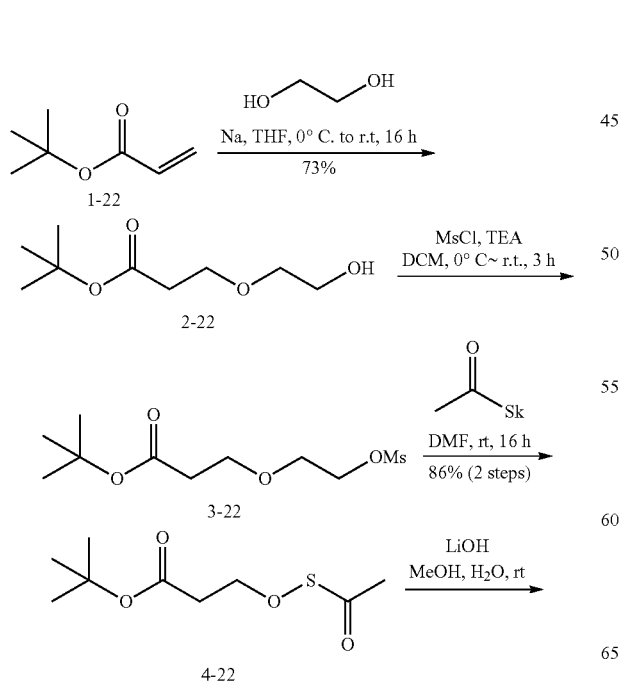

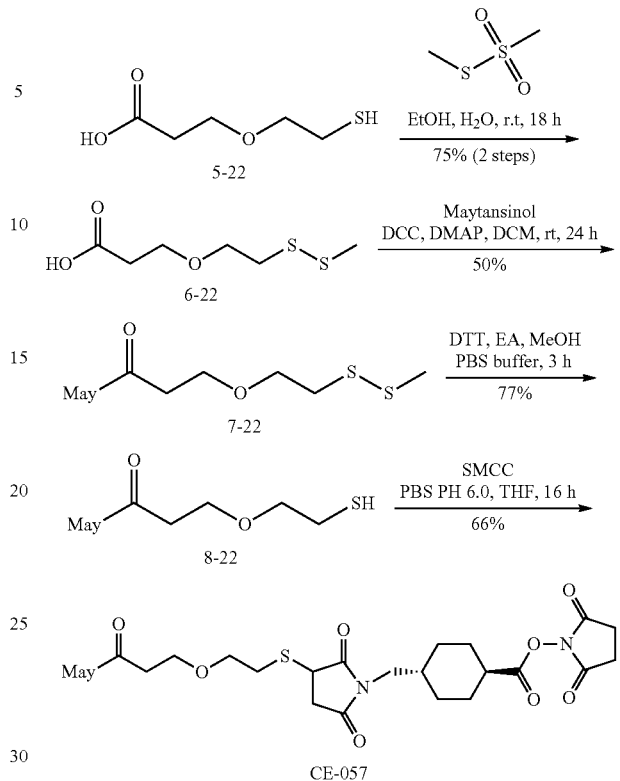

Experimental Procedure

Synthesis of Compound 2-22

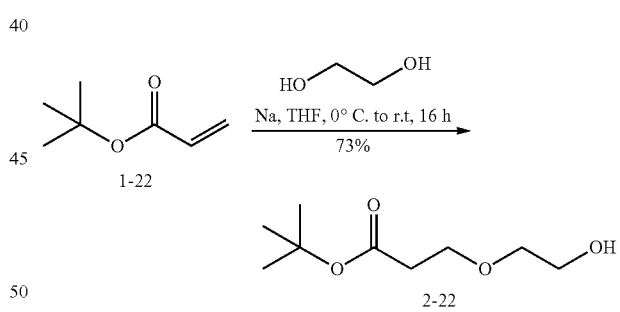

Ethanediol (7.6 mL, 0.15 mol) was dissolved in 100 mL dry THF, 100 mg metal sodium was added, the reaction mixture was stirred at room temperature till the metal sodium was completely consumed, tert-butyl acrylate (14.5 mL, 0.1 mol) was added, then the mixture was stirred overnight at room temperature. THF was removed under reduced pressure, 100 mL EtOAc was added to the residue, the mixture was washed with water for 3 times (50 mL×3), dried over anhydrous sodium sulfate, concentrated, the crude product was purified by silica gel column chromatography (PE/EtOAc=1:1) to give 14 g product 2-22 as colorless oil, yield 73%. LCMS (ESI) m/z 191.1 (M+H)+.

Synthesis of Compound 3-22

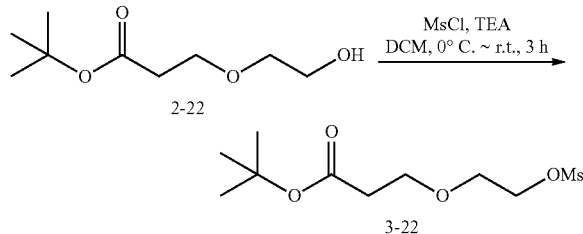

Product 2-22 (7.6 g, 40 mmol) obtained in the previous step and Et₃N (6.6 mL, 48 mmol) were dissolved in 50 mL DCM, the mixture was cooled to 0° C., methanesulfonyl chloride (3.5 mL, 44 mmol) was added dropwise slowly. The reaction mixture was warmed to room temperature and stirred for 2 hours. 50 mL Water was added to quench the reaction, the organic phase was separated, washed with saturated brine for 3 times (50 mL×3), dried over anhydrous sodium sulfate, concentrated to give crude product as light yellow oil, which was used directly for the next step. LCMS (ESI) m/z 269.1 (M+H)$^+$.

Synthesis of Compound 4-22

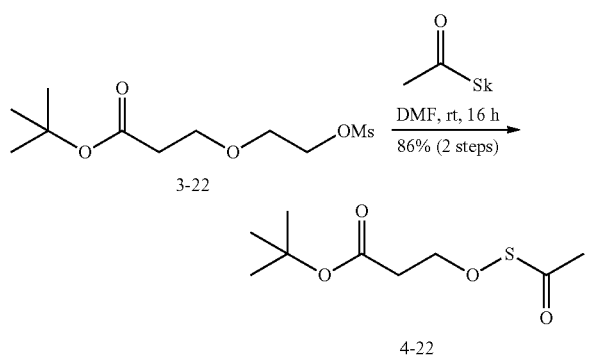

The crude product 3-22 (2.7 g, 10.0 mmol) obtained in the previous step was dissolved in 20 mL DMF, potassium thioacetate (2.3 g, 20 mmol) was added. The reaction mixture was stirred overnight at room temperature, 30 mL water was added, and the resultant mixture was extracted with EtOAc for 3 times (50 mL×3). The organic phases were combined, washed with water for 3 times (30 mL×3) and saturated brine (50 mL), dried over anhydrous sodium sulfate, and concentrated. The crude product was purified by silica gel column chromatography (PE/EtOAc=2:1) to give 2.0 g product 4-22 as brown oil, yield 86%. LCMS (ESI) m/z 248.2 (M+H)$^+$.

Synthesis of Compound 6-22

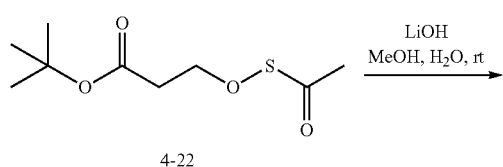

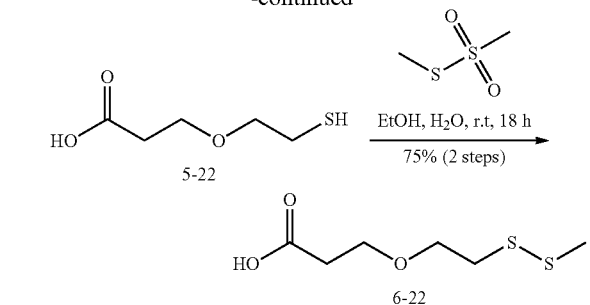

Under nitrogen atmosphere, the product 4-22 (2 g, 8 mmol) obtained in the previous step was dissolved in a mixed solution of 20 mL methanol and 10 mL water, LiOH (0.78 g, 32 mmol) was added. The reaction mixture was stirred for 2 hours at room temperature under nitrogen atmosphere, methyl methanethiosulfonate (1.2 g, 9.6 mmol) was added. The reaction mixture was further stirred overnight at room temperature. 50 mL Water was added, the resultant mixture was extracted with EtOAc for 3 times (50 mL×3). The organic phases were combined, washed with saturated brine for 3 times (50 mL×3), dried over anhydrous sodium sulfate, and concentrated. The crude product was purified by silica gel column chromatography (PE/EtOAc=1:2) to give 1.2 g product 6-22 as light yellow oil, yield 75%.

LCMS (ESI) m/z 197.0 (M+H)$^+$

Synthesis of Compound 7-22

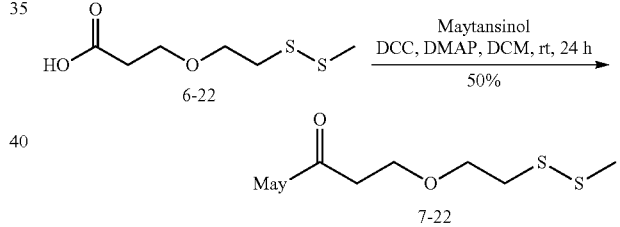

Product 6-22 (47 mg, 0.24 mmol) obtained in the previous step, DCC (132 mg, 0.64 mmol) and DMAP (20 mg, 0.16 mmol) were added to a dry Schlenk tube, the mixture was purged by argon gas for 3 times, 1 mL DCM was added and stirred. Maytansinol (45 mg, 0.08 mmol) in 4 mL dry DCM was added. The reaction mixture was stirred for 2 hours at room temperature, 0.3 mL water was added slowly to quench the reaction, and then 15 mL EtOAc was added, the mixture was filtered, washed with EtOAc. The filtrate was dried over anhydrous sodium sulfate, and concentrated. The crude product was purified by prep-HPLC to give 30 mg product 7-22 as white solid, yield 50%.

Synthesis of Compound 8-22

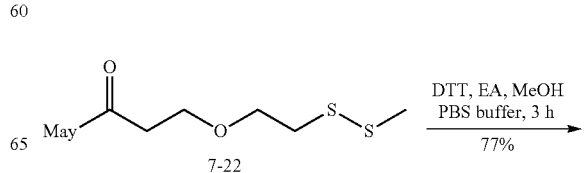

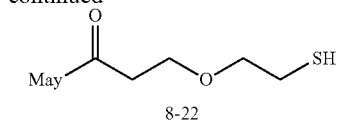

The product 7-22 (15 mg, 0.02 mmol) obtained in the previous step was dissolved in a mixed solution of 0.5 mL EtOAc and 0.5 mL methanol, dithiothreitol (DTT) (15 mg, 0.10 mmol) in 0.5 mL pH=7.5 potassium phosphate buffer was added. The reaction mixture was stirred for 3 hours under nitrogen atmosphere. 1 mL pH=6 potassium phosphate buffer was added to quench the reaction, the mixture was extracted with EtOAc for 3 times (5 mL×3), the organic phases were combined, washed with saturated brine (5 mL), dried over anhydrous sodium sulfate, and concentrated. The crude product was purified by prep-HPLC (CH$_3$CN in H$_2$O-0.05% TFA from 5% to 950%) to give 11 mg product 8-22 as white solid, yield 77%. LCMS (ESI) m/z 697.3 (M+H)$^+$.

Synthesis of Compound CE-057

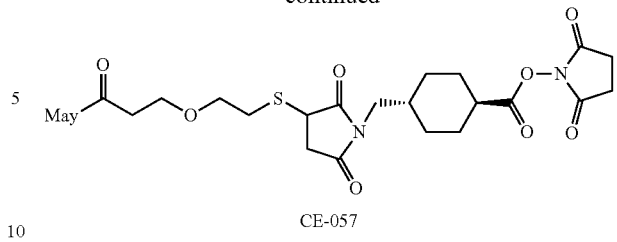

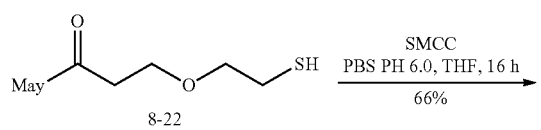

Product 8-22 (10 mg, 0.014 mmol) obtained in the previous step was dissolved in 1.5 mL THF, 1.5 mL pH=6 potassium phosphate buffer and 4-(N-maleimidomethyl) cyclohexanecarboxylic acid N-hydroxysuccinimide ester (23 mg, 0.07 mmol) were added, the mixture was stirred overnight at room temperature under nitrogen atmosphere. The reaction mixture was filtered, purified directly by prep-HPLC to give 9.5 mg product CE-057 as white solid, yield 66%.

LCMS (ESI) m/z 1030.6 (M+H)$^+$.

$^1$H NMR (400 MHz, CDCl$_3$) δ ppm 6.84 (s, 1H), 6.78 (d, J=10.8 Hz, 1H), 6.47 & 6.43 (dd, J$_1$=15.2 Hz, J$_2$=11.2 Hz, 1H), 6.39 (s, 1H), 6.19 (d, J=10.8 Hz, 1H), 5.57 & 5.54 (dd, J$_1$=15.2 Hz, J$_2$=8.8 Hz, 1H), 4.93-4.88 (m, 1H), 4.29-4.21 (m, 1H), 3.99 (s, 3H), 3.92-3.85 (m, 1H), 3.84-3.68 (m, 4H), 3.55-3.47 (m, 2H), 3.39 (t, J=6.8 Hz, 2H), 3.35 (s, 3H), 3.30-3.18 (m, 2H), 3.15 (d, J=17.2 Hz, 3H), 3.10-2.94 (m, 1H), 2.94-2.67 (m, 4H), 2.83 (s, 3H), 2.61-2.47 (m, 3H), 2.16 (d, J=11.2 Hz, 2H), 1.98-1.90 (m, 1H), 1.80-1.78 (m, 2H), 1.68 (s, 3H), 1.64-1.45 (m, 4H), 1.32-1.25 (m, 4H), 1.08 (q, J=8.4 Hz, 3H), 0.84 (s, 3H).

Embodiment 23 the Synthetic Route for CE-063

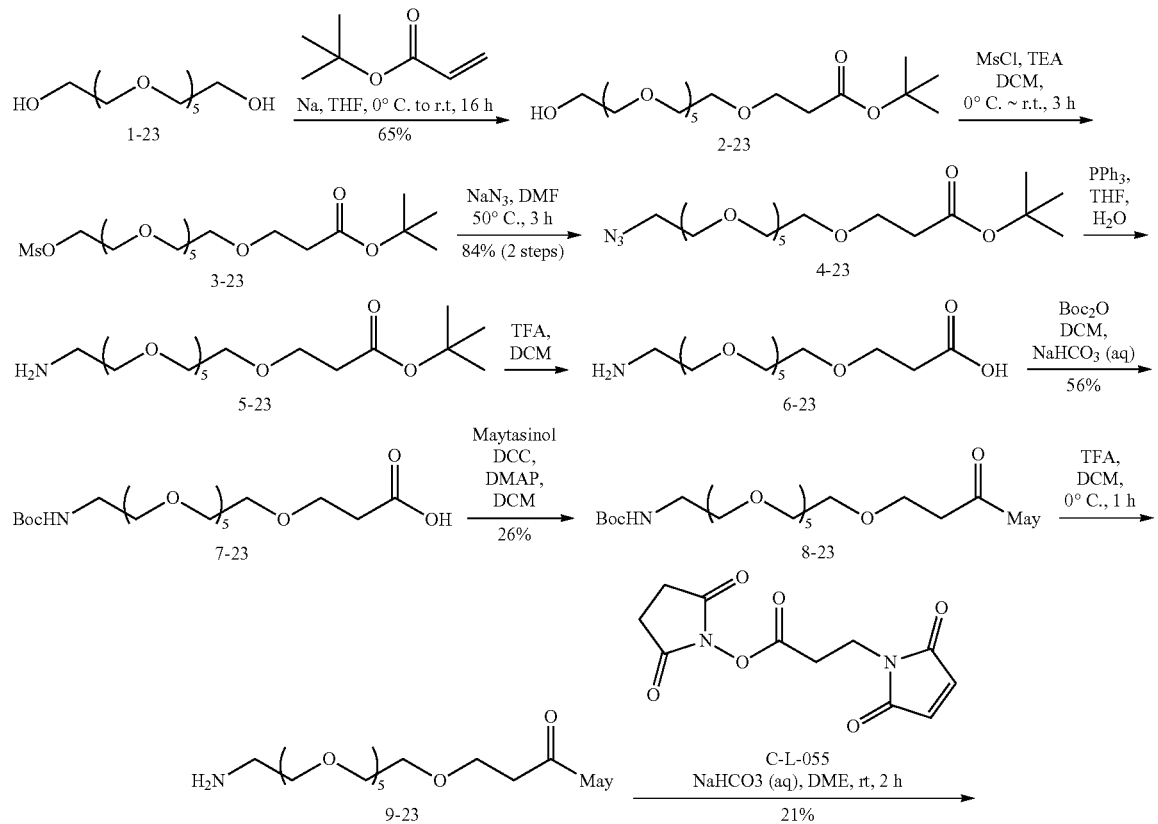

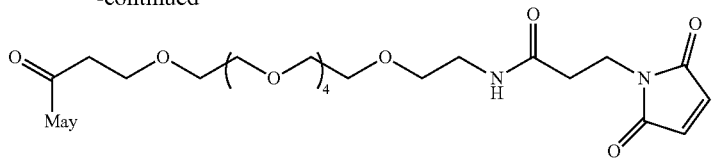

CE-063

Experimental Procedure

Synthesis of Compound 2-23

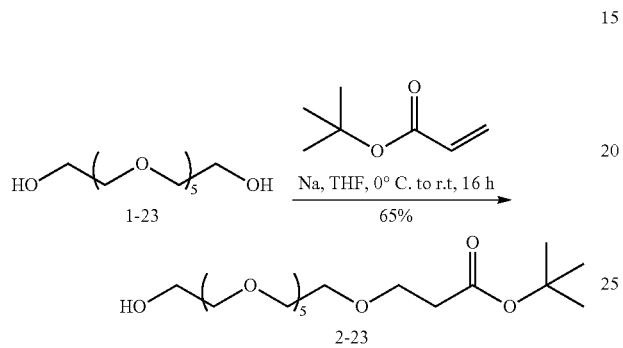

Hexaethylene glycol (11.3 mL, 45 mmol) was dissolved in 80 mL dry THF, 50 mg metallic sodium was added, the reaction mixture was stirred at room temperature till the metallic sodium was completely consumed, tert-butyl acrylate (4.35 mL, 30 mmol) was added, then stirred overnight at room temperature. THF was removed under reduced pressure, 80 mL EtOAc was added into the residue, the mixture was washed with water for 3 times (50 mL×3), dried over anhydrous sodium sulfate, concentrated, the crude product was purified by silica gel column chromatography (DCM/Methanol=20:1) to give 8 g product 2-23 as colorless oil, yield: 65%. LCMS (ESI) m/z 432.9 (M+Na)$^+$.

Synthesis of Compound 3-23

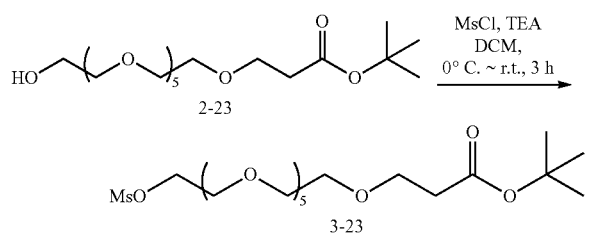

The product 2-23 (2.05 g, 5 mmol) obtained in the previous step and Et$_3$N (0.85 mL, 6 mmol) were dissolved in 30 mL DCM, the mixture was cooled to 0° C., methanesulfonyl chloride (0.45 mL, 5.5 mmol) was added dropwise slowly. The reaction mixture was warmed to room temperature and stirred for 2 hours. 30 mL water was added to quench the reaction, the organic phase was separated, washed with saturated brine for 3 times (30 mL×3), dried over anhydrous sodium sulfate, concentrated to give the crude product as yellow oil, which was used directly for the next step.

Synthesis of Compound 4-23

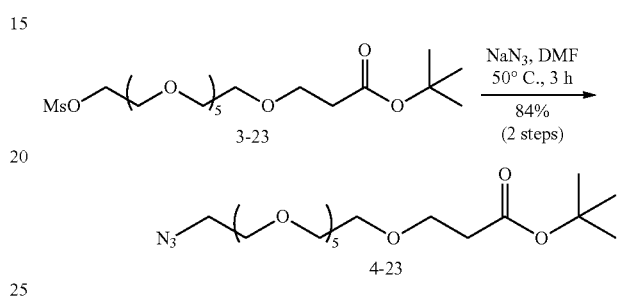

The product 3-23 (2.5 g, 5 mmol) obtained in the previous step was dissolved in 20 mL DMF, NaN$_3$ (390 mg, 6 mmol) was added. The reaction mixture was heated to 50° C. and stirred for 4 hours. The reaction mixture was cooled to room temperature, 30 mL water was added to quench the reaction, extracted with EtOAc for 3 times (30 mL×3), the organic phases were combined, washed with saturated brine for 3 times (30 mL×3), dried over anhydrous sodium sulfate, concentrated to give the crude product, which was purified by silica gel column chromatography (PE/EtOAc=1:1) to give 1.8 g product 4-23 as light yellow oil, the two-step yield 84%. LCMS (ESI) m/z 436.3 (M+H)$^+$.

Synthesis of Compound 5-23

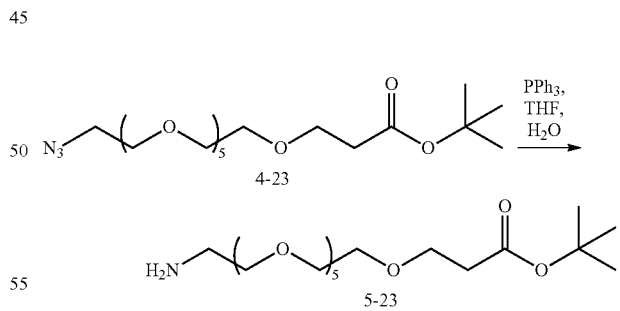

The product 4-23 (1.74 g, 4 mmol) obtained in the previous step was dissolved in 30 mL THF and 5 mL water, PPh$_3$ (1.31 g, 5 mmol) was added. The reaction mixture was stirred overnight at room temperature. THF was removed under reduced pressure, 1 N dilute hydrochloric acid 10 mL was added, the mixture was washed with EtOAc for 3 times (20 mL×3), the aqueous phase was freeze-drying to give 1.5 g crude product 5-23 as light yellow oil. LCMS (ESI) m/z 410.3 (M+H)$^+$.

Synthesis of Compound 6-23

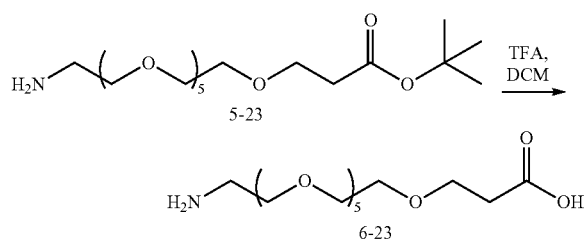

The crude product 5-23 (818 mg, 2 mmol) obtained in the previous step was dissolved in 4 mL dry DCM, the mixture was cooled to 0° C. in an ice bath, 0.8 mL TFA was added dropwise slowly, the reaction mixture was gradually warmed to room temperature and stirred for 1 hour, after the starting material was completely consumed as monitored by LCMS, DCM and TFA were removed under reduced pressure at ambient temperature to give 700 mg crude product 6-23 as light yellow solid, which was used directly for the next step. LCMS (ESI) m/z 354.2 (M+H)$^+$.

Synthesis of Compound 7-23

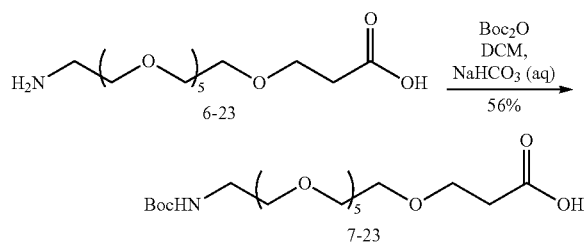

The crude product 6-23 (530 mg, 1.5 mmol) obtained in the previous step was dissolved in 3 mL saturated sodium bicarbonate aqueous solution and 30 mL DCM, the mixture was cooled to 0° C. in an ice-water bath, Boc$_2$O (436 mg, 2 mmol) was added, then warmed to room temperature and stirred for 2 hours. The reaction mixture was washed with water for 2 times (20 mL×2), the aqueous phases were combined, 0.5 M KHSO$_4$ aqueous solution was added to quench the reaction and adjust pH to 3-4, extracted with DCM for 3 times (20 mL×3), the organic phases were combined, dried over anhydrous sodium sulfate, and concentrated, the residue was purified by silica gel column chromatography (DCM/methanol=20:1) to give 380 mg product 7-23 as light yellow oil, yield: 56%. LCMS (ESI) m/z 453.9 (M+H)$^+$, 475.9 (M+Na)$^+$.

Synthesis of Compound 8-23

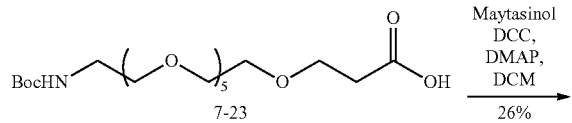

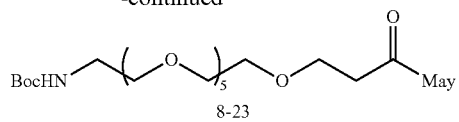

The product 7-23 (136 mg, 0.3 mmol) obtained from the previous step, DCC (165 mg, 0.8 mmol) and DMAP (24 mg, 0.2 mmol) were added into a dry Schlenk tube, the mixture was purged by argon for 3 times, 1 mL DCM was added and stirred. Maytansinol (57 mg, 0.1 mmol) dissolved in 4 mL dry DCM was added. The reaction mixture was stirred for 2 hours at room temperature, 0.3 mL water was added slowly to quench the reaction, then 15 mL EtOAc was added, filtered, washed with EtOAc. The filtrate was dried over anhydrous sodium sulfate, and concentrated. The crude product was purified by prep-HPLC to give 26 mg product 8-28 as white solid, yield: 26%. LCMS (ESI) m/z 1000.7 (M+H).

$^1$H NMR (400 MHz, CDCl$_3$) δ ppm 6.84 (s, 1H), 6.78 (s, 1H), 6.44 & 6.42 (dd, J$_1$=12.4 Hz, J$_2$=8.4 Hz, 1H), 6.40 (s, 1H), 6.21 (d, J=8.8 Hz, 1H), 5.63&5.61 (dd, J$_1$=12.4 Hz, J$_2$=6.8 Hz, 1H), 5.16 (br, 1H), 4.92 (d, J=9.2 Hz, 1H), 4.26 (t, J=8.8 Hz, 1H), 3.99 (s, 3H), 3.84-3.72 (m, 2H), 3.71-3.60 (m, 20H), 3.55-3.51 (m, 2H), 3.47 (d, J=6.8 Hz, 1H), 3.35 (s, 3H), 3.20 (d, J=10.4 Hz, 1H), 3.16 (s, 3H), 2.83-2.78 (m, 2H), 2.72-2.66 (m, 1H), 2.64 (t, J=10.0 Hz, 1H), 2.54-2.49 (m, 1H), 2.18 (t, J=11.2 Hz, 1H), 1.93 (d, J=7.6 Hz, 2H), 1.74-1.69 (m, 2H), 1.68 (s, 3H), 1.64 (d, J=11.2 Hz, 1H), 1.44 (s, 9H), 1.27 (d, J=7.6 Hz, 3H), 0.85 (s, 3H).

Synthesis of Compound 9-23

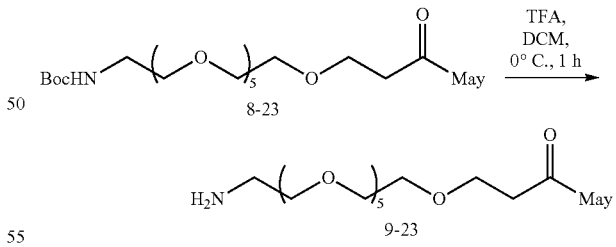

The crude product 8-23 (30 mg, 0.03 mmol) obtained from the previous step was dissolved in 4 mL dry DCM, the mixture was cooled to 0° C. in an ice-water bath, 0.4 mL TFA was added dropwise slowly, the reaction mixture was gradually warmed to room temperature and stirred for 1 hour, after the starting material was completely consumed as monitored by LCMS, DCM and TFA were removed under reduced pressure at ambient temperature to give 20 mg crude product 9-23 as light yellow solid, which was used directly for the next step. LCMS (ESI) m/z 900.7 (M+H)$^+$.

Synthesis of Compound CE-063

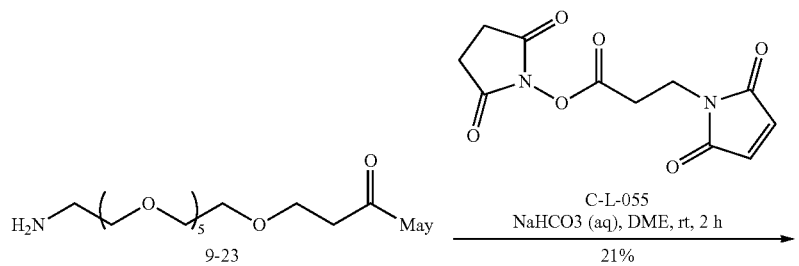

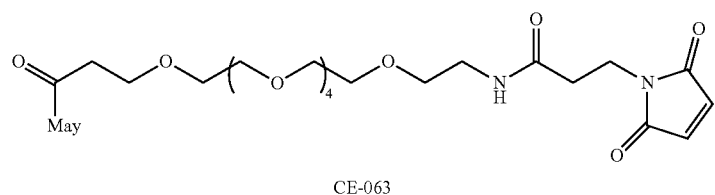

CE-063

Compound 9-23 (20 mg, 0.022 mmol) and CE-L-055 (12 mg, 0.044 mmol) were suspended in 5 mL water, 0.2 mL saturated sodium bicarbonate aqueous solution was added, the reaction mixture was stirred for 2 hours at room temperature. The crude product was purified by prep-HPLC to give 5 mg product CE-063 as white solid, yield: 21%. LCMS (ESI) m/z 1073.3 (M+Na)$^+$.

$^1$H NMR (400 MHz, CDCl$_3$) δ ppm 7.01 (br, 1H), 6.84 (s, 1H), 6.77 (s, 1H), 6.69 (s, 2H), 6.51 (s, 1H), 6.44 & 6.42 (dd, $J_1$=12.4 Hz, $J_2$=8.4 Hz, 1H), 6.21 (d, J=8.4 Hz, 1H), 5.63&5.61 (dd, $J_1$=12.4 Hz, $J_2$=7.2 Hz, 1H), 4.92 (d, J=9.2 Hz, 1H), 4.26 (t, J=8.8 Hz, 1H), 3.99 (s, 3H), 3.84 (t, J=5.6 Hz, 2H), 3.81-3.74 (m, 2H), 3.70-3.60 (m, 22H), 3.56-3.52 (m, 3H), 3.47 (d, J=7.2 Hz, 1H), 3.44-3.39 (m, 2H), 3.35 (s, 3H), 3.20 (d, J=10.4 Hz, 1H), 3.16 (s, 3H), 2.85-2.78 (m, 2H), 2.72-2.66 (m, 1H), 2.53 (d, J=6.0 Hz, 3H), 2.24-2.15 (m, 2H), 1.68 (s, 3H), 1.64 (d, J=11.2 Hz, 1H), 1.50-1.43 (m, 1H), 1.27 (s, 3H), 0.85 (s, 3H).

Embodiment 24 the Synthetic Route for T-CE-040

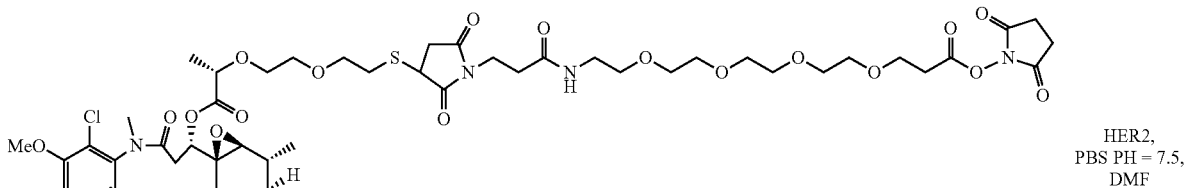

CE-040

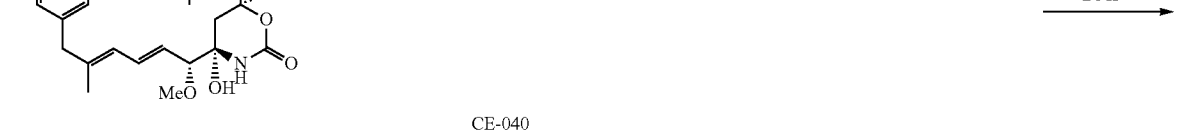

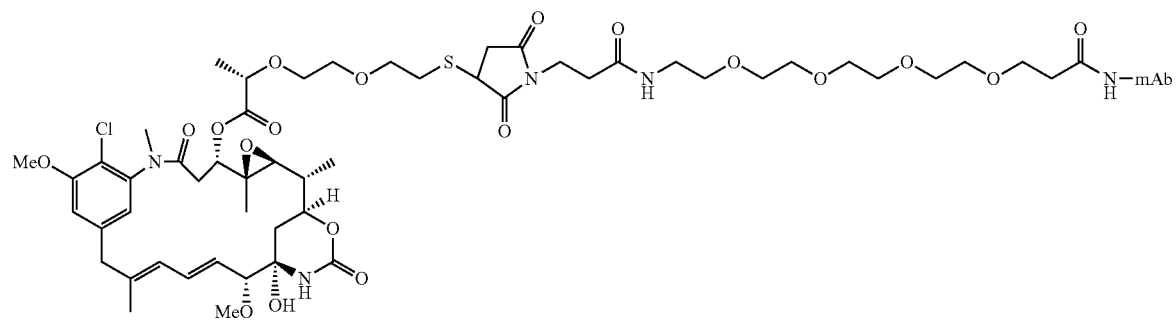

T-CE-040

According to the references Gail D. Lewis Phillips, et al., *Cancer. Res.*, 2008, 68, 9280 and Teemu T. Junttila, et al., *Breast. Cancer. Res. Treat.*, 2011, 128, 347 etc., the anti-HER2 antibodies (anti-human epidermal growth factor receptor 2, Herceptin) prepared in embodiments were dialyzed overnight with solution A (100 mM phosphate buffer, pH=7.5), the dialysate was diluted to 10 mg/mL with solution A. CE-040 was added, the ratio of CW-040 to the anitbody was 6:1 (molar equivalents). Then DMF was added till DMF accounted for 30% of the toatl volume, then the mixture was reacted at 25° C. for 3.5 hours while stirring to mix the reactants. Excessive reagents and small molecule drugs were removed though gel filtration chromatography column with Sephadex G-25 (GE No: 17-0031-01), the chromatography column was pre-balanced with pH=5.0 succinic acid solution, T-CE-040 was obtained after purification. Then the antibody drug conjugate was dialyzed overnight with pH=5.0 succinic acid solution, filtered through a 0.22 m filter, and stored at 4° C. The ultimate number of conjugating CE-040 for each Herceptin antibody was determined by the absorbances of the conjugate at 252 nm and 280 nm as well as LC-MS detection, followed by SEC to determine if the conjugate contained multimers. The drug-antibody ratio (DAR) of CE-040 and Herceptin determined by LC-MS was 3.46:1.

Embodiment 25 the Synthetic Route for T-CE-063

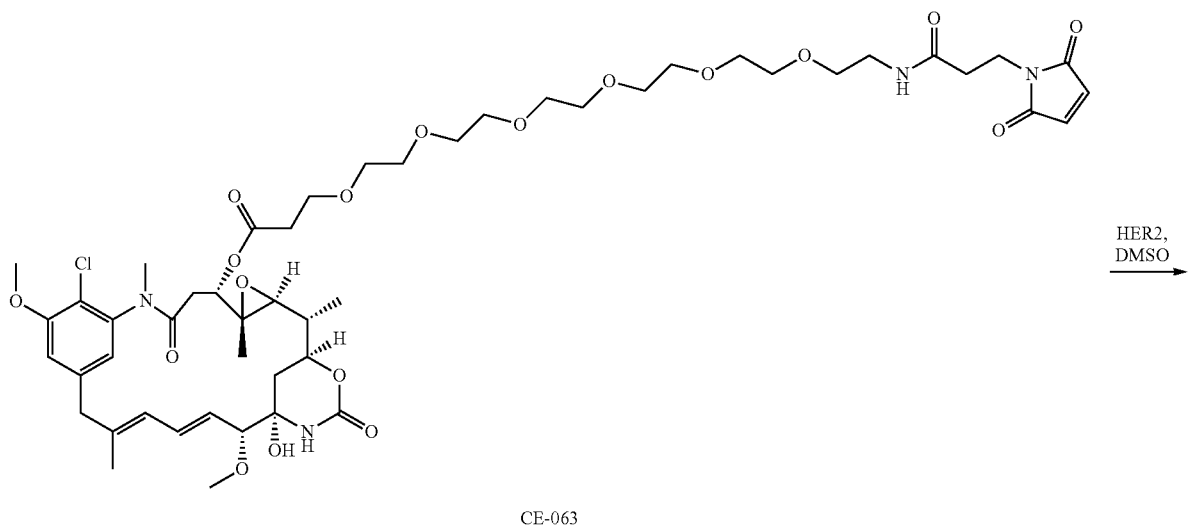

CE-063

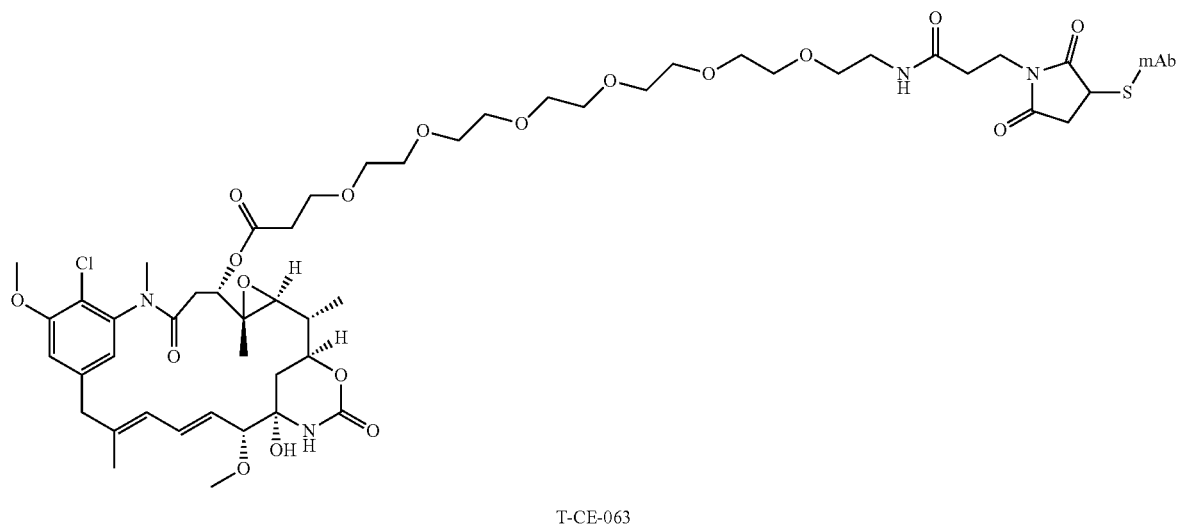

T-CE-063

The anti-HER2 antibodier (anti-human epidermal growth factor receptor 2, Herceptin) prepared in embodiments were dialyzed overnight with solution A (25 mM sodium borate buffer, 25 mM NaC, im MDTPA, pH=7.5), and diluted to 5 mg/mL. 5 mM TCEP was added, the ratio of TCEP to the antibody was 2.5:1 (molar equivalents), then the mixture was reacted at 25° C. for 2 hours while stirring to mix the reactants. Then CE-063 was added till the ratio of CE-063 to the antibody was 10:1 (molar equivalents), and DMSO was added to DMSO accounted for 10% of the total volume, then reacted at 25° C. for 2 hours while stirring to mix the reactants. Excessive reagents and small molecule drugs were removed though gel filtration chromatography column with Sephadex G-25 (GE No: 17-0031-01), the chromatography column was pre-balanced with pH=7.4 phosphate buffer, T-CE-063 was obtained after purification. Then the antibody drug conjugate was dialyzed overnight with pH=7.4 phosphate buffer, filtered through a 0.22 μm filter, and stored at 4° C. The ultimate number of conjugating CE-063 for each Herceptin antibody was determined by HIC detection, followed by SEC to determine if the conjugate contained multimers. The ratio (DAR) of CE-063 and Herceptin determined by HIC was 3.52:1.

Other Antibody Drug Conjugates of the Present Invention could be Prepared according to Embodiments 24-25.

Biological Activity Test

T-CE-040 and T-CE-063 Antibody Drug Conjugates Biological Activity Test

Figure 2:
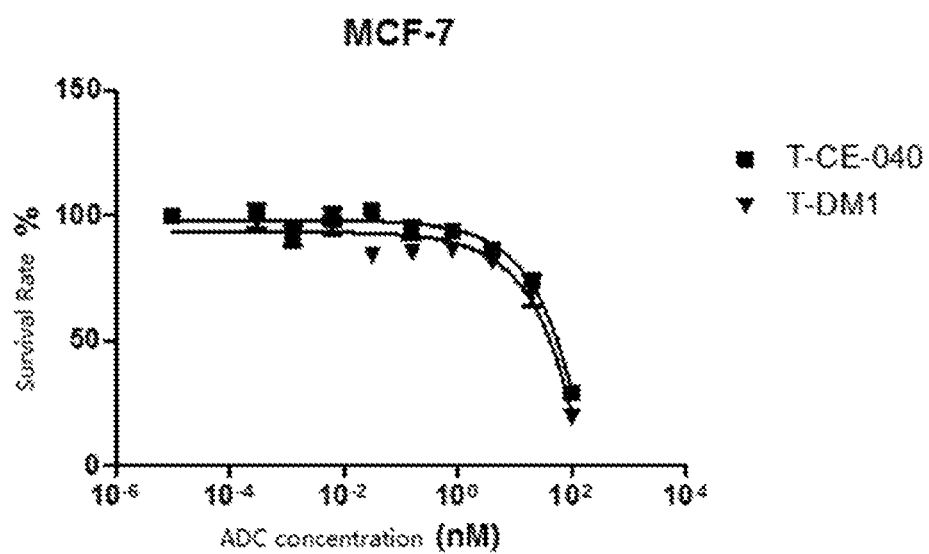
FIG. 2 is a growth inhibition curve graph of T-CE-040 and T-DM1 against MCF-7.
Figure 3:
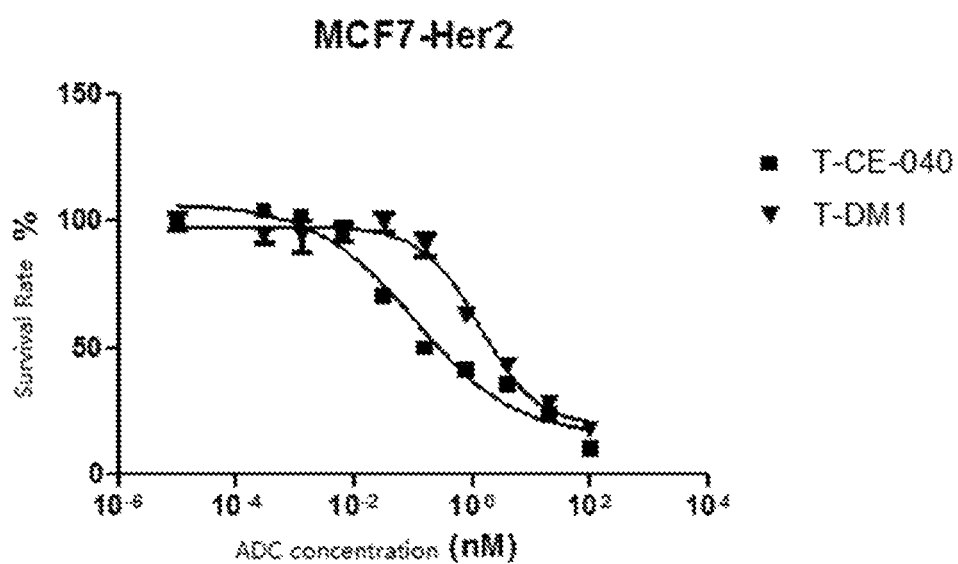
FIG. 3 is a growth inhibition curve graph of T-CE-040 and T-DM1 against MCF-7-Her2.
Figure 4:
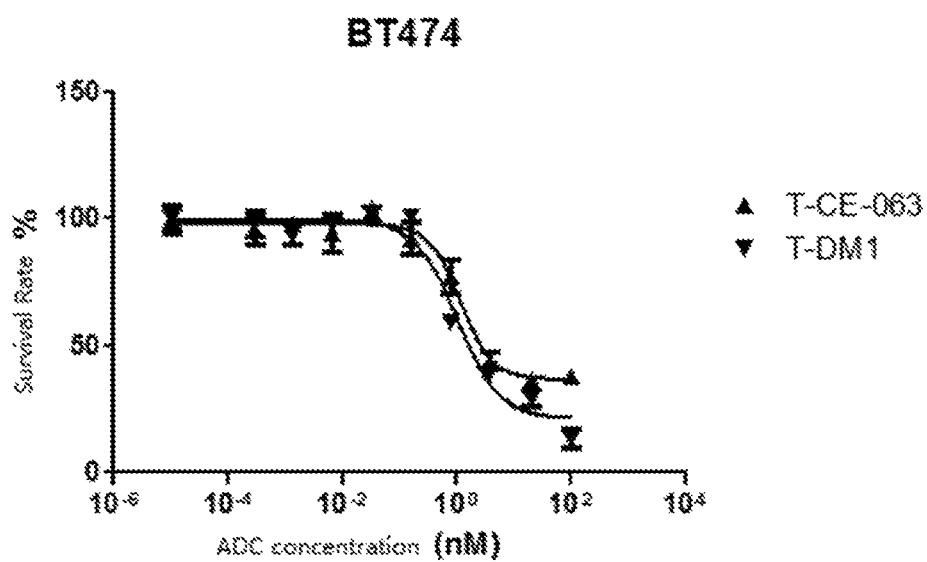
FIG. 4 is a growth inhibition curve graph of T-CE-063 and T-DM1 against BT474.
Figure 5:
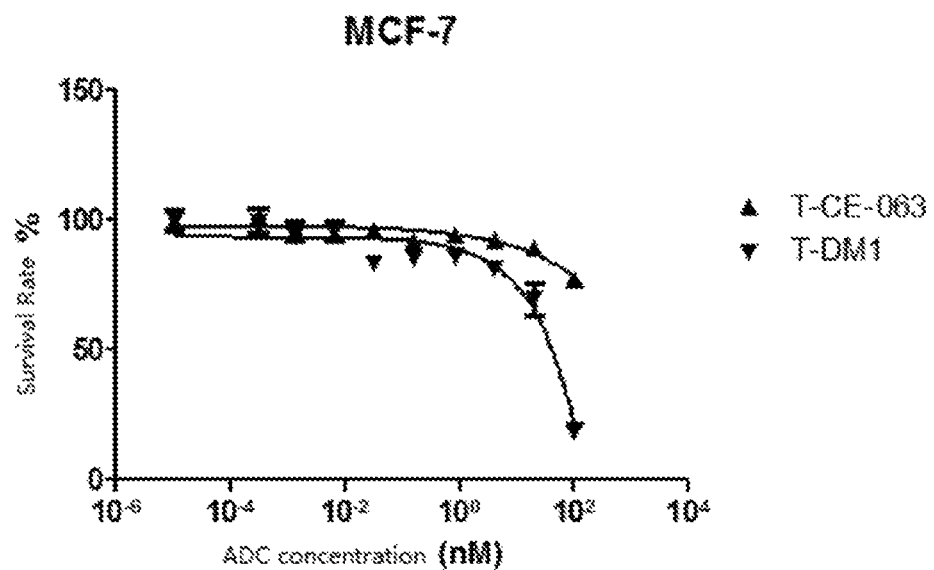
FIG. 5 is a growth inhibition curve graph of T-CE-063 and T-DM1 against MCF-7.
Figure 6:
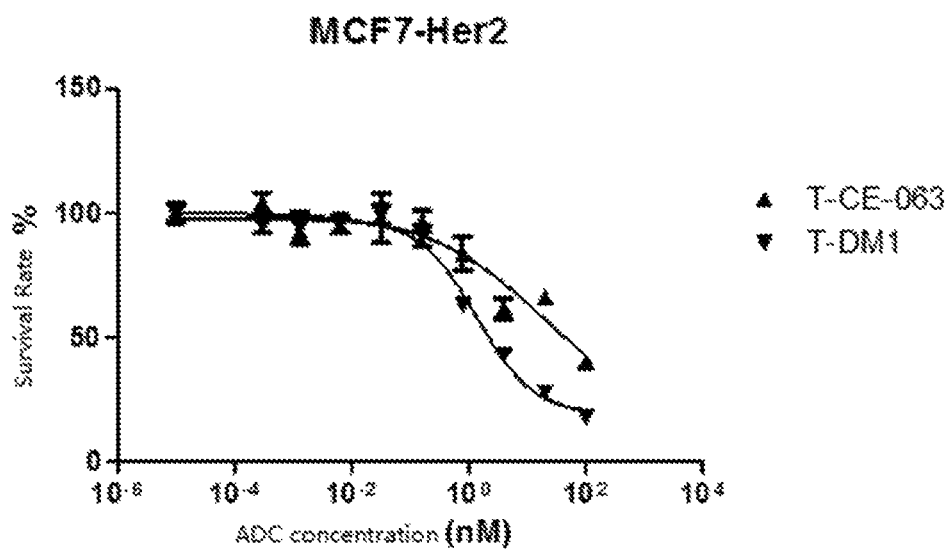
FIG. 6 is a growth inhibition curve graph of T-CE-063 and T-DM1 against MCF-7-Her2.

Her2-positive human BT474 breast tumor cells (BT474 for short), Her2 low expression human MCF-7 breast tumor cells (MCF-7 for short), and human breast tumor cell strain MCF7-Her2 with stable-transfected Her2 outside MCF-7 (MCF-7-Her2 for short) were used (they were prepared by the methods disclosed in the literatures for preparing recombinant cells: Teemu T. Junttila, et al., *Breast. Cancer Res. Treat.*, 2011, 128, 347 and Jeffrey J. Wallin et al., *Clin. Cancer Res.*, 2012, 18, 3901, the contents of which are incorporated herein by reference in their entireties). The growth inhibition of tumor cells by T-CE-040 and T-CE-063 antibody drug conjugates were evaluated. BT474, MCF7-Her2 and MCF-7 were digested with 0.25% (v/v) trypsin and the cells were stripped and then suspended in 100 μL complete medium. 2,000 cells were inoculated in a 96-well plate and cultured, grew adherently overnight at 37° C., then 100 μL T-CE-040 and T-CE-063 antibody drug conjugates with different concentration gradients and the complete medium were added. After 120 hours, relative cell proliferation analysis was performed by adding 50 μL CellTiter-Glo® Fluorescent Cell Activation Reagent (CellTiter-GloB Luminescent, Promega). The growth inhibition curves of tumor cells by T-CE-040, T-CE-063 and T-DM1 were shown in FIG. 1-6, wherein the abscissa indicates drug concentration (i.e. ADC concentration); the ordinate indicates cell survival rate (%). From FIG. 1 to FIG. 6, it can be seen that T-CE-040 can effectively inhibit the proliferation of the above-mentioned three kinds of tumor cells, and the effect is equivalent to or better than that of T-DM1.

Biological activities of other compounds were tested according to the above-mentioned same operations, the results were shown in the following table:

| No. | Structure | Cytotoxicity assay IC$_{50}$ (nM) | | |
|---|---|---|---|---|
| | | BT474 | MCF7 | MCF-Her2 |
| CE-012 | CE-012 | 16.4 | 65.8 | 133 |
| CE-014 | CE-014 | 19.6 | 127 | 68.8 |

| No. | Structure | Cytotoxicity assay IC$_{50}$ (nM) | | |
| --- | --- | --- | --- | --- |
| | | BT474 | MCF7 | MCF-Her2 |
| CE-016 | 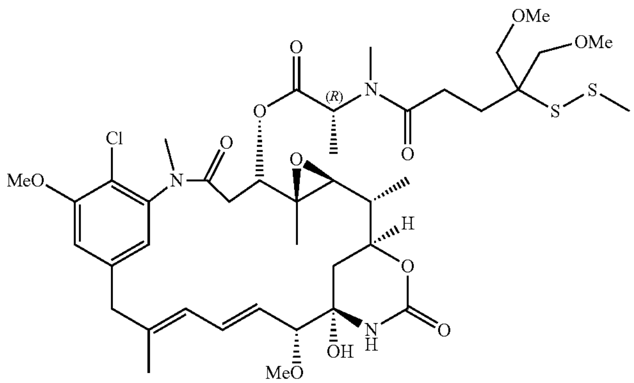 | 23.4 | 67.7 | 42.7 |
| CE-018 | 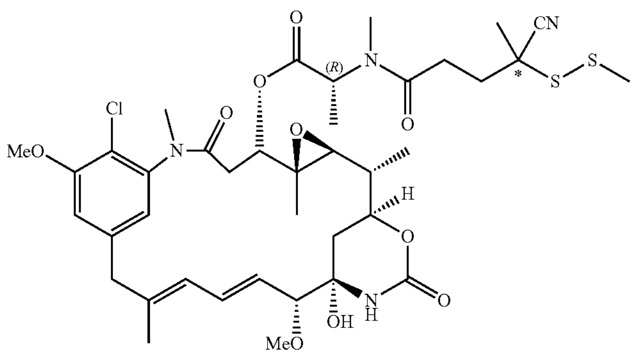 | 41.7 | 1571 | 399 |
| CE-013 | 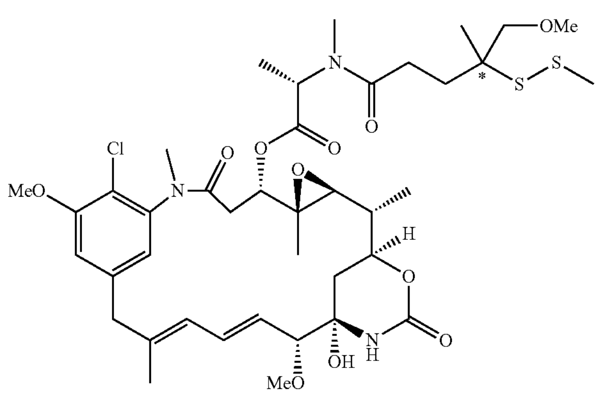 [SMILES: COCC(C)(CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C)SSC] | 21 | 4.3 | 5.9 |

| No. | Structure | Cytotoxicity assay IC$_{50}$ (nM) | | |
|---|---|---|---|---|
| | | BT474 | MCF7 | MCF-Her2 |
| CE-015 | 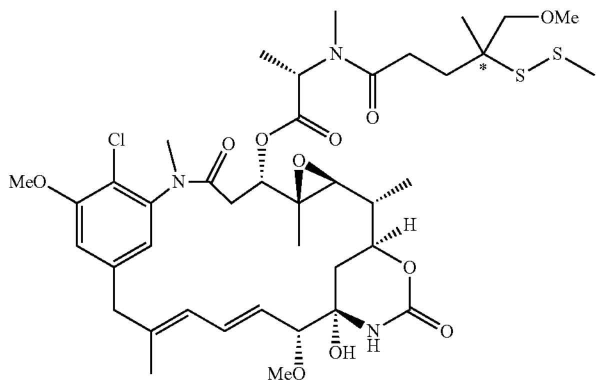 [SMILES: COCC(C)(CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C)SSC] | 6.3 | 3.0 | 7.1 |
| CE-017 | 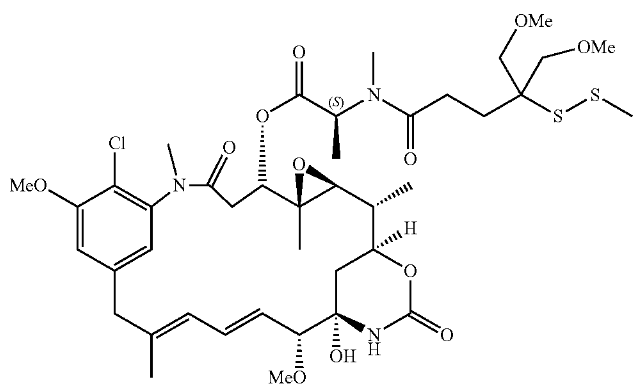 | 14 | 8.9 | 3.1 |
| CE-019 | 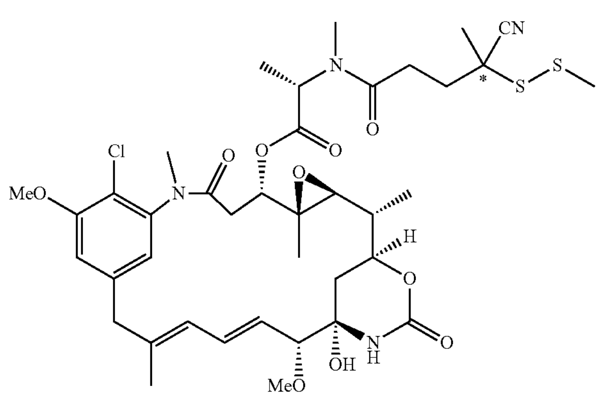 [SMILES: COc1cc2cc(c1Cl)N(C)C(=O)C[C@H](OC(=O)[C@H](C)N(C)C(=O)CCC(C)(C#N)SSC)[C@]1(C)O[C@H]1[C@H](C)[C@@H]1C[C@@](O)(NC(=O)O1)[C@H](OC)/C=C/C=C(\C)C2] | 64 | 150 | 57 |

-continued

| No. | Structure | Cytotoxicity assay IC$_{50}$ (nM) | | |
|---|---|---|---|---|
| | | BT474 | MCF7 | MCF-Her2 |
| CE-021 | *(structure of CE-021)* | 63.9 | 98.6 | 92.9 |
| CE-022 | *(structure of CE-022)* | 13 | 10 | 6.0 |
| CE-023 | *(structure of CE-023)* | 308 | 460 | 352 |

-continued
| No. | Structure | Cytotoxicity assay IC$_{50}$ (nM) | | |
|---|---|---|---|---|
| | | BT474 | MCF7 | MCF-Her2 |
| CE-024 | 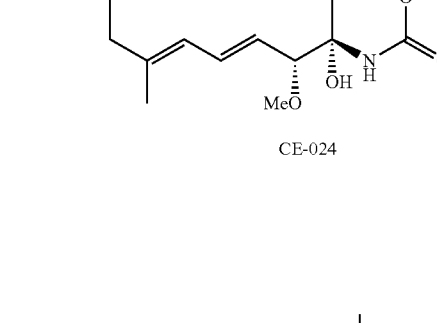 | 20.1 | 23.1 | 50.0 |
| CE-011 | 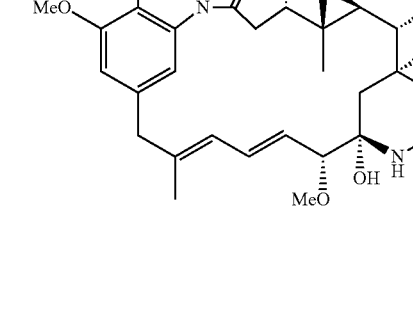 | 1.2 | 2.4 | 1.5 |
| CE-029 | 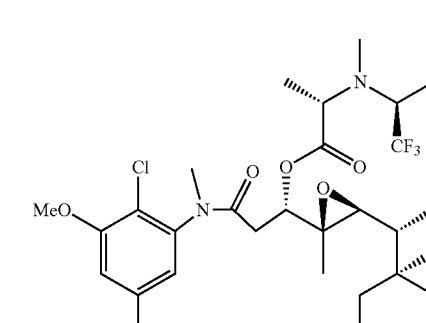 The ortho chiral center of CF$_3$ group is arbitrarily specified | 0.85 | 2.0 | 1.7 |

-continued

| No. | Structure | Cytotoxicity assay IC$_{50}$ (nM) | | |
| --- | --- | --- | --- | --- |
| | | BT474 | MCF7 | MCF-Her2 |
| CE-030 | 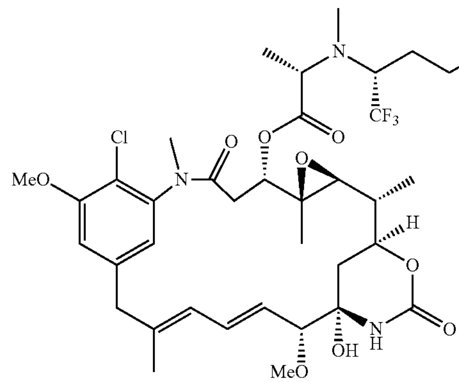 | 2.4 | 6.2 | 3.2 |

The ortho chiral center of CF$_3$ group is arbitrarily specified

| CE-026 | | 14 | 41 | 17 |
| CE-027 | | 15 | 39 | 23 |
| CE-028 | | 12 | 41 | 33 |

-continued
| No. | Structure | Cytotoxicity assay IC$_{50}$ (nM) | | |
|---|---|---|---|---|
| | | BT474 | MCF7 | MCF-Her2 |
| CE-031 | 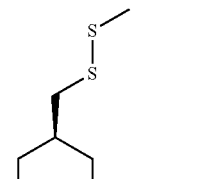 | 7.5 | 15 | 9.2 |
| CE-032 | 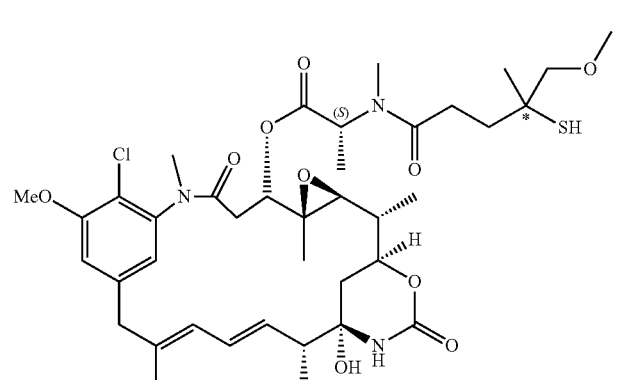 CE-032 | 33.7 | 41.9 | 37.5 |
| CE-038 | 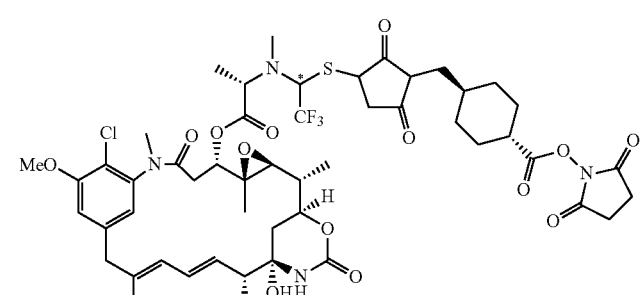 CE-038 | 163 | 873 | 425 |

-continued

| No. | Structure | Cytotoxicity assay IC$_{50}$ (nM) | | |
|---|---|---|---|---|
| | | BT474 | MCF7 | MCF-Her2 |
| CE-039 | 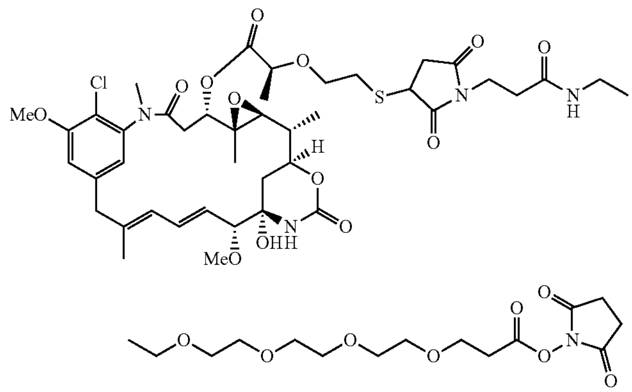 | 420 | 284 | 230 |
| CE-041 | 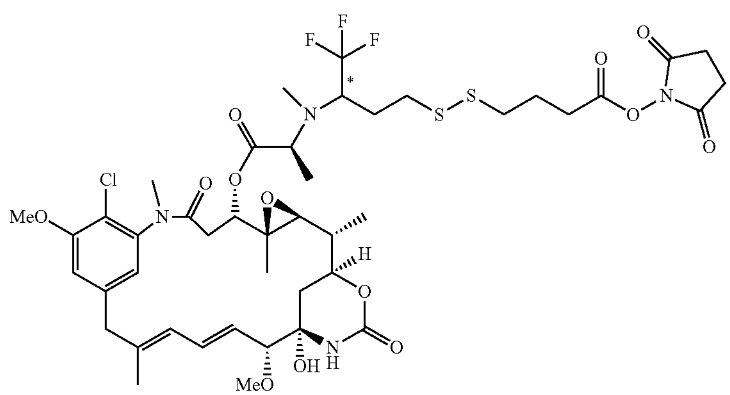 | 68.3 | 185 | 126 |
| CE-045 | 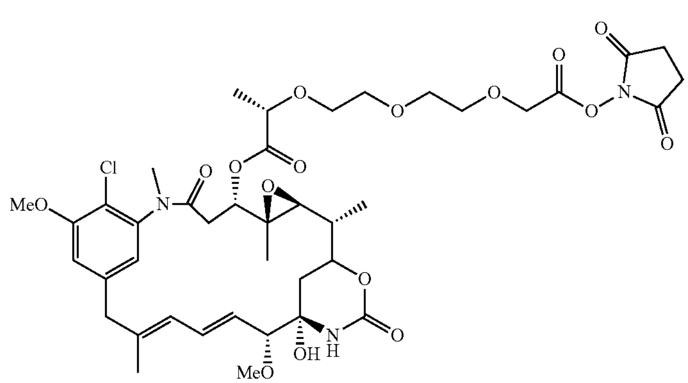 [SMILES: COc1cc2cc(c1Cl)N(C)C(=O)C[C@H](OC(=O)[C@H](C)OCCOCCOCC(=O)ON1C(=O)CCC1=O)[C@]1(C)O[C@H]1[C@H](C)C1C[C@@](O)(NC(=O)O1)[C@H](OC)/C=C/C=C(\C)C2] | 133 | 91.2 | 69.2 |

-continued
| No. | Structure | Cytotoxicity assay IC$_{50}$ (nM) | | |
|---|---|---|---|---|
| | | BT474 | MCF7 | MCF-Her2 |
| CE-046 | 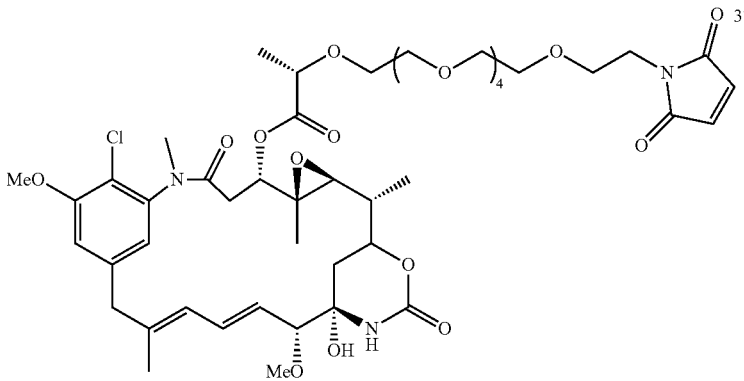 | 375 | 462 | 232 |
| CE-047 | 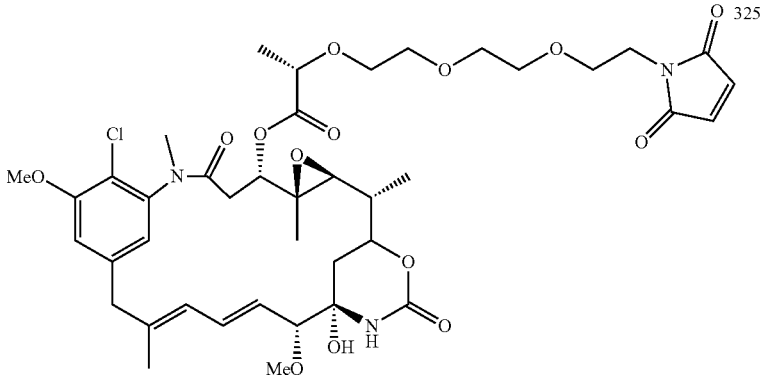 | 325 | 327 | 134 |
| CE-048 | 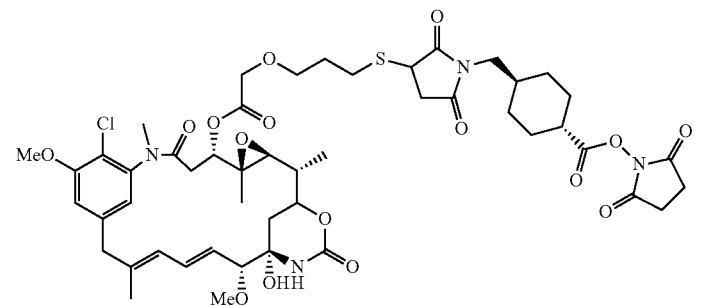 [SMILES: COc1cc2cc(c1Cl)N(C)C(=O)C[C@H](OC(=O)COCCCSC1CC(=O)N(C[C@H]3CC[C@H](C(=O)ON4C(=O)CCC4=O)CC3)C1=O)[C@]1(C)O[C@H]1[C@H](C)C1C[C@@](O)(NC(=O)O1)[C@H](OC)/C=C/C=C(\C)C2] | 266 | 171 | 72.1 |

-continued
| No. | Structure | Cytotoxicity assay IC$_{50}$ (nM) | | |
|---|---|---|---|---|
| | | BT474 | MCF7 | MCF-Her2 |
| CE-049 | 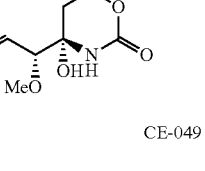 | 138 | 207 | 139 |
| CE-050 | 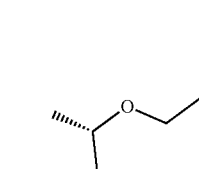 | 26.1 | 14.4 | 7.0 |
| CE-051 | 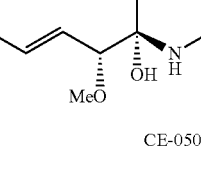 | 112 | 119 | 51.4 |

-continued
| No. | Structure | Cytotoxicity assay IC$_{50}$ (nM) | | |
|---|---|---|---|---|
| | | BT474 | MCF7 | MCF-Her2 |
| CE-052a | 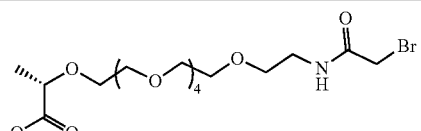 CE-052a | 33.1 | 18.4 | 9.8 |
| CE-053-1 | 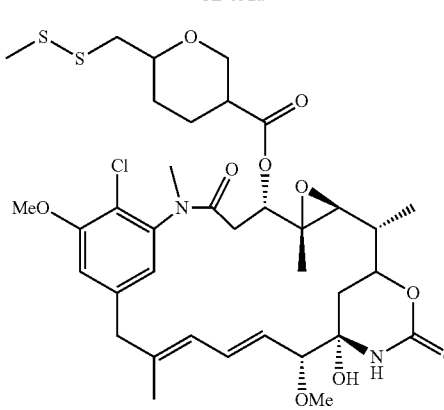 | 22 | 22 | 13 |
| CE-054-1 | 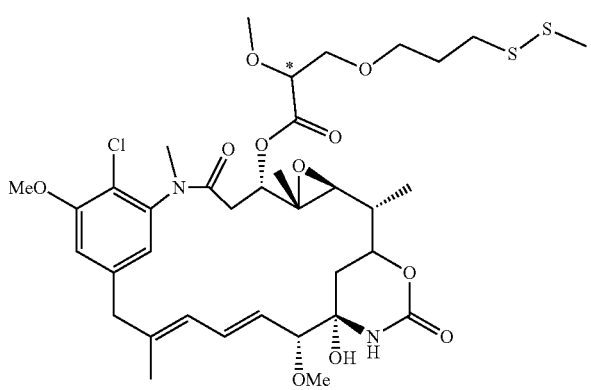 [SMILES: COc1cc2cc(c1Cl)N(C)C(=O)C[C@H](OC(=O)C(COCCCSSC)OC)[C@]1(C)O[C@H]1[C@H](C)C1C[C@@](O)(NC(=O)O1)[C@H](OC)/C=C/C=C(\C)C2] | 10 | 7 | 3.4 |
| CE-055-1 | 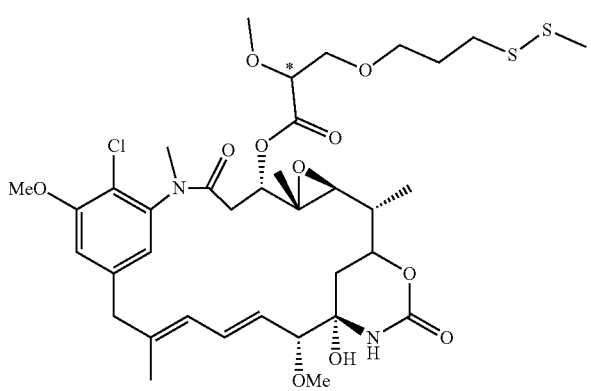 [SMILES: COc1cc2cc(c1Cl)N(C)C(=O)C[C@H](OC(=O)C(COCCCSSC)OC)[C@]1(C)O[C@H]1[C@H](C)C1C[C@@](O)(NC(=O)O1)[C@H](OC)/C=C/C=C(\C)C2] | 8 | 6 | 3 |

-continued
| No. | Structure | Cytotoxicity assay IC$_{50}$ (nM) | | |
|---|---|---|---|---|
| | | BT474 | MCF7 | MCF-Her2 |
| CE-056 | 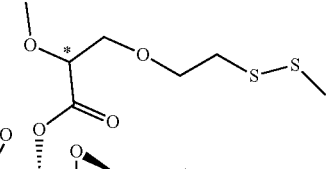 | 39 | 17 | 217 |
| CE-057 | 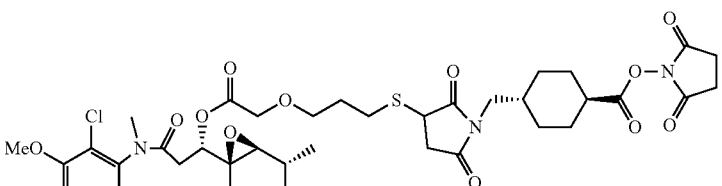 | 270 | 405 | 669 |
| CE-063 | 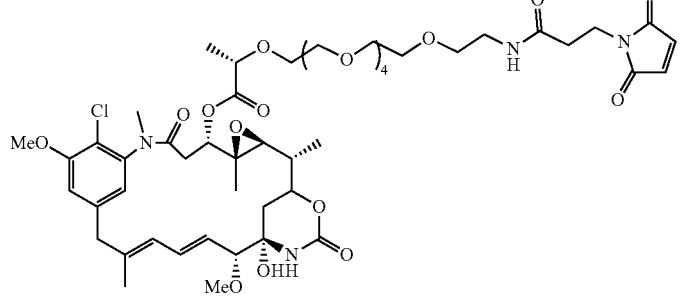 | 439 | 1648 | 1961 |
| T-CE-004 (DAR2.94) | 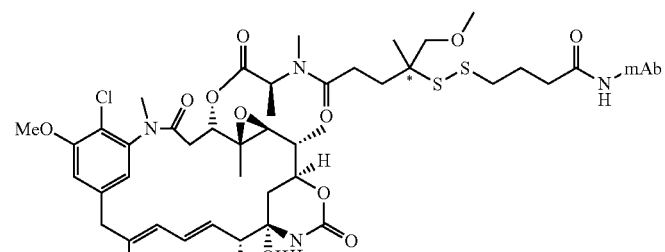 | 1.66 | — | — |
| T-CE-004 (DAR4.82) | | 1.57 | — | 10.42 |

| No. | Structure | Cytotoxicity assay IC$_{50}$ (nM) | | |
|---|---|---|---|---|
| | | BT474 | MCF7 | MCF-Her2 |
| T-CE-005 (DAR3.94) | 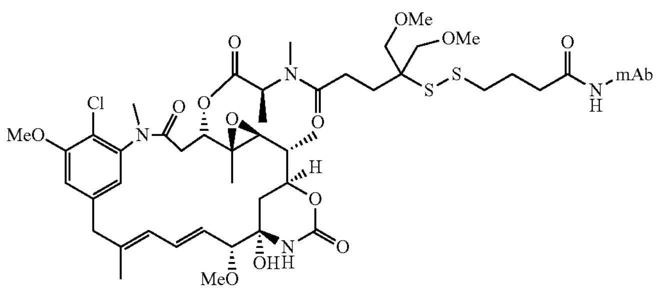 | 3.10 | 12.32 | 7.48 |
| T-CE-005 (DAR5.58) | *T-CE-005* | 0.94 | 3.51 | 7.47 |
| CE-034 | *CE-034* | 19.89 | 14.05 | 14.17 |
| CE-035 | *CE-035* | 26.75 | 25.75 | 15.09 |
| CE-036 | *CE-036* | 8.05 | 13.11 | 6.90 |

-continued

| No. | Structure | Cytotoxicity assay IC$_{50}$ (nM) | | |
|---|---|---|---|---|
| | | BT474 | MCF7 | MCF-Her2 |
| CE-037 | *(structure)* | 49.3 | 135.7 | 70.64 |
| T-CE-034 (DAR2.41) | *(structure)* | 0.94 | 50324 | 1.11 |
| T-CE-034 (DAR3.69) | | 1.22 | 11003 | 0.81 |
| T-CE-035 (DAR2.42) | *(structure)* | 1.30 | — | 0.63 |
| T-CE-035 (DAR4.04) | | 0.85 | — | 0.37 |
| T-CE-036 (DAR2.41) | *(structure)* | 0.96 | 460214 | 3254 |
| T-CE-036 (DAR3.15) | | 1.27 | $6.5 \times 10^6$ | 1.08 |

-continued

| No. | Structure | Cytotoxicity assay IC$_{50}$ (nM) | | |
|---|---|---|---|---|
| | | BT474 | MCF7 | MCF-Her2 |
| T-CE-037 (DAR2.7) | T-CE-037 | 3.1 | — | 2.338 |
| T-CE-037 (DAR3.84) | | 2.6 | — | 2.19 |
| T-CE-038 (DAR2.8) | T-CE-038 | 24.3 | — | 3.89 |
| T-CE-039 (DAR2.49) | T-CE-039 | 2.4 | — | 2.46 |
| T-CE-039 (DAR4.29) | | 2.1 | — | 1.66 |
| T-CE-041 (DAR1.76) | T-CE-041 | 3.8 | — | 351.5 |
| T-CE-041 (DAR4.75) | | 3.3 | — | 108.2 |

-continued
| No. | Structure | Cytotoxicity assay IC$_{50}$ (nM) | | |
|---|---|---|---|---|
| | | BT474 | MCF7 | MCF-Her2 |
| CE-040 | 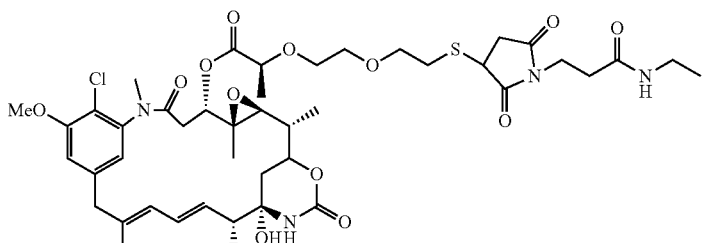 | 10.66 | 9.4 | 5.9 |
| CE-043 | 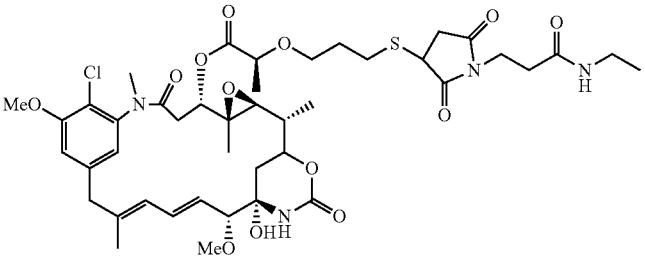 | 548.5 | 231 | 193 |
| T-CE-040 (DAR3.73) | 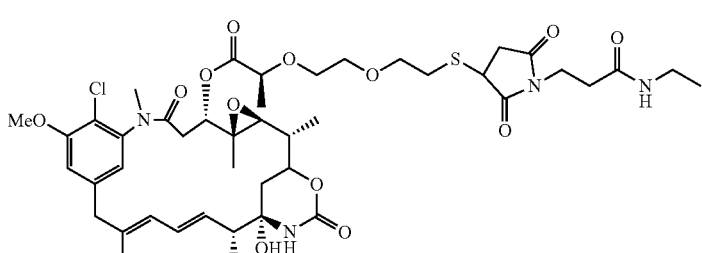 | 1.88 | — | 0.35 |
| T-CE-040 (DAR4.00) | | 1.25 | — | 0.52 |
| T-CE-040 (DAR4.66) | | 1.43 | — | 0.41 |

-continued

| No. | Structure | Cytotoxicity assay IC$_{50}$ (nM) | | |
|---|---|---|---|---|
| | | BT474 | MCF7 | MCF-Her2 |
| T-CE-043 (DAR3.36) | T-CE-043 | 2.32 | — | 0.53 |
| T-CE-043 (DAR4.04) | | 2.10 | — | 0.58 |
| T-CE-043 (DAR4.54) | | 1.56 | — | 0.49 |
| T-CE-045 (DAR3.3) | T-CE-045 | 0.90 | — | — |
| T-CE-045 (DAR2.94) | | 0.79 | — | — |
| T-CE-048 (DAR2.5) | T-CE-048 | 0.51 | — | 0.20 |
| T-CE-048 (DAR3.52) | | 0.30 | — | ~0.14 |
| T-CE-049 (DAR2.42) | T-CE-049 | 1.28 | — | 0.92 |
| T-CE-049 (DAR3.47) | | 0.59 | — | 0.49 |

-continued
| No. | Structure | Cytotoxicity assay IC$_{50}$ (nM) | | |
|---|---|---|---|---|
| | | BT474 | MCF7 | MCF-Her2 |
| T-CE-051 (DAR3.09) | 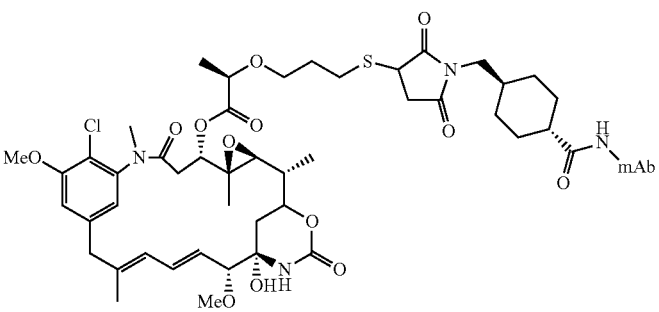 T-CE-051 | 0.50 | — | 0.12 |
| T-CE-051 (DAR5.74) | | 0.39 | — | 0.15 |
| T-CE-057 | 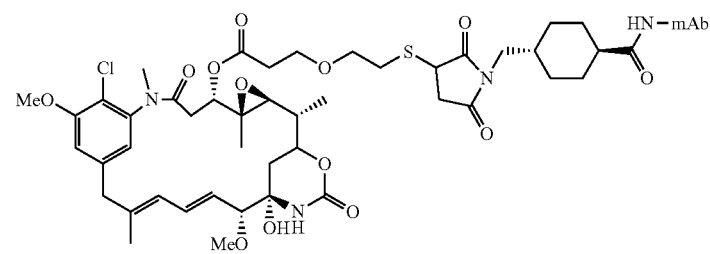 T-CE-057 | 0.632 | — | 25.95 |
| T-CE-063 | 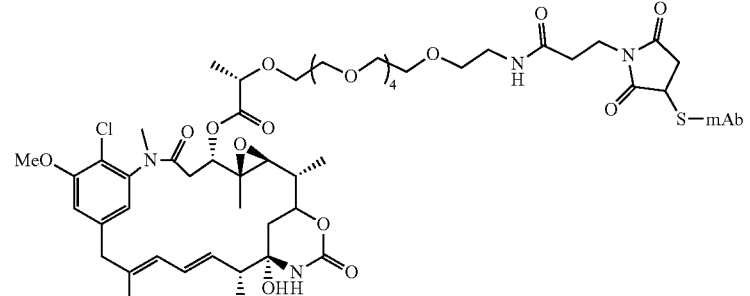 T-CE-063 | 1.14 | — | 28.85 |
| XDCE-M-001 | 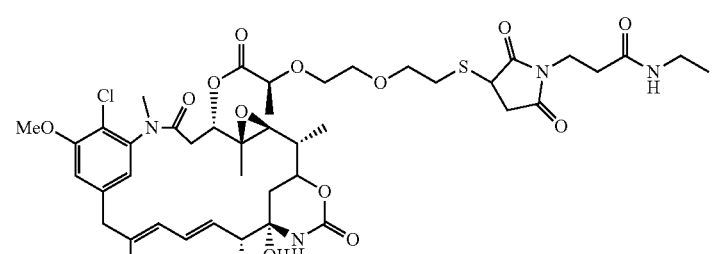 XDCE-M-001 | 455.8 | 330 | 182 |

-continued
| No. | Structure | Cytotoxicity assay IC$_{50}$ (nM) | | |
| --- | --- | --- | --- | --- |
| | | BT474 | MCF7 | MCF-Her2 |
| XDCE-M-002 | 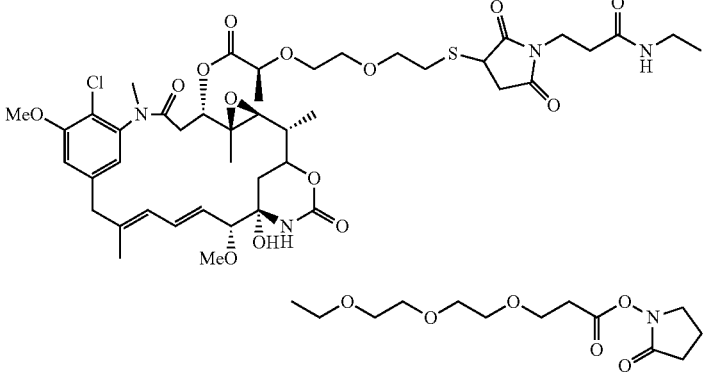 XDCE-M-002 | 41.6 | 51.47 | 64.3 |
| T-XDCE-M-001 (DAR2.92) | 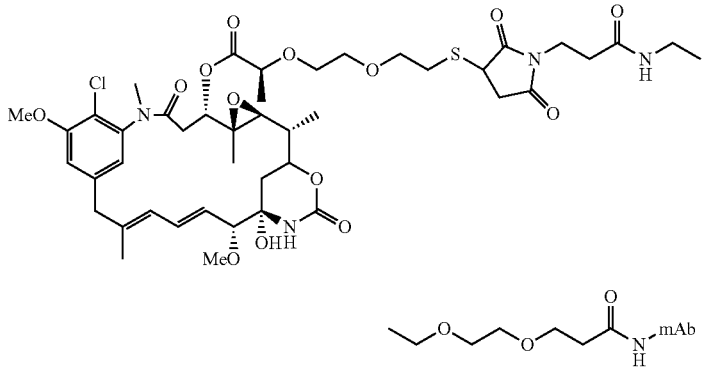 T-XDCE-M-001 | 1.56 | 317 | 0.47 |
| T-XDCE-M-002 (DAR3.15) | 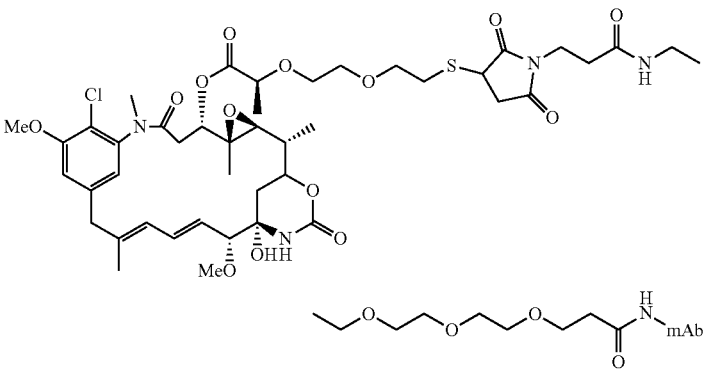 T-XDCE-M-002 | 3.02 | 192 | 0.76 |
| T-DM1 | 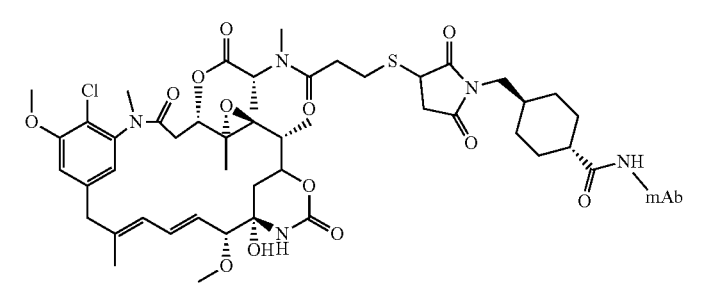 | 1.46 | 57.5 | 0.53 |

-continued

| No. | Structure | Cytotoxicity assay IC$_{50}$ (nM) | | |
|---|---|---|---|---|
| | | BT474 | MCF7 | MCF-Her2 |
| DM1 | 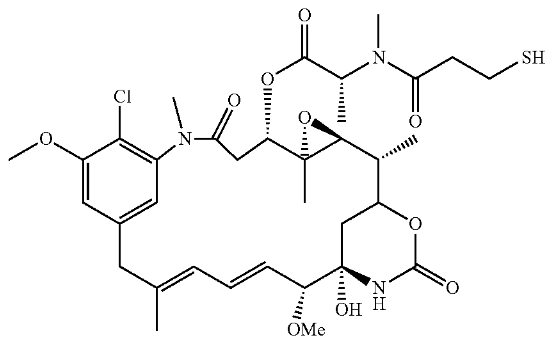 | 21 | 16 | 14 |
| DM1-SMe | 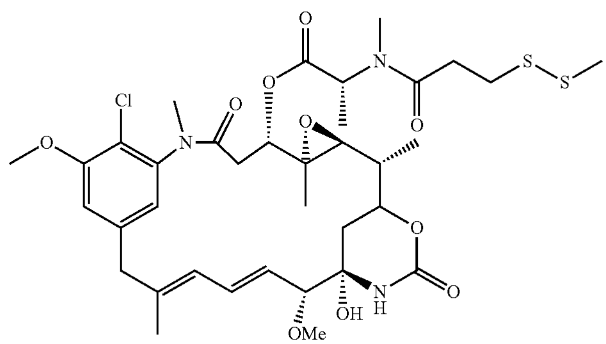 | 9.3 | 9.5 | 7.3 |

It is to be understood that the foregoing description of preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. An antibody drug conjugate, wherein (a) the antibody drug conjugate is represented by formula IB,

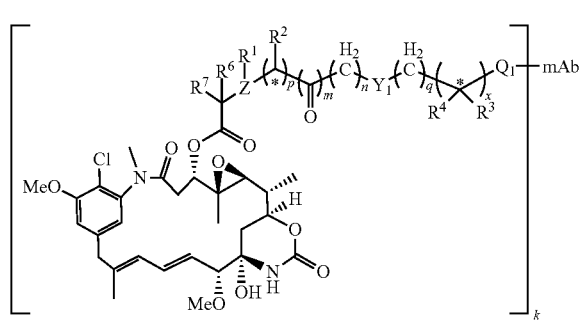

wherein,
Z is a nitrogen atom,

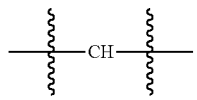 [SMILES: *C*]

or an oxygen atom, when Z is an oxygen atom, $R^1$ is absence; when Z is

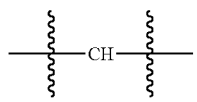

or a nitrogen atom, $R^1$ is a hydrogen or a $C_1$-$C_4$ alkyl;
$R^2$ is a hydrogen or a halogenated $C_1$-$C_4$ alkyl;
p is 0, 1, 2, 3, 4, 5, 6, 7, 8, 9 or 10;
m is 0 or 1;
n is 0, 1, 2, 3, 4, 5, 6, 7, 8, 9 or 10;
$Y_1$ is an oxygen atom, a chemical bond or

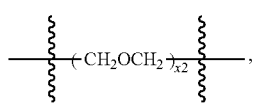

wherein x2 is an integer among 1-24;

q is 0, 1, 2, 3, 4, 5, 6, 7, 8, 9 or 10;

$R^3$ and $R^4$ are independently a hydrogen, a cyano, or a substituted or unsubstituted $C_1$-$C_4$ alkyl; in $R^3$ or $R^4$, the substituent contained in the substituted $C_1$-$C_4$ alkyl refers to a $C_1$-$C_4$ alkoxy;

x is 0, 1, 2, 3, 4, 5, 6, 7, 8, 9 or 10;

Q1 is

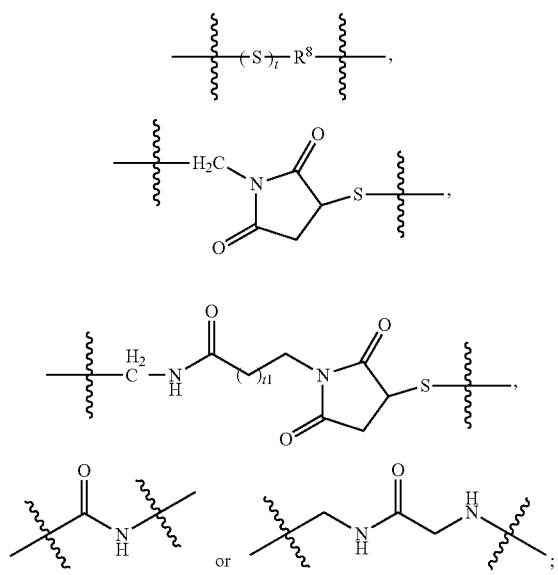

wherein, $R^8$ is a substituted or unsubstituted $C_1$-$C_4$ alkyl,

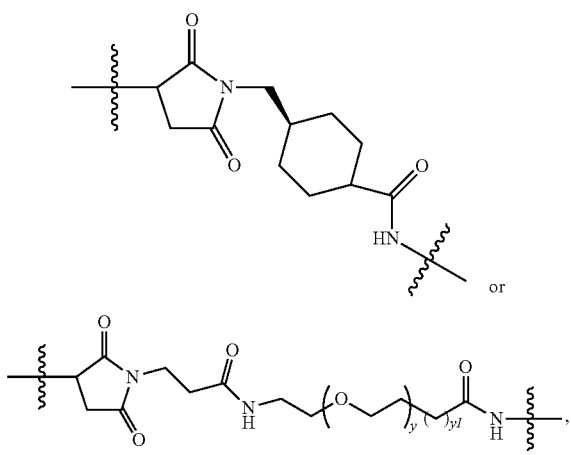

y is 1, 2, 3, 4, 5, 6, 7, 8, 9 or 10; y1 is 0 or 1; in $R^8$, the substituent contained in the substituted $C_1$-$C_4$ alkyl refers to

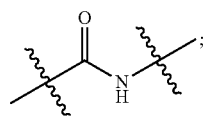 [SMILES: *NC(*)=O]

t is 1 or 2; t1 is 0, 1, 2, 3, 4, 5 or 6;

$R^6$ is a hydrogen or an unsubstituted $C_1$-$C_{12}$ alkyl or

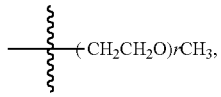

r is 1, 2, 3, 4, 5, 6, 7, 8, 9, 10, 11 or 12;

$R^7$ is a hydrogen or an unsubstituted $C_1$-$C_{12}$ alkyl, an substituted $C_1$-$C_{12}$ alkoxy or

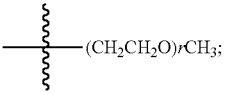

mAb represents a monoclonal antibody;

k is a figure among 1-8;

when Z is nitrogen atom, and both of $R^3$ and $R^4$ are the substituted or unsubstituted $C_1$-$C_4$ alkyl, at least one of $R^3$ and $R^4$ is a $C_1$-$C_4$ alkyl substituted by a $C_1$-$C_4$ alkyloxy;

when Z is nitrogen atom, and one of $R^3$ and $R^4$ is hydrogen, the other one is the unsubstituted $C_1$-$C_4$ alkyl, the unsubstituted $C_1$-$C_4$ alkyl is n-propyl, iso-propyl, n-butyl, tert-butyl or iso-butyl;

when Z is a nitrogen atom, and both of $R^3$ and $R^4$ are hydrogen, m is 0;

when Z is

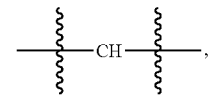

$Y_1$ is an oxygen atom or

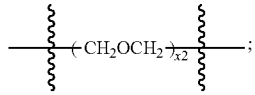

when Z is a nitrogen atom, p is 0, m is 1, and Q1 is

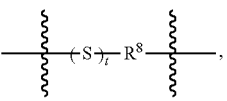

$R^8$ is not

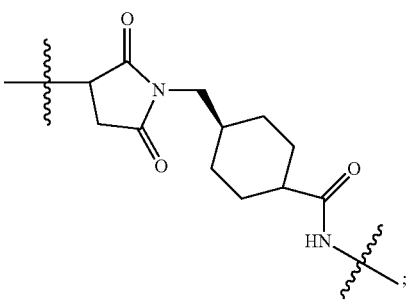

or, (b) the antibody drug conjugate is

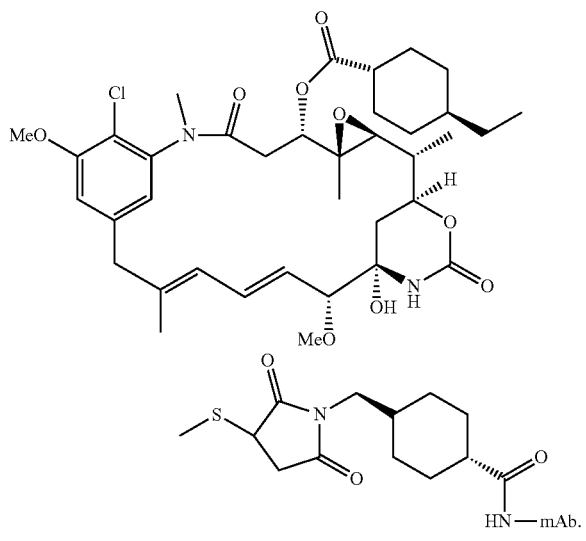

T-CE-036

2. The antibody drug conjugate represented by formula TB according to claim 1, wherein,
$R^1$ is methyl, ethyl, propyl, butyl, iso-propyl, iso-butyl or tert-butyl;
$R^2$ is a halogenated $C_1$-$C_4$ alkyl, the halogen contained in the halogenated $C_1$-$C_4$ alkyl is fluorine, chlorine, or bromine; the halogenated $C_1$-$C_4$ alkyl;
is halogenated methyl, a halogenated ethyl, a halogenated propyl, a halogenated iso-propyl, a halogenated butyl, a halogenated iso-butyl or a halogenated tert-butyl;
p is 0, 1 or 2;
n is 0, 1 or 2;
q is 0, 1 or 2;
when Y1 is a chemical bond, the chemical bond is a single bond,
or, when Y1 is

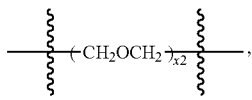

$R^3$ and $R^4$ are independently methyl, ethyl, propyl, butyl, iso-propyl, iso-butyl, tert-butyl, a substituted methyl, a substituted ethyl, a substituted propyl, a substituted butyl, a substituted iso-propyl, a substituted iso-butyl or a substituted tert-butyl;
in $R^3$ or $R^4$, the substituent contained in the substituted or unsubstituted $C_1$-$C_4$ alkyl refers to methoxy, ethoxy, propoxy, butoxy, iso-propoxy, iso-butoxy, tert-butoxy;
x is 0, 1 or 2;
when Q1 is

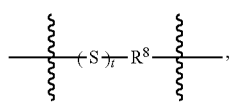

$R^8$ is a substituted or unsubstituted $C_1$-$C_4$ alkyl, the substituted or unsubstituted $C_1$-$C_4$ alkyl is a substituted or unsubstituted methyl, a substituted or unsubstituted ethyl, a substituted or unsubstituted propyl, a substituted or unsubstituted iso-propyl, a substituted or unsubstituted butyl, a substituted or unsubstituted iso-butyl or a substituted or unsubstituted tert-butyl;
$R^6$ is an unsubstituted $C_1$-$C_4$ alkyl;
$R^7$ is an unsubstituted $C_1$-$C_4$ alkyl or an unsubstituted $C_1$-$C_4$ alkoxy;
mAb represents a monoclonal antibody, or Herceptin.

3. The antibody drug conjugate represented by formula TB according to claim 2, wherein,
when $R^2$ is a halogenated methyl, the halogenated methyl is

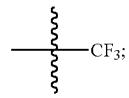

when $R^3$ and $R^4$ are independently a substituted methyl, the substituted methyl is

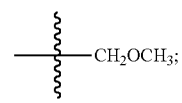

when Q1 is

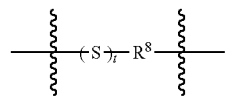

and R8 is a substituted propyl, the substituted propyl is

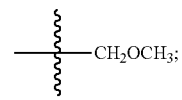

$R^6$ is methyl, ethyl, propyl, iso-propyl, butyl, iso-butyl or tert-butyl;
$R^7$ is methyl, ethyl, propyl, iso-propyl, butyl, iso-butyl, tert-butyl methoxy, ethoxy, propoxy, iso-propoxy, butoxy, iso-butoxy or tert-butoxy.

4. The antibody drug conjugate represented by formula IB according to claim 1, having a structure of formula Ib or Ib1,

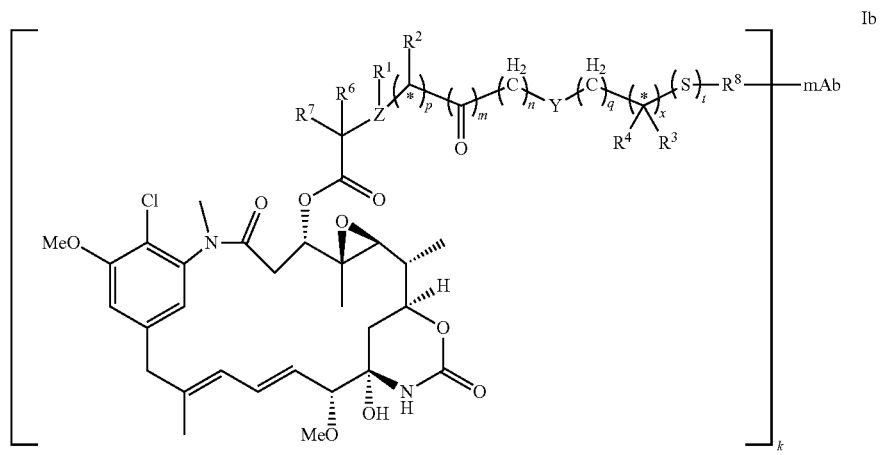
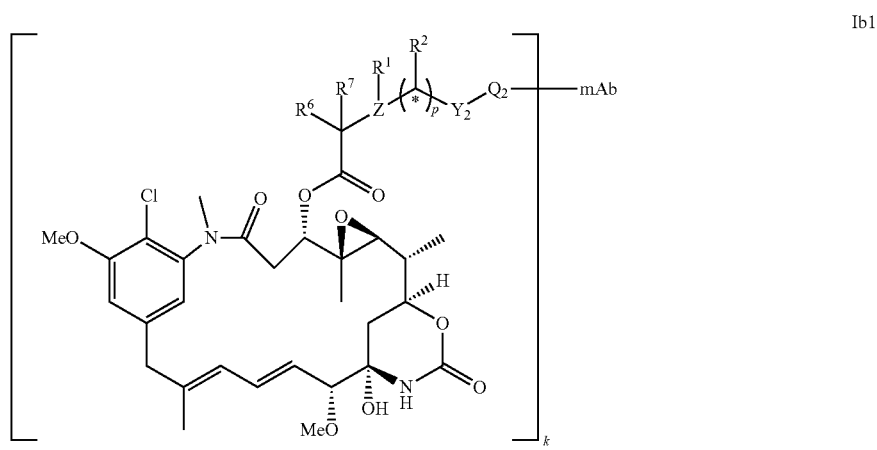
in the antibody drug conjugate represented by formula Ib or Ib1, each letters and groups is defined as that defined in claim 1; Y is an oxygen atom or a chemical bond; $Y_2$ is
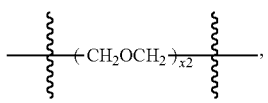
wherein x2 is an integer among 1-24; Q2 is
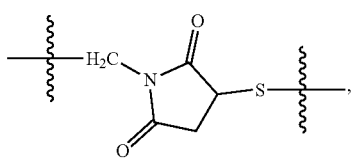
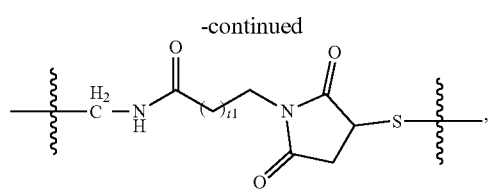
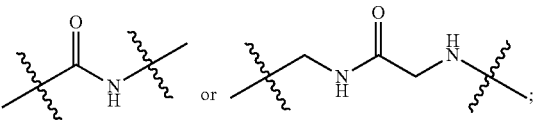
t1 is 0, 1, 2, 3, 4, 5 or 6.
5. The antibody drug conjugate according to claim 1 which is selected from the group consisting of

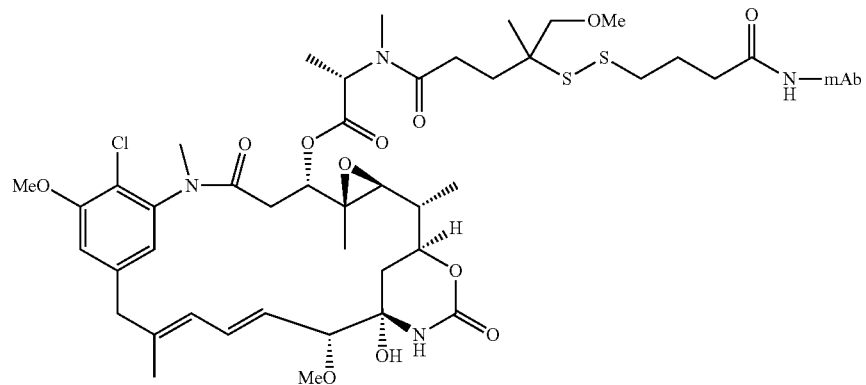
T-CE-004
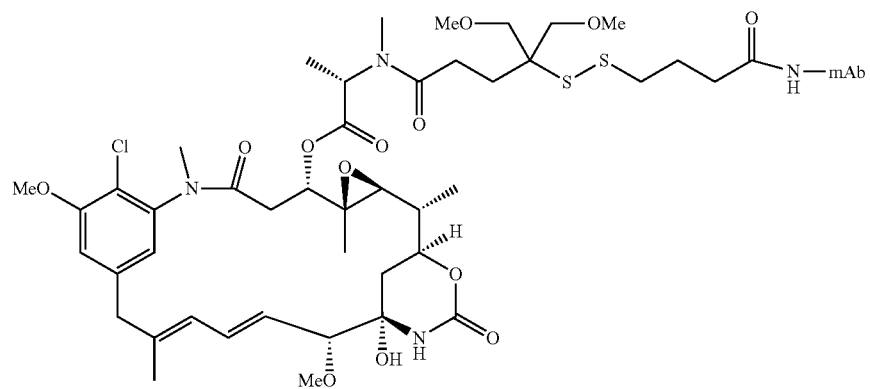
T-CE-005
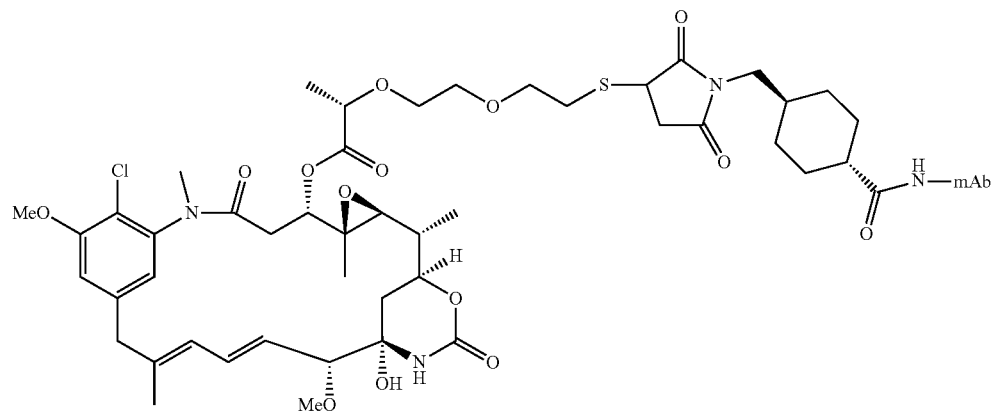
T-CE-034
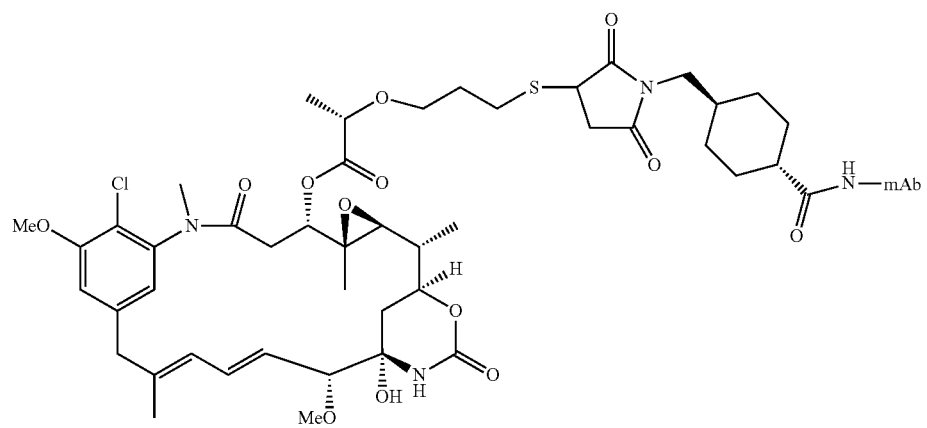
T-CE-035

-continued
T-CE-037
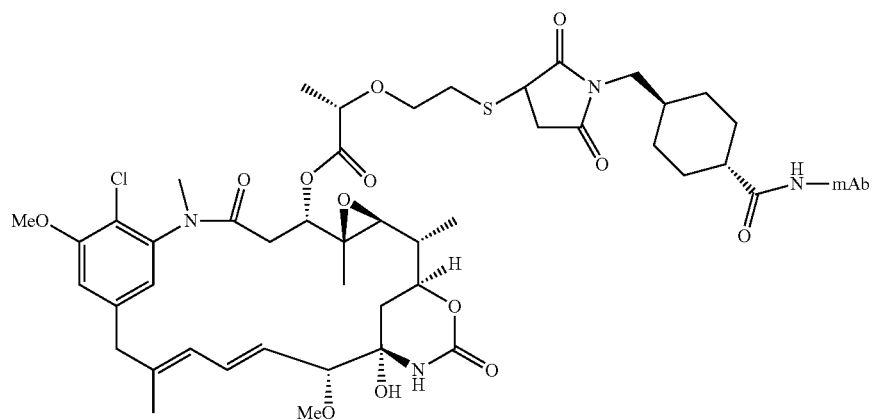
T-CE-041
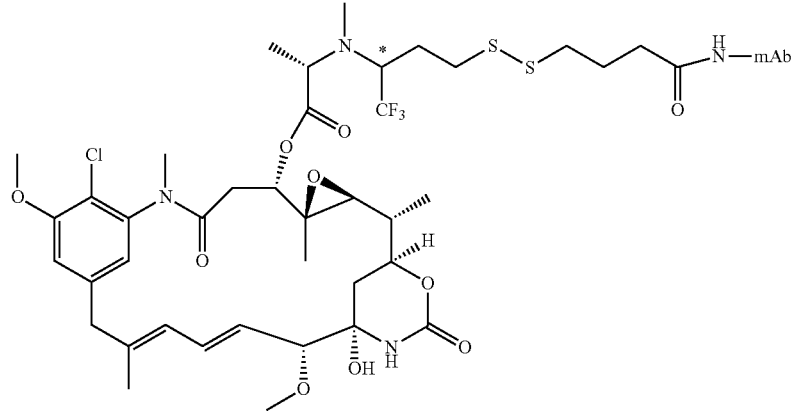
T-CE-038
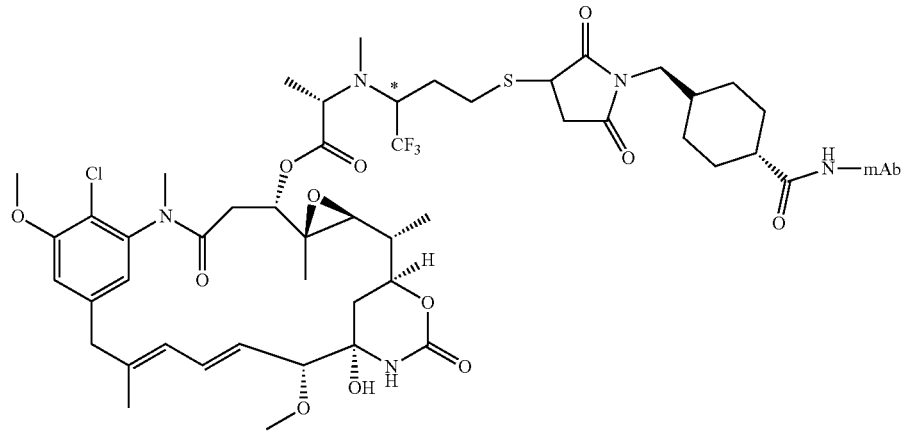
T-CE-039
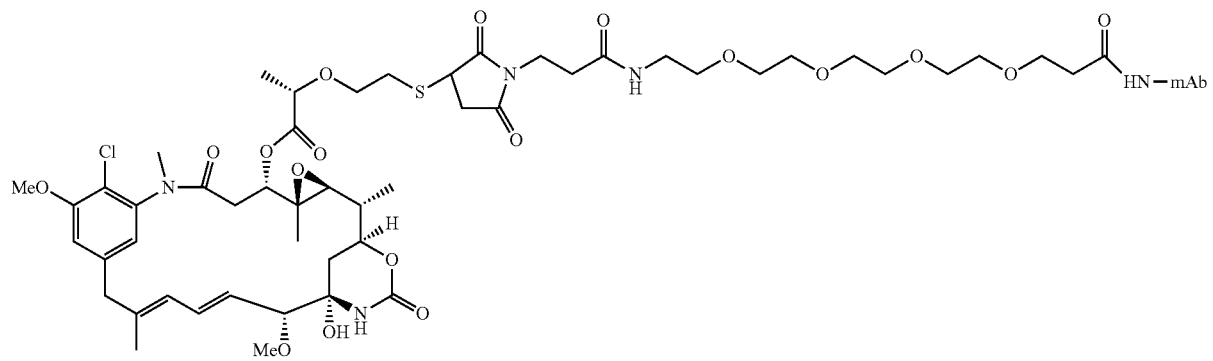

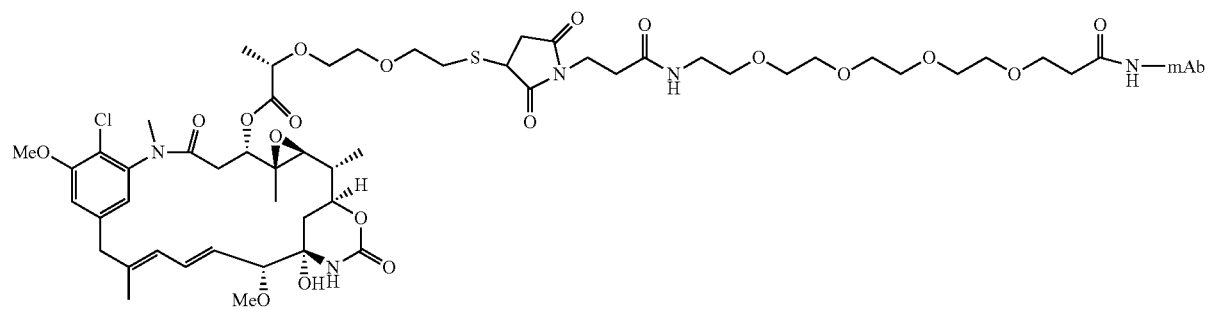
T-CE-040
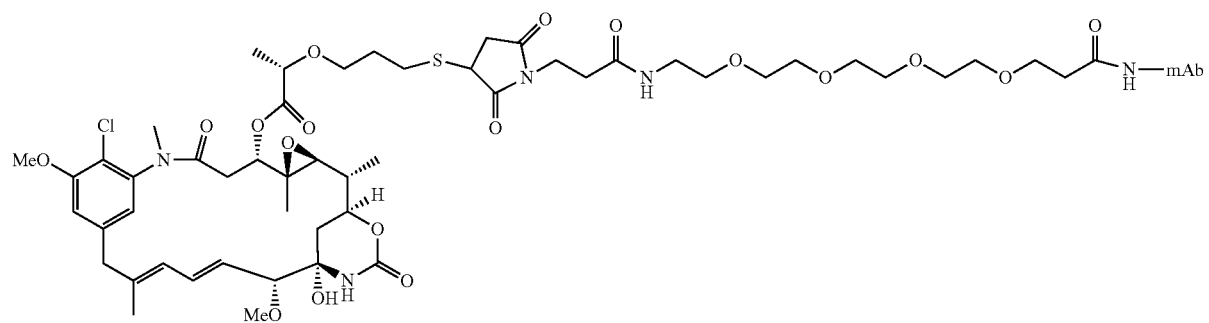
T-CE-043
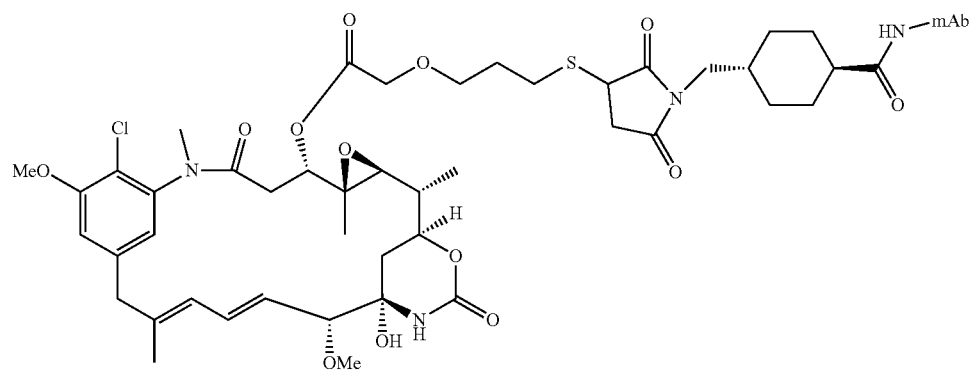
T-CE-048
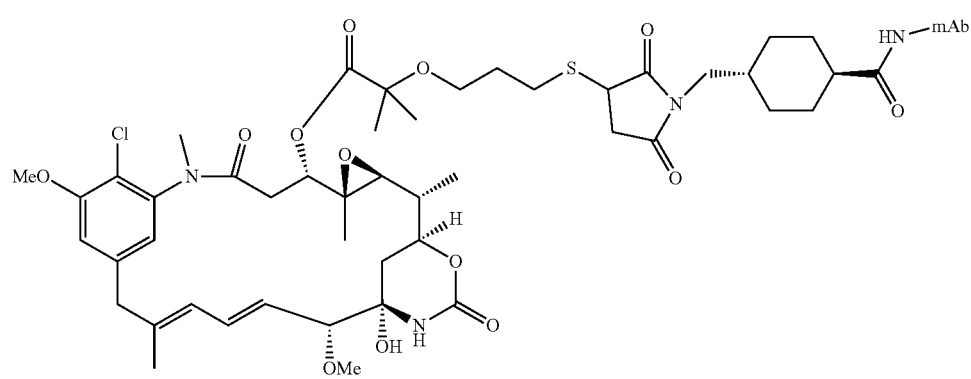
T-CE-049

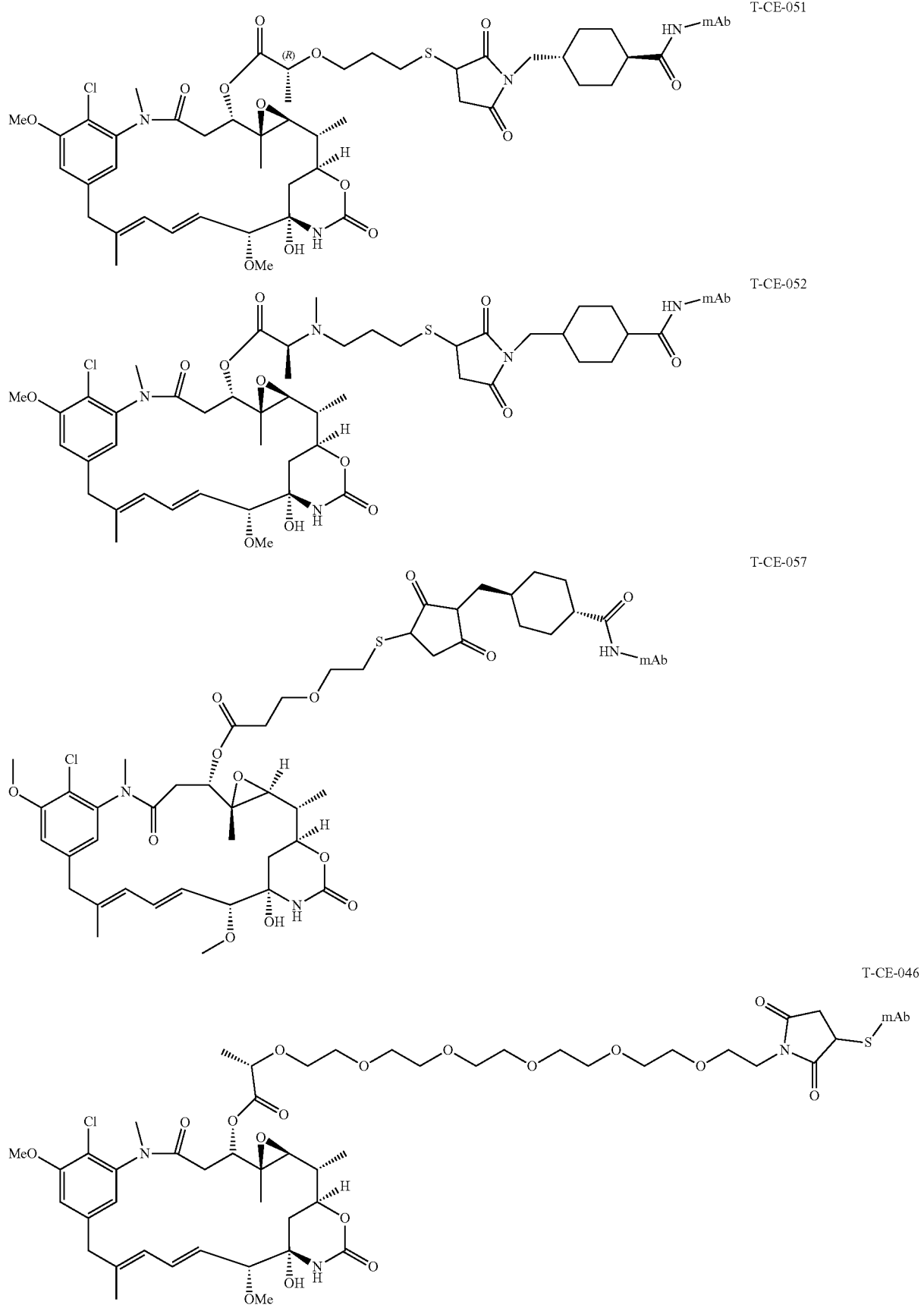

T-CE-047
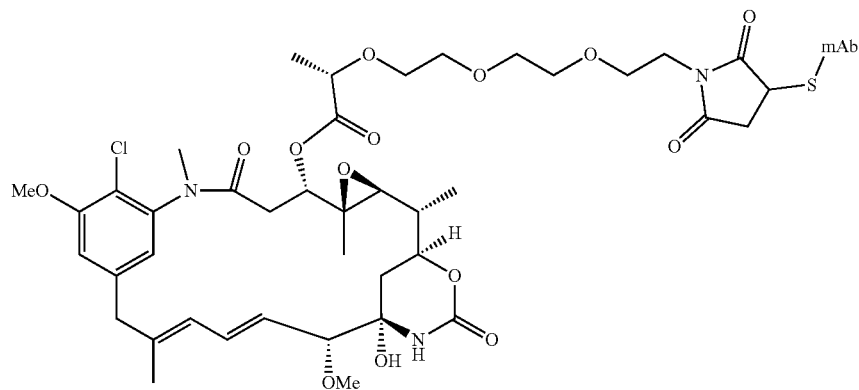
T-CE-063
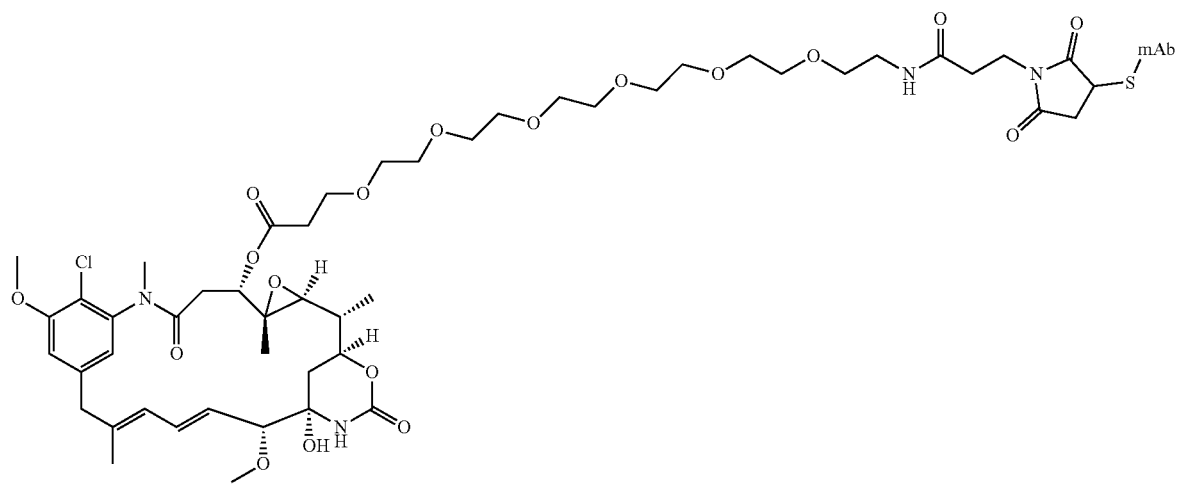
T-CE-045
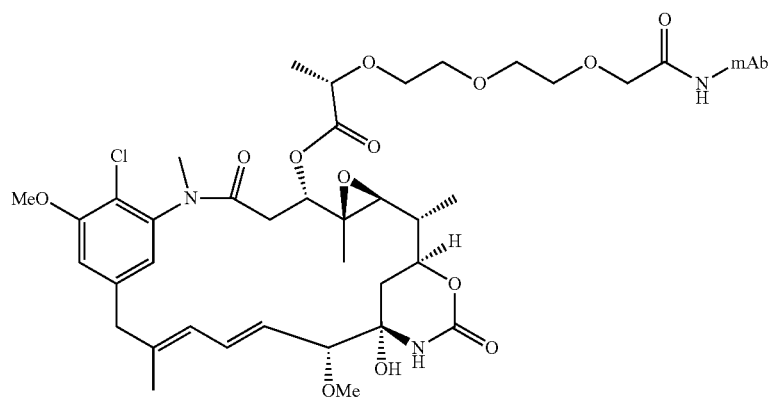

-continued
T-CE-050
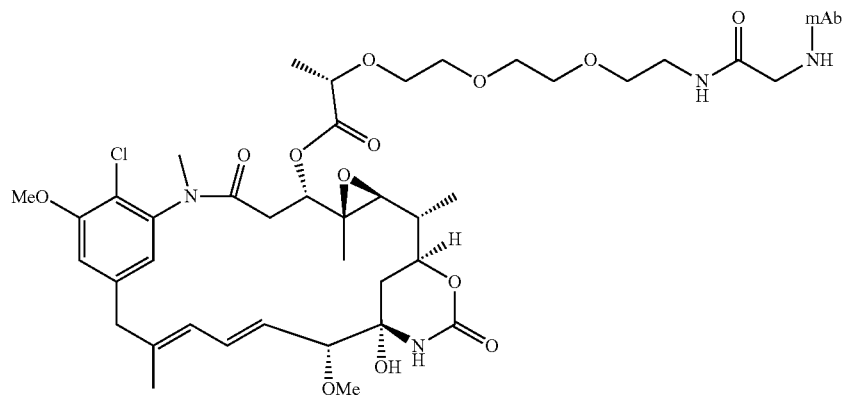
T-CE-052a
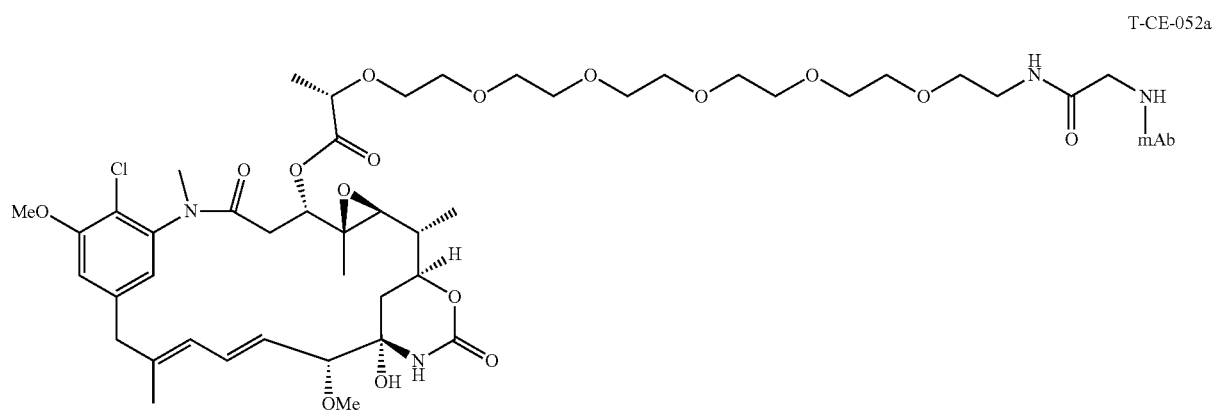
T-XDCE-M-001
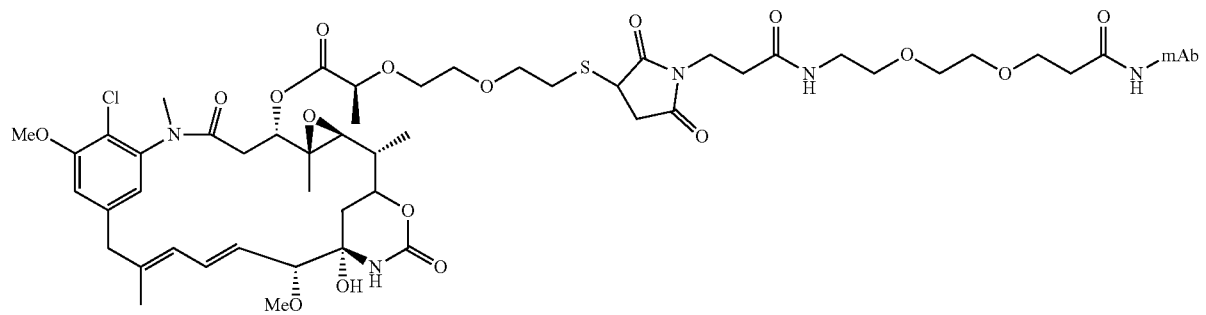
T-XDCE-M-002
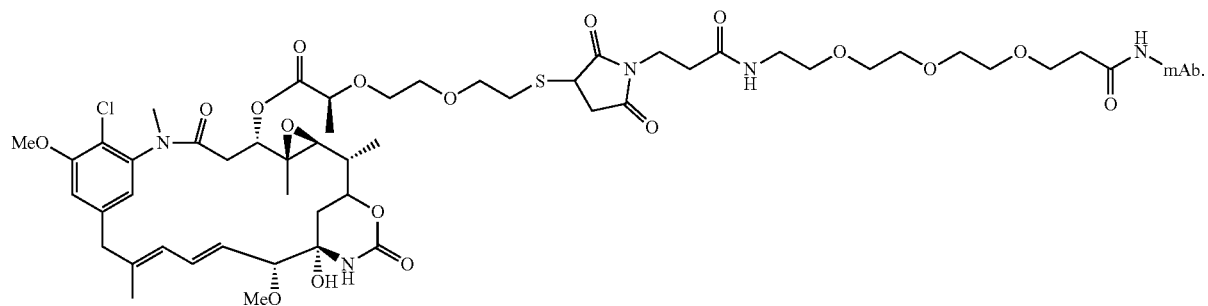

6. An intermediate, wherein (a) the intermediate is represented by formula IA:

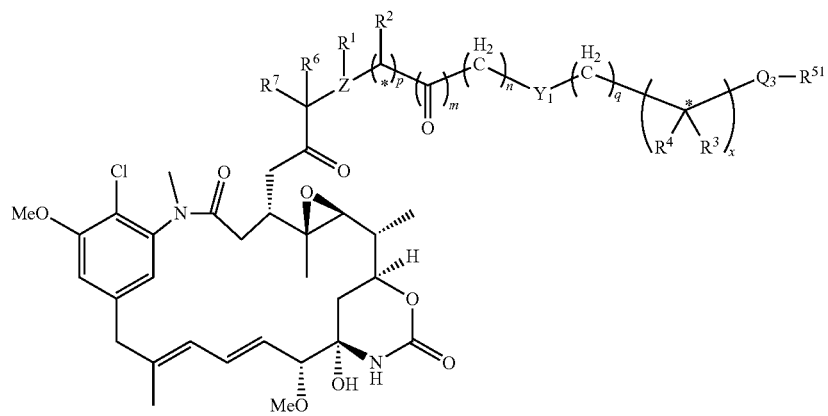

Z is a nitrogen atom,

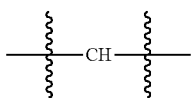 [SMILES: *C*]

or an oxygen atom, when Z is an oxygen atom, $R^1$ is absence; when Z is

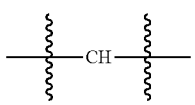 [SMILES: *C*]

or a nitrogen atom, $R^1$ is a hydrogen or a $C_1$-$C_4$ alkyl:
$R^2$ is a hydrogen or a halogenated $C_1$-$C_4$ alkyl;
p is 0, 1, 2, 3, 4, 5, 6, 7, 8, 9 or 10;
m is 0 or 1;
n is 0, 1, 2, 3, 4, 5, 6, 7, 8, 9 or 10
$Y_1$ is an oxygen atom, a chemical bond or

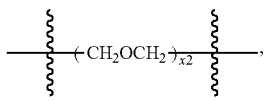

wherein x2 is an integer among 1-24;
q is 0, 1, 2, 3, 4, 5, 6, 7, 8, 9 or 10;
$R^3$ and $R^4$ are independently a hydrogen, a cyano, or a substituted or unsubstituted $C_1$-$C_4$ alkyl; in $R^3$ or $R^4$, the substituent contained in the substituted $C_1$-$C_4$ alkyl refers to a $C_1$-$C_4$ alkoxy;
x is 0, 1, 2, 3, 4, 5, 6, 7, 8, 9 or 10;
$R^6$ is a hydrogen or an unsubstituted $C_1$-$C_{12}$ alkyl or

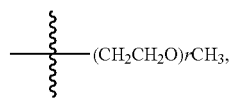

r is 1, 2, 3, 4, 5, 6, 7, 8, 9, 10, 11 or 12:

$R^7$ is a hydrogen or an unsubstituted $C_1$-$C_{12}$ alkyl, an unsubstituted $C_1$-$C_{12}$ alkoxy or

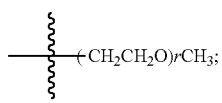

when Z is nitrogen atom, and both of $R^3$ and $R^4$ are the substituted or unsubstituted $C_1$-$C_4$ alkyl, at least one of $R^3$ and $R^4$ is a $C_1$-$C_4$ alkyl substituted by a $C_1$-$C_4$ alkyloxy;
when Z is nitrogen atom, and one of $R^3$ and $R^4$ is hydrogen, the other one is the unsubstituted $C_1$-$C_4$ alkyl, the unsubstituted $C_1$-$C_4$ alkyl is n-propyl, iso-propyl, n-butyl, tert-butyl or iso-butyl;
when Z is a nitrogen atom, and both of $R^3$ and $R^4$ are hydrogen, m is 0:
when Z is

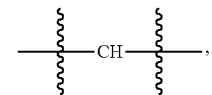 [SMILES: *C*]

$Y_1$ is an oxygen atom or

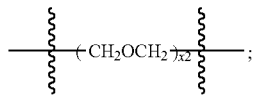

Q is

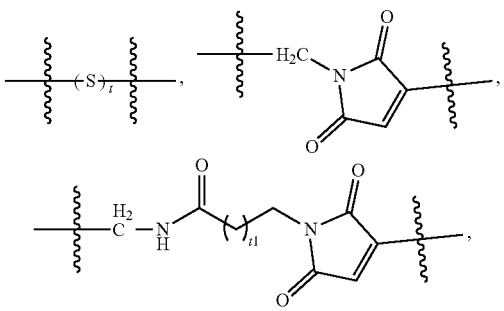

277
-continued
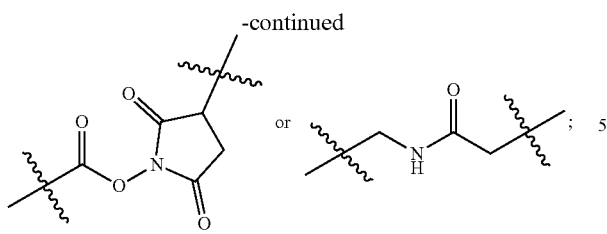
t is 1 or 2; t1 is 0, 1, 2, 3, 4, 5 or 6;
R$^{51}$ is H, a C$_1$-C$_4$ alkyl,
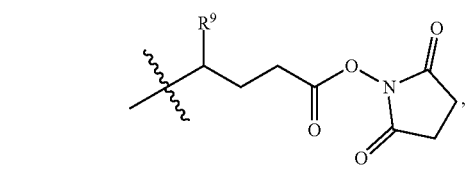
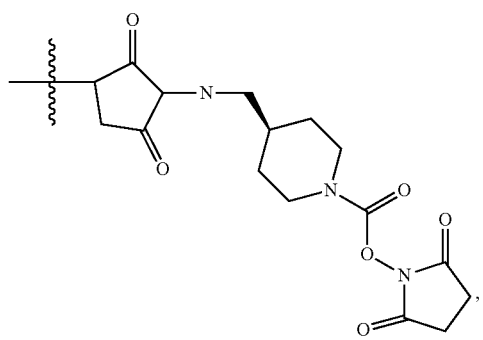
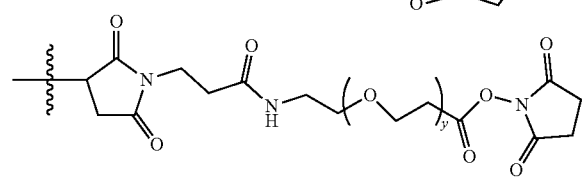
or a halogen; y is 1, 2, 3, 4, 5, 6, 7, 8, 9 or 10; R$^9$ is H or a C$_1$-C$_4$ alkyl;
when Z is a nitrogen atom, p is 0, m is 1, both of R$^3$ and R$^4$ are hydrogen or both of R$^3$ and R$^4$ are unsubstituted C$_1$-C$_4$ alkyl, and Q$_3$ is
278
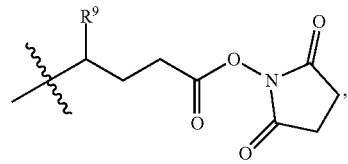
R$^{51}$ is
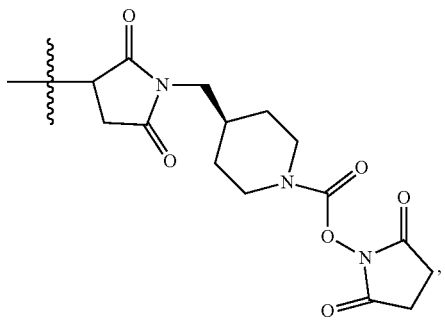
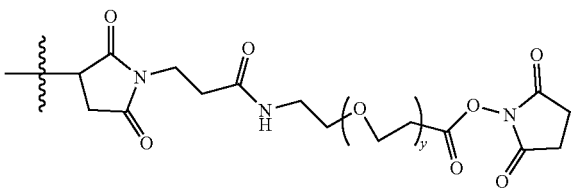
or a halogen; y is 1, 2, 3, 4, 5, 6, 7, 8, 9 or 10; R$^9$ is H or a C$_1$-C$_4$ alkyl;
or, (b) the intermediate is:
CE-033
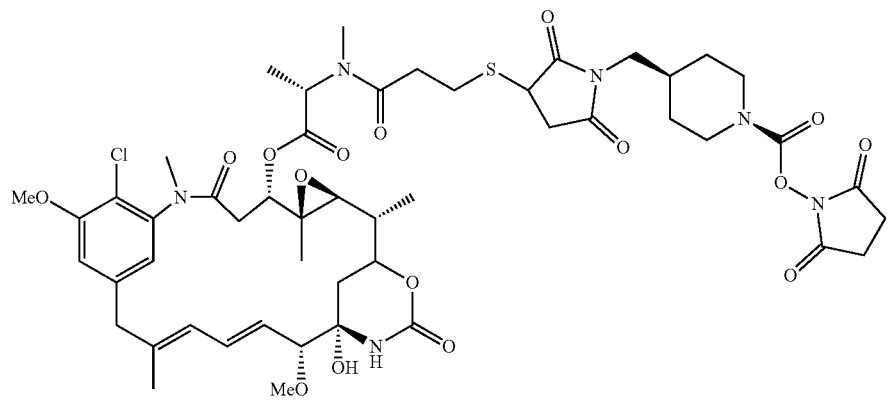

CE-053
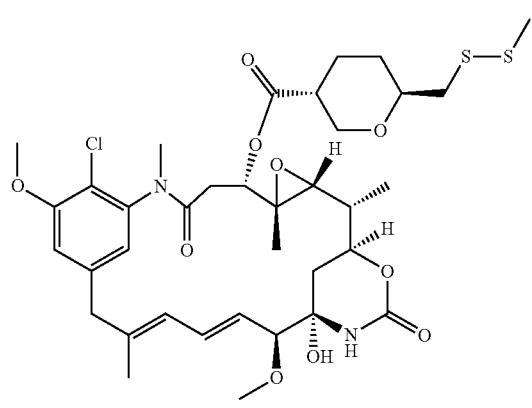
CE-031
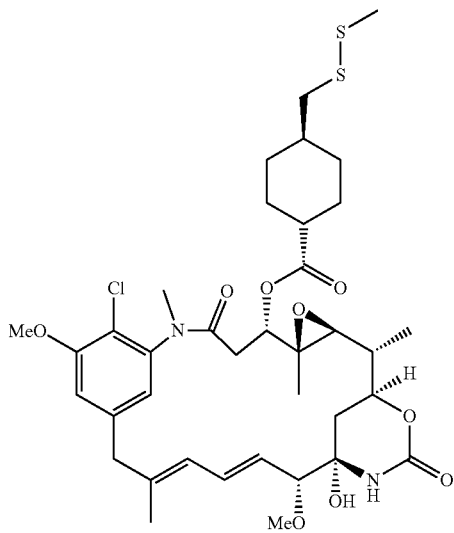
CE-036
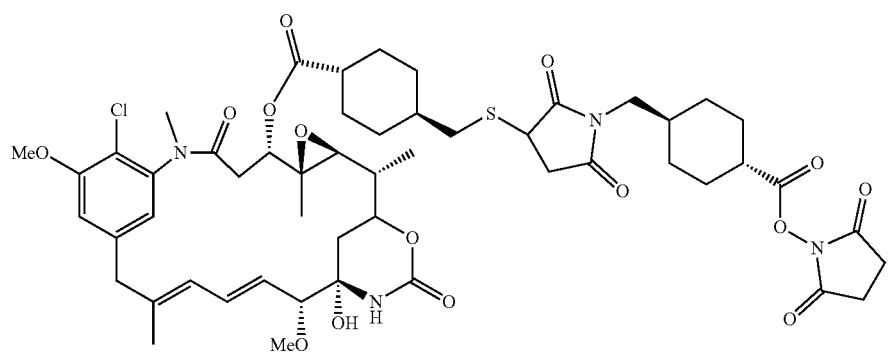
8-9
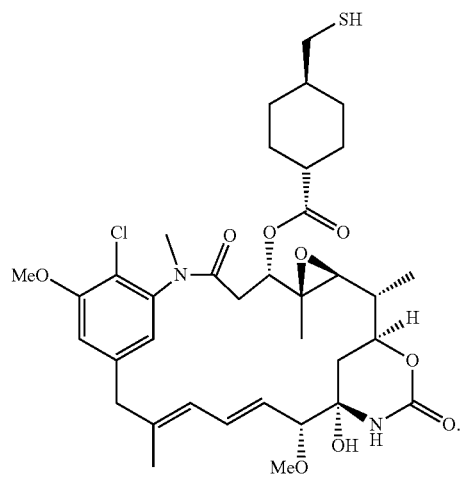
7. The intermediate represented by formula IA according to claim 6, wherein,
$R^{51}$ is methyl, ethyl, propyl, iso-propyl, butyl, iso-butyl, tert-butyl, F, Cl, Br or I;
$R^9$ is methyl, ethyl, propyl, iso-propyl, butyl, iso-butyl or tert-butyl.
8. The intermediate represented by formula IA according to claim 6, having a structure of formula Ia or Ia1:

Ia

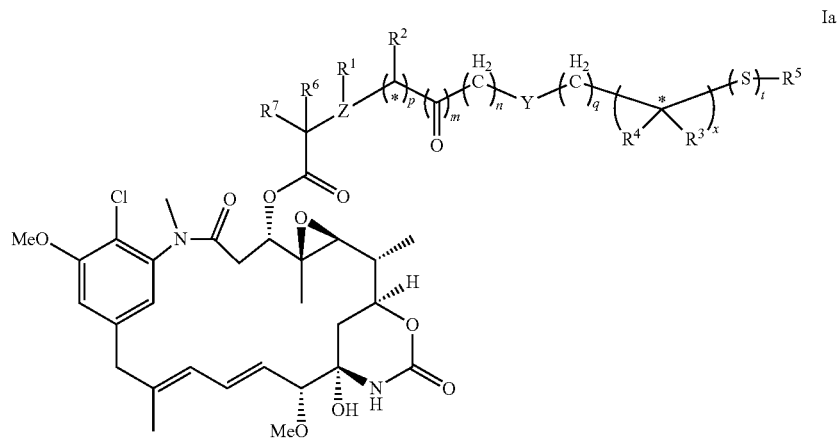

Ia1

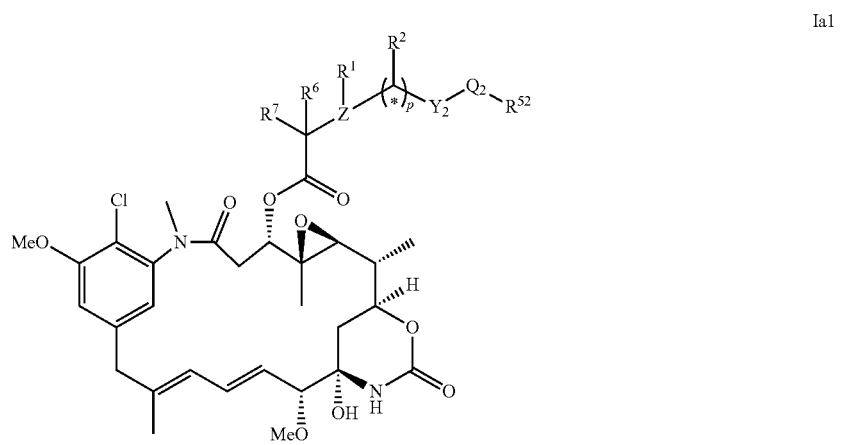

wherein in the intermediate represented by formula Ia or Ia1, each letters and groups is defined as that in claim 6;

in the intermediate represented by formula Ia, $R^5$ is a hydrogen or a $C_1$-$C_4$ alkyl;

or the $C_1$-$C_4$ alkyl-in $R^5$ is methyl, ethyl, propyl, butyl, iso-propyl, iso-butyl or tert-butyl,

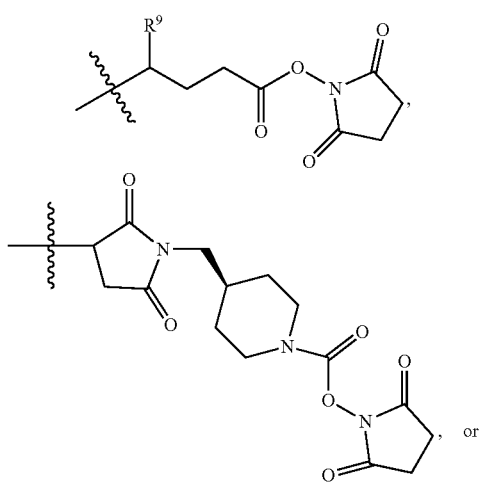

y is 1, 2, 3, 4, 5, 6, 7, 8, 9 or 10; y1 is 0 or 1; $R^9$ is a hydrogen or a $C_1$-$C_4$ alkyl, or, the $C_1$-$C_4$ alkyl in $R^9$ is methyl, ethyl, propyl, butyl, iso-propyl, iso-butyl or tert-butyl;

in the intermediate represented by formula Ia1, $R^{52}$ is a hydrogen or a halogen, or, the halogen in $R^{52}$ is F, Cl, Br, or I.

9. The intermediate according to claim 6 is selected from the group consisting of

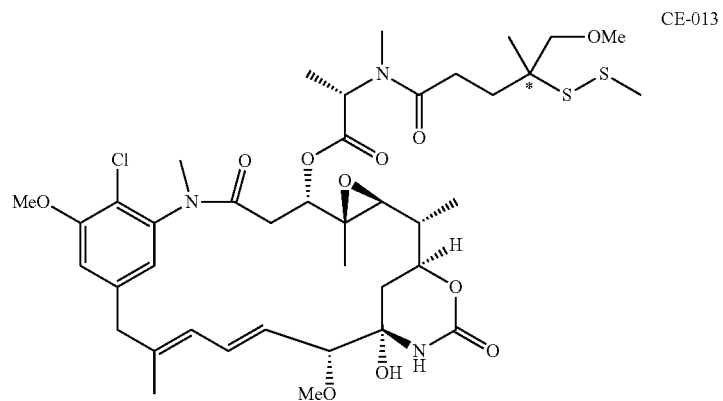
CE-013
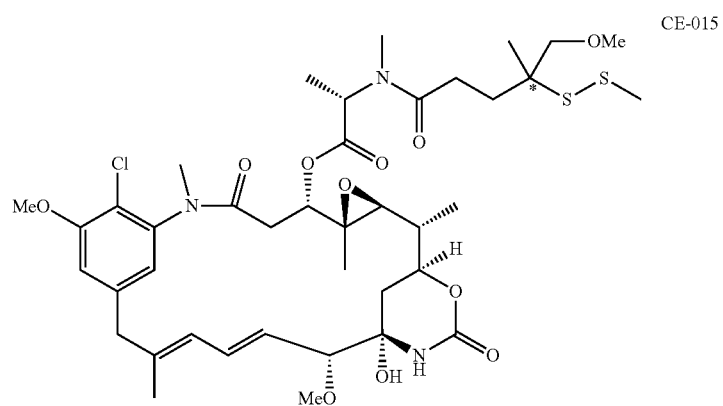
CE-015
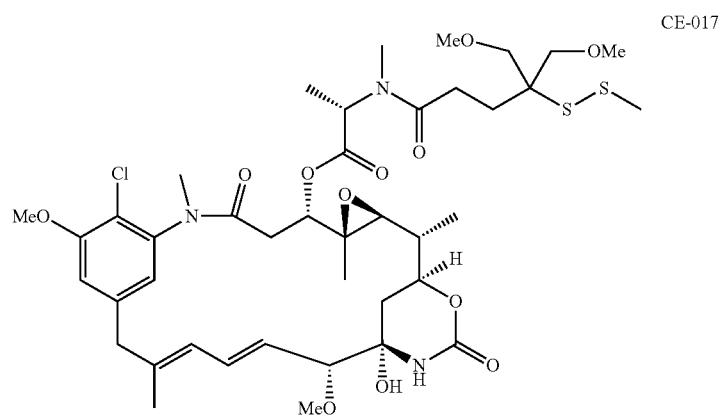
CE-017
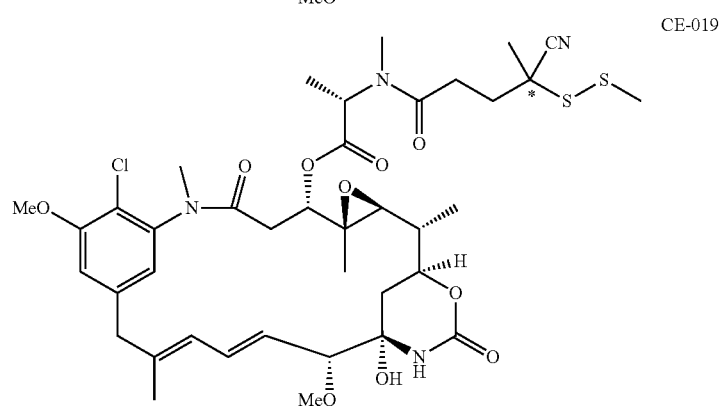
CE-019

-continued
CE-022
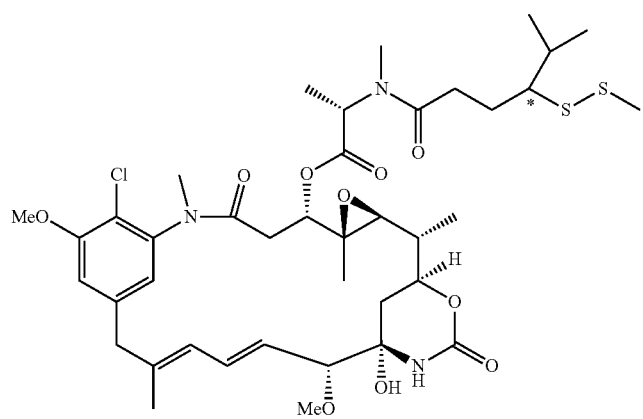
CE-011
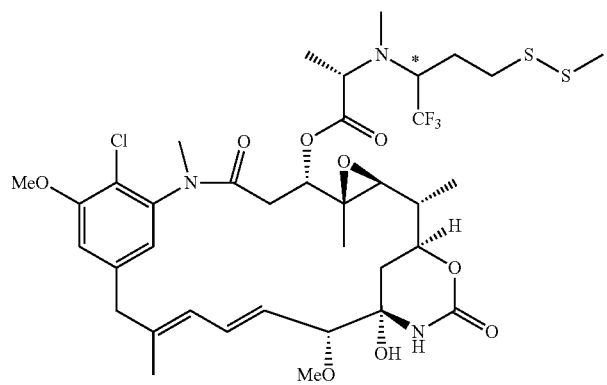
CE-029
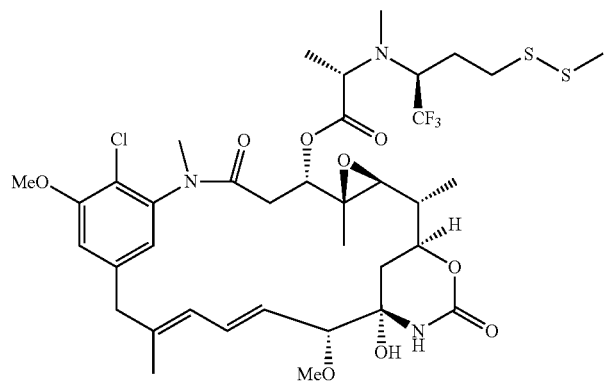
CE-030
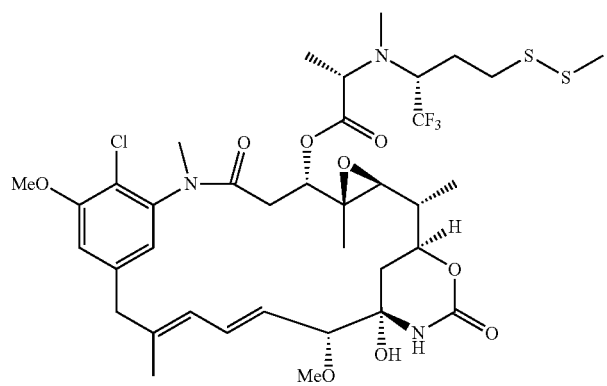

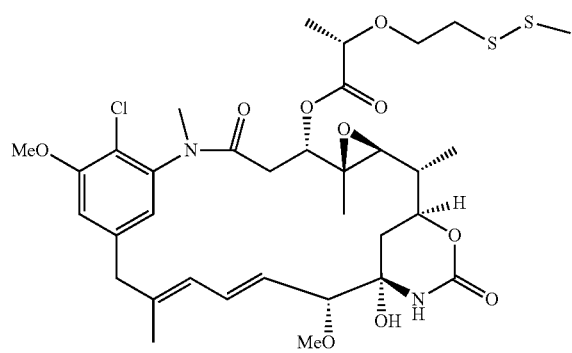
CE-026
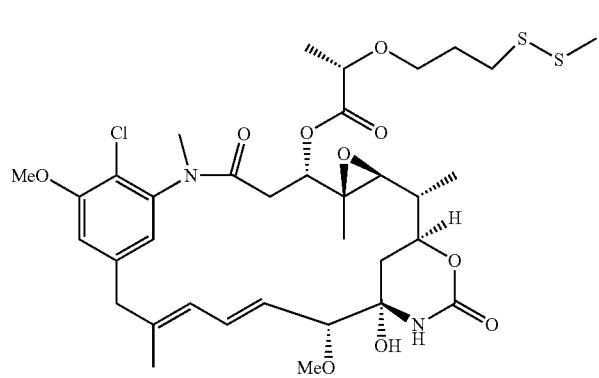
CE-027
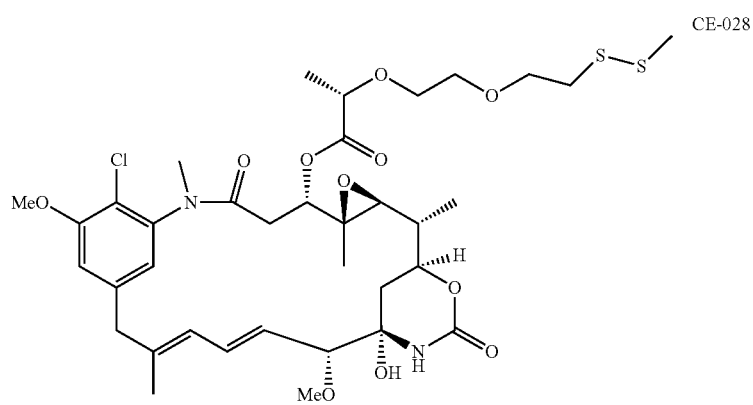
CE-028
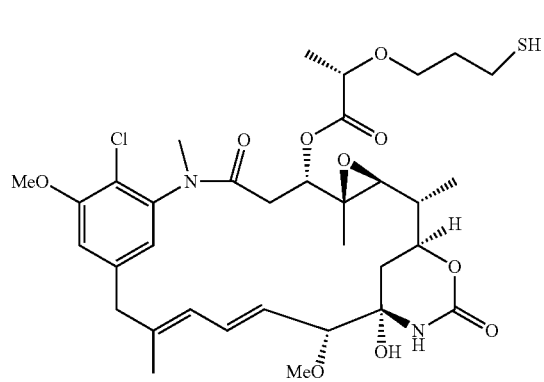
8-8

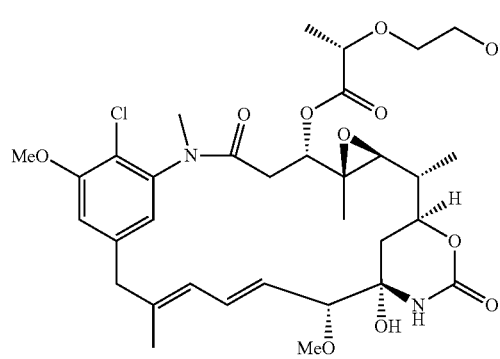
9-7
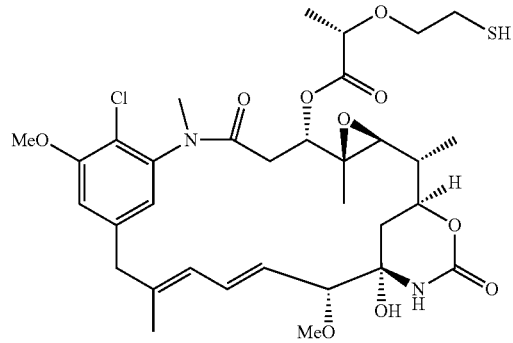
10-10
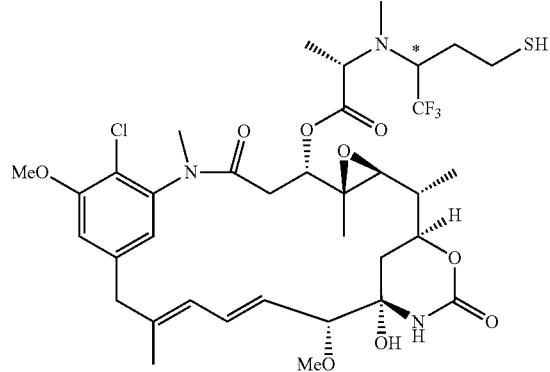
7-2
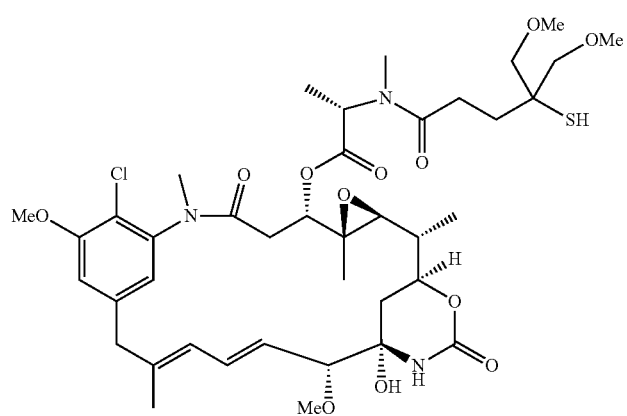
CE-024

CE-032
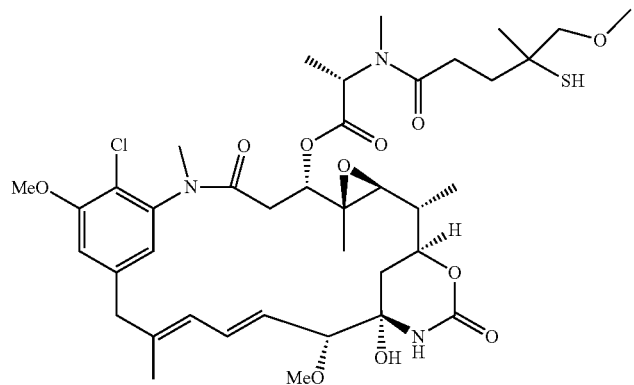
CE-054/055
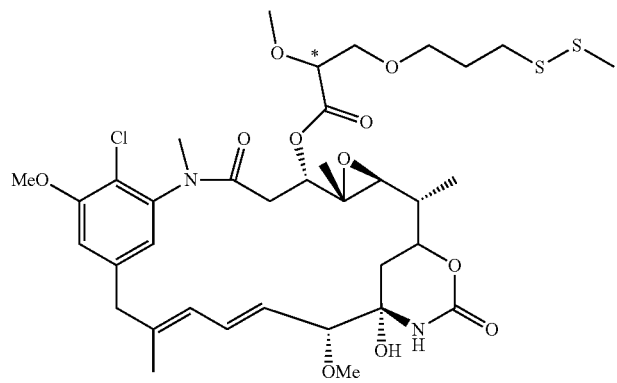
CE-056
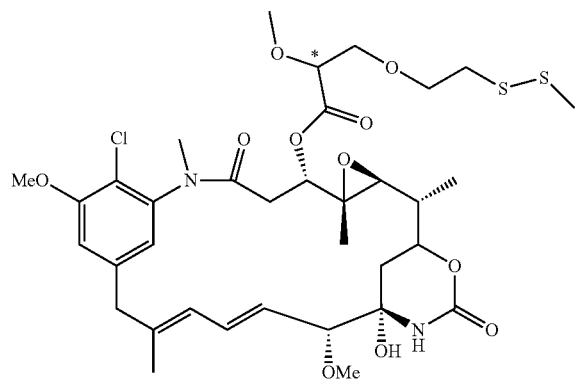
CE-002
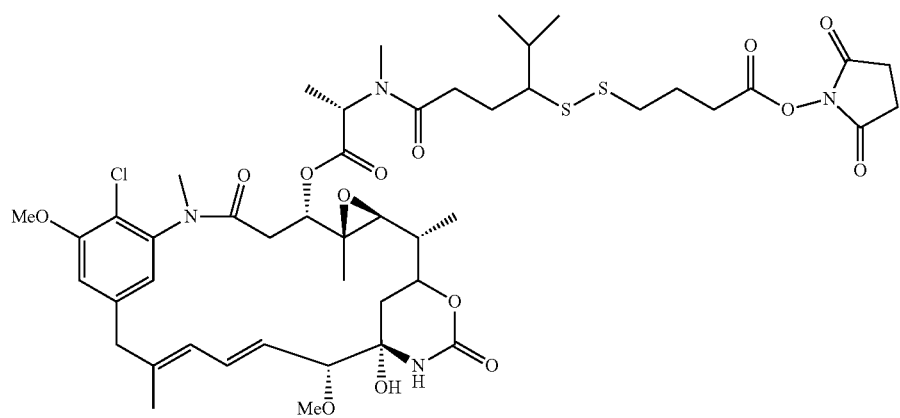

-continued
CE-004
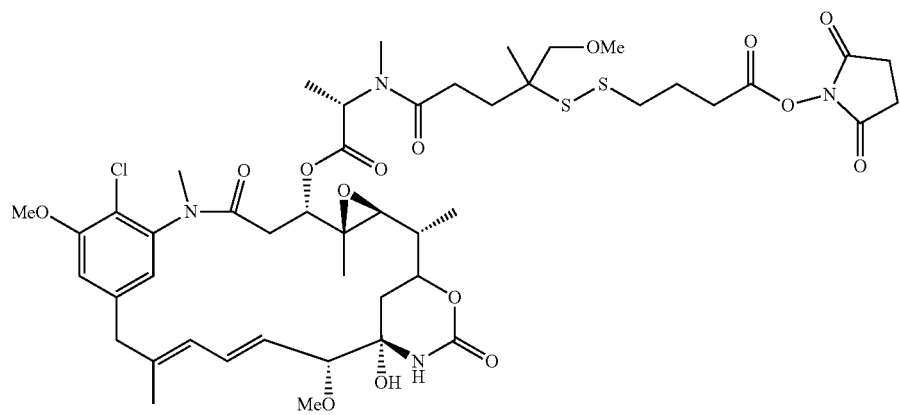
CE-005
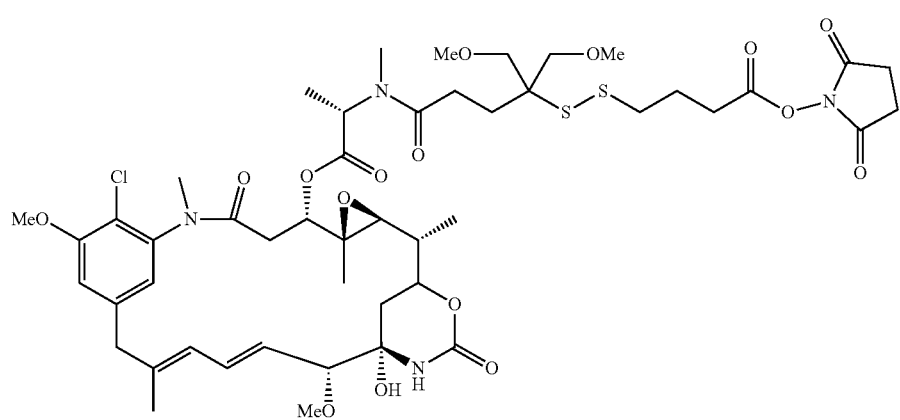
CE-034
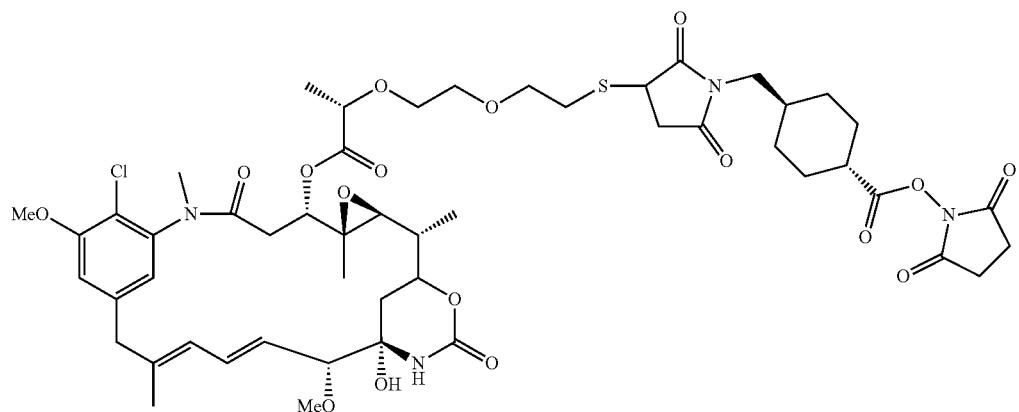
CE-035
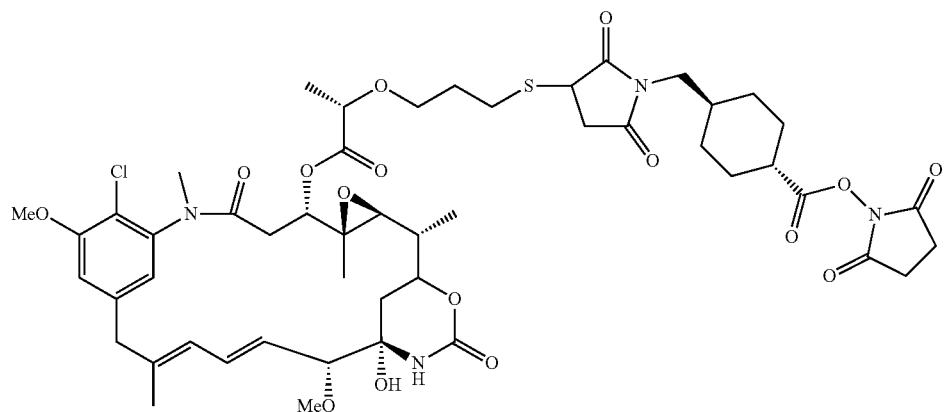

-continued
CE-037
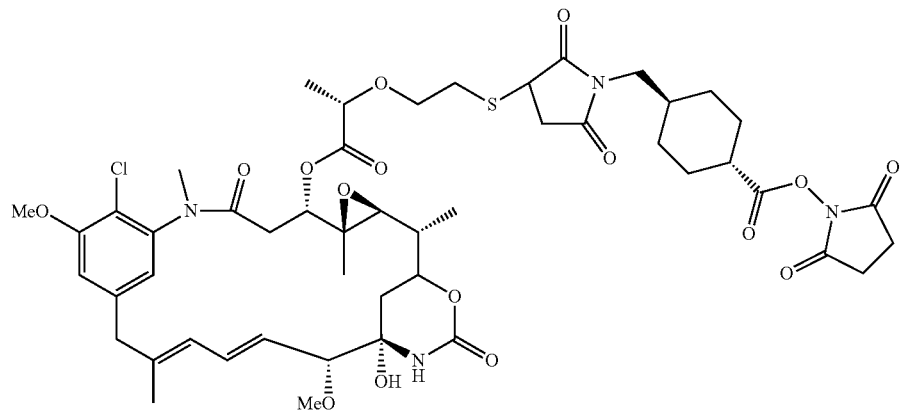
CE-007
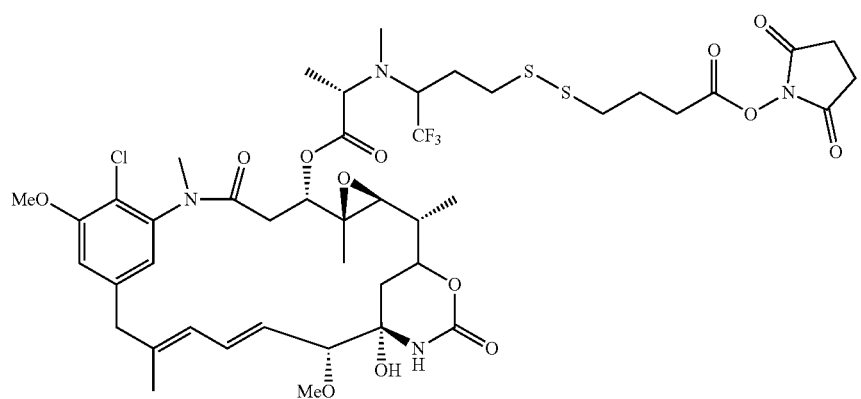
CE-041
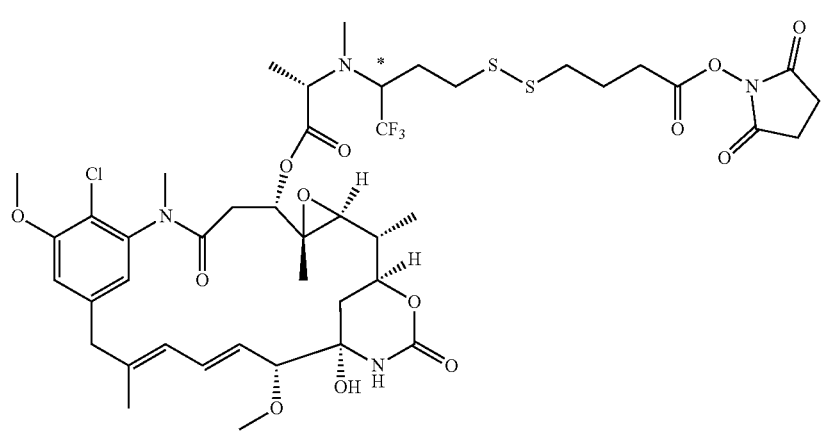

-continued
CE-038
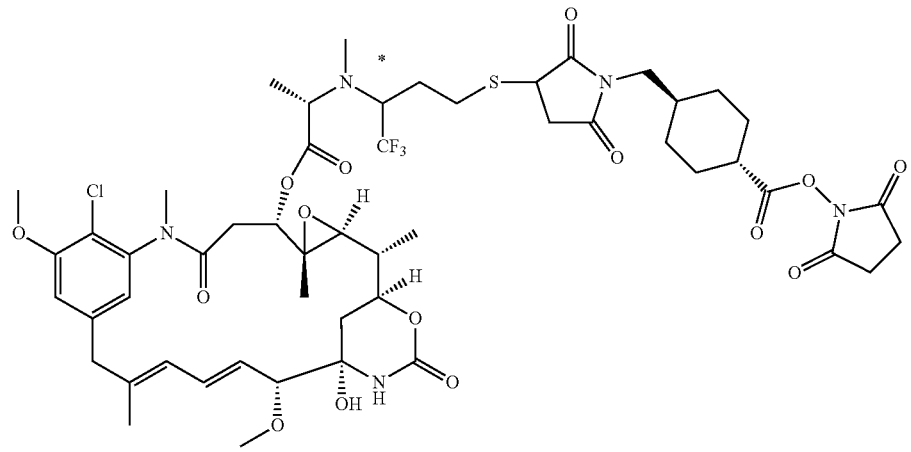
CE-039
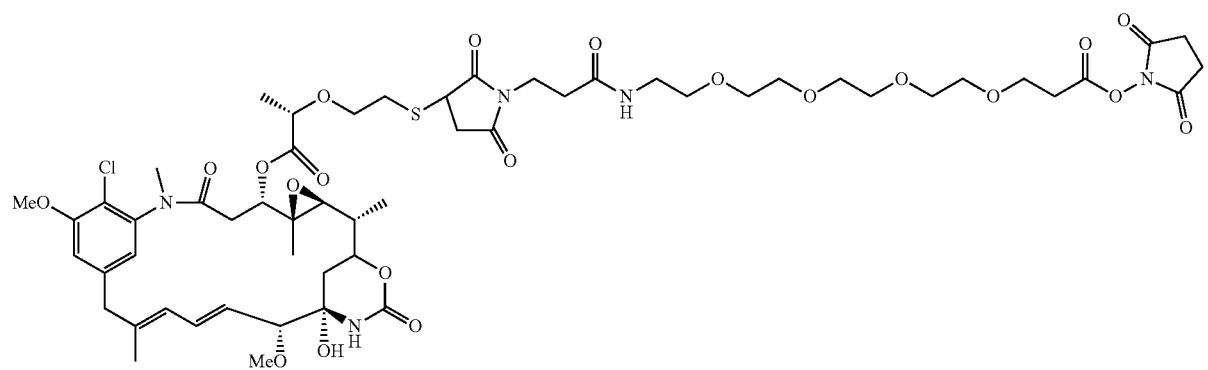
CE-040
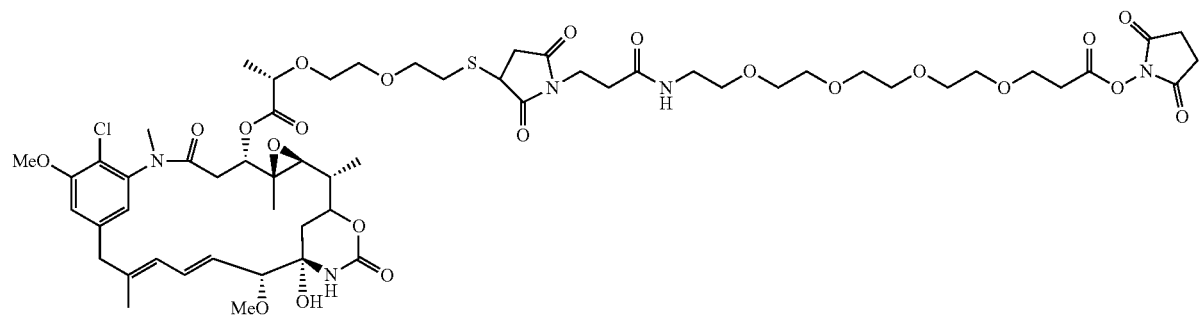
CE-043
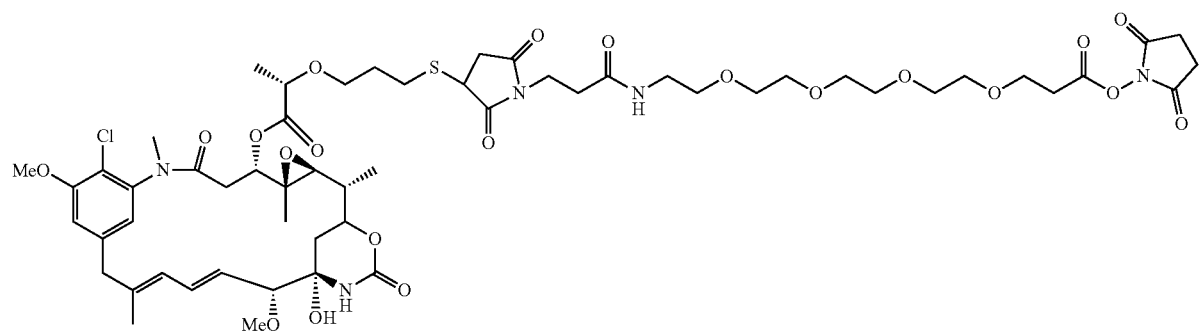

CE-048
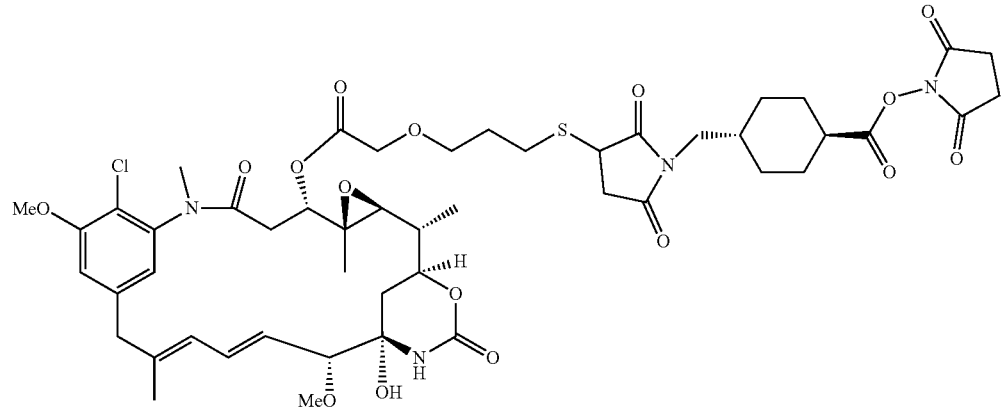
CE-049
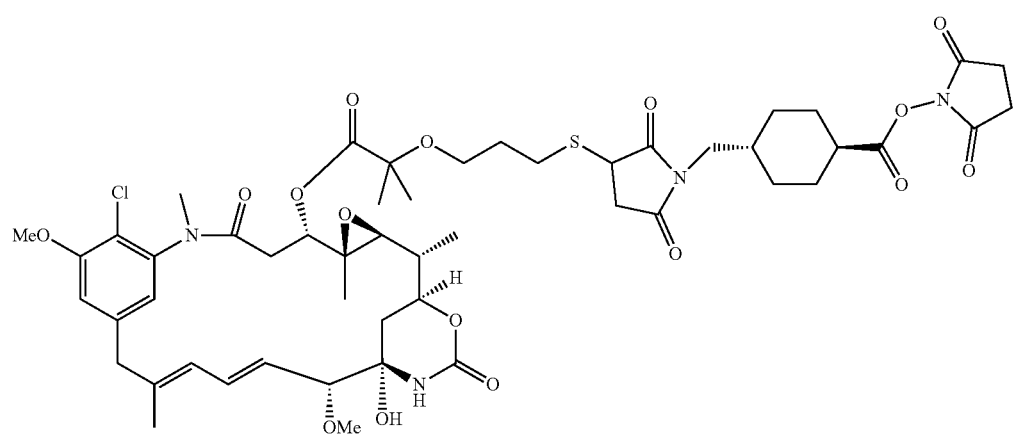
CE-051
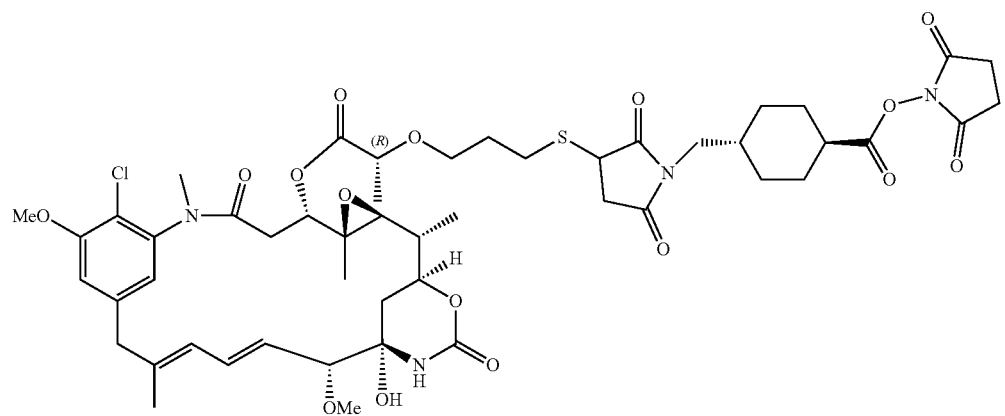

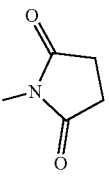
CE-052
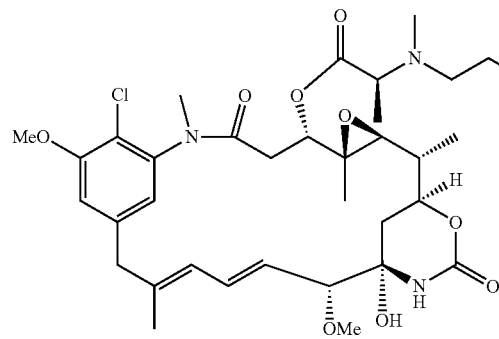
XDCE-M-001
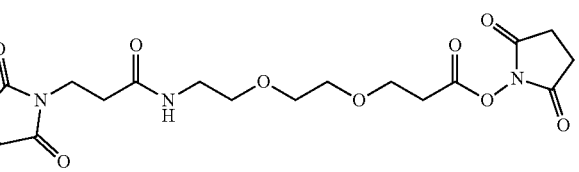
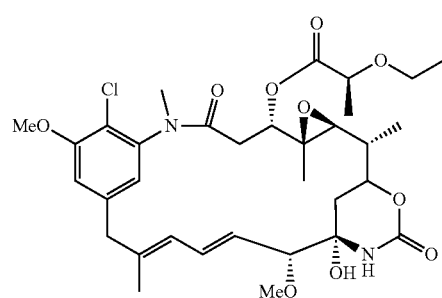
XDCE-M-002
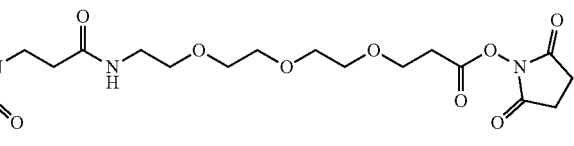
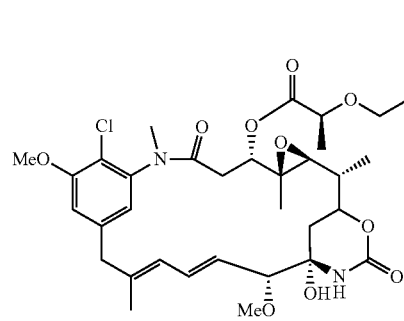
CE-045
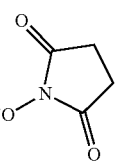
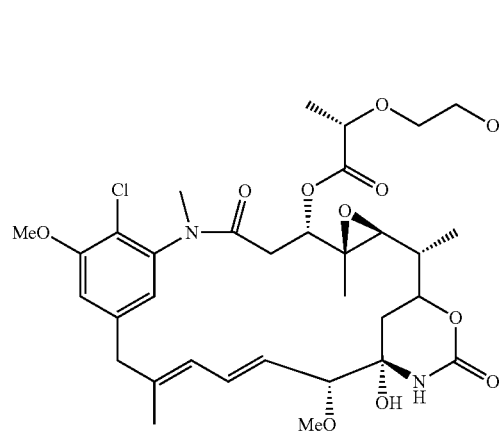

CE-047
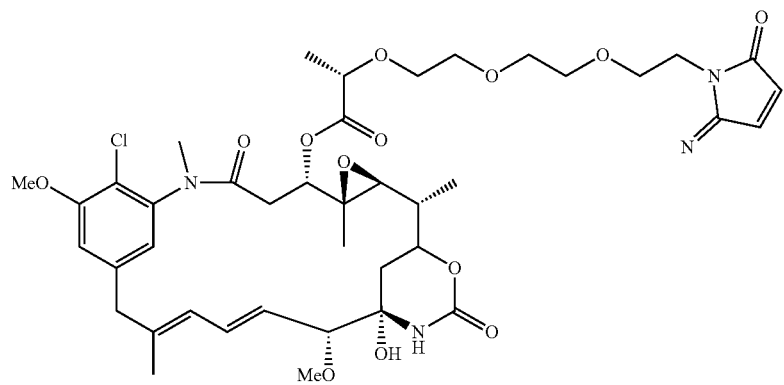
CE-050
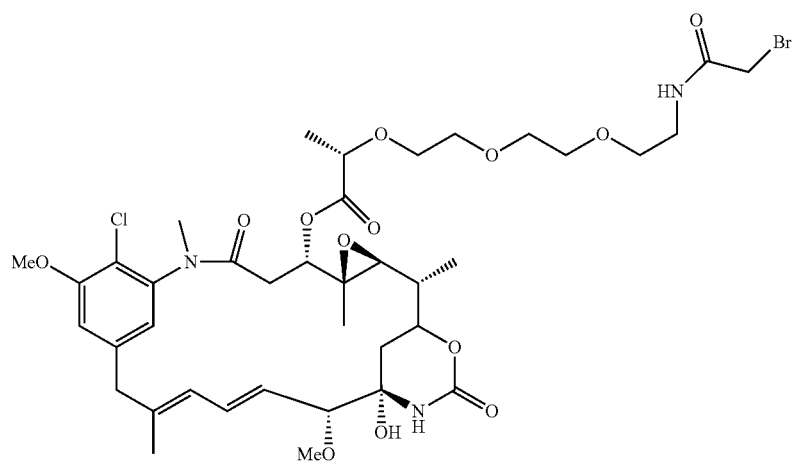
CE-046
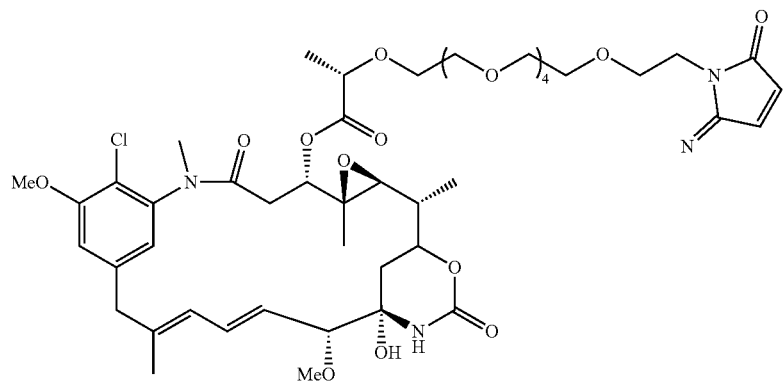
CE-063
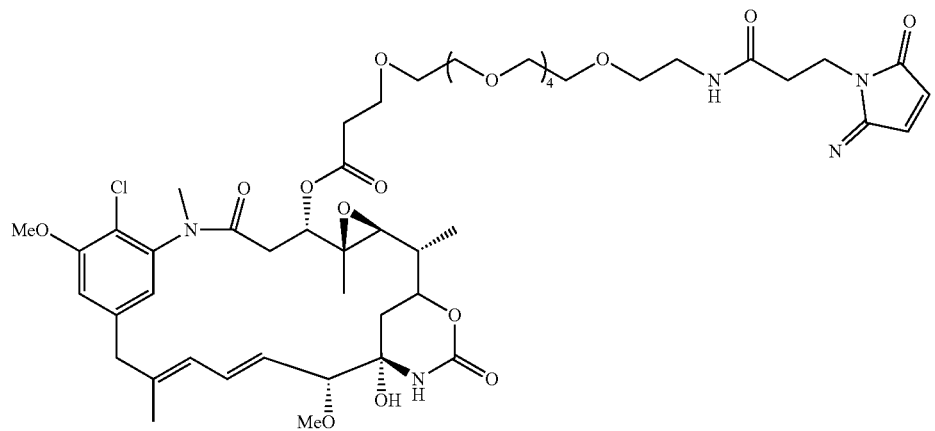

-continued
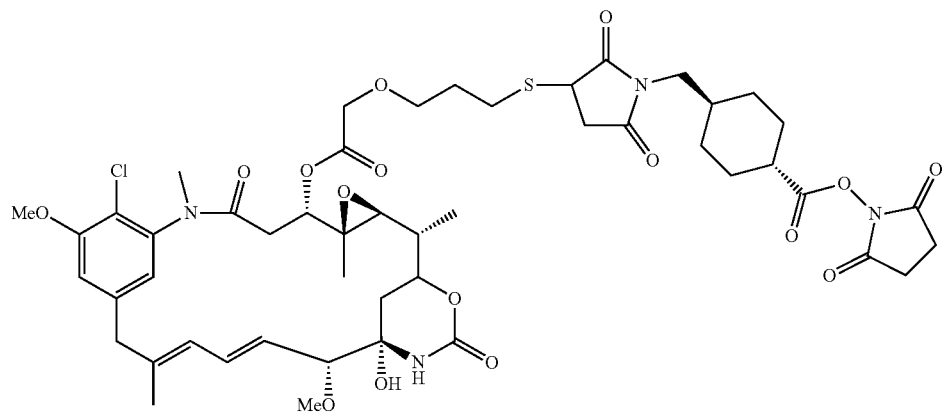
CE-048
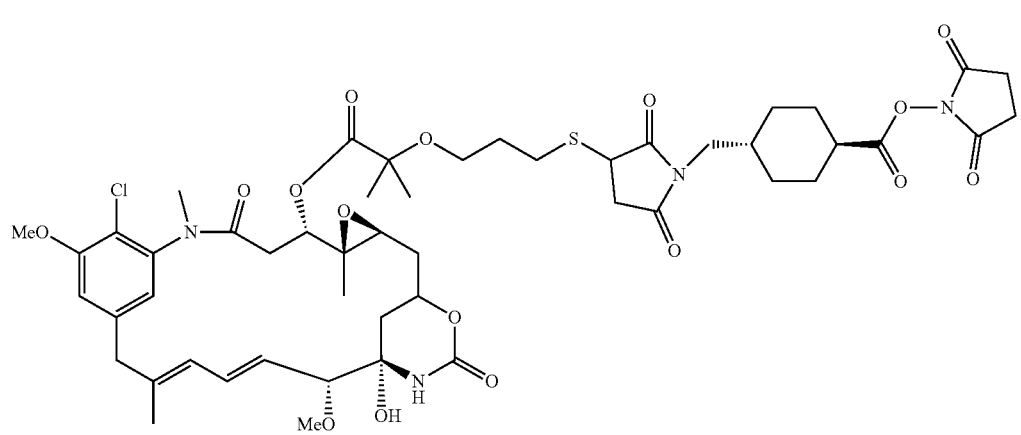
CE-049
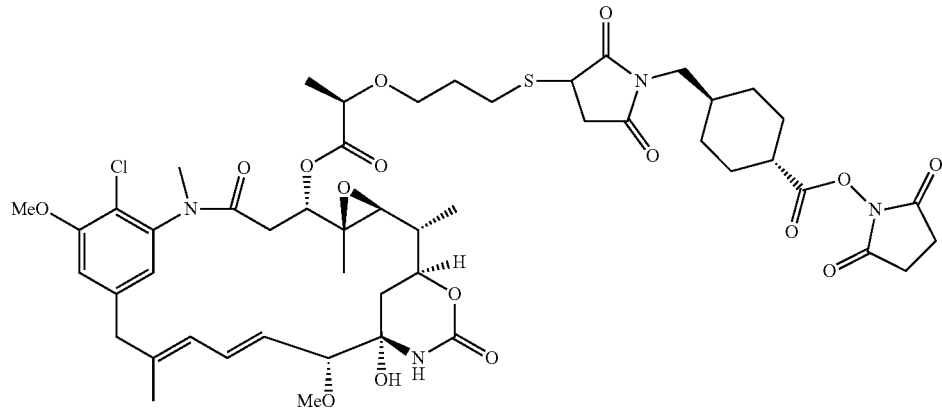
CE-051
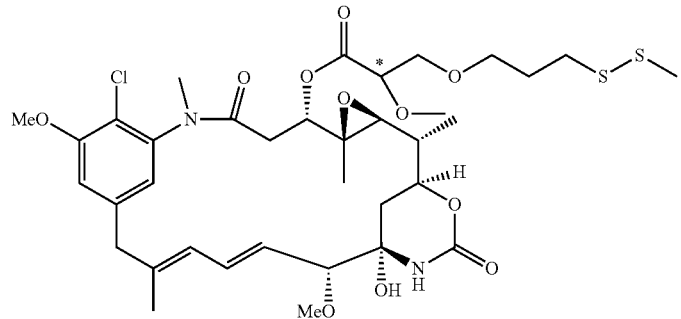
CE-054/CE-055

CE-056
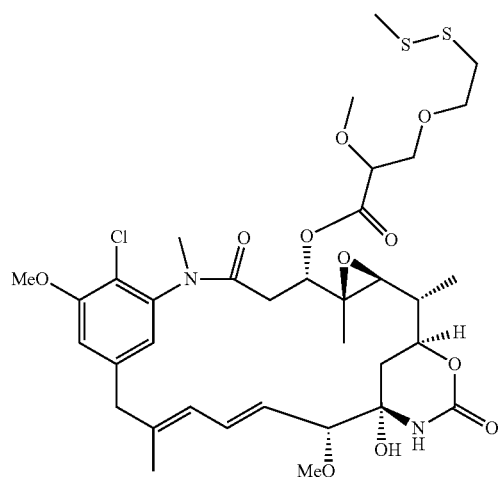
CE-057
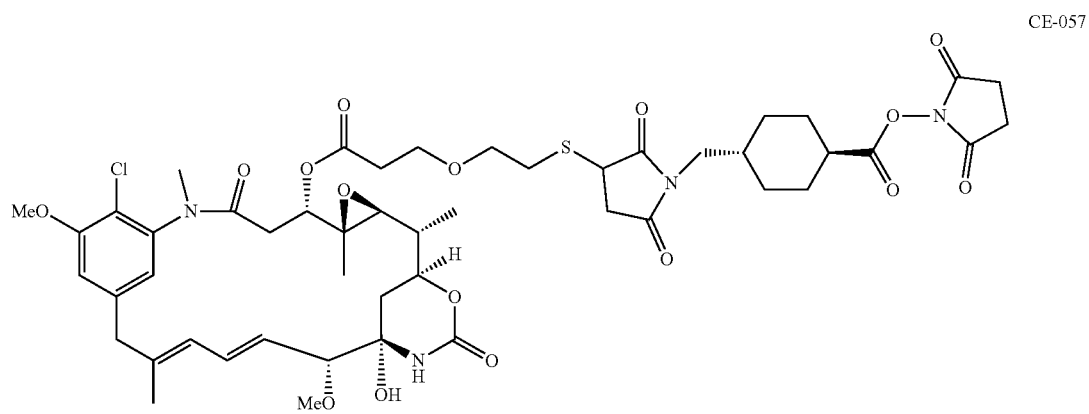
CE-052a
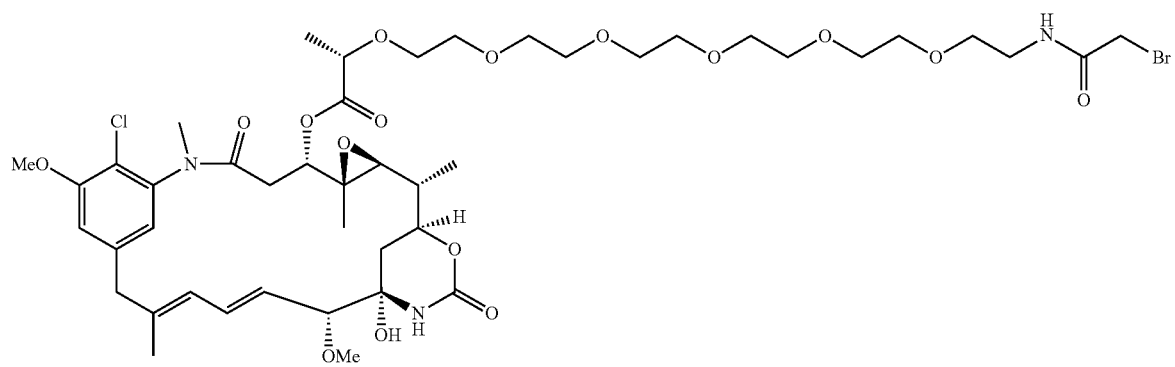
10-16
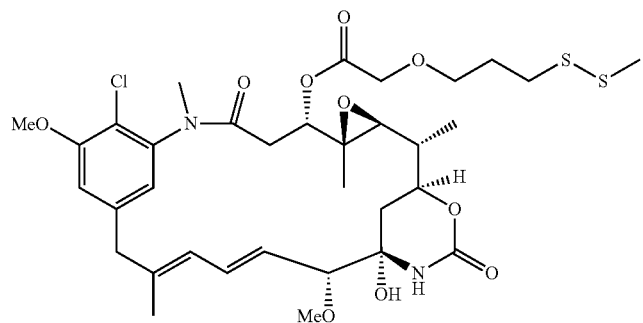

11-16
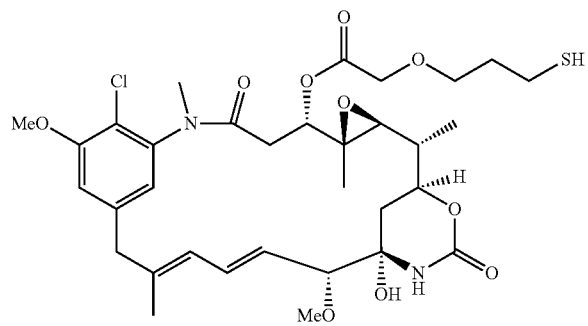
8-17
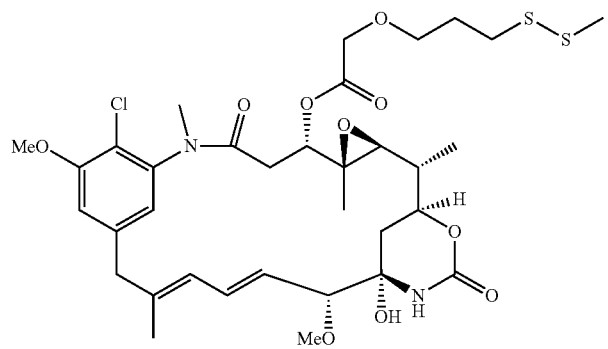
9-17
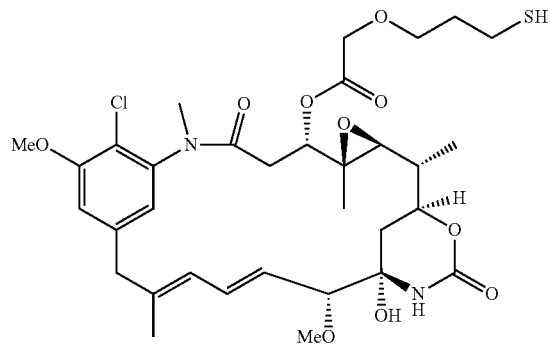
8-18
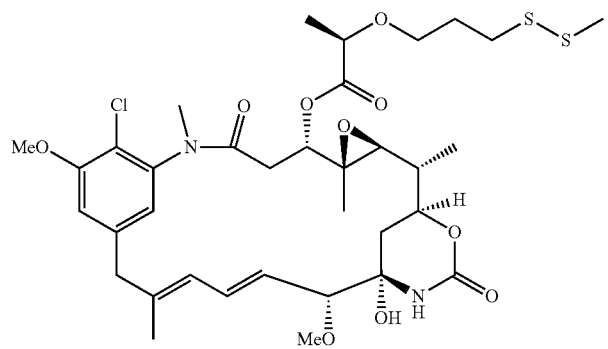

-continued
9-18
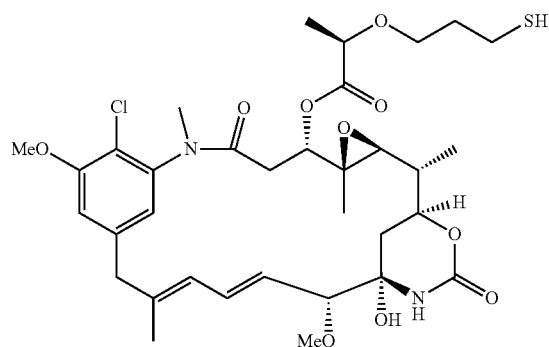
7-22
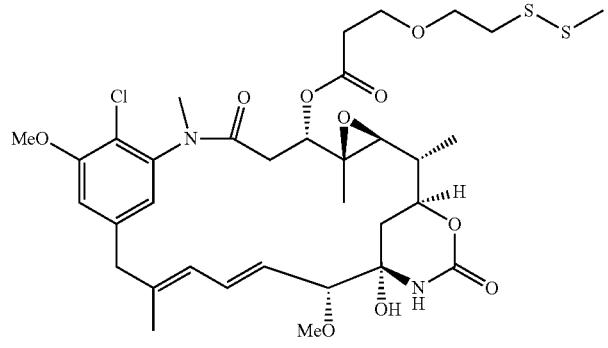
and
8-22
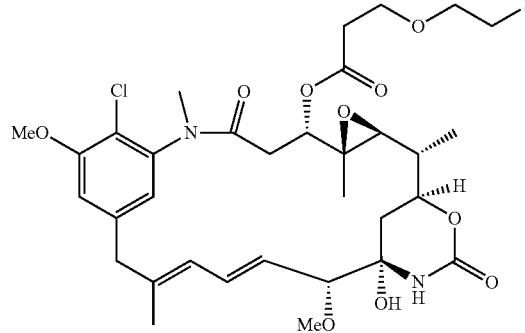
10. A process for preparing the antibody drug conjugate represented by formula IB according to claim 1, comprising in an organic solvent, under the condition of pH 6-8, conjugating the intermediate IA with a monoclonal antibody to deliver the antibody drug conjugate represented by formula IB;
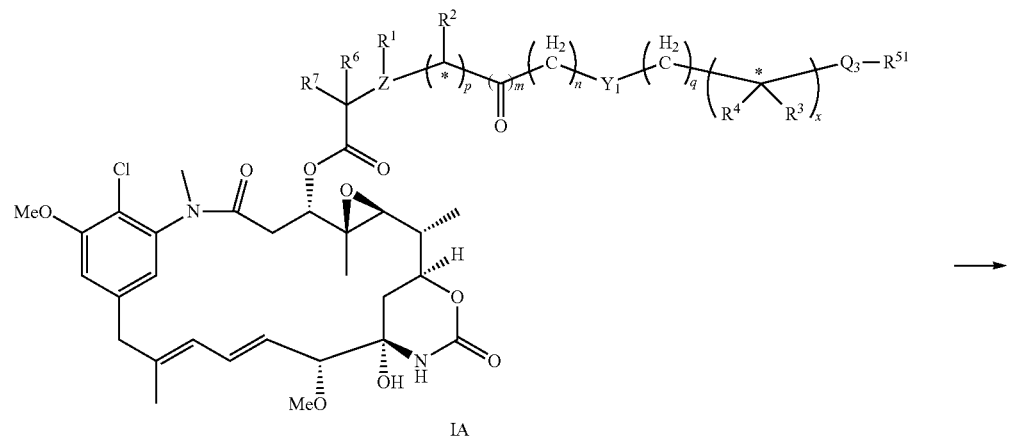

-continued

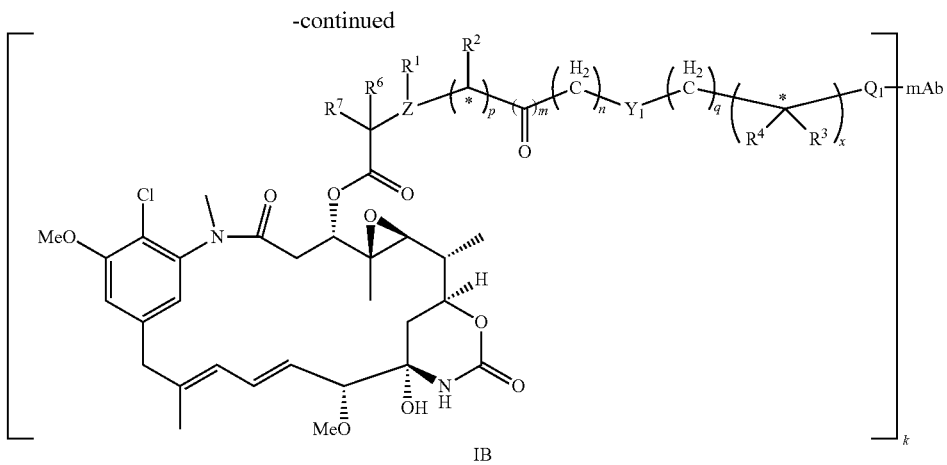

in the compound represented by formula IA or IB, each letters and groups is defined as that in claim 1.

11. A method for treating breast cancer in a subject in need thereof, comprising: administering an effective amount of the antibody drug conjugate according to claim 1 to the subject.

12. A pharmaceutical composition, comprising the antibody drug conjugate according to claim 1, as well as one or more than one pharmaceutically acceptable excipients.

13. The antibody drug conjugate represented by formula TB according to claim 4, wherein, in the antibody drug conjugate represented by formula Ib or Ib1,
- $R^1$ is methyl, ethyl, propyl, butyl, iso-propyl, iso-butyl or tert-butyl;
- $R^2$ is a halogenated $C_1$-$C_4$ alkyl, the halogen contained in the halogenated $C_1$-$C_4$ alkyl is fluorine, chlorine, or bromine;
- the halogenated $C_1$-$C_4$ alkyl is a halogenated methyl, a halogenated ethyl, a halogenated propyl, a halogenated iso-propyl, a halogenated butyl, a halogenated iso-butyl or a halogenated tert-butyl;
- p is 0, 1 or 2;
- n is 0, 1 or 2;
- q is 0, 1 or 2;
- when Y is a chemical bond, the chemical bond is a single bond,
- when Y2 is

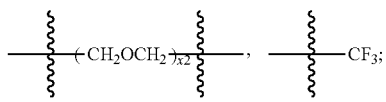

x2 is 1, 2, 3, 4, 5, 6, 7, 8, 9 or 10;
- $R^3$ and $R^4$ are independently methyl, ethyl, propyl, butyl, iso-propyl, iso-butyl, tert-butyl, a substituted methyl, a substituted ethyl, a substituted propyl, a substituted butyl, a substituted iso-propyl, a substituted iso-butyl or a substituted tert-butyl;
- in $R^3$ or $R^4$, the substituent contained in the substituted or unsubstituted $C_1$-$C_4$ alkyl refers to methoxy, ethoxy, propoxy, butoxy, iso-propoxy, iso-butoxy, tert-butoxy;
- x is 0, 1 or 2;
- when $R^8$ is a substituted or unsubstituted $C_1$-$C_4$ alkyl, the substituted or unsubstituted $C_1$-$C_4$ alkyl is a substituted or unsubstituted methyl, a substituted or unsubstituted ethyl, a substituted so-propyl, a substituted or unsubstituted iso-propyl, a substituted or unsubstituent contained butyl, a substituted or unsubstituted iso-butyl or a substituted or unsubstituted tert-butyl;
- $R^6$ is an unsubstituted $C_1$-$C_4$ alkyl;
- $R^7$ is an unsubstituted $C_1$-$C_4$ alkyl or an unsubstituted $C_1$-$C_4$ alkoxy;
- mAb represents a monoclonal antibody, or Herceptin.

14. The antibody drug conjugate represented by formula IB according to claim 13, wherein, in the antibody drug conjugate represented by formula Ib or Ib1,
when $R^2$ is a halogenated methyl, the halogenated methyl is

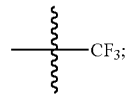

when $R^3$ and $R^4$ are independently a substituted methyl, the substituted methyl is

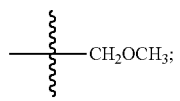

when $R^8$ is a substituted propyl, the substituted propyl is

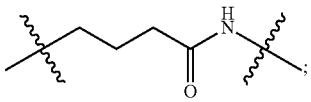 [SMILES: *CCCC(=O)N*]

$R^6$ is methyl, ethyl, propyl, iso-propyl, butyl, iso-butyl or tert-butyl;
$R^7$ is methyl, ethyl, propyl, iso-propyl, butyl, iso-butyl, tert-butyl methoxy, ethoxy, propoxy, iso-propoxy, butoxy, iso-butoxy or tert-butoxy.

15. An intermediate represented by formula IA according to claim 6, wherein, in formula IA,
$R^1$ is methyl, ethyl, propyl, butyl, iso-propyl, iso-butyl or tert-butyl;

$R^2$ is a halogenated $C_1$-$C_4$ alkyl, the halogen contained in the halogenated $C_1$-$C_4$ alkyl is fluorine, chlorine, or bromine;

the halogenated $C_1$-$C_4$ alkyl is a halogenated methyl, a halogenated ethyl, a halogenated propyl, a halogenated iso-propyl, a halogenated butyl, a halogenated iso-butyl or a halogenated tert-butyl;

p is 0, 1 or 2;
n is 0, 1 or 2;
q is 0, 1 or 2;

when Y1 is a chemical bond, the chemical bond is a single bond, when Y1 is

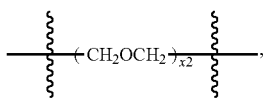

x2, is 1, 2, 3, 4, 5, 6, 7, 8, 9 or 10;

$R^3$ and $R^4$ are independently methyl, ethyl, propyl, butyl iso-propyl, iso-butyl, tert-butyl, a substituted methyl, a substituted ethyl, a substituted propyl, a substituted butyl, a substituted iso-propyl, a substituted iso-butyl or a substituted tert-butyl;

in $R^3$ or $R^4$, the substituent contained in the substituted or unsubstituted $C_1$-$C_4$ alkyl refers to methoxy, ethoxy, propoxy, butoxy, iso-propoxy, iso-butoxy, tert-butoxy;

x is 0, 1 or 2;
$R^6$ is an unsubstituted $C_1$-$C_4$ alkyl;
$R^7$ is an unsubstituted $C_1$-$C_4$ alkyl or an unsubstituted $C_1$-$C_4$ alkoxy.

16. An intermediate represented by formula IA according to claim 15, wherein, in formula IA, when $R^2$ is a halogenated methyl, the halogenated methyl is

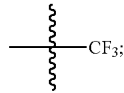

when $R^3$ and $R^4$ are independently a substituted methyl, the substituted methyl is

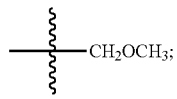

$R^6$ is methyl, ethyl, propyl, iso-propyl, butyl, iso-butyl or tert-butyl;

$R^7$ is methyl, ethyl, propyl, iso-propyl, butyl, iso-butyl, tert-butyl methoxy, ethoxy, propoxy, iso-propoxy, butoxy, iso-butoxy or tert-butoxy.

17. A method for treating breast cancer in a subject in need thereof, comprising: administering an effective amount of the intermediate according to claim 6 to the subject.

18. A pharmaceutical composition, comprising the intermediate according to claim 6, as well as one or more than one pharmaceutically acceptable excipients.

\* \* \* \* \*